US012558323B2

(12) United States Patent
Brown et al.

(10) Patent No.: US 12,558,323 B2
(45) Date of Patent: *Feb. 24, 2026

(54) PARTICLE FORMATION AND MORPHOLOGY

(71) Applicant: Elektrofi, Inc., Boston, MA (US)

(72) Inventors: Paul Brown, Boston, MA (US); Lyndon Fitzgerald Charles, Jr., Medford, MA (US); Chase Spenser Coffman, Newton, MA (US); Daniel Benjamin Dadon, East Boston, MA (US); James W. Ivey, Reading, MA (US); Lisa Liu, Somerville, MA (US); Chaitanya Sudrik, Stoneham, MA (US)

(73) Assignee: Elektrofi, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/659,740

(22) Filed: May 9, 2024

(65) Prior Publication Data

US 2024/0293332 A1 Sep. 5, 2024

Related U.S. Application Data

(63) Continuation of application No. 18/344,142, filed on Jun. 29, 2023, which is a continuation of application No. 17/351,937, filed on Jun. 18, 2021, now Pat. No. 11,717,488, which is a continuation of application No. PCT/US2020/015957, filed on Jan. 30, 2020.

(60) Provisional application No. 62/799,696, filed on Jan. 31, 2019.

(51) Int. Cl.
| | |
|---|---|
| *A61K 9/16* | (2006.01) |
| *A61K 9/10* | (2006.01) |
| *A61K 9/50* | (2006.01) |
| *A61K 9/51* | (2006.01) |
| *A61K 47/14* | (2017.01) |
| *C07K 16/00* | (2006.01) |

(52) U.S. Cl.
CPC ............... *A61K 9/51* (2013.01); *C07K 16/00* (2013.01)

(58) Field of Classification Search
None
See application file for complete search history.

(56) References Cited

U.S. PATENT DOCUMENTS

| | | | |
|---|---|---|---|
| 3,013,007 | A | 12/1961 | Dale et al. |
| 3,882,036 | A | 5/1975 | Krezanoski et al. |
| 4,172,896 | A | 10/1979 | Uno et al. |
| 4,531,056 | A | 7/1985 | Labowsky et al. |
| 5,358,970 | A | 10/1994 | Ruff et al. |
| 5,427,798 | A | 6/1995 | Ludwig et al. |
| 5,541,231 | A | 7/1996 | Ruff et al. |
| 5,595,721 | A | 1/1997 | Kaminski et al. |
| 5,612,055 | A | 3/1997 | Bedford et al. |
| 5,677,180 | A | 10/1997 | Robinson et al. |
| 5,731,000 | A | 3/1998 | Ruff et al. |
| 5,736,137 | A | 4/1998 | Anderson et al. |
| 5,739,169 | A | 4/1998 | Ocain et al. |
| 5,763,493 | A | 6/1998 | Ruff et al. |
| 5,801,005 | A | 9/1998 | Cheever et al. |
| 5,824,311 | A | 10/1998 | Greene et al. |
| 5,830,880 | A | 11/1998 | Sedlacek et al. |
| 5,840,731 | A | 11/1998 | Mayer et al. |
| 5,846,945 | A | 12/1998 | McCormick |
| 5,874,029 | A | 2/1999 | Subramaniam et al. |
| 6,095,134 | A | 8/2000 | Sievers et al. |
| 6,110,973 | A | 8/2000 | Young |
| 7,001,888 | B2 | 2/2006 | Tidmarsh et al. |
| 8,013,022 | B2 | 9/2011 | Deangelo et al. |
| 8,512,754 | B2 | 8/2013 | Needham |
| 8,728,525 | B2 | 5/2014 | Brown et al. |
| 8,779,094 | B2 | 7/2014 | Johnston et al. |
| 8,939,388 | B1 | 1/2015 | Beetz et al. |
| 9,259,701 | B2 | 2/2016 | Palmer et al. |
| 9,364,542 | B2 | 6/2016 | Chang |
| 9,597,385 | B2 | 3/2017 | Caplan |
| 9,643,996 | B2 | 5/2017 | Petrel et al. |
| 11,077,059 | B2 * | 8/2021 | Coffman ............... B01J 13/206 |
| 11,459,376 | B2 * | 10/2022 | Brown ................... A61K 47/14 |
| 11,510,995 | B2 | 11/2022 | Sanchez Martin et al. |
| 11,654,112 | B2 * | 5/2023 | Coffman ................. A61K 9/14 424/59 |
| 11,717,488 | B2 * | 8/2023 | Brown ................ A61K 9/5192 424/489 |

(Continued)

FOREIGN PATENT DOCUMENTS

| | | |
|---|---|---|
| CN | 1750811 A | 3/2006 |
| CN | 103908432 A | 7/2014 |

(Continued)

OTHER PUBLICATIONS

Elektrofi (2021, 11 pages), (Year: 2021).*
Oxford Dictionary (2024, one page) (Year: 2024).*
English language abstract for JP 2010609243 A5, 2011, 1 page. (Year: 2011).*
Allahham, D. et al., "Development and application of a microcapillary rheometer for in-vitro evaluation of parenteral injectability," Journal of Pharmacy and Pharmacology, vol. 56; 709-716 (2004).
Aniket et al., "Microglassification Tm: A novel technique for protein dehydration," J Pharm Sci. 103(3): 810-820 (2014).
Banerjee et al., "Electrospray ionization mass spectrometry: a technique to access the information beyond the molecular weight of the analyte," Int J Anal Chem. Article 282574 (2012) (40 pages).

(Continued)

*Primary Examiner* — Michael Szperka
*Assistant Examiner* — Marianne Dibrino
(74) *Attorney, Agent, or Firm* — Hamilton, Brook, Smith & Reynolds, P.C.

(57) ABSTRACT
The present disclosure relates to compositions and methods that enable the formation of pharmaceutically relevant particles that can be used for therapy. In particular, the methods disclosed herein allow the controlled formation of circular particles having low internal void spaces comprising bioactive therapeutic agents.

10 Claims, 18 Drawing Sheets

(56) References Cited

U.S. PATENT DOCUMENTS

| | | |
|---|---|---|
| 11,795,429 B2 | 10/2023 | Bitterfield et al. |
| 12,115,262 B2 | 10/2024 | Coffman et al. |
| 12,178,913 B2 | 12/2024 | Coffman et al. |
| 12,263,249 B2 | 4/2025 | Coffman et al. |
| 12,263,253 B2 | 4/2025 | Coffman et al. |
| 12,377,050 B2 | 8/2025 | Auer et al. |
| 2001/0031801 A1 | 10/2001 | Lyons et al. |
| 2002/0081732 A1 | 6/2002 | Bowlin et al. |
| 2003/0055010 A1 | 3/2003 | De Haan |
| 2004/0197469 A1 | 10/2004 | Lyons et al. |
| 2005/0013868 A1 | 1/2005 | Brynjelsen et al. |
| 2005/0019410 A1 | 1/2005 | Johnson |
| 2005/0186183 A1 | 8/2005 | Deangelo et al. |
| 2006/0002862 A1 | 1/2006 | Truong-Le et al. |
| 2006/0147400 A1 | 7/2006 | Piot |
| 2006/0292224 A1 | 12/2006 | Moore et al. |
| 2008/0026068 A1 | 1/2008 | Brown et al. |
| 2008/0095849 A1 | 4/2008 | Wu et al. |
| 2009/0035381 A1 | 2/2009 | Stankus et al. |
| 2009/0226530 A1 | 9/2009 | Lassner et al. |
| 2009/0274765 A1 | 11/2009 | Beduneau et al. |
| 2010/0047248 A1 | 2/2010 | Darvari et al. |
| 2010/0092526 A1 | 4/2010 | Baker, Jr. et al. |
| 2010/0092778 A1 | 4/2010 | Watanabe et al. |
| 2010/0305500 A1 | 12/2010 | Lambert et al. |
| 2010/0330169 A1 | 12/2010 | Bunick et al. |
| 2011/0223208 A1 | 9/2011 | Hill et al. |
| 2011/0280864 A1 | 11/2011 | Johnston et al. |
| 2012/0076800 A1* | 3/2012 | Dai .................... A61K 47/44 |
| | | 424/158.1 |
| 2012/0157591 A1 | 6/2012 | Rufner et al. |
| 2012/0244196 A1 | 9/2012 | Okubo et al. |
| 2012/0258914 A1 | 10/2012 | Kumar et al. |
| 2013/0256931 A1 | 10/2013 | Palmer et al. |
| 2014/0052020 A1 | 2/2014 | Allen et al. |
| 2014/0262694 A1 | 9/2014 | Knigge |
| 2014/0263694 A1 | 9/2014 | Lin et al. |
| 2014/0271843 A1 | 9/2014 | Ma et al. |
| 2014/0288282 A1 | 9/2014 | Petrel et al. |
| 2014/0303356 A1 | 10/2014 | Gramer et al. |
| 2014/0308270 A1 | 10/2014 | Lobo et al. |
| 2014/0348852 A1 | 11/2014 | Vos et al. |
| 2014/0378370 A1 | 12/2014 | Johnston et al. |
| 2014/0378655 A1 | 12/2014 | Anderson |
| 2015/0079395 A1 | 3/2015 | Cruise et al. |
| 2015/0157576 A1 | 6/2015 | Shum et al. |
| 2016/0015640 A1 | 1/2016 | Propst et al. |
| 2016/0128944 A1 | 5/2016 | Chawrai et al. |
| 2016/0250329 A1 | 9/2016 | Bukrinski et al. |
| 2016/0271064 A1 | 9/2016 | Sell et al. |
| 2017/0210554 A1 | 7/2017 | Black et al. |
| 2018/0333493 A1 | 11/2018 | Shenoy |
| 2019/0142957 A1 | 5/2019 | Teran et al. |
| 2019/0374470 A1 | 12/2019 | Coffman et al. |
| 2020/0253875 A1 | 8/2020 | Coffman et al. |
| 2020/0268695 A1 | 8/2020 | Sanders |
| 2021/0220289 A1* | 7/2021 | Coffman .............. A61K 9/1688 |
| 2021/0309724 A1 | 10/2021 | Brown et al. |
| 2021/0315827 A1 | 10/2021 | Brown et al. |
| 2021/0322317 A1 | 10/2021 | Coffman et al. |
| 2021/0403599 A1 | 12/2021 | Badovinac-Crnjevic et al. |
| 2022/0211627 A1 | 7/2022 | Arrighi et al. |
| 2022/0389084 A1 | 12/2022 | Brown et al. |
| 2023/0065628 A1 | 3/2023 | Auer et al. |
| 2023/0094393 A1 | 3/2023 | Charles et al. |
| 2023/0181473 A1 | 6/2023 | Auer et al. |
| 2023/0338299 A1 | 10/2023 | Paul et al. |
| 2023/0355530 A1 | 11/2023 | Coffman et al. |
| 2024/0255517 A1 | 8/2024 | Carter et al. |
| 2024/0270864 A1 | 8/2024 | Brown et al. |
| 2024/0415782 A1 | 12/2024 | Coffman et al. |
| 2025/0025425 A1 | 1/2025 | Brown et al. |
| 2025/0026811 A1 | 1/2025 | Brown et al. |
| 2025/0064744 A1 | 2/2025 | Coffman et al. |
| 2025/0082736 A1 | 3/2025 | Brown et al. |
| 2025/0186348 A1 | 6/2025 | Coffman et al. |
| 2025/0228790 A1 | 7/2025 | Coffman et al. |

FOREIGN PATENT DOCUMENTS

| | | | |
|---|---|---|---|
| EP | 0677332 A2 | 10/1995 | |
| EP | 3236987 B1 | 3/2020 | |
| EP | 2773330 B1 | 9/2020 | |
| JP | 2003-513710 A | 4/2003 | |
| JP | 2005-504090 A | 2/2005 | |
| JP | 2005-504764 A | 2/2005 | |
| JP | 2008-266128 A | 11/2008 | |
| JP | 2010-524948 A | 5/2010 | |
| JP | 2011-079747 A | 4/2011 | |
| JP | 2011-241223 A | 12/2011 | |
| JP | 2012-500799 A | 1/2012 | |
| JP | 2012-508744 A | 4/2012 | |
| JP | 2013-166100 A | 8/2013 | |
| JP | 2014-058466 A | 4/2014 | |
| JP | 2014-510077 A | 4/2014 | |
| JP | 2014-129357 A | 7/2014 | |
| JP | 2019-535832 A | 12/2019 | |
| WO | 99/11196 A1 | 3/1999 | |
| WO | 03/35301 A1 | 5/2003 | |
| WO | 2006/087354 A2 | 8/2006 | |
| WO | 2007/059782 A1 | 5/2007 | |
| WO | 2008/062908 A1 | 5/2008 | |
| WO | 2008/092084 A2 | 7/2008 | |
| WO | 2010/044867 A1 | 4/2010 | |
| WO | 2010/082543 A1 | 7/2010 | |
| WO | 2011/131943 A2 | 10/2011 | |
| WO | 2012/042274 A1 | 4/2012 | |
| WO | 2014/057424 A2 | 4/2014 | |
| WO | 2015/085898 A1 | 6/2015 | |
| WO | 2015/138844 A1 | 9/2015 | |
| WO | 2015/196091 A1 | 12/2015 | |
| WO | 2016/014497 A1 | 1/2016 | |
| WO | 2016/089309 A1 | 6/2016 | |
| WO | 2017/106716 A1 | 6/2017 | |
| WO | WO 2018/098376 A1 * | 5/2018 | |
| WO | 2018/234489 A1 | 12/2018 | |
| WO | 2019/023392 A1 | 1/2019 | |
| WO | 2019/226969 A1 | 11/2019 | |
| WO | 2020/051307 A1 | 3/2020 | |
| WO | 2020/160323 A2 | 8/2020 | |
| WO | 2021/050953 A1 | 3/2021 | |
| WO | 2021/158959 A2 | 8/2021 | |
| WO | 2021/168271 A1 | 8/2021 | |
| WO | 2021/212019 A1 | 10/2021 | |
| WO | 2022/256840 A2 | 12/2022 | |
| WO | 2023/212721 A1 | 11/2023 | |
| WO | 2024/177927 A1 | 8/2024 | |
| WO | 2025/054552 A1 | 3/2025 | |

OTHER PUBLICATIONS

Bock et al., "Electrospraying of polymers with therapeutic molecules: state of the art," Prog Polym Sci. 37(11): 1510-1551 (2012) (67 pages).

Bogelein et al., "Cyclone selection influences protein damage during drying in a mini spray-dryer," Int J Pharm. 401 (1-2): 68-71 (2010).

Capelle, M.A.H. et al., "High throughout screening of protein formulation stability: Practical considerations," European Journal of Pharmaceutics and Biopharmaceutics, vol. 65; 131-148 (2007).

Cloupeau et al., "Electrostatic spraying of liquids: Main functioning modes," J Electrostat. 25(2): 165-184 (1990).

Clackson, T. et al., "Making antibody fragments using phage display libraries," Nature vol. 352; 624-628 (1991).

Cloupeau et al., "Electrohydrodynamic spraying functioning modes: a critical review," J Aerosol Sci. 25(6): 1021-1036 (1994).

Dias et al., "Tolerability of High-vol. Subcutaneous Injections of a Viscous Placebo Buffer: A Randomized, Crossover Study in Healthy Subjects," AAPS PharmSciTech. 16(5): 1101-1107 (2015).

English translation of Office Action issued in Chinese Patent Application No. 201780072350.0, issued May 17, 2021 (16 pages).

(56) References Cited

OTHER PUBLICATIONS

European Search Report and Search Opinion Received for EP Application No. 18838118, mailed on May 6, 2021, 12 pages.
Fernandez de la Mora et al., "The current emitted by highly conducting taylor cones," J Fluid Mech. 260: 155-184 (1994).
Fernandez de la Mora et al., "The fluid dynamics of Taylor cones," Annu Rev Fluid Mech. 39: 217-43 (2007) (29 pages).
Forgacs, E. et al., "Direct (Normal)-Phase High-Performance Liquid Chromatography," Chapter II.B. in Molecular Basis of Chromatographic Separation, CRC Press, Baco Raton, FL; 120-131 (1997).
Galam et al., "High-throughput assay for the identification of Hsp90 inhibitors based on Hsp90- dependent refolding of firefly luciferase," available in PMC Mar. 1, 2008, published in final edited form as: Bioorg Med Chem. 15(5): 1939-1946 (2007) (16 pages).
Ganan-Calvo et al., "Current and droplet size in the electrospraying ofliquids. Scaling laws," J Aerosol Sci. 28(2): 249-275 (1997).
Gapinski et al., "Structure and dimensions of core-shell nanoparticles comparable to the confocal vol. studied by means of fluorescence correlation spectroscopy," Langmuir. 32(10): 2482-2491 (Feb. 2016).
Gikanga et al., "Manufacturing of High-Concentration Monoclonal Antibody Formulations via Spray Drying-the Road to Manufacturing Scale," PDA J Pharm Sci Technol. 69(1): 59-73 (2015) (16 pages).
Giugliano et al., "Efficacy, safety, and tolerability of a monoclonal antibody to proprotein convertase subtilisin/kexin type 9 in combination with a statin in patients with hypercholesterolaemia (LAPLACE-TIMI 57): a randomised, placebo-controlled, dose-ranging, phase 2 study," available in PMC Mar. 3, 2015, published in final edited form as: Lancet. 380(9858): 2007-17 (2012) (20 pages).
Haggag et al., "Evaluation of nano spray drying as a method for drying and formulation of therapeutic peptides and proteins," Front Pharmacol. 6:140 (2015) (5 pages).
Hickey, J.W. et al., "Biologically Inspired Design ofNanoparticle Artificial Antigen-Presenting Cells for Immunomodulation," Nano Letters, vol. 17; 7045-7054 )2017).
Hui et al., "Progress in preparation of peptide protein drug microspheres," The medicine herald, Issue 10, 2007, pp. 1-32. (Concise explanation met by English Translation of Search report cited concurrently as Other Document 11).
International Preliminary Report on Patentability received for PCT Patent Application No. PCT/US2020/015957, mailed on Aug. 12, 2021, 7 pages.
International Search Report and Written Opinion for International Application No. PCT/US2020/015957, entitled: "Particle Formation and Morphology," mailed Jun. 24, 2020.
Janssen Biotech Inc., "Highlights of prescribing information," <jans-senlabels.com/package-inserl/product-monograph/prescribinginformation/DARZALEX-pi.pdl>, dated Jul. 2019, retrieved on Aug. 22, 2019 (13 pages).
Kaltashov et al., "Estimates of Protein Surface Areas in Solution by Electrospray Ionization Mass Spectrometry," available in PMC Jan. 27, 2009, published in final edited form as: Anal Chem. 77(16): 5370-5379 (2005) (21 pages).
Kim et al., "Controlled production of emulsion drops using an electric field in a flow-focusing microfluidic device," Appl Phys Lett. 91: 133106 (2007) (3 Pages).
Ku et al., "Electrospray characteristics of highly viscous liquids," J Aerosol Sci. 33(10): 1361-1378 (2002).
Lal et al., "Clean western blot signals from immunoprecipitated samples," available in PMC Jan. 25, 2006, published in final edited form as: Mol Cell Probes. 19(6): 385-388 (2005) (5 pages).
Lavorini et al., "New inhaler devices—the good, the bad and the ugly," Respiration. 88(1): 3-15 (2014).
Lee et al., "Solid-state stabilization of α Chymotrypsin and catalase with carbohydrates," Ind Eng Chem Res. 45(14): 5134-5147 (2006).
Lee, Spray-Drying of Proteins. Rational Design of Stable Protein Formulations. Carpenter and Manning, 135-158 (2002).

Li et al., "Effects of pulsed electric fields and heat treatment on stability and secondary structure of bovine immunoglobulin G," J Agric Food Chem. 53(3): 663-670 (2005).
Longman et al., "Identifying differences in solution Conformations of two chimeric IgG3 antibodies through triple detection SEC," LCGC North America. 18(21): (2005) (10 pages).
Lopez-Herrera et al., "Coaxial jets generated from eleclified Taylor cones. Scaling laws," J Aerosol Sci. 34(5): 535-552 (2003).
Loscertales et al., "Micro/nano encapsulation via electrified coaxial liquid jets," Science. 295(5560): 1695-8 (2002).
Makadia et al., "Poly lactic-co-glycolic acid (PLGA) as biodegradable controlled drug delivery carrier," Polymers (Basel). 3(3): 1377-1397 (2011).
Marks, J.D. et al., "By-passing Immunization Human Antibodies from V-gene Libraries Displayed on Phage," J. Mol. Biol., vol. 222; 581-597 (1991).
Miller et al., "Antibody nanoparticle dispersions formed with mixtures of crowding molecules retain activity and in vivo bioavailability," available in PMC Oct. 1, 2013, published in final edited form as: J Pharm Sci. 101(10): 3763-3778 (2012) (25 pages).
Miller et al., "Low viscosity highly concentrated injectable nonaqueous suspensions of lysozyme microparticles," available in PMC Feb. 17, 2011, published in final edited form as: Langmuir. 26(2): 1067-1074 (2010) (22 pages).
Morales-Cruz et al., "Two-step nanoprecipitation for the production of protein-loaded PLGA nanospheres," Results Pharma Sci. 2: 79-85 (2012).
Mueller et al., "The rheology of suspensions of solid particles," Proc R Soc A. 466: 1201-1228 (2010).
Naqvi et al., "Living cell factories—electrosprayed microcapsules and microcarriers for minimally invasive delivery," Adv Maler. 28(27): 5662-71 (2016)(10 pages).
Nguyen et al., "Pharmaceutical applications of electrospraying," J Pharm Sci. 105(9): 2601-2620 (2016).
Non-Final Office Action for U.S. Appl. No. 17/351,937, mailed Mar. 2, 2023.
Notice of Allowance for U.S. Appl. No. 17/351,937, mailed Jun. 23, 2023.
Park et al., "One step immobilization of protein encapsulated core/shell particles onto nanofibers," Macromol Maler Eng. 295(6): 544-550 (2010).
Patel et al., "Poloxamers: a pharmaceutical excipients with therapeutic behaviors," International Journal of PharmTech Research. 1(2):299-303 (2009).
Persic, L. et al., "An integrated vector system for the eukaryotic expression of antibodies or their fragments after selection from phage display libraries," Gene; 9-18 (1997).
Pivnik, A.V., "Use of rituximab for treatment of HIV-infected patients with hematological disorders," Genotekhnologiya Medical Center, Moscow, 7 pages; English Abstract Only (2013).
Press, O.W. et al., "Monoclonal Antibody 1F5 (Anti-CD20) Serotherapy of Human B Cell Lymphoma," Blood, vol. 69; No. 2; 584-591 (1987).
Reichardt, C., "Solvatochromic Dyes as Solvent Polarity Indicators," Chem. Rev., vol. 94; 2319-2358 (1994).
Richardson, H. et al., "Influence of the glass transition on solvent loss from spin-cast glassy polymer thin films," Eur. Phys. J. E, vol. 12; 021; S87-S91 (2003).
Saglam et al., "Preparation of high protein micro-particles using two-step emulsification," Food Hydrocolloids. 25(5):1139-48 (2011).
Sblattero, D. and Bradbury, A., "Exploiting recombination in single bacteria to make large phage antibody libraries," Nature Biotechnology, vol. 18; 75-80 (2000).
Serra-Peinado, C., et al., "Expression of CD20 after viral reactivation renders HIV-reservoir cells susceptible to Rituximab," Nature Communications, vol. 10; 15 pages (2019).
Shire et al., "Challenges in the development of high protein concentration formulations," J Pharm Sci. 93(6): 1390-402 (2004).
Supplementary Partial European Search Report for European Patent Application No. 17873547.8, dated Jun. 15, 2020 (9 pages).
Takats et al., "Electrosonic spray ionization. A gentle technique for generating folded proteins and protein complexes in the gas phase

(56) References Cited

OTHER PUBLICATIONS and for studying ion-molecule reactions at atmospheric pressure," Anal Chem. 76(14): 4050-58 (2004).

Torchilin, "Multifunctional nanocarriers," Adv Drug Deliv Rev. 58(14): 1532-55 (2006).

U.S. Department of Health and Human Services, "Q3C—Tables and List: Guidance for Industry," Aug. 2018 (10 pages).

Vonhoff, Sebastian, Thesis: "The Influence of Atomization Conditions on Protein Secondary and Tertiary Structure During Microparticle Formation by Spray-Freezing-Drying," Doktorgrades Dr. rer. nat, Der Naturwissenschaftlichen Fakultat, der Friedrich-Alexander Universitat Erlangen-Nurnberg, 2010 (195 pages).

Vehring, "Pharmaceutical particle engineering via spray drying," Pharm Res. 25(5): 999-1022 (2008).

Wang et al., "FDA's regulatory science program for generic PLA/PLGA-based drug products," Am Pharm Rev. americanpharmaceuticalreview.com/Featured-Articles/188841-FDA-s- Regulatory-Science-Program-for-Generic-PLA-PLGA-Based-Drug-Products/>, dated Jun. 15, 2016, retrieved on Aug. 22, 2019 (5 pages).

Wanning et al., "Pharmaceutical spray freeze drying," Int J Pharm. 488(1-2): 136-53 (2015).

Xie et al., "Encapsulation of protein drugs in biodegradable microparticles by co-axial electrospray," J Colloid Interface Sci. 317(2): 469-76 (2008).

Yuan et al., "Coaxial electrospray of curcumin-loaded microparticles for sustained drug release," PLoS One. 10(7):e0132609 (2015) (15 pages).

Yuan et al., "One-step fabrication of triple-layered microcapsules by a tri-axial flow focusing device for microencapsulation of soluble drugs and imaging agents," Proc SPIE vol. 9711, Imaging, Manipulation, and Analysis of Biomolecules, Cells, and Tissues IX (2016) (12 pages).

Zhang et al., "Coaxial electrospray of microparticles and nanoparticles for biomedical applications," Expert Rev Med Devices. 9(6): 595-612 (2012).

Zhiqi, L., et al., "Functional Emulsifiers and Emulsions", China Light Industry Press, Apr. 30, 2000, 2 pages. (Concise explanation met by Translation of Search report being cited as Other Document 10 in IDS being cited concurrently).

Zliabicki et al., "Crystal nucleation in an electric field," Macromol Symp. 104(1): 65-87 (1996).

CN Search report Mailed on Jan. 13, 2024 for CN Application No. 2021800293477; 4 pages (with English Translation).

CN Search report Mailed on Jul. 28, 2022 for CN Application No. 202080012222.9; 5 pages (With English Translation).

Elektrofi, Inc., Redefining the Delivery of Biologics, 11 pages, retrieved from Internet URL: https://www.elektrofi.com/welcome#technology, on Nov. 15, 2021; 11 pages.

English translation of Chinese Application No. 202080064558 Office Action; 17 pages; dated Sep. 2, 2024.

English Translation of CN Office Action Mailed on Aug. 3, 2022 for CN Application No. 202080012222.9; 4 pages.

Fenn et al., "Electrospray ionization for mass spectrometry of large biomolecules," Science. 246(4926):64-71 (Oct. 6, 1989).

Frost, G.I., "Recombinant human hyaluronidase (rHuPH20): an enabling platform for subcutaneous drug and fluid administration," Expert Opinion Drug Deliv., vol. 4; No. 4; 427-440 (2007).

Imamura, K. et al., "Evaluation of Hydration States of Protein in Freeze-Dried Amorphous Sugar Matrix," J. Pharm. Sci., vol. 90; 1955-1963 (2001).

Imamura, K., "Sugar-Protein Interaction and Stabilization of Protein in Amorphous Sugar Matrix," Cryobiology and Cryotechnology, vol. 51; No. 1; 31-35 (2005). English Abstract included.

Jones, A.J.S., "Analysis of Polypeptides and Proteins," Advanced Drug Delivery Reviews, vol. 10; p. 29-90 (1993).

Jun, L., "Guizho Science and Technology Press", Agricultural building materials, Aug. 31, 1999, 4 pages (Concise explanation met by the English Translation of CN Appl 202080064558 office action provided herewith).

Mardles. E. W. J., "Viscosity of Suspensions and the Einstein Equation," Nature. 145: 970 (Jun. 22, 1940).

Nema et al., Pharmaceutical Dosage Forms: Parenteral Medications, Third Edition, vol. 3: Requlations, Validation and the Future. Informa Healthcare, vii-304 (2010) (328 pages).

Non-Final Office Action for U.S. Appl. No. 18/907,018 mailed Dec. 31, 2024.

Final Office Action for U.S. Appl. No. 18/907,018, mailed Apr. 11, 2025, 13 pages.

Gulfam, M. et al., "Anticancer Drug-Loaded Gliadin Nanoparticles Induce Apoptosis in Breast Cancer Cells," American Chemical Society, Langmuir, vol. 28; 8216-8223 (2012).

Miller et al. (Low viscosity highly concentrated injectable non-aqueous suspension of lysosome microparticles, Languir, Jan. 19, 2010; 26 (2): 1067-1074). (Year: 2010).

Papir, Y.S. and Krieger, I.M., "Rheological Studies on Dispersions of Uniform Colloidal Spheres," Journal of Colloid and Interface Science, vol. 34; No. 1; 126-130 (1970).

Pearlman, R. and Nguyen, T.H., "Analysis of Protein Drugs," Peptide and Protein Drug Delivery, Vincent Lee Ed., Marcel Dekker, Inc., New York, NY, pp. 247-301 (1991).

Plückthun, A., "Antibodies from *Escherichia coli*," In: The pharmacology of monoclonal antibodies, M. Rosenberg and G. P. Moore, Eds. (Springer Verlag, Berlin, 1994), vol. 113, pp. 269-315.

Sridhar et al. (Electrosprayed nanoparticles for drug delivery and pharmaceutical applications, Biomatter, Mar. 19, 2013; 3(3)) (Year: 2013).

Sridhar, R. and Ramakrishna, S., "Electrosprayed nanoparticles for drug delivery and pharmaceutical applications," Biomatter, vol. 3; No. 3; e24281-1; 14 pages (2013).

Vehring, R. et al., "Particle formation in spray drying," Aerosol Science, vol. 38; 728-746 (2007).

Zhang, J. et al., "Fundamentals and applications of inertial microfluidics: a review," Lab Chip, vol. 16; 10-34 (2016).

Ziabicki, A. and Jarecki, L., "Crystal Nucleation in an Electric Field," Macromol. Symp., vol. 104; 65-87 (1996).

Gross-Rother et al., "Particle Detection and Characterization for Biopharmaceutical Applications: Current Principles of Established and Alternative Techniques", Pharmaceutics, vol. 12, No. 11, Nov. 19, 2020, 49 pages.

Jack et al., "Analysis of particulate contaminations of infusion solutions in a pediatric intensive care unit", Intensive Care Medicine, vol. 36, No. 4, Feb. 18, 2010, pp. 707-711.

Non-Final Office Action for U.S. Appl. No. 18/907,018, mailed Sep. 4, 2025, 8 pages.

Sah et al.; "Recent Trends in Preparation of Poly(lactide-co-glycolide) Nanoparticles by Mixing Polymeric Organic Solution with Antisolvent," 2015; Hindawi Publishing Corporation; Journal of Nanomaterials, vol. 2015, Article ID 794601, pp. 1-22. (Year: 2015).

* cited by examiner

Dispersive Surface Energy Profile

Acid-Base Surface Energy Profile

Time = 0

Time = 6hrs

1 μm

1 μm

PARTICLE FORMATION AND MORPHOLOGY

RELATED APPLICATION(S)

This application is a continuation of U.S. patent application Ser. No. 18/344,142, filed on Jun. 29, 2023, which is a continuation of U.S. patent application Ser. No. 17/351,937, filed on Jun. 18, 2021, which is a Continuation of International Application No. PCT/US2020/015957, filed on Jan. 30, 2020, published in English, which claims the benefit of U.S. Provisional Application No. 62/799,696, filed on Jan. 31, 2019. The entire teachings of the above applications are incorporated herein by reference.

TECHNICAL FIELD

The present disclosure relates to compositions and methods that enable the formation of pharmaceutically relevant particles that can be used for therapy. In particular, the methods disclosed herein allow the formation of circular particles having low internal void spaces comprising bioactive therapeutic agents.

BACKGROUND

Materials science and the application of nanotechnology calls for more efficient, reproducible and innovative technologies to synthesize novel functional particles. Recent advances in synthesis and the controlled assembly of bioactive particles have enabled their applications for use in therapy. Current efforts have been directed to developing new synthetic approaches for non-circular microparticles that often exhibit physical properties unobtainable by simply tuning the size and form of the particles. However, the application of these techniques to circular particles have been limited due to the lack of sufficient control over size uniformity, shape selectivity, surface functionality and skeletal density of the particles which are often difficult to obtain. Therefore, a highly robust and controlled method for circular particle preparation is needed.

SUMMARY

Provided herein is a particle, or a composition comprising a plurality of particles, comprising an agent, wherein the particle comprises less than about 25% internal void spaces and the circularity of the particle is from about 0.10 to about 1.00.

In one aspect, the disclosure provides a particle comprising an agent, wherein the particle comprises less than about 25% internal void spaces and the circularity of the particle is from about 0.10 to about 1.00.

In another aspect, the disclosure provides a composition comprising a plurality of particles comprising an agent suspended in a liquid, wherein the particles comprise less than about 25% internal void spaces and the circularity of the particles are from about 0.10 to about 1.00.

The present disclosure also provides a method of forming particles.

In one aspect, the disclosure provides a method of forming particles, the method comprising:
  a) providing droplets comprising a first liquid and an agent;
  b) contacting the droplets with a second liquid;
  c) allowing the droplets to dry; and
  d) removing the first and second liquids, thereby forming particles comprising an agent, wherein the particles comprise less than about 25% internal void spaces and the circularity of the particles is from about 0.10 to about 1.00 after removing the first and second liquids.

Also provided herein, is a method of controlling the morphology of particles.

In one aspect, the disclosure provides a method of controlling the morphology of particles, the method comprising:
  a) providing droplets comprising a first liquid and an agent;
  b) contacting the droplets with a second liquid under a specified Peclet number;
  c) allowing the droplets to dry; and
  d) removing the first and second liquids,
  wherein the specified Peclet number controls the morphology of the particles.

The present disclosure also provides herein a method of controlling the surface properties of particles.

In one aspect, the disclosure provides a method of controlling the surface properties of particles, the method comprising:
  a) providing droplets comprising a first liquid, a first component, and a second component, wherein the first component is present in an amount closer to its solubility limit than the second component, the first component has a higher Peclet number than the second component, or a combination thereof;
  b) contacting the droplets with a second liquid;
  c) allowing the droplets to dry; and
  d) removing the first and second liquids,
  thereby forming particles, wherein the first component is enriched at the surface of the particles relative to the second component.

The present compositions and methods may be useful for the formation of pharmaceutically relevant particles that can be used for therapy. In preferred embodiments, the methods disclosed herein may allow the formation of circular particles having low internal void spaces comprising bioactive therapeutic agents.

BRIEF DESCRIPTION OF THE DRAWINGS

The foregoing will be apparent from the following more particular description of example embodiments, as illustrated in the accompanying drawings in which like reference characters, refer to the same parts throughout the different views. The drawings are not necessarily to scale, emphasis instead being placed upon illustrating embodiments.

DETAILED DESCRIPTION

Figure 1A:
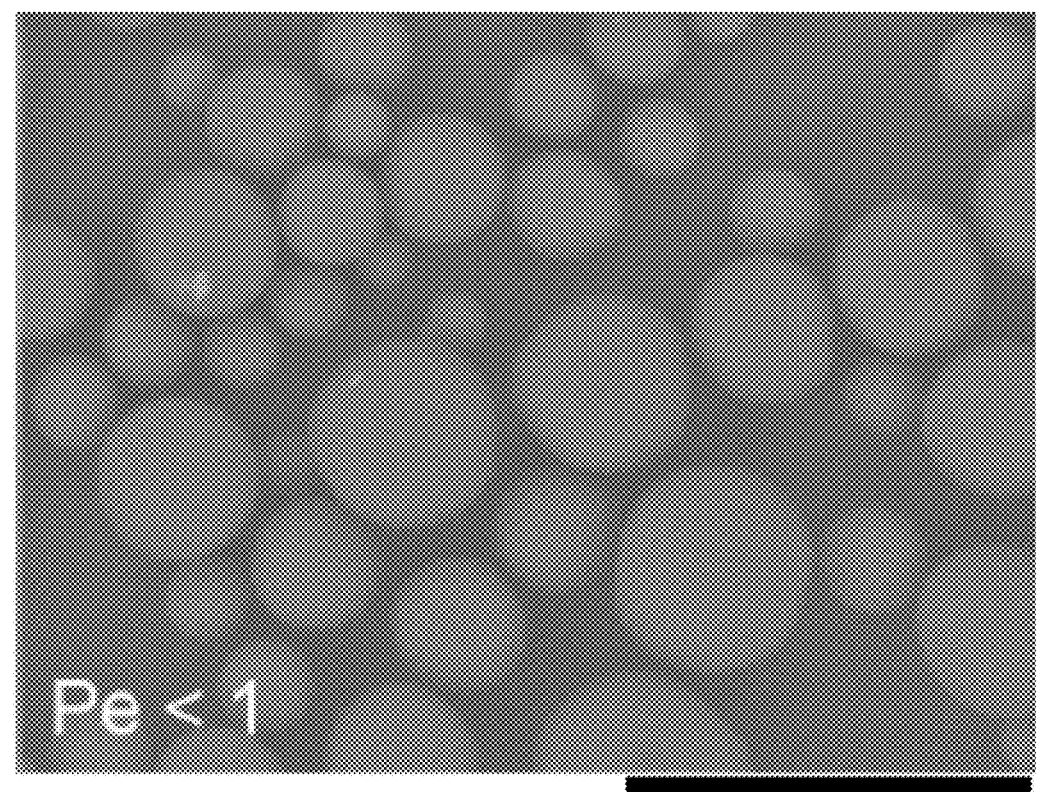
FIG. 1A shows an image of human IgG particles produced using a second liquid for which the Peclet number substantially less than 1.

Particles have been produced using various techniques. For example, the generation of particles can be accomplished by producing a droplet of a liquid comprising an active agent dissolved in a solvent. The solvent can then be extracted from the droplets by depositing the droplets into a liquid in which the solvent, but not the active agent, is soluble leaving behind a solid particle. Isolation of the particles occur following evaporation of the liquids. However, the application of these techniques to form functional circular particles have been limited due to the lack of sufficient control over size uniformity, shape selectivity, surface functionality and skeletal density of the particles which are often difficult to obtain. The present disclosure seeks to mitigate the control issues that are associated with forming functional particles by providing a robust and controlled method for particle preparation.

The present disclosure generally relates to a particle comprising an agent or a composition comprising a plurality of particles comprising an agent suspended in a liquid, wherein the particle or the plurality of particles comprises less than about 25% internal void spaces and the circularity of the particle is from about 0.10 to about 1.00.

The present disclosure also relates to methods of forming particles, the method comprising: a) providing droplets comprising a first liquid and an agent; b) contacting the droplets with a second liquid; c) allowing the droplets to dry; and d) removing the first and second liquids, thereby forming particles comprising an agent, wherein the particles comprise less than about 25% internal void spaces and the circularity of the particles is from about 0.10 to about 1.00 after removing the first and second liquids.

In certain aspects, the disclosure generally relates to a method of controlling the morphology of particles, the method comprising: a) providing droplets comprising a first liquid and an agent; b) contacting the droplets with a second liquid under a specified Peclet number; c) allowing the droplets to dry; and d) removing the first and second liquids, wherein the specified Peclet number controls the morphology of the particles.

In certain other aspects, the disclosure generally relates to a method of controlling the surface properties of particles, the method comprising: a) providing droplets comprising a first liquid, a first component, and a second component, wherein the first component is present in an amount closer to its solubility limit than the second component, the first component has a higher Peclet number than the second component, or a combination thereof; b) contacting the droplets with a second liquid; c) allowing the droplets to dry; and d) removing the first and second liquids, thereby forming particles, wherein the first component is enriched at the surface of the particles relative to the second component.

As described herein, the disclosure provides methods for the preparation of particles including one or more agents, e.g., therapeutic or diagnostic agents. The particles can be formed by creating droplets of a first liquid, e.g., including an agent, and removing the first liquid, e.g., through its dispersal in a second liquid and/or evaporation, to solidify the droplets. The process of forming the particles as described herein, significantly alters the structure or morphology of the particles and may enhance the stability of the agents. For example, the particles may be stored for extended periods of time without significant loss of activity or the need for refrigeration. These particles may be used to generate stabilized pharmaceutical compositions, pharmaceutical suspension formulations, pharmaceutical powder formulations (e.g., inhalable powders, injectable powders), creams or other topical pastes, nutraceuticals, or cosmetics. The term "pharmaceutical composition" as used herein, denotes a composition in which a therapeutic or diagnostic agent retains, or partially retains, its intended biological activity or functional form, and in which only pharmaceutically acceptable components are included.

It will be readily understood that the aspects and embodiments, as generally described herein, are exemplary. The following more detailed description of various aspects and embodiments are not intended to limit the scope of the present disclosure, but is merely representative of various aspects and embodiments. Moreover, the compositions and methods disclosed herein may be changed by those skilled in the art without departing from the scope of the present disclosure. Unless defined otherwise, all technical and scientific terms used herein have the same meaning as is commonly understood by one of skill in the art to which this disclosure belongs. All publications and patents referred to herein are incorporated by reference.

Definitions

For purposes of the present disclosure, the following definitions will be used unless expressly stated otherwise:

The terms "a", "an", "the" and similar referents used in the context of describing the present disclosure are to be construed to cover both the singular and the plural, unless otherwise indicated herein or clearly contradicted by context. All methods described herein, can be performed in any suitable order unless otherwise indicated herein or otherwise clearly contradicted by context. The use of any and all examples, or exemplary language (e.g., "such as") provided herein, is intended merely to better illuminate the present disclosure and does not pose a limitation on the scope of the disclosure otherwise claimed. No language in the present specification should be construed as indicating any unclaimed element is essential to the practice of the disclosure.

The term "about" in relation to a given numerical value, such as for temperature and period of time, is meant to include numerical values within 10% of the specified value.

As used herein, an "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, iso-butyl, sec-butyl, tert-butyl, n-pentyl, tert-pentyl, neo-pentyl, iso-pentyl, sec-pentyl, 3-pentyl, sec-iso-pentyl, active-pentyl, hexyl, heptyl, octyl, ethylhexyl, and the like. A $C_{1-8}$ straight chained or branched alkyl group is also referred to as a "lower alkyl" group. An alkyl group with two open valences is sometimes referred to as an alkylene group, such as methylene, ethylene, propylene and the like. Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, an alkyl, a halogen, a hydroxyl, a carbonyl (such as a carboxyl, and alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamide, sulfamoyl and sulfonate), and silyl groups, as well as ethers, alkylthios, carbonyls (including ketones, aldehydes, carboxylates, and esters), —CF$_3$, —CN and the like. Exemplary substituted alkyls are described below. Cycloalkyls can be further substituted with alkyls, alkenyls, alkoxys, alkylthios, aminoalkyls, carbonyl-substituted alkyls, —CF$_3$, —CN and the like. In other embodiments, the term "alkyl" can mean "cycloalkyl" which refers to a non-aromatic carbocyclic ring having 3 to 10 carbon ring atoms, which are carbon atoms bound together to form the ring. The ring may be saturated or have one or more carbon-carbon double bonds. Examples of cycloalkyl include, but not limited to cyclopropyl, cyclobutyl, cyclopentyl, cyclopentenyl, cyclohexyl, cyclohexenyl, and cycloheptyl, as well as bridged and caged saturated ring groups such as norbornyl and adamantyl. As described herein, organic solvents include, but are not limited to aliphatic hydrocarbon solvents, aromatic hydrocarbon solvents, alcohols or alkylalcohols, alkylethers, sulfoxides, alkylketones, alkylacetates, trialkylamines, alkylformates, trialkylamines, or a combination thereof. Aliphatic hydrocarbon solvents can be pentane, hexane, heptane, octane, cyclohexane, and the like or a combination thereof. Aromatic hydrocarbon solvents can be benzene, toluene, and the like or a combination thereof. Alcohols or alkylalcohols include, for example, methanol, ethanol, propanol, butanol, pentanol, hexanol, heptanol, octanol, decanol, amylalcohol, or a combination thereof. Alkylethers include methyl, ethyl, propyl, butyl, and the like, e.g., diethylether, diisopropylether or a combination thereof. Sulfoxides include dimethyl sulfoxide (DMSO), decylmethyl sulfoxide, tetradecylmethyl sulfoxide, and the like or a combination thereof. The term "alkylketone" refers to a ketone substituted with an alkyl group, e.g., acetone, ethylmethylketone, and the like or a combination thereof. The term "alkylacetate" refers to an acetate substituted with an alkyl group, e.g., ethylacetate, propylacetate (n-propylacetate, iso-propylacetate), butylacetate (n-butylacetate, isobutylacetate, sec-butylacetate, tert-butylacetate), amylacetate (n-pentylacetate, tert-pentylacetate, neo-pentylacetate, iso-pentylacetate, sec-pentylacetate, 3-pentylacetate, sec-iso-pentylacetate, active-pentylacetate), 2-ethylhexylacetate, and the like or a combination thereof. The term "alkylformate" refers to a formate substituted with an alkyl group, e.g., methylformate, ethylformate, propylformate, butylformate, and the like or a combination thereof. The term "trialkylamine" refers to an amino group substituted with three alkyl groups, e.g., triethylamine.

As used herein, an "amino acid" or "residue" refers to any naturally or non-naturally occurring amino acid, any amino acid derivative or any amino acid mimic known in the art. Included are the L- as well as the D-forms of the respective amino acids, although the L-forms are usually preferred. In some embodiments, the term relates to any one of the 20 naturally occurring amino acids: glycine (Gly), alanine (Ala), valine (Val), leucine (Leu), isoleucine (Ile), proline (Pro), cysteine (Cys), methionine (Met), serine (Ser), threonine (Thr), glutamine (Gin), asparagine (Asn), glutamic acid (Glu), aspartic acid (Asp), lysine (Lys), histidine (His), arginine (Arg), phenylalanine (Phe), tryptophan (Trp), and tyrosine (Tyr) in their L-form. In certain embodiments, the amino acid side-chain may be a side-chain of Gly, Ala, Val, Leu, Ile, Met, Cys, Ser, Thr, Trp, Phe, Lys, Arg, His, Tyr, Asn, Gln, Asp, Glu, or Pro.

As used herein, except where the context requires otherwise, the term "comprise" and variations of the term, such as "comprising", "comprises" and "comprised", are not intended to exclude further additives, components, integers or steps. The terms "including" and "comprising" may be used interchangeably. As used herein, the phrases "selected from the group consisting of", "chosen from", and the like, include mixtures of the specified materials. Where a numerical limit or range is stated herein, the endpoints are included. Also, all values and subranges within a numerical limit or range are specifically included as if explicitly written out. References to an element in the singular is not intended to mean "one and only one" unless specifically stated, but rather "one or more." Unless specifically stated otherwise, terms such as "some" refer to one or more, and singular terms such as "a", "an" and "the" refer to one or more.

The term "oligopeptide" is used to refer to a peptide with fewer members of amino acids as opposed to a polypeptide or protein. Oligopeptides described herein, are typically comprised of about two to about forty amino acid residues. Oligopeptides include dipeptides (two amino acids), tripeptides (three amino acids), tetrapeptides (four amino acids), pentapeptides (five amino acids), hexapeptides (six amino acids), heptapeptides (seven amino acids), octapeptides (eight amino acids), nonapeptides (nine amino acids), decapeptides (ten amino acids), undecapeptides (eleven amino acids), dodecapeptides (twelve amino acids), icosapeptides (twenty amino acids), tricontapeptides (thirty amino acids), tetracontapeptides (forty amino acids), etc. Oligopeptides may also be classified according to molecular structure: aeruginosins, cyanopeptolins, microcystins, microviridins, microginins, anabaenopeptins and cyclamides, etc. Homo-oligopeptides are oligopeptides comprising the same amino acid. In preferred embodiments, homo-oligopeptides comprise 10 amino acid poly-valine, poly-alanine, and poly-glycine hexamers.

The meaning of the term "peptides" are defined as small proteins of two or more amino acids linked by the carboxyl group of one to the amino group of another. Accordingly, at its basic level, peptide synthesis of whatever type comprises the repeated steps of adding amino acid or peptide molecules to one another or to an existing peptide chain. The term "peptide" generally has from about 2 to about 100 amino acids, whereas a polypeptide or protein has about 100 or more amino acids, up to a full length sequence which may be translated from a gene. Additionally, as used herein, a peptide can be a subsequence or a portion of a polypeptide or protein. In certain embodiments, the peptide consists of 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acid residues. In preferred embodiments, the peptide is from between about 30 to about 100 amino acids in length. In some embodiments, the peptide is from between about 40 to about 100 amino acids in length.

As used herein, the term "pharmaceutically acceptable" refers to compositions that are physiologically tolerable and do not typically produce an allergic or similar untoward reaction when administered to a subject, preferably a human subject. Preferably, as used herein, the term "pharmaceutically acceptable" means approved by a regulatory agency of a federal or state government or listed in the U.S. Pharmacopeia or other generally recognized pharmacopeia for use in animals, and more particularly in humans.

As used herein, the term "prodrug" is intended to encompass therapeutic biologics which, under physiologic conditions, are converted into the therapeutically active biologics of the present disclosure. A common method for making a prodrug is to include one or more selected moieties which are hydrolyzed under physiologic conditions to reveal the desired molecule. In other embodiments, the prodrug is converted by an enzymatic activity of the host animal. For example, esters or carbonates (e.g., esters or carbonates of alcohols or carboxylic acids) are preferred prodrugs of the present disclosure. In certain embodiments, some or all of the molecules in a composition represented above can be replaced with the corresponding suitable prodrug, e.g., wherein a hydroxyl in the parent molecule is presented as an ester or a carbonate or carboxylic acid present in the parent therapeutic biologic is presented as an ester.

The meaning of the term "protein" is defined as a linear polymer built from about 20 different amino acids. The type and the sequence of amino acids in a protein are specified by the DNA that produces them. In certain embodiments, the sequences can be natural and unnatural. The sequence of amino acids determines the overall structure and function of a protein. In some embodiments, proteins can contain 50 or more residues. In preferred embodiments, proteins can contain greater than about 101 residues in length. A protein's net charge can be determined by two factors: 1) the total count of acidic amino acids vs. basic amino acids; and 2) the specific solvent pH surroundings, which expose positive or negative residues. As used herein, "net positively or net negatively charged proteins" are proteins that, under non-denaturing pH surroundings, have a net positive or net negative electric charge. In general, those skilled in the art will recognize that all proteins may be considered "net negatively charged proteins", regardless of their amino acid composition, depending on their pH and/or solvent surroundings. For example, different solvents can expose negative or positive side chains depending on the solvent pH. Proteins or peptides are preferably selected from any type of enzyme or antibodies or fragments thereof showing substantially the same activity as the corresponding enzyme or antibody. Proteins or peptides may serve as a structural material (e.g. keratin), as enzymes, as hormones, as transporters (e.g. hemoglobin), as antibodies, or as regulators of gene expression. Proteins or peptides are required for the structure, function, and regulation of cells, tissues, and organs.

The term "substantially" as used herein, refers to a majority of, or mostly, as in at least about 50%, 60%, 70%, 80%, 90%, 95%, 96%, 97%, 98%, 99%, 99.5%, 99.9%, 99.99%, or at least about 99.999% or more.

It is understood that the specific order or hierarchy of steps in the methods or processes disclosed is an illustration of exemplary approaches. Based upon design preferences, it is understood that the specific order or hierarchy of steps in the methods or processes may be rearranged. Some of the steps may be performed simultaneously. The accompanying methods claims present elements of the various steps in a sample order, and are not meant to be limited to a specific hierarchy or order presented. A phrase such as "embodiment" does not imply that such embodiment applies to all configurations of the subject technology. A disclosure relating to an embodiment may apply to all embodiments, or one or more embodiments. A phrase such as an embodiment may refer to one or more embodiments and vice-versa.

Particles

Unless otherwise defined, all terms of art, notations and other scientific terminology used herein, are intended to have the meanings commonly understood by those of skill in the art to which this disclosure pertains. In some cases, terms with commonly understood meanings are defined herein, for clarity and/or for ready reference, and the inclusion of such definitions herein, should not necessarily be construed to represent a substantial difference over what is generally understood in the art. The techniques and procedures described or referenced herein, are generally well understood and commonly employed using conventional methodology by those skilled in the art. As appropriate, procedures involving the use of commercially available kits and reagents are generally carried out in accordance with manufacturer defined protocols and/or parameters unless otherwise noted.

In some aspects, the disclosure relates to a particle comprising an agent, wherein the particle comprises less than about 25% internal void spaces and the circularity of the particle is from about 0.10 to about 1.00.

The terms "particle" or "particles" or "microparticle" or "microparticles" are used herein, interchangeably in the broadest sense, refers to a discrete body or bodies. The particles described herein, are circular, spheroidal and of controlled dispersity with a characteristic size from sub-micrometers to tens of micrometers, in contrast to, e.g., a porous monolithic "cake", which is typically produced during conventional lyophilization. This morphology allows for a flowable powder (as described by low Hausner ratios) without post-processing. In some embodiments, the term "particle" refers to a quantity of an agent or agents which is either in a state of matter that is substantially solid as compared to a liquid droplet or in a gel form. In other embodiments, the particle may include a core and a shell, where the shell may be viewed as an encapsulant. In still other embodiments, the particle does not include a shell, in which case, the particle is made up entirely of a core. The term "proto-particle" refers to a stage of particle formation in which one or more of the components comprising the particle are in an at least a partial state of desiccation. The total liquid content of the proto-particle is less than that of the droplet and greater than that of the formed particle. Similarly, the average concentration of the solutes is higher than that of the drop but typically less than that of the formed particle. The term "encapsulant" refers to a substance that can be dried or gelled around a particle core to form a shell.

As disclosed herein, the agent may be a therapeutic or diagnostic agent. In some embodiments, the agent is not a diagnostic or therapeutic agent. In other embodiments, the agent can be a metal or other element, silica, titania, a metal salt, a metal oxide, a metal nitride, a metal sulfide, a metal alkoxide, a polymer, or a combination thereof. Exemplary therapeutic or diagnostic agents include, but are not limited to nucleic acids, oligonucleotides, antibodies or fragment thereof, amino acids, peptides, proteins, cells, bacteria, gene therapeutics, genome engineering therapeutics, epigenome engineering therapeutics, carbohydrates, chemical drugs, contrast agents, magnetic particles, polymer beads, metal nanoparticles, metal microparticles, quantum dots, antioxidants, antibiotic agents, hormones, nucleoproteins, polysaccharides, glycoproteins, lipoproteins, steroids, analgesics, local anesthetics, anti-inflammatory agents, anti-microbial agents, chemotherapeutic agents, exosomes, outer membrane vesicles, vaccines, viruses, bacteriophages, adjuvants, vitamins, minerals, organelles, or a combination thereof. In preferred embodiments, the therapeutic agent is a therapeutic biologic. Therapeutic and diagnostic agents may have a molecular weight of about 20 to about 200 kDa, e.g., about 40 to about 150 kDa, or about 50 to about 100 kDa. Table 1 provides a list of therapeutic and diagnostic agents and the typical concentration range for the general class of compound in a pharmaceutical composition.

TABLE 1

| Therapeutic/ diagnostic agent | Concentration range (mg/mL) |
| --- | --- |
| proteins | 20-1500 (e.g., 20-600) (or crystalline density, if higher) |
| peptides | 20-1500 (e.g., 20-600) (or crystalline density, if higher) |
| chemical drugs | 0.0001-2000 (e.g., 0.0001-1000) (or crystalline density, if higher) |
| magnetic particles | 0.001-5400 (e.g., 0.001-500) (iron oxide density) |
| carbohydrates | 0.001-400 |
| nucleic acids | 0.001-100 |

In other embodiments, the particles may include, but are not limited to, agents such as silica, titania, metals or other elements, metal salts, metal oxides, metal nitrides, metal sulfides, metal alkoxides, and/or polymers. The methods as described herein, may present an alternative to sol-gel synthesis and can provide particles for a diverse set of applications, including semiconductor particles (e.g., lead sulfide), surface plasmon resonance (e.g., gold), magnetism (e.g., iron oxide), UV-blocking (e.g., zinc oxide), imaging agents (e.g., silicon), or laser applications (e.g., poly(methyl methacrylate) and silicon dioxide mixtures).

A therapeutic biologic, also known as a biologic medical product, or biopharmaceutical, is any pharmaceutical drug product manufactured in, extracted from, or semisynthesized from biological sources. Therapeutic biologics can include a wide range of products such as vaccines, blood and blood components, allergenics, somatic cells, gene therapy, tissues, and recombinant therapeutic proteins. In some embodiments, the biologics can be composed of sugars, proteins, or nucleic acids or complex combinations of these substances, or may be living entities such as cells and tissues. Biologics can be isolated from a variety of natural sources, e.g., a human, animal, or microorganism, and may be produced by biotechnology methods or other technologies. Gene-based and cellular biologics, for example, are often used to treat a variety of medical conditions for which no other treatments are available. In preferred embodiments of the disclosure, the therapeutic biologic is an antibody.

The terms "antibody" and "immunoglobulin" are used interchangeably in the broadest sense and include monoclonal antibodies, polyclonal antibodies, multivalent antibodies, and multispecific antibodies, regardless of how they are produced (i.e., using immunization, recombinant, synthetic methodologies). Antibodies can be gamma globulin proteins that are found in blood, or other bodily fluids of vertebrates that function in the immune system to bind antigen, hence identifying and/or neutralizing foreign objects. Antibodies can be assigned to different classes or isotypes. There are five classes of immunoglobulins: IgA, IgD, IgE, IgG, and IgM, having heavy chains designated alpha, delta, epsilon, gamma, and mu, respectively. The gamma class is further divided into subclasses based on the differences in sequences and function, e.g., humans express the following subclasses: IgG1, IgG2, IgG3, IgG4, IgA1, and IgA2. In certain embodiments of the disclosure, the IgG antibody is an IgG1 antibody. In preferred embodiments of the disclosure, the IgG1 antibody is a monoclonal IgG1 antibody. The L chain from any vertebrate species can be assigned to one of two clearly distinct types, e.g., kappa and lambda, based on the amino acid sequences of their constant domains.

The recognized immunoglobulin genes include the kappa, lambda, alpha, gamma, delta, epsilon and mu constant region genes, as well as the myriad immunoglobulin variable region genes. In some embodiments, light chains are classified as either kappa or lambda. In other embodiments, heavy chains are classified as gamma, mu, alpha, delta, or epsilon, which in turn define the immunoglobulin classes, IgG, IgM, IgA, IgD and IgE, respectively. In preferred embodiments of the disclosure, the antibody is an IgG antibody.

An exemplary antibody (immunoglobulin) structural unit comprises a tetramer. Each tetramer is composed of two identical pairs of polypeptide chains, each pair having one "light" (about sss25 kD) and one "heavy" chain (about 50-70 kD). The N-terminus of each chain defines a variable region of about 100 to 110 or more amino acids primarily responsible for antigen recognition. The terms "variable light" chain, domain, region and component are used interchangeably, are abbreviated by "VL" or "$V_L$" and refer to the light chain of an antibody or antibody fragment. Similarly, terms "variable heavy" chain, domain, region and component are used interchangeably, are abbreviated by "VH" or "$V_H$" and refer to the heavy chain of an antibody or antibody fragment. Antibodies are generally a heterotetrameric glycoprotein composed of two identical light (L) chains and two identical heavy (H) chains. Each L chain is linked to a H chain by one covalent disulfide bond. The two H chains are linked to each other by one or more disulfide bonds depending on the H chain isotype. Each H and L chain also has regularly spaced intra-chain disulfide bridges. H and L chains define specific Ig domains. In particular, each H chain has at the N-terminus, a variable domain (VH) followed by three constant domains (CH) for each of the alpha and gamma chains and four CH domains for p and c isotypes. Each L chain has at the N-terminus, a variable domain (VL) followed by a constant domain (CL) at its other end. The VL is aligned with the VH and the CL is aligned with the first constant domain of the heavy chain (CHL). The constant domain includes the Fc portion which comprises the carboxy-terminal portions of both H chains held together by disulfides. The effector functions of antibodies such as ADCC are determined by sequences in the Fc region, which is also the part recognized by Fc receptors (FcR) found on certain types of cells.

As disclosed herein, the pairing of a VH and VL together form a "variable region" or "variable domain" including the amino-terminal domains of the heavy or light chain of the antibody. The variable domain of the heavy chain may be referred to as "VH". The variable domain of the light chain may be referred to as "VL". The V domain contains an "antigen binding site" which affects antigen binding and defines specificity of a particular antibody for its particular antigen. V regions span about 110 amino acid residues and consist of relatively invariant stretches called framework regions (FRs) (generally about 4) of 15-30 amino acids separated by shorter regions of extreme variability called "hypervariable regions" (generally about 3) that are each generally 9-12 amino acids long. The FRs largely adopt a p-sheet configuration and the hypervariable regions form loops connecting, and in some cases forming part of, the p-sheet structure. In certain embodiments, the "hypervariable region" refers to the regions of an antibody variable domain which are hypervariable in sequence and/or form structurally defined loops. Generally, antibodies comprise six hypervariable regions; three in the VH (H1, H2, H3), and three in the VL (L1, L2, L3). "Framework" or "FR" residues are those variable domain residues other than the hypervariable region residues defined herein.

The terms "full length antibody", "intact antibody" and "whole antibody" are used herein, interchangeably, to refer to an antibody in its substantially intact form, not as antibody fragments as defined above. The terms particularly refer to an antibody with heavy chains that contain the Fc region. A full length antibody can be a native sequence antibody or an antibody variant. In certain embodiments, an "intact" or "whole" antibody is one which comprises an antigen-binding site as well as a CL and at least heavy chain constant domains, CH1, CH2 and CH3. The constant domains may be native sequence constant domains (e.g. human native sequence constant domains) or amino acid sequence variants thereof.

As disclosed herein, "whole antibody fragments including a variable domain" include Fab, Fab', F(ab')₂, and Fv fragments; diabodies; linear antibodies, single-chain antibody molecules; and multispecific antibodies formed from antibody fragments. The "Fab fragment" consists of an entire L chain along with the variable region domain of the H chain (VH), and the first constant domain of one heavy chain (CHI). Each Fab fragment is monovalent with respect to antigen binding, i.e., it has a single antigen-binding site. A "Fab' fragment" differs from Fab fragments by having additional few residues at the carboxy terminus of the CHI domain including one or more cysteines from the antibody hinge region. Fab'-SH is the designation herein for Fab' in which the cysteine residue(s) of the constant domains bear a free thiol group. A "F(ab')₂ fragment" roughly corresponds to two disulfide linked Fab fragments having divalent antigen-binding activity and is still capable of cross-linking antigen. An "Fv" is the minimum antibody fragment which contains a complete antigen-recognition and binding site. This fragment consists of a dimer of one heavy and one light chain variable region domain in tight, non-covalent association. In a single-chain Fv (scFv) species, one heavy and one light chain variable domain can be covalently linked by a flexible peptide linker such that the light and heavy chains can associate in a "dimeric" structure analogous to that in a two-chain Fv species. From the folding of these two domains emanate six hypervariable loops (3 loops each from the H and L chain) that contribute the amino acid residues for antigen binding and confer antigen binding specificity to the antibody. "Single-chain Fv" also abbreviated as "sFv" or "scFv" are antibody fragments that comprise the VH and VL antibody domains connected to form a single polypeptide chain. In preferred embodiments, the scFv polypeptide further comprises a polypeptide linker between the VH and VL domains which enables the scFv to form the desired structure for antigen binding. In some embodiments, a "single variable domain" is half of an Fv (comprising only three CDRs specific for an antigen) that has the ability to recognize and bind antigen, although at a lower affinity than the entire binding site.

In some embodiments, "diabodies" refer to antibody fragments with two antigen-binding sites, which fragments comprise a heavy-chain variable domain (VH) connected to a light-chain variable domain (VL) in the same polypeptide chain (VH-VL). The small antibody fragments are prepared by constructing sFv fragments with short linkers (about 5-10 residues) between the VH and VL domains such that interchain but not intra-chain pairing of the V domains is achieved, resulting in a bivalent fragment, i.e., fragment having two antigen-binding sites. In other embodiments, diabodies may be bivalent or bispecific. In certain embodiments, bispecific diabodies are heterodimers of two "crossover" sFv fragments in which the VH and VL domains of the two antibodies are present on different polypeptide chains. Triabodies and tetrabodies are also generally known in the art.

"Antigen binding fragments" of antibodies as described herein, comprise only a portion of an intact antibody, generally including an antigen binding site of the intact antibody and thus retaining the ability to bind antigen. Exemplary examples of antibody fragments encompassed by the present definition include but are not limited to: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v) the Fv fragment having the VL and VH domains of a single arm of an antibody; (vi) the dAb fragment which consists of a VH domain; (vii) isolated CDR regions; (viii) F(ab')₂ fragments, a bivalent fragment including two Fab' fragments linked by a disulfide bridge at the hinge region; (ix) single chain antibody molecules (e.g. single chain Fv; scFv); (x) "diabodies" with two antigen binding sites, comprising a heavy chain variable domain (VH) connected to a light chain variable domain (VL) in the same polypeptide chain; (xi)

"linear antibodies" comprising a pair of tandem Fd, segments (VH-CH1-VH-CH1) which, together with complementary light chain polypeptides, form a pair of antigen binding regions. In some embodiments, an "antigen binding site" generally refers to a molecule that includes at least the hypervariable and framework regions that are required for imparting antigen binding function to a V domain. An antigen binding site may be in the form of an antibody or an antibody fragment, (such as a dAb, Fab, Fd, Fv, F(ab')$_2$ or scFv) in a method described herein.

In some embodiments, the term "single-chain Fv" or "scFv" or "single chain" antibody can refer to antibody fragments comprising the VH and VL domains of antibody, wherein these domains are present in a single polypeptide chain. Generally, the Fv polypeptide further comprises a polypeptide linker between the VH and VL domains which enables the sFv to form the desired structure for antigen binding. For a review of sFv, see Pluckthun, THE PHARMACOLOGY OF MONOCLONAL ANTIBODIES, vol. 113, Rosenburg and Moore eds. Springer-Verlag, New York, pp. 269-315 (1994).

As used herein, the term "monoclonal antibody" refers to an antibody obtained from a population of substantially homogeneous antibodies, i.e., the individual antibodies comprising the population are identical except for possible naturally occurring mutations that may be present in minor amounts. Monoclonal antibodies (mAbs) are highly specific, being directed against a single antigenic site or determinant on the antigen. In addition to their specificity, the monoclonal antibodies are advantageous in that they may be synthesized uncontaminated by other antibodies. Monoclonal antibodies may be prepared by the hybridoma methodology. The monoclonal antibodies may also be isolated from phage antibody libraries using molecular engineering techniques. The monoclonal antibodies of the disclosure may be generated by recombinant DNA methods, and are sometimes referred to as "recombinant antibodies" or "recombinant monoclonal antibodies" as described herein. In some embodiments, a monoclonal antibody is a single species of antibody wherein every antibody molecule recognizes the same epitope because all antibody producing cells are derived from a single B-lymphocyte cell line. The methods for generating monoclonal antibodies (mAbs) generally begin along the same lines as those for preparing polyclonal antibodies. In other embodiments, rodents such as mice and rats are used in generating monoclonal antibodies. In certain embodiments, rabbit, sheep, or frog cells are used in generating monoclonal antibodies. The use of rats is well known and may provide certain advantages. Mice (e.g., BALB/c mice) are routinely used and generally give a high percentage of stable fusions. In still other embodiments of the disclosure, the antibody is a monoclonal antibody. In preferred embodiments of the disclosure, the IgG antibody is monoclonal.

In other embodiments, recombinant antibody fragments may be isolated from phage antibody libraries using techniques well known in the art. See, for example, Clackson et al., 1991, Nature 352: 624-628; Marks et al., 1991, J. Mol. Biol. 222: 581-597. Recombinant antibody fragments may be derived from large phage antibody libraries generated by recombination in bacteria (Sblattero and Bradbury, 2000, Nature Biotechnology 18:75-80; and as described herein). Polynucleotides encoding the VH and VL components of antibody fragments (i.e., scFv) may be used to generate recombinant full length immunoglobulins using methods known in the art (see, for example, Persic et al., 1997, Gene 187: 9-18).

An "isolated antibody" is one that has been identified and separated and/or recovered from a component of its pre-existing environment. Contaminant components are materials that would interfere with therapeutic uses for the antibody, and may include enzymes, hormones, and other proteinaceous or nonproteinaceous solutes.

As used herein, a "human antibody" refers to an antibody that possesses an amino acid sequence that corresponds to that of an antibody produced by a human. Human antibodies can be produced using various techniques known in the art, including phage-display libraries. Human antibodies can be prepared by administering the antigen to a transgenic animal that has been modified to produce such antibodies in response to antigenic challenge, but whose endogenous loci has been disabled. "Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin.

An "affinity matured" antibody is one with one or more alterations in one or more hypervariable region thereof that result in an improvement in the affinity of the antibody for antigen, compared to a parent antibody that does not possess those alterations. In some embodiments, affinity matured antibodies can have micromolar affinities for the target antigen. In other embodiments, affinity matured antibodies can have nanomolar or even picomolar affinities for the target antigen. Affinity matured antibodies are produced by procedures known in the art.

A "blocking" antibody or an "antagonist" antibody is one that inhibits or reduces biological activity of the antigen it binds. In some embodiments, blocking antibodies or antagonist antibodies substantially or completely inhibit the biological activity of the antigen. An "agonist antibody", as used herein, is an antibody, which mimics at least one of the functional activities of a polypeptide of interest.

"Binding affinity" generally refers to the strength of the sum total of noncovalent interactions between a single binding site of a molecule, e.g., an antibody, and its binding partner, e.g., an antigen. Unless indicated otherwise, as used herein, "binding affinity" refers to intrinsic binding affinity, which reflects a 1:1 interaction between members of a binding pair, e.g., antibody and antigen. The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present disclosure. "Epitope" generally refers to that part of an antigen that is bound by the antigen binding site of an antibody. In some embodiments, an epitope may be "linear" in the sense that the hypervariable loops of the antibody CDRs that form the antigen binding site bind to a sequence of amino acids as in a primary protein structure. In other embodiments, the epitope is a "conformational epitope", i.e. one in which the hypervariable loops of the CDRs bind to residues as they are presented in the tertiary or quaternary protein structure.

In some embodiments of any of the foregoing composition of matter and methods, the therapeutic biologic is an antibody. In other embodiments, the antibody includes but are not limited to 3F8, Abagovomab, Abatacept, Abciximab, Abituzumab, Abrezekimab, Abrilumab, Acritumomab, Actoxumab, Abituzumab, Adalimumab-adbm, Adalimumab-atto, Adalimumab-bwwb, Adecatumumab, Ado-trastuzumab emtansine, Aducanumab, Afasevikumab, Afelimomab, Aflibercept, Afutuzumab, Alacizumab pegol, ALD518, Alefacept, Alemtuzumab, Alirocumab, Altumomab pentetate, Amatuximab, Anatumomab mafenatox, Andecaliximab, Anetumab ravtansine, Anifrolumab, Anrukinzumab, Apolizumab, Aprutumab ixadotin, Arcitumomab, Ascrinvacumab, Aselizumab, Atezolizumab, Atidortoxumab, Atinumab, Atlizumab, Atorolimumab, Avelumab, Azintuxizumab vedotin, Bapineuzumab, Basiliximab, Bavituximab, BCD-100, Bectumomab, Begelomab, Belantamab mafodotin, Belatacept, Belimumab, Bemarituzumab, Benralizumab, Bermekimab, Bersanlimab, Bertilimumab, Besilesomab, Bevacizumab, Bevacizumab-awwb, Bezlotoxumab, Biciromab, Bimagrumab, Bimekizumab, Birtamimab, Bivatuzumab mertansine, Bleselumab, Blinatumomab, Blontuvetmab, Blosozumab, Bococizumab, Brazikumab, Brentuximab vedotin, Briakinumab, Brodalumab, Brolucizumab, Brontictuzumab, Burosumab, Cabiralizumab, Camidanlumab tesirine, Camrelizumab, Canakinumab, Cantuzumab mertansine, Cantuzumab ravtansine, Caplacizumab, Capromab pendetide, Carlumab, Carotuximab, Catumaxomab, cBR96-doxorubicin immunoconjugate, Cedelizumab, Cemiplimab, Cergutuzumab amunaleukin, Cergutuzumab amunaleukin, Certolizumab pegol, Cetrelimab, Cetuximab, Cibisatamab, Cirmtuzumab, Citatuzumab bogatox, Cixutumumab, Clazakizumab, Clenoliximab, Clivatuzumab tetraxetan, Codrituzumab, Cofetuzumab pelidotin, Coltuximab ravtansine, Conatumumab, Concizumab, Cosfroviximab, Crenezumab, CR6261, Crizanlizumab, Crotedumab, Cusatuzumab, Dacetuzumab, Daclizumab, Dalotuzumab, Dapirolizumab pegol, Daratumumab, Dectrekumab, Demcizumab, Denileukin diftitox, Denintuzumab mafodotin, Denosumab, Depatuxizumab mafodotin, Derlotuximab biotin, Detumomab, Dezamizumab, Dinutuximab, Diridavumab, Domagrozumab, Dorlimomab aritox, Dostarlimab, Drozitumab, DS-8201, Duligotumab, Dupilumab, Durvalumab, Dusigitumab, Duvortuxizumab, Ecromeximab, Eculizumab, Edobacomab, Edrecolomab, Efalizumab, Efungumab, Eldelumab, Elezanumab, Elgemtumab, Elotuzumab, Elsilimomab, Emactuzumab, Emibetuzumab, Emicizumab, Enapotamab vedotin, Enavatuzumab, Enfortumab vedotin, Enlimomab pegol, Enoblituzumab, Enokizumab, Enoticumab, Ensituximab, Epitumomab cituxetan, Epoetin-alfa, Epoetin-alfa-epbx, Epratuzumab, Eptinezumab, Erenumab, Erlizumab, Ertumaxomab, Etanercept, Etanercept-szzs, Etaracizumab, Etigilimab, Etrolizumab, Evinacumab, Evolocumab, Exbivirumab, Factor VIII Fc fusion protein, Factor IX Fc fusion protein, Fanolesomab, Faralimomab, Faricimab, Farletuzumab, Fasinumab, Felvizumab, Fezakinumab, Fibatuzumab, Ficlatuzumab, Figitumumab, Filgrastim, Filgrastim-sndz, Firivumab, Flanvotumab, Fletikumab, Flotetuzumab, Fontolizumab, Foralumab, Foravirumab, Fremanezumab, Fresolimumab, Frovocimab, Frunevetmab, Fulranumab, Futuximab, Galcanezumab, Galiximab, Ganitumab, Gantenerumab, Gatipotuzumab, Gavilimomab, Gedivumab, Gemtuzumab ozogamicin, Gevokizumab, Gilvetmab, Gimsilumab, Girentuximab, Glembatumumab vedotin, Golimumab, Gomiliximab, Gosuranemab, Guselkumab, Ibalizumab, IBI308, Ibritumomab tiuxetan, Ierucumab, Idarucizumab, Ifabotuzumab, Igovomab, Iladatuzumab vedotin, IMAB362, Imalumab, Imaprelimab, Imciromab, Imgatuzumab, Inclacumab, Indatuximab ravtansine, Indusatumab vedotin, Inebilizumab, Infliximab, Infliximab-abda, Infliximab-dyyb, Infliximab-qbtx, Intetumumab, Inolimomab, Inotuzumab ozogamicin, Ipilimumab, Iomab-B, Iratumumab, Isatuximab, Iscalimab, Istiratumab, Itolizumab, Ixekizumab, Keliximab, Labetuzumab, Lacnotuzumab, Ladiratuzumab vedotin, Lambrolizumab, Lampalizumab, Lanadelumab, Landogrozumab, Laprituximab emtansine, Larcaviximab, Lebrikizumab, Lemalesomab, Lendalizumab, Lenvervimab, Lenzilumab, Lerdelimumab, Leronlimab, Lesofavumab, Letolizumab, Lexatumumab, Libivirumab, Lifastuzumab vedotin, Ligelizumab, Loncastuximab tesirine, Losatuxizumab vedotin, Lilotomab satetraxetan, Lintuzumab, Lirilumab, Lodelcizumab, Lokivetmab, Lorvotuzumab mertansine, Lucatumumab, Lulizumab pegol, Lumiliximab, Lumretuzumab, Lupartumab amadotin, Lutikizumab, Mapatumumab, Margetuximab, Marstacimab, Maslimomab, Mavrilimumab, Matuzumab, Mepolizumab, Metelimumab, Milatuzumab, Minretumomab, Mirikizumab, Mirvetuximab soravtansine, Mitumomab, Modotuximab, Mogamulizumab, Monalizumab, Morolimumab, Mosunetuzumab, Motavizumab, Moxetumomab pasudotox, Muromonab-CD3, Nacolomab tafenatox, Namilumab, Naptumomab estafenatox, Naratuximab emtansine, Narnatumab, Natalizumab, Navicixizumab, Navivumab, Naxitamab, Nebacumab, Necitumumab, Nemolizumab, NEOD001, Nerelimomab, Nesvacumab, Netakimab, Nimotuzumab, Nirsevimab, Nivolumab, Nofetumomab merpentan, Obiltoxaximab, Obinutuzumab, Ocaratuzumab, Ocrelizumab, Odulimomab, Ofatumumab, Olaratumab, Oleclumab, Olendalizumab, Olokizumab, Omalizumab, Omburtamab, OMS721, Onartuzumab, Ontuxizumab, Onvatilimab, Opicinumab, Oportuzumab monatox, Oregovomab, Orticumab, Otelixizumab, Otilimab, Otlertuzumab, Oxelumab, Ozanezumab, Ozoralizumab, Pagibaximab, Palivizumab, Pamrevlumab, Panitumumab, Pankomab, Panobacumab, Parsatuzumab, Pascolizumab, Pasotuxizumab, Pateclizumab, Patritumab, PDR001, Pegfilgrastim-jmdb, Pembrolizumab, Pemtumomab, Perakizumab, Pertuzumab, Pexelizumab, Pidilizumab, Pinatuzumab vedotin, Pintumomab, Placulumab, Plozalizumab, Pogalizumab, Polatuzumab vedotin, Ponezumab, Porgaviximab, Prasinezumab, Prezalizumab, Priliximab, Pritoxaximab, Pritumumab, PRO 140, Quilizumab, Racotumomab, Radretumab, Rafivirumab, Ralpancizumab, Ramucirumab, Ranevetmab, Ranibizumab, Raxibacumab, Ravagalimab, Ravulizumab, Refanezumab, Regavirumab, Relatlimab, Remtolumab, Reslizumab, Rilonacept, Rilotumumab, Rinucumab, Risankizumab, Rituximab, Rituximab-abbs, Rituximab-pvvr, Rivabazumab pegol, Rivabazumab pegol, Robatumumab, Rmab, Roledumab, Romilkimab, Romiplostim, Romosozumab, Rontalizumab, Rosmantuzumab, Rovalpituzumab tesirine, Rovalpituzumab tesirine, Rovelizumab, Rozanolixizumab, Ruplizumab, Sacituzumab govitecan, Samalizumab, Samrotamab vedotin, Sapelizumab, Sarilumab, Satralizumab (SA237), Satumomab pendetide, Secukinumab, Selicrelumab, Seribantumab, Setoxaximab, Setrusumab, Sevirumab, Sibrotuzumab, SGN-CD19A, SGN-CD33A, SHP647, Sifalimumab, Siltuximab, Simtuzumab, Siplizumab, Sirtratumab vedotin, Sirukumab, Sofituzumab vedotin, Solanezumab, Solitomab, Sonepcizumab, Sontuzumab, Spartalizumab, Stamulumab, Sulesomab, Suptavumab, Sutimlimab, Suvizumab, Suvratoxumab, Tabalumab, Tacatuzumab tetraxetan, Tadocizumab, Talacotuzumab, Talizumab, Tamtuvetmab, Tanezumab, Taplitumomab paptox, Tarextumab, Tavolimab, Tefibazumab, Telimomab aritox, Telisotuzumab vedotin, Tenatumomab, Teneliximab, Teplizumab, Tepoditamab, Teprotumumab, Tesidolumab, Tetulomab, Tezepelumab, TGN1412, Tibulizumab, Ticilimumab, Tildrakizumab, Tigatuzumab, Timigutuzumab, Timolumab, Tiragotumab, Tislelizumab, Tisotumab vedotin, TNX-650, Tocilizumab, Tomuzotuximab, Toralizumab, Tosatoxumab, Tositumomab, Tovetumab, Tralokinumab, Trastuzumab, Trastuzumab-anns, Trastuzumab-dkst, Trastuzumab emtansine, Tregalizumab, Tremelimumab, Trevogrumab, Tucotuzumab celmoleukin, Tuvirumab, Ublituximab, Ulocuplumab, Urelumab, Urtoxazumab, Ustekinumab, Utomilumab, Vadastuximab talirine, Vanalimab, Vandortuzumab vedotin, Vantictumab, Vanucizumab, Vapaliximab, Varisacumab, Varlilumab, Vatelizumab, Vedolizumab, Veltuzumab, Vepalimomab, Vesencumab, Visilizumab, Vobarilizumab, Volociximab, Vonlerolizumab, Vopratelimab, Vorsetuzumab mafodotin, Votumumab, Xentuzumab, XMAB-5574, Zalutumumab, Zanolimumab, Zatuximab, Zenocutuzumab, Ziralimumab, Zolbetuximab (IMAB362, Claudiximab), Ziv-aflibercept, or Zolimomab aritox.

In other embodiments of any of the foregoing composition of matter and methods, the antibody is monoclonal. In certain embodiments, the monoclonal antibody includes but are not limited to 3F8, 8H9, Abatacept, Abagovomab, Abciximab, Abituzumab, Adalimumab-adbm, Adalimumab-atto, Adalimumab-bwwb, Abrilumab, Actoxumab, Abituzumab, Abrezekimab, Abrilumab, Actoxumab, Adalimumab, Adecatumumab, Ado-trastuzumab emtansine, Aducanumab, Afasevikumab, Afelimomab, Aflibercept, Afutuzumab, Alacizumab pegol, ALD518, Alefacept, Alemtuzumab, Alirocumab, Altumomab pentetate, Amatuximab, Anatumomab mafenatox, Andecaliximab, Anetumab ravtansine, Anifrolumab, Anrukinzumab (IMA-638) Apolizumab, Arcitumomab, Ascrinvacumab, Aselizumab, Atezolizumab, Atidortoxumab, Atinumab, Atlizumab (tocilizumab), Atorolimumab, Avelumab, Bapineuzumab, Basiliximab, Bevacizumab, Bevacizumab-awwb, BCD-100, Bectumomab, Begelomab, Belatacept, Belimumab, Bemarituzumab, Benralizumab, Bermekimab, Bersanlimab, Bertilimumab, Besilesomab, Bezlotoxumab, Biciromab, Bimagrumab, Bimekizumab, Birtamimab, Bivatuzumab mertansine, Bleselumab, Blinatumomab, Blontuvetmab, Blosozumab, Bococizumab, Brazikumab, Brentuximab vedotin, Briakinumab, Brodalumab, Brolucizumab, Brontictuzumab, Burosumab, Cabiralizumab, Camrelizumab, Canakinumab, Cantuzumab mertansine, Cantuzumab ravtansine, Caplacizumab, Capromab pendetide, Carlumab, Carotuximab, Catumaxomab, Cedelizumab, Cemiplimab, Certolizumab pegol, Cetrelimab, Cetuximab, Cibisatamab, Cirmtuzumab, Ch. 14.18, Citatuzumab bogatox, Cixutumumab, Clazakizumab, Clenoliximab, Clivatuzumab tetraxetan, Codrituzumab, Cofetuzumab pelidotin, Coltuximab ravtansine, Conatumumab, Concizumab, Cosfroviximab, Crenezumab, CR6261, Crizanlizumab, Crotedumab, Cusatuzumab, Dacetuzumab, Daclizumab, Dalotuzumab, Dapirolizumab pegol, Daratumuma, Dectrekumab, Demcizumab, Denileukin diftitox, Deninotuzumab mafodotin, Denosumab, Derlotuximab biotin, Detumomab, Dezamizumab, Dinutuximab, Diridavumab, Domagrozumab, Dorlimomab aritox, Dostarlimab, Drozitumab, Duligotumab, Dupilumab, Durvalumab, Dusigitumab, Duvortuxizumab, Ecromeximab, Eculizumab, Edobacomab, Edrecolomab, Efalizumab, Efungumab, Eldelumab, Elezanumab, Elgemtumab, Elotuzumab, Elsilimomab, Emactuzumab, Emibetuzumab, Emicizumab, Enavatuzumab, Enfortumab vedotin, Enlimomab pegol, Enoblituzumab, Enokizumab, Enoticumab, Ensituximab, Epitumomab cituxetan, Epoetin-alfa, Epoetin-alfa-epbx, Epratuzumab, Eptinezumab, Erenumab, Erlizumab, Ertumaxomab, Etanercept, Etanercept-szzs, Etaracizumab, Etigilimab, Etrolizumab, Evinacumab, Evolocumab, Exbivirumab, Factor VIII Fc fusion protein, Factor IX Fc fusion protein, Fanolesomab, Faralimomab, Faricimab, Farletuzumab, Fasinumab, FBTA05, Felvizumab, Fezakinumab, Fibatuzumab, Ficlatuzumab, Figitumumab, Filgrastim, Filgrastim-sndz, Firivumab, Flanvotumab, Fletikumab, Flotetuzumab, Fontolizumab, Foralumab, Foravirumab, Fremanezumab, Fresolimumab, Frovocimab, Frunevetmab, Fulranumab, Futuximab, Galcanezumab, Galiximab, Ganitumab, Gantenerumab, Gatipotuzumab, Gavilimomab, Gedivumab, Gemtuzumab ozogamicin, Gevokizumab, Gilvetmab, Gimsilumab, Girentuximab, Glembatumumab vedotin, Golimumab, Gomiliximab, Gosuranemab, Guselkumab, Ibalizumab, IBI308, Ibritumomab tiuxetan, Icrucumab, Idarucizumab, Ifabotuzumab, Igovomab, IMAB362, Imalumab, Imaprelimab, Imciromab, Imgatuzumab, Inclacumab, Indatuximab ravtansine, Indusatumab vedotin, Inebilizumab, Infliximab, Infliximab-abda, Infliximab-dyyb, Infliximab-qbtx, Intetumumab, Inolimomab, Inotuzumab ozogamicin, Ipilimumab, Iratumumab, Isatuximab, Iscalimab, Istiratumab, Itolizumab, Ixekizumab, Keliximab, Labetuzumab, Lacnotuzumab, Lambrolizumab, Lampalizumab, Lanadelumab, Landogrozumab, Larcaviximab, Lebrikizumab, Lemalesomab, Lendalizumab, Lenvervimab, Lenzilumab, Lerdelimumab, Leronlimab, Lesofavumab, Letolizumab, Lexatumumab, Libivirumab, Lifastuzumab vedotin, Ligelizumab, Lilotomab satetraxetan, Lintuzumab, Lirilumab, Lodelcizumab, Lokivetmab, Lorvotuzumab mertansine, Lucatumumab, Lulizumab pegol, Lumiliximab, Lumretuzumab, Lutikizumab, Mapatumumab, Margetuximab, Marstacimab, Maslimomab, Mavrilimumab, Matuzumab, Mepolizumab, Metelimumab, Milatuzumab, Minretumomab, Mirikizumab, Mirvetuximab soravtansine, Mitumomab, Modotuximab, Mogamulizumab, Monalizumab, Morolimumab, Mosunetuzumab, Motavizumab, Moxetumomab pasudotox, Muromonab-CD3, Nacolomab tafenatox, Namilumab, Naptumomab estafenatox, Narnatumab, Natalizumab, Navicixizumab, Navivumab, Naxitamab, Nebacumab, Necitumumab, Nemolizumab, NEOD001, Nerelimomab, Nesvacumab, Netakimab, Nimotuzumab, Nirsevimab, Nivolumab, Nofetumomab merpentan, Obiltoxaximab, Obinutuzumab, Ocaratuzumab, Ocrelizumab, Odulimomab, Ofatumumab, Olaratumab, Oleclumab, Olendalizumab, Olokizumab, Omalizumab, Omburtamab, OMS721, Onartuzumab, Ontuxizumab, Onvatilimab, Opicinumab, Oportuzumab monatox, Oregovomab, Orticumab, Otelixizumab, Otilimab, Otlertuzumab, Oxelumab, Ozanezumab, Pagibaximab, Palivizumab, Pamrevlumab, Panitumumab, Pankomab, Panobacumab, Parsatuzumab, Pascolizumab, Pasotuxizumab, Pateclizumab, Patritumab, PDR001, Pegfilgrastim-jmdb, Pembrolizumab, Pemtumomab, Peraki-zumab, Pertuzumab, Pexelizumab, Pidilizumab, Pinatuzumab vedotin, Pintumomab, Placulumab, Plozali-zumab, Pogalizumab, Polatuzumab vedotin, Ponezumab, Porgaviximab, Prasinezumab, Prezalizumab, Priliximab, Pritoxaximab, Pritumumab, PRO 140, Quilizumab, Tetulo-mab, Racotumomab, Radretumab, Rafivirumab, Ralpanci-zumab, Ramucirumab, Ranevetmab, Ranibizumab, Raxi-bacumab, Ravagalimab, Ravulizumab, Refanezumab, Regavirumab, Relatlimab, Remtolumab, Reslizumab, Rilonacept, Rilotumumab, Rinucumab, Risankizumab-rzaa, Rituximab, Rituximab-abbs, Rituximab-pvvr, Robatu-mumab, Rmab, Roledumab, Romilkimab, Romiplostim, Romosozumab, Rontalizumab, Rosmantuzumab, Roveli-zumab, Rozanolixizumab, Ruplizumab, Sacituzumab govitecan, Samalizumab, Sarilumab, Satralizumab (SA237), Satumomab pendetide, Secukinumab, Selicrelumab, Serib-antumab, Setoxaximab, Setrusumab, Sevirumab, Sibro-tuzumab, SGN-CD19A, SGN-CD33A, SHP647, Sifalim-umab, Siltuximab, Simtuzumab, Siplizumab, Sirukumab, Sofituzumab vedotin, Solanezumab, Solitomab, Sonepci-zumab, Sontuzumab, Spartalizumab, Stamulumab, Suleso-mab, Suptavumab, Sutimlimab, Suvizumab, Suvratoxumab, Tabalumab, Tacatuzumab tetraxetan, Tadocizumab, Tala-cotuzumab, Talizumab, Tamtuvetmab, Tanezumab, Taplitu-momab paptox, Tarextumab, Tavolimab, Tefibazumab, Teli-momab aritox, Tenatumomab, Teneliximab, Teplizumab, Tepoditamab, Teprotumumab, Tesidolumab, Tetulomab (lilotomab), Tezepelumab, TGN1412, Tibulizumab, Ticili-mumab (tremelimumab), Tildrakizumab, Tigatuzumab, Timigutuzumab, Timolumab, Tiragotumab, Tislelizumab, TNX-650, Tocilizumab (atlizumab), Tomuzotuximab, Toralizumab, Tosatoxumab, Tositumomab, Tovetumab, Tralokinumab, Trastuzumab, Trastuzumab-anns, Trastuzumab-dkst, Trastuzumab emtansine, TRBS07, Tregalizumab, Tremelimumab, Trevogrumab, Tucotuzumab celmoleukin, Tuvirumab, Ublituximab, Ulocuplumab, Ure-lumab, Urtoxazumab, Ustekinumab, Utomilumab, Vanal-imab, Vandortuzumab vedotin, Vantictumab, Vanucizumab, Vapaliximab, Varisacumab, Varlilumab, Vatelizumab, Ved-olizumab, Veltuzumab, Vepalimomab, Vesencumab, Visili-zumab, Vobarilizumab, Volociximab, Vonlerolizumab, Vopratelimab, Vorsetuzumab mafodotin, Votumumab, Xen-tuzumab, XMAB-5574, Zalutumumab, Zanolimumab, Zatuximab, Zenocutuzumab, Ziralimumab, Zolbetuximab (IMAB362, Claudiximab), Ziv-aflibercept, Zolimomab ari-tox or the corresponding anti-drug antibody in a sample from a human patient. In preferred embodiments, the mono-clonal antibody is Rituximab, Rituximab-abbs, or Ritux-imab-pvvr.

In some embodiments, the monoclonal antibody is a biosimilar. In other embodiments, the biosimilar includes but are not limited to Adalimumab-adbm, Adalimumab-atto, Adalimumab-bwwb, Bevacizumab-awwb, Epoetin alfa-epbx, Etanercept-szzs, Infliximab-abda, Infliximab-dyyb, Infliximab-qbtx, Filgrastim-sndz, Pegfilgrastim-jmdb, Peg-filgrastim-bmez, Risankizumab-rzaa, Rituximab-abbs, Rit-uximab-pvvr, Trastuzumab-anns, or Trastuzumab-dkst. In certain embodiments, the active biosimilar substance is Adalimumab, Bevacizumab, Enoxaparin sodium, Epoetin alfa, Epoetin zeta, Etanercept, Filgrastim, Follitropin alfa, Infliximab, Insulin glargine, Insulin lispro, Pegfilgrastim, Risankizumab, Rituximab, Rituximab-abbs, Rituximab-pvvr, Somatropin, Teriparatide, or Trastuzumab. In preferred embodiments, the biosimilar is Rituximab, Rituximab-abbs, or Rituximab-pvvr.

In other embodiments, the targeting moiety is an antibody from an intact polyclonal antibody, an intact monoclonal antibody, an antibody fragment, a single chain Fv (scFv) mutant, a multispecific antibody, a bispecific antibody, a chimeric antibody, a humanized antibody, a human antibody, a fusion protein comprising an antigenic determinant portion of an antibody, or other modified immunoglobulin mol-ecules comprising antigen recognition sites.

In some embodiments, the therapeutic biologic is an immunotherapy. In other embodiments, the immunotherapy is an anti-CD20 antibody. In certain embodiments, the anti-CD20 antibody is rituximab. In certain other embodi-ments, the therapeutic biologic is an anti-CD20 antibody. As described herein, any antibody capable of binding the CD20 antigen may be used in the methods of the instant disclosure. Antibodies which bind the CD20 antigen include, for example: C2B8 (rituximab; RITUXAN® anti-CD20 anti-body™.) (U.S. Pat. No. 5,736,137, expressly incorporated herein by reference); the yttrium-[90]-labeled 2138 murine antibody designated Y2B8 (U.S. Pat. No. 5,736,137, expressly incorporated herein by reference); murine IgG2a 131 optionally labeled with 131 1 to generate the 131 1-B1 antibody (BEXXAR® therapeutic regimen) (U.S. Pat. No. 5,595,721, expressly incorporated herein by reference); murine monoclonal antibody 1F5 (Press et al. Blood 69 (2): 584-591 (1987)); chimeric 2H7 antibody (U.S. Pat. No. 5,677,180 expressly incorporated herein by reference); and monoclonal antibodies L27, G28-2, 93-1 133, B—Cl or NU-B2 available from the International Leukocyte Typing Workshop (Valentine et al., In: Leukocyte TypingIII (McMi-chael, Ed., p. 440, Oxford University Press (1987)).

In certain embodiments of the disclosure, the anti-CD20 antibody is rituximab. Rituximab is a genetically engineered chimeric murine/human monoclonal antibody. Rituximab is an IgG, kappa immunoglobulin containing murine light and heavy chain variable region sequences and human constant region sequences. Rituximab has a binding affinity for the CD20 antigen of approximately 8.0 nM and is commercially available, e.g., from Genentech (South San Francisco, Calif.).

In some embodiments, the therapeutic biologic is an immunotherapeutic. In other embodiments, the immuno-therapeutic is a PD-1 inhibitor such as a PD-1 antibody, a PD-L1 inhibitor such as a PD-L1 antibody, a CTLA-4 inhibitor such as a CTLA-4 antibody, a CSF-1R inhibitor, an IDO inhibitor, an A1 adenosine inhibitor, an A2A adenosine inhibitor, an A2B adenosine inhibitor, an A3A adenosine inhibitor, an arginase inhibitor, or an HDAC inhibitor. In still other embodiments, the immunotherapeutic is a PD-1 inhibi-tor (e.g., nivolumab, pembrolizumab, pidilizumab, BMS 936559, and MPDL328OA). In some embodiments, the immunotherapy is a PD-L1 inhibitor (e.g., atezolizumab and MEDI4736). In some embodiments, the immunotherapeutic is a CTLA-4 inhibitor (e.g., ipilimumab). In certain other embodiments, the immunotherapeutic is a CSF-1R inhibitor (e.g., pexidartinib and AZD6495). In certain embodiments, the immunotherapeutic is an IDO inhibitor (e.g., norhar-mane, rosmarinic acid, and alpha-methyl-tryptophan). In some embodiments, the immunotherapeutic is an A1 adenosine inhibitor (e.g., 8-cyclopentyl-1,3-dimethylxan-thine, 8-cyclopentyl-1,3-dipropylxanthine, 8-phenyl-1,3-dipropylxanthine, bamifylline, BG-9719, BG-9928, FK-453, FK-838, rolofylline, or N-0861). In other embodi-ments, the immunotherapeutic is an A2A adenosine inhibitor (e.g., ATL-4444, istradefylline, MSX-3, preladenant, SCH-58261, SCH-412,348, SCH-442,416, ST-1535, VER-6623, VER-6947, VER-7835, viadenant, or ZM-241,385). In still other embodiments, the immunotherapeutic is an A2B adenosine inhibitor (e.g., ATL-801, CVT-6883, MRS-1706, MRS-1754, OSIP-339,391, PSB-603, PSB-0788, or PSB-1115). In certain other embodiments, the immunotherapeutic is an A3A adenosine inhibitor (e.g., KF-26777, MRS-545, MRS-1191, MRS-1220, MRS-1334, MRS-1523, MRS-3777, MRE-3005-F20, MRE-3008-F20, PSB-11, OT-7999, VUF-5574, and SSR161421). In certain embodiments, the immunotherapeutic is an arginase inhibitor (e.g., an arginase antibody, (2s)-(+)-amino-5-iodoacetamidopentanoic acid, NG-hydroxy-L-arginine, (2S)-(+)-amino-6-iodoacetamido-hexanoic acid, or (R)-2-amino-6-borono-2-(2-(piperidin-1-yl)ethyl)hexanoic acid. In some embodiments, the immunotherapeutic is an HDAC inhibitor (e.g., valproic acid, SAHA, or romidepsin). In other embodiments, the immunotherapeutic is a toll-like receptor activator. In still other embodiments, the immunotherapy is a RIG-I-like receptor activator. In certain other embodiments, the immunotherapeutic is a stimulator of interferon genes (STING) pathway activator. In certain embodiments, the immunotherapeutic is an Interleukin-1 receptor agonist, e.g., an IL-R1 antagonist. In some embodiments, the immunotherapeutic is a PTEN inhibitor, e.g., a bisperoxovanadium compound. In other embodiments, the immunotherapeutic is a tumor necrosis factor receptor (TNFR), e.g., TNFR-1 or TNFR-2 inhibitor. In certain embodiments, the immunotherapeutic is a Lym-phocyte-activation gene 3 (LAG-3) inhibitor, e.g., GSK2831781.

In other embodiments, the therapeutic biologic is ledipas-vir/sofosbuvir, insulin glargine, lenalidomide, pneumococ-cal 13-valent conjugate vaccine, fluticasone/salmeterol, elvitegravir/cobicistat/emtricitabine/tenofovir alafenamide, emtricitabine, rilpivirine and tenofovir alafenamide, emtric-itabine/tenofovir alafenamide, grazoprevir/elbasvir, coagu-lation factor VIIa recombinant, epoetin alfa, Aflibercept or etanercept.

In some embodiments, the therapeutic or diagnostic agent is Abatacept, AbobotulinumtoxinA, Agalsidase beta, Albig-lutide, Aldesleukin, Alglucosidase alfa, Alteplase (cathflo activase), Anakinra, Asfotase alfa, Asparaginase, Asparagi-nase *Erwinia chrysanthemi*, Becaplermin, Belatacept, Col-lagenase, Collagenase clostridium histolyticum, Darbepo-etin alfa, Denileukin diftitox, Dornase alfa, Dulaglutide, Ecallantide, Elosulfase alfa, Etanercept-szzs, Filgrastim, Fil-grastim-sndz, Galsulfase, Glucarpidase, Idursulfase, Inco-botulinumtoxinA, Interferon alfa-2b, Interferon alfa-n3, Interferon beta-1a, Interferon beta-1b, Interferon gamma-1b, Laronidase, Methoxy polyethylene glycol-epoetin beta, Metreleptin, Ocriplasmin, OnabotulinumtoxinA, Oprelvekin, Palifermin, Parathyroid hormone, Pegaspar-gase, Pegfilgrastim, Peginterferon alfa-2a, Peginterferon alfa-2a co-packaged with ribavirin, Peginterferon alfa-2b, Peginterferon beta-1a, Pegloticase, Rasburicase, Reteplase, Rilonacept, RimabotulinumtoxinB, Romiplostim, Sargra-mostim, Sebelipase alfa, Tbo-filgrastim, Tenecteplase, or Ziv-aflibercept.

In other embodiments, the diagnostic agent is tuberculin purified protein derivative, hyrotropin alpha, secretin, soluble transferrin receptor, troponin, B-type natriuretic pep-tide, iobenguane 1123, florbetapir F 18, perflutren, gadoter-ate meglumine, florbetaben F 18, flutemetamol F 18, gad-oterate meglumine, isosulfan blue, regadenoson, technetium Tc 99m tilmanocept, florbetaben F 18, perflutren, regade-noson, or flutemetamol F 18.

The therapeutic or diagnostic agent in the particles may have an activity per unit of about 0.5 to about 1.0, about 0.75 to about 1.0 activity per unit, or about 0.9 to about 1.0 activity per unit. Activity is measured relative to the same therapeutic or diagnostic agent prior to particle formation. In certain embodiments, the therapeutic agent has an activity per unit of about 0.5 to about 1.0. In preferred embodiments, the therapeutic biologic has an activity per unit of about 0.5 to about 1.0. The term "activity" refers to the ratio of a functional or structural aspect of an agent, e.g., a therapeutic or diagnostic agent, at two points in time. The denominator of the ratio corresponds to a measure of the functional or structural aspect of the agent in the feed solution, immedi-ately in advance of droplet formation. The numerator of the ratio corresponds to the same measure of a functional or structural aspect of the agent at a later point in time, e.g., immediately after particle formation.

In certain embodiments, the particles include a loading of therapeutic or diagnostic agents from about 1 to about 100 wt %, e.g., from about 50 to about 100 wt %, from about 75 to about 100 wt %, from about 90 to about 100 wt %, from about 95 to about 100 wt %, from about 99 to about 100 wt %, or from about 99.9 to about 100 wt %. At these loadings the therapeutic or diagnostic agents retain from about 0.5 to about 1.0 activity during particle formation, e.g., from about 0.75 to about 1.0 activity, from about 0.9 to about 1.0 activity, from about 0.95 to about 1.0 activity, from about 0.99 to about 1.0 activity, or from about 0.999 to about 1.0 activity. This includes the activity retained through primary desiccation (i.e., desiccation utilizing a second liquid) and, in some cases, secondary desiccation.

In some embodiments, the particles have less than about 25% internal void spaces, e.g., less than about 24, 20, 15, 10, 9, 8, 7, 6, 5, 4, 3, 2, 1, 0.5, or 0.1% internal void spaces. In certain embodiments, the particle may include less than 10% internal void spaces, less than 5% internal void spaces, less than 1% internal void spaces, less than 0.1% internal void spaces, or less than 0.01% internal void spaces. In preferred embodiments, the particle is substantially free from any internal void spaces. Suitable methods for determining inter-nal void space can be accomplished by using Focused Ion Beam Scanning Electron Microscopy (FIB-SEM). For example, internal void space can be calculated using the following formula: internal void space=$A_v/A_p$, where $A_v$ is the total area of void spaces and $A_p$ is the total area of the particle.

In other embodiments, the particles may exhibit a porosity from about 0 to about 50%, e.g., from about 0 to about 10%, from about 0 to about 5%, from about 0 to about 1%, from about 0 to about 0.5%, from about 0 to about 0.1%, or from about 0 to about 0.01%. Exemplary pore size measurements include scanning electron microscopy (SEM), transmission electron microscopy (TEM), and confocal laser scanning microscopy analysis. The specific surface area of porous micro- and nanospheres may also be investigated by nitro-gen adsorption/desorption analysis and a Brunauer-Emmett-Teller adsorption model. In certain embodiments where the pore sizes are sufficiently large, mercury-intrusion porosim-etry may be employed.

The particles according to the disclosure are circular. Circularity can serve as an indicator of the shape of the particle. The particles described herein, can have a charac-teristic circularity, e.g., have a relative shape, that is sub-stantially circular. This characteristic describes and defines the form of a particle on the basis of its circularity. The circularity is 1.0 when the particle has a completely circular structure. Particles as described herein, can have a circular-ity of about 0.8, 0.9, 0.95, 0.96, 0.97, 0.98, or 0.99; greater than about 0.80, greater than about 0.90, or greater than about 0.95. In some embodiments, the circularity of the particle is greater than about 0.88. In other embodiments, the circularity of the particle is greater than about 0.90. In certain embodiments, the circularity of the particle is greater than about 0.93. In preferred embodiments, the circularity of the particle is greater than about 0.97. The diameter and the circularity of the particles can be determined by the image processing of an image observed under an electron microscope or the like or a flow-type particle image analyzer. The circularity can also be determined by subjecting particles to circularity measurement and averaging the resulting values. For example, circularity (circ) can be calculated using the following formula:

$$circ = 4 * \pi * \frac{Area}{Perimeter^2}. \qquad \text{Eq. 1}$$

The term "perimeter", as used herein, refers to the boundary of a closed plane figure or the sum of all borders of a two-dimensional image. As used herein, the term "area", refers to the crossectional area of a two-dimensional image of a particle. The circularity of a particle can also be described as the ratio of the smallest diameter of the particle to its largest diameter. For a perfect circle, the ratio is 1. The percentage circularity can be calculated by multiplying the circularity by 100. The circularity can be calculated, for example, by measuring the aspect ratio using any software adapted to deal with images, for example, images obtained by microscopy, in particular, scanning electron microscopy (SEM) or transmission electron microscopy (TEM). In some embodiments, the circularity of the particles is at least about 10%, e.g., at least about 20, 30, 40, 50, 55, 60, 65, 70, 75, 80, 85, 90, 91, 92, 93, 94, 95, 96, 97, 98, 99, or about 100%. In other embodiments, the circularity of the particles is at least about 88%. In certain embodiments, the circularity of the particles is at least about 90%. In still other embodiments, the circularity of the particles is at least about 93%. In preferred embodiments, the circularity of the particles is at least about 97%.

In other embodiments, the circularity of the particle is from about 0.10 to about 1.00, e.g., from about 0.20, 0.30, 0.40, 0.50. 0.60, 0.70, 0.75, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, or 0.99 to about 1.00. In certain embodiments, the circularity of the particle is from about 0.88 to about 1.00. In still other embodiments, the circularity of the particle is from about 0.90 to about 1.00. In certain other embodiments, the circularity of the particle is from about 0.93 to about 1.00. In preferred embodiments, the circularity of the particle is from about 0.97 to about 1.00. In some embodiments, methods of measuring particle circularity include image analysis of scanning electron micrographs of the particles in which the average roundness is calculated on the basis of the cross-sectional shapes of the particles projected onto the plane of the image. Such roundness factors can be extended to identify the corresponding circularity.

The particles according to the disclosure are spherical. The coefficient of sphericity of a particle is the ratio of the smallest diameter of the particle to its largest diameter. For a perfect sphere, the ratio is 1. The sphericity coefficient can be calculated by measuring the aspect ratio using any software adapted to deal with images, for example, images obtained by microscopy, in particular, scanning electron microscopy (SEM) or transmission electron microscopy (TEM). In some embodiments, the sphericity of the particles are at least about 50%, e.g., at least about 55, 60, 65, 70, 75, 80, 85, 90, 91, 92, 93, 94, 95, 96, 97, 98, 99, or about 100%. In other embodiments, the sphericity of the particle is from about 0.10 to about 1.00, e.g., from about 0.20, 0.30, 0.40, 0.50. 0.60, 0.70, 0.75, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, or 0.99 to about 1.00. In preferred embodiments, the sphericity of the particle is about 1.00.

In certain embodiments, the sphericity of the particles may range from about 0.10 to about 1.00, e.g., at least about 0.20, about 0.40, about 0.60, or about 0.80 to about 1.00. In some embodiments, methods of measuring particle sphericity include image analysis of scanning electron micrographs of the particles in which the average roundness is calculated on the basis of the cross-sectional shapes of the particles projected onto the plane of the image. Sphericity ($\psi$) is a measure of the roundness of an object. Sphericity is the ratio of the surface area of a sphere (which has the same volume as the particle being compared) to the surface of the particle being tested. Sphericity can be calculated according to the following formula:

$$\Psi = \frac{\pi^{\frac{1}{3}}(6V_p)^{\frac{2}{3}}}{A_p}, \qquad \text{Eq. 2}$$

where Vp is the volume of the sphere and Ap is the surface area of the sphere. The term "surface area" as used herein, refers to the external surface of a particle.

In other embodiments, the sphericity (minor axis/major axis) can be determined by using an image analyzer, or an electron microscopic photograph taken with a scanning electron microscope (SEM). For example, the average sphericity can be calculated as the average of the sphericity values calculated for randomly selected particles in the electron microscopic photograph by determining their minor axis and major axis based on visual observation.

In some embodiments of the disclosure, the drying operation may be controlled to provide particles having particular characteristics, such as particles having a substantially smooth surface. "Surface roughness", as used herein, means a particle having numerous wrinkles or creases, e.g., being ridged or wrinkled. The term "pit", as used herein, refers to an indentation or crevice in the particle, either an indentation or crevice in the two-dimensional image or an indentation or crevice in an object. The term "spike", as used herein, refers to a projection pointing outward from the centroid of a particle, a projection pointing outward from the centroid of a two-dimensional image or a sharp projection pointing outward from an object.

In preferred embodiments of the disclosure, the particles as described herein, have a surface morphology that is smooth rather than ridged or wrinkled. The surface roughness of the particles may be decreased by controlling the formulation and/or process to form the particles as described herein. In certain embodiments, the drying conditions can be selected to control the particle morphology in order to enhance the smoothness of the particle's surface. In particular, the drying conditions can be selected to provide particles having a substantially smooth surface. In certain preferred embodiments, the particles have a substantially smooth surface. A person of ordinary skill in the field of this disclosure can readily assess the surface morphology of the disclosed particles using routine and standard techniques.

In other embodiments, the particle has a diameter between about 0.1 to about 1000 μm, e.g., about 0.1 to about 900, 800, 700, 600, 500, 400, 300, 200, 100, 90, 80, 70, 60, 50, 45, 40, 35, 30, 25, 20, 19, 18, 17, 16, 15, 14, 13, 12, 11, 10, 9, 8, 7, 6, 5, 4, 3, 2, 1, 0.9, 0.8, 0.7, 0.6, 0.5, 0.4, 0.3, or about 0.2 μm. In certain embodiments, the particle has a diameter between about 1 to about 100 μm, e.g., about 2, 3, 4, 5, 6, 7, 8, 9, 10, 11, 12, 13, 14, 15, 16, 17, 18, 19, 20, 25, 30, 35, 40, 45, or 50 to about 100 μm. In still other embodiments, the particle has a diameter between about 4 to about 100 μm. In certain other embodiments, the particle has a diameter between about 10 to about 100 μm. In preferred embodiments, the particle has a diameter between about 20 to about 50 μm. In certain preferred embodiments, the particle is intentionally controlled in its diameter. In some embodiments, the particles have diameters from about 0.1 to about 1000 μm, e.g., about 1 to about 400 μm, about 1 to about 200 μm, about 1 to about 100 μm, about 1 to about 50 μm, about 1 to about 25 μm, about 1 to about 10 μm, about 10 to about 100 μm, about 50 to about 100 μm, about 50 to about 75 μm, or about 75 to about 100 μm. In other embodiments, the particles have diameters from about 1 to about 100 μm, e.g., from about 4 to about 100 μm, from about 10 to about 100 μm, or from about 20 to about 50 μm.

In certain embodiments, the particle has a diameter between about 0.1 to about 100 μm. In certain other embodiments, the particle has a diameter between about 0.5 to about 50 μm. In still other embodiments, the particle has a diameter between about 20 to about 50 μm. In certain preferred embodiments, the particle has a diameter between about 1 to about 40 μm. In preferred embodiments, the particle has a diameter between about 2 to about 15 μm.

In some embodiments, the particle has a surfactant content of less than about 10% by mass, e.g., less than about 9, 8, 7, 6, 5, 4, 3, 2, 1, 0.9, 0.8, 0.7, 0.6, 0.5, 0.4, 0.3, 0.2, 0.1, 0.09, 0.08, 0.07, 0.06, 0.05, 0.04, 0.03, 0.02, 0.01, 0.009, 0.008, 0.007, 0.006, 0.005, 0.004, 0.003, 0.002, 0.001% by mass. In other embodiments, the particle has a surfactant content of less than about 5% by mass. In certain embodiments, the particle has a surfactant content of less than about 3% by mass. In still other embodiments, the particle has a surfactant content of less than about 0.1% by mass. In certain other embodiments, the particle has a surfactant content of less than about 0.01% by mass. In some embodiments, the particle has a surfactant content of less than about 0.001% by mass. In preferred embodiments, the particle has a surfactant content of less than about 1% by mass. In certain preferred embodiments, the particle is substantially free from any surfactant content.

In other embodiments, the surfactant content of the particles is from 0 to 10 wt %, e.g., from 0 to 5 wt %, from 0 to 3 wt %, from 0 to 2 wt %, from 0 to 1 wt %, from 0 to 0.5 wt %, from 0 to 0.2 wt %, from 0 to 0.1 wt %, from 0 to 0.01 wt %, or from 0 to 0.001 wt %. Exemplary methods of measuring the surfactant content include reconstitution of the particles in an appropriate medium, e.g., deionized water, and subsequent analysis of the reconstituted solution through liquid chromatography. The chromatographic technique may include the use of a charged aerosol detector (CAD) or an evaporative light scattering detector (ELSD).

In some embodiments, the surfactant is polysorbate, magnesium stearate, sodium dodecyl sulfate, TRITON™ N-101, glycerin, polyoxyethylated castor oil, docusate, sodium stearate, decyl glucoside, nonoxynol-9, cetyltrimethylammonium bromide, sodium bis(2-ethylhexyl) sulfosuccinate, sodium laureth sulfate, lecithin, or a combination thereof. In some embodiments, the surfactant includes, but is not limited to: (i) cationic surfactants such as; cetyltrimethylammonium chloride, hexadecyltrimethylammonium chloride, benzalkonium chloride, benzethonium chloride, dioctadecyldimethylammonium bromide; (ii) anionic surfactants such as magnesium stearate, sodium dodecyl sulfate, dioctyl sodium sulfosuccinate, sodium myreth sulfate, perfluorooctanesulfonate, alkyl ether phosphates; (iii) non-ionic surfactants such as alkylphenol ethoxylates (TRITONX™-100), fatty alcohol ethoxylates (octaethylene glycol monododecyl ether, cocamide diethanolamine, poloxamers, glycerolmonostearate, fatty acid esters of sorbitol (sorbitan monolaurate, Tween 80, Tween 20; and (iv) zwitterionic surfactants such as cocamidopropyl hydroxysultaine, and 3-[(3-Cholamidopropyl)dimethylammonio]-1-propanesulfonate (CHAPS). In other embodiments, the surfactant is polysorbate, magnesium stearate, sodium dodecyl sulfate, TRITON™ N-101, glycerin, polyoxyethylated castor oil, docusate, sodium stearate, decyl glucoside, nonoxynol-9, cetyltrimethylammonium bromide, sodium bis(2-ethylhexyl) sulfosuccinate, lecithin, sorbitan ester, or a combination thereof. In certain embodiments, the surfactant is polysorbate, docusate or lecithin. In preferred embodiments, the surfactant is polysorbate 20, polysorbate 60, or polysorbate 80. In certain preferred embodiments, the surfactant is polysorbate 20 or polysorbate 80. In certain other embodiments, the fatty acid ester of sorbitol is a sorbitan ester, e.g., span 20, span 40, span 60, or span 80. In still other embodiments, the surfactant is an ionic surfactant.

In other embodiments, the particles exhibit a skeletal density from about 1.00 to about 6.00 $g/cm^3$, e.g., from about 1.00 to about 5.00 $g/cm^3$, from about 1.00 to about 3.00 $g/cm^3$, from about 1.00 to about 2.00 $g/cm^3$, from about 1.00 to about 1.50 $g/cm^3$, from about 1.30 to about 1.50 $g/cm^3$, from about 1.32 to about 1.50 $g/cm^3$, or from about 1.10 to about 1.40 $g/cm^3$. In some embodiments, the particles exhibit a skeletal density from about 0.10 to about 5.00 $g/cm^3$, e.g., from about 0.10 to about 2.50 $g/cm^3$, from about 0.10 to about 1.40 $g/cm^3$, from about 0.50 to about 1.40 $g/cm^3$, or from about 1.00 to about 1.40 $g/cm^3$. In certain embodiments, the particle has a skeletal density of about 0.09 to about 1.60 $g/cm^3$. In still other embodiments, the particle has a skeletal density of about 1.30 to about 1.58 $g/cm^3$. In preferred embodiments, the particle has a skeletal density of about 1.32 to about 1.50 $g/cm^3$. Exemplary methods of skeletal density measurements include gas displacement pycnometry.

In certain embodiments, the particles have a skeletal density of about 1000 mg/mL to about 1500 mg/mL, about 1050 mg/mL to about 1500 mg/mL, about 1100 mg/mL to about 1500 mg/mL, about 1150 mg/mL to about 1500 mg/mL, about 1200 mg/mL to about 1500 mg/mL, about 1250 mg/mL to about 1500 mg/mL, about 1300 mg/mL to about 1500 mg/mL, about 1310 mg/mL to about 1500 mg/mL, about 1320 mg/mL to about 1500 mg/mL, about 1330 mg/mL to about 1500 mg/mL, about 1340 mg/mL to about 1500 mg/mL, about 1350 mg/mL to about 1500 mg/mL, about 1360 mg/mL to about 1500 mg/mL, about 1370 mg/mL to about 1500 mg/mL, about 1380 mg/mL to about 1500 mg/mL, about 1390 mg/mL to about 1500 mg/mL, about 1400 mg/mL to about 1500 mg/mL, about 1410 mg/mL to about 1500 mg/mL, about 1420 mg/mL to about 1500 mg/mL, about 1430 mg/mL to about 1500 mg/mL, about 1440 mg/mL to about 1500 mg/mL, about 1450 mg/mL to about 1500 mg/mL, about 1460 mg/mL to about 1500 mg/mL, about 1470 mg/mL to about 1500 mg/mL, about 1480 mg/mL to about 1500 mg/mL, or about 1490 mg/mL to about 1500 mg/mL.

In some embodiments, the particles can be characterized by a glass transition temperature of about 0° C. to about 250° C., e.g., of about 34° C. to about 200° C., of about 50° C. to about 200° C., of about 60° C. to about 200° C., of about 40 to about 160° C., of about 50 to about 110° C., of about 60 to about 100° C., or of about 75 to about 80° C. The term "glass transition" as used herein, refers to a thermodynamic transition of an amorphous material characterized by step changes in specific heat capacity and modulus. At temperatures above the glass transition temperature, molecular mobility is increased as are the rates of physical and chemical changes. Exemplary analytical methods for the determination of the glass transition temperature include differential scanning calorimetry and dynamic mobility analysis. In other embodiments, the particle has a glass transition temperature of about 40 to about 160° C. In still other embodiments, the particle has a glass transition temperature of about 50 to about 110° C. In certain embodiments, the particle has a glass transition temperature of about 60 to about 100° C. In preferred embodiments, the particle has a glass transition temperature of about 75 to about 80° C.

In certain embodiments, the particle has a glass transition temperature that is higher than about 160° C. In certain other embodiments, the particle has a glass transition temperature that is higher than about 90° C. In certain preferred embodiments, the particle has a glass transition temperature that is higher than about 50° C.

In other embodiments, the particles are heated to about ±30° C., e.g., to about ±20, ±10, ±5, ±1° C., of the glass transition temperature of the particles during drying.

In some embodiments, the particle further comprises a carbohydrate, a pH adjusting agent, a salt, a chelator, a mineral, a polymer, a surfactant, a protein stabilizer, an emulsifier, an antiseptic, an amino acid, an antioxidant, a protein, an organic solvent, a paraben, a bactericide, a fungicide, a vitamin, a preservative, a nutrient media, an oligopeptide, a biologic excipient, a chemical excipient, or a combination thereof. In certain embodiments, the particle further comprises a carbohydrate, a pH adjusting agent, a salt, a surfactant, a protein stabilizer, an emulsifier, an amino acid, or a combination thereof.

In other embodiments, the carbohydrate may be from the families of monosaccharides, disaccharides, oligosaccharides, or polysaccharides. In some embodiments, the carbohydrate is dextran, trehalose, sucrose, agarose, mannitol, lactose, sorbitol, maltose, starch, alginates, xanthan, galactomanin, agar, agarose, or a combination thereof. In certain embodiments, the carbohydrate is dextran, trehalose, sucrose, agarose, mannitol, lactose, sorbitol, maltose, hydroxypropyl beta-cyclodextrin, or a combination thereof. In preferred embodiments, the carbohydrate is trehalose, cyclodextrins, hydroxypropyl beta-cyclodextrin, or a combination thereof. Cyclodextrins are available in three different forms α, β, and γ based on the number of number of glucose monomers. The number of glucose monomers in α, β, and γcyclodextrin can be 6, 7, or 8, respectively.

In some embodiments, the pH adjusting agent is acetate, citrate, glutamate, glycinate, histidine, lactate, maleate, phosphate, succinate, tartrate, bicarbonate, aluminum hydroxide, phosphoric acid, hydrochloric acid, DL-lactic/glycolic acids, phosphorylethanolamine, tromethamine, imidazole, glyclyglycine, monosodium glutamate, sodium hydroxide, potassium hydroxide, or a combination thereof. In other embodiments, the pH adjusting agent is citrate, histidine, phosphate, succinate, sodium hydroxide, potassium hydroxide, or a combination thereof. In certain embodiments, the pH adjusting agent is hydrochloric acid or citric acid.

In other embodiments, the salt is sodium chloride, calcium chloride, potassium chloride, sodium hydroxide, stannous chloride, magnesium sulfate, sodium glucoheptonate, sodium pertechnetate, guanidine hydrochloride, potassium hydroxide, or a combination thereof. In preferred embodiments, the salt is sodium chloride.

In other embodiments, the surfactant is polysorbate, magnesium stearate, sodium dodecyl sulfate, TRITON™ N-101, glycerin, polyoxyethylated castor oil, docusate, sodium stearate, decyl glucoside, nonoxynol-9, cetyltrimethylammonium bromide, sodium bis(2-ethylhexyl) sulfosuccinate, sodium laureth sulfate, lecithin, or a combination thereof. In some embodiments, the surfactant includes, but is not limited to: (i) cationic surfactants such as; cetyltrimethylammonium chloride, hexadecyltrimethylammonium chloride, benzalkonium chloride, benzethonium chloride, dioctadecyldimethylammonium bromide; (ii) anionic surfactants such as magnesium stearate, sodium dodecyl sulfate, dioctyl sodium sulfosuccinate, sodium myreth sulfate, perfluorooctanesulfonate, alkyl ether phosphates; (iii) non-ionic surfactants such as alkylphenol ethoxylates (TRITONX™-100), fatty alcohol ethoxylates (octaethylene glycol monododecyl ether, cocamide diethanolamine, poloxamers, glycerolmonostearate, fatty acid esters of sorbitol (sorbitan monolaurate, Tween 80, Tween 20; and (iv) zwitterionic surfactants such as cocamidopropyl hydroxysultaine, and 3-[(3-Cholamidopropyl)dimethylammonio]-1-propanesulfonate (CHAPS). In certain embodiments, the surfactant is polysorbate, docusate or lecithin. In preferred embodiments, the surfactant is polysorbate 20, polysorbate 60, or polysorbate 80. In certain preferred embodiments, the surfactant is polysorbate 20 or polysorbate 80. In certain other embodiments, the fatty acid ester of sorbitol is a sorbitan ester, e.g., span 20, span 40, span 60, or span 80.

In other embodiments, the surfactant is polysorbate, magnesium stearate, sodium dodecyl sulfate, TRITON™ N-101, glycerin, polyoxyethylated castor oil, docusate, sodium stearate, decyl glucoside, nonoxynol-9, cetyltrimethylammonium bromide, sodium bis(2-ethylhexyl) sulfosuccinate, sodium laureth sulfate, lecithin, or a combination thereof. In some embodiments, the surfactant includes, but is not limited to: (i) cationic surfactants such as; cetyltrimethylammonium chloride, hexadecyltrimethylammonium chloride, benzalkonium chloride, benzethonium chloride, dioctadecyldimethylammonium bromide; (ii) anionic surfactants such as magnesium stearate, sodium dodecyl sulfate, dioctyl sodium sulfosuccinate, sodium myreth sulfate, perfluorooctanesulfonate, alkyl ether phosphates; (iii) non-ionic surfactants such as alkylphenol ethoxylates (TritonX-100), fatty alcohol ethoxylates (octaethylene glycol monododecyl ether, cocamide diethanolamine, poloxamers, glycerolmonostearate, fatty acid esters of sorbitol (sorbitan monolaurate, Tween 80, Tween 20; and (iv) zwitterionic surfactants such as cocamidopropyl hydroxysultaine, and 3-[(3-Cholamidopropyl)dimethylammonio]-1-propanesulfonate (CHAPS). In certain embodiments, the surfactant is polysorbate, docusate or lecithin. In preferred embodiments, the surfactant is polysorbate 20, polysorbate 60, or polysorbate 80. In certain preferred embodiments, the surfactant is polysorbate 20 or polysorbate 80. In certain other embodiments, the fatty acid ester of sorbitol is a sorbitan ester, e.g., span 20, span 40, span 60, or span 80.

In some embodiments, the protein stabilizer is acetyltryptophanate, caprylate, N-acetyltryptophan, trehalose, PEG 200, PEG 300, PEG 3350, PEG 8000, PEG 10000, PEG 20000, polyoxamers, polyvinylpyrrolidone, polyacrylic acids, poly(vinyl) polymers, polyesters, polyaldehydes, tert-polymers, polyamino acids, hydroxyethylstarch, N-methyl-2-pyrrolidone, sorbitol, sucrose, mannitol, or a combination thereof. In certain embodiments, the protein stabilizer is trehalose, PEG 200, PEG 300, PEG 3350, PEG 8000, PEG 10000, PEG 20000, polyoxamers, polyvinylpyrrolidone, polyacrylic acids, poly(vinyl) polymers, polyesters, polyaldehydes, tert-polymers, polyamino acids, hydroxyethylstarch, N-methyl-2-pyrrolidone, sorbitol, sucrose, mannitol, cyclodextrin, saccharides, hydroxypropyl beta-cyclodextrin, or a combination thereof. In preferred embodiments, the protein stabilizer is trehalose, cyclodextrin, hydroxypropyl beta-cyclodextrin, or a combination thereof. The stabilizers, used synonymously with the term "stabilizing agent", as described herein, can be a salt, a carbohydrate, saccharides or amino acids, preferably a carbohydrate or saccharide admitted by the authorities as a suitable additive or excipient in pharmaceutical compositions. The term "excipient" refers to an additive to a preparation or formulation, which may be useful in achieving a desired modification to the characteristics of the preparation or formulation. Such modifications include, but are not limited to, physical stability, chemical stability, and therapeutic efficacy. Exemplary excipients include, but are not limited to a carbohydrate, a pH adjusting agent, a salt, a chelator, a mineral, a polymer, a surfactant, an amino acid, an oligopeptide, a biologic excipient, a chemical excipient, an antiseptic, an antioxidant, a paraben, a bactericide, a fungicide, a vitamin, a preservative, an analgesic, and/or nutrient media.

Examples of emulsifiers suitable for use in the particles include, but are not limited to, lipophilic agents having an HLB of less than 7, such as mixed fatty acid monoglycerides; mixed fatty acid diglycerides; mixtures of fatty acid mono- and diglycerides; lipophilic polyglycerol esters; glycerol esters including glyceryl monooleate, glyceryl dioleate, glyceryl monostearate, glyceryl distearate, glyceryl monopalmitate, and glyceryl dipalmitate; glyceryl-lacto esters of fatty acids; propylene glycol esters including propylene glycol monopalmitate, propylene glycol monostearate, and propylene glycol monooleate; sorbitan ester including sorbitan monostearate, sorbitan sesquioleate; fatty acids and their soaps including stearic acid, palmitic acid, and oleic acid; and mixtures thereof glyceryl monooleate, glyceryl dioleate, glyceryl monostearate, glyceryl distearate, glyceryl monopalmitate, and glyceryl dipalmitate; glyceryl-lacto esters of fatty acids; propylene glycol esters including propylene glycol monopalmitate, propylene glycol monostearate, and propylene glycol monooleate; sorbitan ester including sorbitan monostearate, sorbitan sesquioleate; fatty acids and their soaps including stearic acid, palmitic acid, and oleic acid; or a combination thereof. In some embodiments, the emulsifier is polysorbate 80, polysorbate 60, polysorbate 20, sorbitan monooleate, ethanolamine, polyoxyl 35 castor oil, poloxyl 40 hydrogenated castor oil, carbomer 1342, a corn oil-mono-di-triglyceride, a polyoxyethylated oleic glyceride, a poloxamer, or a combination thereof. In preferred embodiments, the fatty acid ester of sorbitol is a sorbitan ester, e.g., span 20, span 40, span 60, or span 80. In certain preferred embodiments, the emulsifier is polysorbate 80, sorbitan monooleate, or a combination thereof.

In other embodiments, the antiseptic is phenol, m-cresol, benzyl alcohol, 2-phenyloxyethanol, chlorobutanol, neomycin, benzethonium chloride, gluteraldehyde, beta-propiolactone, or a combination thereof.

In certain embodiments, the amino acid is alanine, aspartic acid, cysteine, isoleucine, glutamic acid, leucine, methionine, phenylalanine, pyrrolysine, serine, selenocysteine, threonine, tryptophan, tyrosine, valine, asparagine, L-arginine, histidine, glycine, glutamine, proline, or various salts thereof (arginine hydrochloride, arginine glutamate, etc.) or a combination thereof. In preferred embodiments, the amino acid is L-arginine, histidine, proline, or a combination thereof.

In some embodiments, the antioxidant is glutathione, ascorbic acid, cysteine, N-acetyl-L-tryptophanate, tocopherol, histidine, methionine, or a combination thereof. In other embodiments, the protein is protamine, protamine sulfate, gelatin, or a combination thereof. In certain embodiments, the organic solvent is dimethyl sulfoxide, N-methyl-2-pyrrolidone, or a combination thereof. In still other embodiments, the preservative is methyl hydroxybenzoate, thimerosal, parabens, formaldehyde, castor oil, or a combination thereof. The paraben can be a parahydroxybenzoate. In some embodiments, the bactericide is benzalkonium chloride (cationic surfactants), hypochlorites, peroxides, alcohols, phenolic compounds (e.g. carbolic acid), benzyl benzoate, or a combination thereof. In preferred embodiments, the bactericide is benzyl benzoate.

In other embodiments, the fungicide is acibenzolar, 2-phenylphenol, anilazine, carvone, natamycin, potassium azide, or a combination thereof. In preferred embodiments, the fungicide is benzyl benzoate. In certain embodiments, the vitamin is thiamine, riboflavin, niacin, pantothenic acid, biotin, vitamin $B_6$, vitamin $B_{12}$, folate, niacin, ascorbic acid, calciferols, retinols, quinones, or a combination thereof. In still other embodiments, the preservative is sodium nitrate, sulfur dioxide, potassium sorbate, sodium sorbate, sodium benzoate, benzoic acid, methyl hydroxybenzoate, thimerosal, parabens, formaldehyde, castor oil, or a combination thereof. In preferred embodiments, the preservative is methyl hydroxybenzoate, thimerosal, parabens, formaldehyde, castor oil, or a combination thereof.

A number of nutrient media, preferably serum free, alone or in combination, may be used in the present disclosure, including commercially available media or other media well known in the art. Examples of such media (all without serum or having had the serum removed) include ADC-1, LPM (Bovine Serum Albumin-free), F10 (HAM), F12 (HAM), DCCM1, DCCM2, RPMI 1640, BGJ Medium (Fitton-Jackson Modification), Basal Medium Eagle (BME—with the addition of Earle's salt base), Dulbecco's Modified Eagle Medium (DMEM-without serum), Glasgow Modification Eagle Medium (GMEM), Leibovitz L-15 Medium, McCoy's 5 A Medium, Medium M199 (M199E—with Earle's salt base), Medium M199 (M199H—with Hank's salt base), Minimum Essential Medium Eagle (MEM-E—with Earle's salt base), Minimum Essential Medium Eagle (MEM-H—with Hank's salt base) and Minimum Essential Medium Eagle (MEM-NAA—with non-essential amino acids), among numerous others. In addition, serum-containing nutrient media may also be used in compositions according to the present disclosure, but the use of serum-containing media is less preferred because of the possibility that the serum may be contaminated with microbial agents and because the patient may develop immunological reactions to certain antigenic components contained in the serum.

In some embodiments, the oligopeptide is trileucine. In other embodiments, the biologic excipient are nucleic acids, oligonucleotides, antibodies or fragment thereof, amino acids, polyamino acids, peptides, proteins, cells, bacteria, gene therapeutics, genome engineering therapeutics, epigenome engineering therapeutics, hormones, nucleoproteins, glycoproteins, lipoproteins, exosomes, outer membrane vesicles, vaccines, viruses, bacteriophages, organelles, nutrient media, or a combination thereof. In certain embodiments, the chemical excipient are chemical drugs, contrast agents, dyes, magnetic particles, polymer beads, metal nanoparticles, metal microparticles, quantum dots, antioxidants, antibiotic agents, steroids, analgesics, local anesthetics, antiinflammatory agents, parabens, anti-microbial agents, chemotherapeutic agents, vitamins, minerals, bactericides, antiseptics, or a combination thereof.

In other embodiments, the particle has less than 20% aggregation or less than 20% fragmentation of the therapeutic biologic, e.g., less than about 19, 18, 17, 16, 15, 14, 13, 12, 10, 9, 8, 7, 6, 5, 4, 3, 2, 1.9, 1.8, 1.7, 1.6, 1.5, 1.4, 1.3, 1.2, 1.1, 1, 0.9, 0.8, 0.7, 0.6, 0.5, 0.4, 0.3, 0.2, or 0.1%. In some embodiments, the particle has less than 10% aggregation or less than 10% fragmentation of the therapeutic biologic, e.g., less than about 9, 8, 7, 6, 5, 4, 3, 2, 1.9, 1.8, 1.7, 1.6, 1.5, 1.4, 1.3, 1.2, 1.1, 1, 0.9, 0.8, 0.7, 0.6, 0.5, 0.4, 0.3, 0.2, or 0.1%. In certain embodiments, the particle has about 3% to about 1% aggregation of the therapeutic biologic. In certain other embodiments, the particle has about 1% to about 0.5% aggregation of the therapeutic biologic. In preferred embodiments, the particle is substantially free from any aggregation of the therapeutic biologic. In still other embodiments, the particle has less than about 1% fragmentation of the therapeutic biologic. In certain preferred embodiments, the particle is substantially free from any fragmentation of the therapeutic biologic. Suitable methods for measuring aggregation and fragmentation of a biologic can be accomplished by using size-exclusion chromatography (SEC).

In some embodiments, the process of particle formation provides less than a 50% change in charge variants in the population of a diagnostic or therapeutic agent, e.g., an antibody or an antibody fragment, (e.g., less than 40, 30, 20, 10, 8, 5, 4, 3, or 1%) as compared to the therapeutic or diagnostic agent prior to particle formation. Charge variants may be acidic, basic, or neutral, and the variation may be caused post-translation modifications at terminal amino acids, such as asparagine deamidation or lysine glycation. For example, charge variants include the loss of a positive charge by the loss of a C-terminal lysine residue, covalent bonding of the amine portions of two lysine residues by reducing sugars, or the conversion of an N-terminal amine to a neutral amide by the cyclization of N-terminal glutamines. Negative charges on proteins, e.g., antibodies, can appear by the conversion of asparagine residues to aspartic acid and/or isoaspartic residues via a deamidation reaction. Exemplary methods of measuring charge variants include cation exchange chromatography (CIEX), where the variants are quantified by dividing the area under the peak corresponding to the variant, e.g., acidic, basic, or neutral population by the cumulative area contained beneath all peaks in the sample spectrum. Changes in charge variant population percentage between two samples, e.g., Sample A and Sample B, are computed as the numerical difference in the respective population variant percentages, i.e., by subtracting the specific variant, e.g., acidic, percentage of Sample B from the specific variant, e.g., acidic, percentage of Sample A, or vice versa. In certain embodiments, the analysis may be extended similarly for all variants within a population.

In certain embodiments, the particle has less than about 50% change in charge variants of the therapeutic biologic, e.g., less than about 45, 40, 35, 30, 25, 20, 15, 10, 9, 8, 7, 6, 5, 4, 3, 2, 1, 0.5, 0.1%, compared to the starting biologic prior to particle formation. In preferred embodiments, the particle is substantially free from any change in charge variants of the therapeutic biologic compared to the starting biologic prior to particle formation. Suitable methods for measuring a change in charge variants of a biologic can be accomplished by using cation exchange chromatography (CIEX).

In other embodiments, the residual moisture or solvent content of the dry component is less than about 7% by weight, e.g., less than about 6, 5, 4, 3, 2, 1.9, 1.8, 1.7, 1.6, 1.5, 1.4, 1.3, 1.2, 1.1, 1, 0.9, 0.8, 0.7, 0.6, 0.5, 0.4, 0.3, 0.2, or 0.1% by weight. In some embodiments, the particle has less than about 7% residual moisture by weight. In still other embodiments, the particle has less than about 5% residual moisture by weight. In certain embodiments, the particle has less than about 3% residual moisture by weight. In preferred embodiments, the particle has less than about 1% residual moisture by weight.

In some embodiments, the particle has about 1% to about 7% residual moisture by weight. In still other embodiments, the particle has about 1% to about 5% residual moisture by weight. In certain embodiments, the particle has about 1% to about 3% residual moisture by weight. In preferred embodiments, the particle is substantially free from any residual moisture by weight.

Exemplary methods for the measurement of moisture content include chemical titration methods, e.g., Karl Fischer titration involving a vacuum oven. A variety of solvents, including water, may also be measured using weight loss methods involving thermal excitation. Exemplary methods include Thermogravimetric Analysis with Infrared Spectroscopy (TGA-IR).

In some embodiments, the particle has greater than about 60% therapeutic biologic by weight, e.g., greater than about 65, 70, 75, 80, 85, 86, 87, 88, 89, 90, 91, 92, 93, 94, 95, 96, 97, 98, 99, 99.1, 99.2, 99.3, 99.4, 99.5, 99.6, 99.7, 99.8, 99.9% therapeutic biologic by weight. In other embodiments, the particle has greater than about 90% therapeutic biologic by weight. In certain embodiments, the particle has greater than about 95% therapeutic biologic by weight. In still other embodiments, the particle has greater than about 98% therapeutic biologic by weight. In preferred embodiments, the particle has greater than about 98% therapeutic biologic by weight. In certain preferred embodiments, the particle has greater than about 99% therapeutic biologic by weight.

The particles comprising at least one therapeutic biologic described herein, can be prepared in a number of ways, as well as any methods of forming the particles disclosed in, for example, PCT/US2017/063150, PCT/US2018/043774, PCT/US2019/033875, and U.S. 62/799,696, each of which is hereby incorporated by reference in its entirety.

As used herein, the term "dispersity index" (DI) is a parameter characterizing the degree of non-uniformity of a size distribution of particles. The term "polydispersity index" (PDI) is a parameter characterizing the width of the particle size distribution within a given sample. The numerical value of PDI ranges from 0.0 (for a perfectly uniform sample with respect to the particle size) to 1.0 and greater (for a highly polydisperse sample with multiple particle size populations). As the value decreases, the particles have more narrowly distributed particle sizes, and greater homogeneity of the plurality of particles. Particle diameter may be collected using microscopy (FLOWCAM™, SEM) as well as laser diffraction.

In some embodiments, the polydispersity index (PDI) calculation used for Dynamic Light Scattering (DLS) measurement is: Polydispersity index from DLS=(the square of standard deviation)/(the square of mean diameter). In other embodiments, the PDI calculation can be: the statistical characteristics of particles namely number-average diameter (Dn), weight-average diameter (Dw), and polydispersity index (PDI), wherein the calculation can be accomplished using the following equations, where di represents the diameters of the microspheres, and n is the number of particles:

$$D_n = \frac{\sum d_i}{M} \tag{1}$$

$$D_w = \frac{\sum (d_i)^4}{\sum (d_i)^3} \tag{2}$$

$$PDI = \frac{D_w}{D_n} \tag{3}$$

In still other embodiments, polydispersity can be represented through coefficient of variation, which is calculated as: Coefficient of variation (CV=(Standard deviation×100)/mean).

In certain embodiments, the particles may include one or more agents, e.g., therapeutic biologic. In other embodiments, the particles can have diameters from about 0.1 to about 1000 μm, e.g., about 0.1 to about 90 μm, about 90 to about 230 μm, or about 0.1 to about 1 μm. In still other embodiments, the particles can have a size dispersity from about 0 to about 0.9, e.g., from about 0 to about 0.7, from about 0 to about 0.5, or from about 0 to about 0.2. Methods of measuring the particle size and distribution include imaging flow cytometry and image analysis of scanning electron micrographs of the particles in which an average spherical radius or diameter can be calculated on the basis of the cross-sectional areas of the particles projected onto the plane of the image. In certain other embodiments of the disclosure, the particle may have a diameter between about 0.1 to about 1000 μm, a skeletal density of about 1.00 to about 6.00 g/cm3, and a glass transition temperature of about 0 to about 250° C.

While each of the elements of the present disclosure is described herein, as containing multiple embodiments, it should be understood that, unless indicated otherwise, each of the embodiments of a given element of the present disclosure is capable of being used with each of the embodiments of the other elements of the present disclosure and each such use is intended to form a distinct embodiment of the present disclosure.

It will be understood by one of ordinary skill in the relevant arts that other suitable modifications and adaptations to the compositions and methods described herein are readily apparent from the description of the disclosure contained herein, in view of information known to the ordinarily skilled artisan, and may be made without departing from the scope of the disclosure or any embodiment thereof.

Pharmaceutical Compositions

In certain embodiments, the disclosure relates to a composition comprising a plurality of particles comprising any one of the aforementioned agents suspended in a low viscosity liquid. In certain preferred embodiments, the disclosure relates to a pharmaceutical composition comprising a plurality of particles comprising any one of the aforementioned therapeutic biologics suspended in a low viscosity pharmaceutically acceptable liquid.

In preferred embodiments according to the disclosure as described herein, the composition comprising a plurality of particles has improved stability of the therapeutic biologic compared to an aqueous composition comprising the therapeutic biologic in monomeric form.

In other aspects, the disclosure relates to composition comprising a plurality of particles comprising an agent suspended in a liquid, wherein the particles comprise less than about 25% internal void spaces and the circularity of the particles are from about 0.10 to about 1.00. As disclosed herein, the agent may be a therapeutic or diagnostic agent. In certain embodiments, the therapeutic agent has an activity per unit of about 0.5 to about 1.0. In preferred embodiments, the therapeutic biologic has an activity per unit of about 0.5 to about 1.0.

In some embodiments, the disclosure provides a composition containing a plurality of particles that include an agent, e.g., a therapeutic or diagnostic agent, where the storage stability of the agent in the particles is improved with respect to the storage stability of the agent in the first liquid. In other embodiments, storage conditions are defined by time (e.g., more than about 2 years, more than about 1 year, more than about 6 months, more than about 3 months, more than about 1 month, or more than about 1 week) and temperature (e.g., about −80° C. to about 100° C., about −80° C. to about 60° C., about −20° C. to about 60° C., about 4 to about 60° C.), among potentially other variables. In still other embodiments, the storage time is about 3 days, about 7 days, about 30 days, about 90 days, about 180 days, about 1 year, or about 2 years. In certain other embodiments, this temperature is about −80° C., about −40° C., about −20° C., about 4° C., about 25° C., about 40° C., or about 40 to about 60° C. In certain embodiments, the storage stability of the therapeutic or diagnostic agent in the particles is improved with respect to the storage stability of a first liquid of the therapeutic or diagnostic agent.

In other embodiments, the particles have less than about 25% internal void spaces, e.g., less than about 24, 20, 15, 10, 9, 8, 7, 6, 5, 4, 3, 2, 1, 0.5, or 0.1% internal void spaces. In certain embodiments, the particles may include less than 10% internal void spaces, less than 5% internal void spaces, less than 1% internal void spaces, less than 0.1% internal void spaces, or less than 0.01% internal void spaces. In preferred embodiments, the particles are substantially free from any internal void spaces. In other embodiments, the particles may exhibit a porosity from about 0 to about 50%, e.g., from about 0 to about 10%, from about 0 to about 5%, from about 0 to about 1%, from about 0 to about 0.5%, from about 0 to about 0.1%, or from about 0 to about 0.01%. Exemplary pore size measurements include scanning electron microscopy (SEM), transmission electron microscopy (TEM), and confocal laser scanning microscopy analysis. A gallium focused ion beam (FIB) was used to cut one of the particles in half to reveal a cross-section of the particle interior. The specific surface area of porous micro- and nanospheres may also be investigated by nitrogen adsorption/desorption analysis and a Brunauer-Emmett-Teller adsorption model. In certain embodiments where the pore sizes are sufficiently large, mercury-intrusion porosimetry may be employed.

In some embodiments, the circularity of the particles are at least about 10%, e.g., at least about 20, 30, 40, 50, 55, 60, 65, 70, 75, 80, 85, 90, 91, 92, 93, 94, 95, 96, 97, 98, 99, or about 100%. In other embodiments, the circularity of the particles are at least about 88%. In certain embodiments, the circularity of the particles are at least about 90%. In still other embodiments, the circularity of the particles are at least about 93%. In preferred embodiments, the circularity of the particles are at least about 97%.

In other embodiments, the circularity of the particles are from about 0.10 to about 1.00, e.g., from about 0.20, 0.30, 0.40, 0.50. 0.60, 0.70, 0.75, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, or 0.99 to about 1.00. In certain embodiments, the circularity of the particles are from about 0.88 to about 1.00. In still other embodiments, the circularity of the particles are from about 0.90 to about 1.00. In certain other embodiments, the circularity of the particles are from about 0.93 to about 1.00. In preferred embodiments, the circularity of the particles are rom about 0.97 to about 1.00.

In certain embodiments, the circularity of the particles may range from at least about 0.10 to about 1.00, e.g., at least about 0.88, about 0.90, about 0.93, or about 0.97 to about 1.00.

In some embodiments, the sphericity of the particles are at least about 50%, e.g., at least about 55, 60, 65, 70, 75, 80, 85, 90, 91, 92, 93, 94, 95, 96, 97, 98, 99, or about 100%. In other embodiments, the sphericity of the particles are from about 0.10 to about 1.00, e.g., from about 0.20, 0.30, 0.40, 0.50. 0.60, 0.70, 0.75, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, or 0.99 to about 1.00. In preferred embodiments, the sphericity of the particles are about 1.00.

In certain embodiments, the sphericity of the particles may range from about 0.10 to about 1.00, e.g., at least about 0.20, about 0.40, about 0.60, or about 0.80 to about 1.00.

In preferred embodiments, the particles have a substantially smooth surface.

In some embodiments, the particles have a diameter between about 0.1 to about 1000 µm, e.g., about 0.1 to about 900, 800, 700, 600, 500, 400, 300, 200, 100, 90, 80, 70, 60, 50, 45, 40, 35, 30, 25, 20, 19, 18, 17, 16, 15, 14, 13, 12, 11, 10, 9, 8, 7, 6, 5, 4, 3, 2, 1, 0.9, 0.8, 0.7, 0.6, 0.5, 0.4, 0.3, or about 0.2 µm. In certain embodiments, the particles have a diameter between about 1 to about 100 µm, e.g., about 2, 3, 4, 5, 6, 7, 8, 9, 10, 11, 12, 13, 14, 15, 16, 17, 18, 19, 20, 25, 30, 35, 40, 45, or 50 to about 100 µm. In still other embodiments, the particles have a diameter between about 4 to about 100 µm. In certain other embodiments, the particles have a diameter between about 10 to about 100 µm. In preferred embodiments, the particles have a diameter between about 20 to about 50 µm. In certain preferred embodiments, the particles are intentionally controlled in its diameter. In some embodiments, the particles have diameters from about 0.1 to about 1000 µm, e.g., about 1 to about 400 µm, about 1 to about 200 µm, about 1 to about 100 µm, about 1 to about 50 µm, about 1 to about 25 µm, about 1 to about 10 µm, about 10 to about 100 µm, about 50 to about 100 µm, about 50 to about 75 µm, or about 75 to about 100 µm. In other embodiments, the particles have diameters from about 1 to about 100 µm, e.g., from about 4 to about 100 µm, from about 10 to about 100 µm, or from about 20 to about 50 µm.

In certain embodiments, the particles have a diameter between about 0.1 to about 100 µm. In certain other embodiments, the particles have a diameter between about 0.5 to about 50 µm. In still other embodiments, the particles have a diameter between about 20 to about 50 µm. In certain preferred embodiments, the particles have a diameter between about 1 to about 40 µm. In preferred embodiments, the particles have a diameter between about 2 to about 15 µm.

In some embodiments, the particles have a surfactant content of less than about 10% by mass, e.g., less than about 9, 8, 7, 6, 5, 4, 3, 2, 1, 0.9, 0.8, 0.7, 0.6, 0.5, 0.4, 0.3, 0.2, 0.1, 0.09, 0.08, 0.07, 0.06, 0.05, 0.04, 0.03, 0.02, 0.01, 0.009, 0.008, 0.007, 0.006, 0.005, 0.004, 0.003, 0.002, 0.001% by mass. In other embodiments, the particles have a surfactant content of less than about 5% by mass. In certain embodiments, the particles have a surfactant content of less than about 3% by mass. In still other embodiments, the particles have a surfactant content of less than about 0.1% by mass. In certain other embodiments, the particles have a surfactant content of less than about 0.01% by mass. In some embodiments, the particles have a surfactant content of less than about 0.001% by mass. In preferred embodiments, the particles have a surfactant content of less than about 1% by mass. In certain preferred embodiments, the particles are substantially free from any surfactant content.

In other embodiments, the surfactant content of the particles are from 0 to 10 wt %, e.g., from 0 to 5 wt %, from 0 to 3 wt %, from 0 to 2 wt %, from 0 to 1 wt %, from 0 to 0.5 wt %, from 0 to 0.2 wt %, from 0 to 0.1 wt %, from 0 to 0.01 wt %, or from 0 to 0.001 wt %.

In some embodiments, the surfactant is polysorbate, magnesium stearate, sodium dodecyl sulfate, TRITON™ N-101, glycerin, polyoxyethylated castor oil, docusate, sodium stearate, decyl glucoside, nonoxynol-9, cetyltrimethylammonium bromide, sodium bis(2-ethylhexyl) sulfosuccinate, lecithin, sorbitan ester, or a combination thereof. In certain embodiments, the surfactant is polysorbate, docusate or lecithin. In preferred embodiments, the surfactant is polysorbate 20, polysorbate 60, or polysorbate 80. In certain preferred embodiments, the surfactant is polysorbate 20 or polysorbate 80. In certain other embodiments, the fatty acid ester of sorbitol is a sorbitan ester, e.g., span 20, span 40, span 60, or span 80. In still other embodiments, the surfactant is an ionic surfactant.

In other embodiments, the particles exhibit a skeletal density from about 1.00 to about 6.00 $g/cm^3$, e.g., from about 1.00 to about 5.00 $g/cm^3$, from about 1.00 to about 3.00 $g/cm^3$, from about 1.00 to about 2.00 $g/cm^3$, from about 1.00 to about 1.50 $g/cm^3$, from about 1.30 to about 1.50 $g/cm^3$, from about 1.32 to about 1.50 $g/cm^3$, or from about 1.10 to about 1.40 $g/cm^3$. In some embodiments, the particles exhibit a skeletal density from about 0.10 to about 5.00 $g/cm^3$, e.g., from about 0.10 to about 2.50 $g/cm^3$, from about 0.10 to about 1.40 $g/cm^3$, from about 0.50 to about 1.40 $g/cm^3$, or from about 1.00 to about 1.40 $g/cm^3$. In certain embodiments, the particles have a skeletal density of about 0.09 to about 1.60 $g/cm^3$. In still other embodiments, the particles have a skeletal density of about 1.30 to about 1.58 $g/cm^3$. In preferred embodiments, the particles have a skeletal density of about 1.32 to about 1.50 $g/cm^3$.

In certain embodiments, the particles have a skeletal density of about 1000 mg/mL to about 1500 mg/mL, about 1050 mg/mL to about 1500 mg/mL, about 1100 mg/mL to about 1500 mg/mL, about 1150 mg/mL to about 1500 mg/mL, about 1200 mg/mL to about 1500 mg/mL, about 1250 mg/mL to about 1500 mg/mL, about 1300 mg/mL to about 1500 mg/mL, about 1310 mg/mL to about 1500 mg/mL, about 1320 mg/mL to about 1500 mg/mL, about 1330 mg/mL to about 1500 mg/mL, about 1340 mg/mL to about 1500 mg/mL, about 1350 mg/mL to about 1500 mg/mL, about 1360 mg/mL to about 1500 mg/mL, about 1370 mg/mL to about 1500 mg/mL, about 1380 mg/mL to about 1500 mg/mL, about 1390 mg/mL to about 1500 mg/mL, about 1400 mg/mL to about 1500 mg/mL, about 1410 mg/mL to about 1500 mg/mL, about 1420 mg/mL to about 1500 mg/mL, about 1430 mg/mL to about 1500 mg/mL, about 1440 mg/mL to about 1500 mg/mL, about 1450 mg/mL to about 1500 mg/mL, about 1460 mg/mL to about 1500 mg/mL, about 1470 mg/mL to about 1500 mg/mL, about 1480 mg/mL to about 1500 mg/mL, or about 1490 mg/mL to about 1500 mg/mL.

In other embodiments, the particles can be characterized by a glass transition temperature of about 0° C. to about 250° C., e.g., of about 34° C. to about 200° C., of about 50° C. to about 200° C., of about 60° C. to about 200° C., of about 40 to about 160° C., of about 50 to about 110° C., of about 60 to about 100° C., or of about 75 to about 80° C. In other embodiments, the particles have a glass transition temperature of about 40 to about 160° C. In still other embodiments, the particles have a glass transition temperature of about 50 to about 110° C. In certain embodiments, the particles have a glass transition temperature of about 60 to about 100° C. In preferred embodiments, the particles have a glass transition temperature of about 75 to about 80° C. In still other embodiments, the particles are heated to about ±30° C., e.g., to about ±20, ±10, ±5, ±1° C., of the glass transition temperature of the particles during drying.

In certain embodiments, the particles have a glass transition temperature that is higher than about 160° C. In certain other embodiments, the particles have a glass transition temperature that is higher than about 90° C. In certain preferred embodiments, the particles have a glass transition temperature that is higher than about 50° C.

In some embodiments, the particles further comprise a carbohydrate, a pH adjusting agent, a salt, a chelator, a mineral, a polymer, a surfactant, a protein stabilizer, an emulsifier, an antiseptic, an amino acid, an antioxidant, a protein, an organic solvent, a paraben, a bactericide, a fungicide, a vitamin, a preservative, a nutrient media, an oligopeptide, a biologic excipient, a chemical excipient, or a combination thereof. In certain embodiments, the particle further comprises a carbohydrate, a pH adjusting agent, a salt, a surfactant, a protein stabilizer, an emulsifier, an amino acid, or a combination thereof.

In certain embodiments, the liquid is non-aqueous or aqueous. In other embodiments, the liquid is non-aqueous. In still other embodiments, the liquid is aqueous.

In other embodiments, the non-aqueous liquid is an organic solvent or an ionic liquid. In some embodiments, the organic solvent is benzyl benzoate, coconut oil, cottonseed oil, fish oil, grape seed oil, hazelnut oil, hydrogenated vegetable oils, olive oil, palm seed oil, peanut oil, peppermint oil, safflower oil, sesame oil, soybean oil, sunflower oil, walnut oil, acetone, ethyl acetate, ethyl lactate, dimethylacetamide, dimethyl isosorbide, dimethyl sulfoxide, glycofurol, diglyme, methyl tert-butyl ether, N-methyl pyrrolidone, perfluorodecalin, polyethylene glycol, 2-pyrrolidone, tetrahydrofurfuryl alcohol, trigylcerides, triglycerides of the fractionated plant fatty acids C8 and C10, propylene glycol diesters of saturated plant fatty acids C8 and C10, ethyl oleate, ethyl caprate, dibutyl adipate, fatty acid esters, hexanoic acid, octanoic acid, triacetin, diethyl glycol monoether, gamma-butyrolactone, eugenol, clove bud oil, citral, limonene, polyoxyl 40 hydrogenated castor oil, polyoxyl 35 castor oil, simple alcohols such as ethanol, octanol, hexanol, decanol, propanol, and butanol, gamma-butyrolactone, tocopherol, octa-fluoropropane, (perfluorohexyl)octane, n-acetyltryptophan, ethyl laurate, methyl caprylate, methyl caprate, methyl myristate, methyl oleate, methyl linoleate, dimethyl adipate, dibutyl suberate, diethyl sebacate, ethyl macadamiate, trimethylolpropane triisosterate, isopropyl laurate, isopropyl myristate, diethyl succinate, polysorbate esters, ethanol amine, propanoic acid, citral, anisole, anethol, benzaldehyde, linalool, caprolactone, phenol, thioglycerol, dimethylacetamide, diethylene glycol monoethyl ether, propylene carbonate, solketal, isosorbide dimethyl ether, ethyl formate, and ethyl hexyl acetate, or a combination thereof. In preferred embodiments, the organic solvent is ethyl oleate, ethyl laureate, ethyl macadamiate, ethyl caprate, diethyl succinate, diethylene glycol monoethyl ether, propylene carbonate, or a combination thereof. In certain preferred embodiments, the organic solvent is ethyl oleate. Exemplary ionic liquids of the disclosure contain (i) cations such as pyridinium, pyridazinium, pyrimidinium, pyrazinium, imidazolium, pyrazolium, thiazolium, oxazolium, triazolium, ammonium, sulfonium; and (ii) anions such as halides, sulfates, sulfonates, carbonates, phosphates, bicarbonates, nitrates, acetates, $PF_6$—, $BF_4$—, triflate, nonaflate, bis(triflyl)amide, trifluoroacetate, heptafluorobutanoate, haloaluminate, or a combination thereof. In certain embodiments, the ionic liquid comprises pyridinium, pyridazinium, pyrimidinium, pyrazinium, imidazolium, pyrazolium, thiazolium, oxazolium, triazolium, ammonium, sulfonium, halides, sulfates, sulfonates, carbonates, phosphates, bicarbonates, nitrates, acetates, $PF_6$—, $BF_4$—, triflate, nonaflate, bis(trifyl)amide, trifluoroacetate, heptafluorobutanoate, haloaluminate, or a combination thereof.

In certain embodiments, the organic solvent is acetonitrile, chlorobenzene, chloroform, cyclohexane, cumene, 1,2-dichloroethene, dichloromethane, 1,2-dimethoxyethane, N,N-dimethylacetamide, N,N-dimethylformamide, 1,4-dioxane, 2-ethoxyethanol, ethyleneglycol, formamide, hexane, methanol, 2-methoxyethanol, methylbutyl ketone, methylcyclohexane, methylisobutylketone, N-methylpyrrolidone, nitromethane, pyridine, sulfolane, tetrahydrofuran, tetralin, toluene, 1,1,2-trichloroethene, xylene, acetic acid, acetone, anisole, 1-butanol, 2-butanol, butylacetate, tert-butylmethyl ether, dimethyl sulfoxide, ethanol, ethylacetate, ethyl ether, ethyl formate, formic acid, heptane, isobutylacetate, isopropylacetate, methylacetate, 3-methyl-1-butanol, methylethyl ketone, 2-methyl-1-propanol, pentane, 1-pentanol, 1-propanol, 2-propanol, propylacetate, triethylamine, 1,1-diethoxypropane, 1,1-dimethoxymethane, 2,2-dimethoxypropane, isooctane, isopropyl ether, methylisopropyl ketone, methyltetrahydrofuran, petroleum ether, trichloroacetic acid, trifluoroacetic acid, decanol, 2-ethylhexylacetate, amylacetate, or a combination thereof.

In some embodiments, the aqueous liquid is water, 0.9% saline, lactated Ringer's solution, buffers, dextrose 5%, or a combination thereof. In preferred embodiments, the aqueous liquid is water. Exemplary buffers of the disclosure may include acetate buffer, histidine buffer, succinate buffer, HEPES buffer, tris buffer, carbonate buffer, citrate buffer, phosphate buffer, phosphate-buffered saline, glycine buffer, barbital buffer, cacodylate buffer, ammonium formate buffer, urea solution, or a combination thereof.

The phrase "pharmaceutically acceptable" is employed herein, to refer to those therapeutic biologics, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The term "pharmaceutically acceptable" can refer to particles and compositions comprising a plurality of particles that do not produce an adverse, allergic, or other untoward reaction when administered to a mammal, such as a human, as appropriate. The preparation of a pharmaceutical composition comprising an antibody or additional active ingredient will be known to those of skill in the art in light of the present disclosure. Moreover, for mammal (e.g., human) administration, it will be understood that preparations should meet sterility, pyrogenicity, general safety, and purity standards as required by FDA Office of Biological Standards.

The phrase "pharmaceutically acceptable liquid" includes any and all aqueous solvents (e.g., water, alcoholic/aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters. In certain preferred embodiments, the plurality of particles is suspended in a pharmaceutically acceptable liquid. In preferred embodiments, the liquid is a pharmaceutically acceptable liquid.

A pharmaceutical composition (formulation) as disclosed herein, can be administered to a subject by any of a number of routes of administration including, for example, parenterally (including intramuscularly, intravenously, subcutaneously or intrathecally as, for example, a sterile solution or suspension); intraperitoneally; or subcutaneously. In certain embodiments, a composition may be simply suspended in a non-aqueous liquid carrier. Details of appropriate routes of administration and compositions suitable for same can be found in, for example, U.S. Pat. Nos. 6,110,973; 5,763,493; 5,731,000; 5,541,231; 5,427,798; 5,358,970 and 4,172,896, as well as in patents cited therein. The term "suspension formulation" refers to a liquid formulation including solid particles disposed within a carrier liquid in which they are not soluble on an appropriate timescale. The particles may settle over time, i.e., the physical stability of the suspension is not indefinite, but may be re-suspended using a form of agitation or excitation.

A "therapeutic amount" refers to an amount of a therapeutic or diagnostic agent required to produce the desired effect. As used herein, the terms "treat," "treated," and "treating" mean both therapeutic treatment and prophylactic or preventative measures wherein the object is to prevent or slow down (lessen) an undesired physiological condition, disorder, or disease, or obtain beneficial or desired clinical results. Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total), whether detectable or undetectable; an amelioration of at least one measurable physical parameter, not necessarily discernible by the patient; or enhancement or improvement of condition, disorder, or disease. Treatment includes eliciting a clinically significant response without excessive levels of side effects. Treatment also includes prolonging survival as compared to expected survival if not receiving treatment.

In certain embodiments, the liquid further comprises a carbohydrate, a pH adjusting agent, a salt, a chelator, a mineral, a polymer, a surfactant, a protein stabilizer, an emulsifier, an antiseptic, an amino acid, an antioxidant, a protein, an organic solvent, a paraben, a bactericide, a fungicide, a vitamin, a preservative, a nutrient media, analgesic, or a combination thereof. In preferred embodiments, the liquid further comprises a carbohydrate, a pH adjusting agent, a salt, a surfactant, a protein stabilizer, an emulsifier, an amino acid, or a combination thereof. In certain preferred embodiments, the aqueous liquid further comprises a carbohydrate, a pH adjusting agent, a salt, a surfactant, a protein stabilizer, an emulsifier, an amino acid, or a combination thereof.

In other embodiments, the carbohydrate may be from the families of monosaccharides, disaccharides, oligosaccharides, or polysaccharides. In some embodiments, the carbohydrate is dextran, trehalose, sucrose, agarose, mannitol, lactose, sorbitol, maltose, starch, alginates, xanthan, galactomanin, agar, agarose, or a combination thereof. In certain embodiments, the carbohydrate is dextran, trehalose, sucrose, agarose, mannitol, lactose, sorbitol, maltose, hydroxypropyl beta-cyclodextrin, or a combination thereof. In preferred embodiments, the carbohydrate is trehalose, cyclodextrins, hydroxypropyl beta-cyclodextrin, or a combination thereof. Cyclodextrins are available in three different forms α, β, and γ based on the number of number of glucose monomers. The number of glucose monomers in a, 3, and γ cyclodextrin can be 6, 7, or 8, respectively.

In some embodiments, the pH adjusting agent is acetate, citrate, glutamate, glycinate, histidine, lactate, maleate, phosphate, succinate, tartrate, bicarbonate, aluminum hydroxide, phosphoric acid, hydrochloric acid, DL-lactic/glycolic acids, phosphorylethanolamine, tromethamine, imidazole, glyclyglycine, monosodium glutamate, sodium hydroxide, potassium hydroxide, or a combination thereof. In other embodiments, the pH adjusting agent is citrate, histidine, phosphate, succinate, sodium hydroxide, potassium hydroxide, or a combination thereof. In certain embodiments, the pH adjusting agent is hydrochloric acid or citric acid.

In other embodiments, the salt is sodium chloride, calcium chloride, potassium chloride, sodium hydroxide, stannous chloride, magnesium sulfate, sodium glucoheptonate, sodium pertechnetate, guanidine hydrochloride, potassium hydroxide, or a combination thereof. In preferred embodiments, the salt is sodium chloride.

In some embodiments, the chelator is disodium edetate, ethylenediaminetetraacetic acid, pentetic acid, or a combination thereof. In other embodiments, the mineral is calcium, zinc, titanium dioxide, or a combination thereof. In certain embodiments, the polymer is propyleneglycol, glucose star polymer, silicone polymer, polydimethylsiloxane, polyethylene glycol, carboxymethylcellulose, poly(glycolic acid), poly(lactic-co-glycolic acid), polylactic acid, polycaprolactone (PCL), polyvinylpyrrolidone (PVP), ficoll, dextran, or a combination thereof.

In other embodiments, the surfactant is polysorbate, magnesium stearate, sodium dodecyl sulfate, TRITON™ N-101, glycerin, polyoxyethylated castor oil, docusate, sodium stearate, decyl glucoside, nonoxynol-9, cetyltrimethylammonium bromide, sodium bis(2-ethylhexyl) sulfosuccinate, sodium laureth sulfate, lecithin, or a combination thereof. In some embodiments, the surfactant includes, but is not limited to: (i) cationic surfactants such as; cetyltrimethylammonium chloride, hexadecyltrimethylammonium chloride, benzalkonium chloride, benzethonium chloride, dioctadecyldimethylammonium bromide; (ii) anionic surfactants such as magnesium stearate, sodium dodecyl sulfate, dioctyl sodium sulfosuccinate, sodium myreth sulfate, perfluorooctanesulfonate, alkyl ether phosphates; (iii) non-ionic surfactants such as alkylphenol ethoxylates (TRITONX™-100), fatty alcohol ethoxylates (octaethylene glycol monododecyl ether, cocamide diethanolamine, poloxamers, glycerolmonostearate, fatty acid esters of sorbitol (sorbitan monolaurate, Tween 80, Tween 20; and (iv) zwitterionic surfactants such as cocamidopropyl hydroxysultaine, and 3-[(3-Cholamidopropyl)dimethylammonio]-1-propanesulfonate (CHAPS). In certain embodiments, the surfactant is polysorbate, docusate or lecithin. In preferred embodiments, the surfactant is polysorbate 20 or polysorbate 80.

In some embodiments, the protein stabilizer is acetyltryptophanate, caprylate, N-acetyltryptophan, trehalose, PEG 200, PEG 300, PEG 3350, PEG 8000, PEG 10000, PEG 20000, polyoxamers, polyvinylpyrrolidone, polyacrylic acids, poly(vinyl) polymers, polyesters, polyaldehydes, tert-polymers, polyamino acids, hydroxyethylstarch, N-methyl-2-pyrrolidone, sorbitol, sucrose, mannitol, or a combination thereof. In certain embodiments, the protein stabilizer is trehalose, PEG 200, PEG 300, PEG 3350, PEG 8000, PEG 10000, PEG 20000, polyoxamers, polyvinylpyrrolidone, polyacrylic acids, poly(vinyl) polymers, polyesters, polyal-dehydes, tert-polymers, polyamino acids, hydroxyethyl-starch, N-methyl-2-pyrrolidone, sorbitol, sucrose, mannitol, cyclodextrin, saccharides, or a combination thereof. In preferred embodiments, the protein stabilizer is trehalose, PEG 200, PEG 300, PEG 3350, PEG 8000, PEG 10000, PEG 20000, cyclodextrin, hydroxypropyl beta-cyclodextrin, or a combination thereof. The stabilizers, used synonymously with the term "stabilizing agent", as described herein, can be a salt, a carbohydrate, saccharides or amino acids, preferably a carbohydrate or saccharide admitted by the authorities as a suitable additive or excipient in pharmaceutical compositions. The term "stabilizer" refers to an excipient or a mixture of excipients which stabilizes the physical and/or chemical properties of agents, e.g., therapeutic or diagnostic agents. In some embodiments, stabilizers prevent, e.g., degradation of the therapeutic or diagnostic agents during droplet formation, desiccation, and/or storage of the particulate matter. Exemplary stabilizers include, but are not limited to, sugars, salts, hydrophobic salts, detergents, reducing agents, cyclodextrins, polyols, carboxylic acids, and amino acids. A "stable" formulation as described herein, refers to a formulation in which the therapeutic or diagnostic agent retains an acceptable portion of its essential physical, chemical, or biological properties over an acceptable period of time. In the case of proteins and peptides, e.g., exemplary methods of assessing stability are reviewed in (i) Peptide and Protein Drug Delivery, 247-301, Vincent Lee Ed., Marcel Dekker, Inc., New York, NY, 1991, and (ii) Jones, A., Adv. Drug Delivery Rev. 10: 29-90 (1993). In certain embodiments, chemical stability of a protein is assessed by measuring the size distribution of the sample at several stages. These include, e.g., before particle formation (assessment of the feed solution), immediately after particle formation, and again after a period of storage, where storage takes place either within or in the absence of a suspension formulation carrier medium. In certain other embodiments, the size distribution is assessed by size exclusion chromatography (SEC-HPLC).

Examples of emulsifiers suitable for use in the liquid include, but are not limited to, lipophilic agents having an HLB of less than 7, such as mixed fatty acid monoglycerides; mixed fatty acid diglycerides; mixtures of fatty acid mono- and diglycerides; lipophilic polyglycerol esters; glycerol esters including glyceryl monooleate, glyceryl dioleate, glyceryl monostearate, glyceryl distearate, glyceryl monopalmitate, and glyceryl dipalmitate; glyceryl-lacto esters of fatty acids; propylene glycol esters including propylene glycol monopalmitate, propylene glycol monostearate, and propylene glycol monooleate; sorbitan ester including sorbitan monostearate, sorbitan sesquioleate; fatty acids and their soaps including stearic acid, palmitic acid, and oleic acid; and mixtures thereof glyceryl monooleate, glyceryl dioleate, glyceryl monostearate, glyceryl distearate, glyceryl monopalmitate, and glyceryl dipalmitate; glyceryl-lacto esters of fatty acids; propylene glycol esters including propylene glycol monopalmitate, propylene glycol monostearate, and propylene glycol monooleate; sorbitan ester including sorbitan monostearate, sorbitan sesquioleate; fatty acids and their soaps including stearic acid, palmitic acid, and oleic acid; or a combination thereof. In some embodiments, the emulsifier is polysorbate 80, polysorbate 20, sorbitan monooleate, ethanolamine, polyoxyl 35 castor oil, poloxyl 40 hydrogenated castor oil, carbomer 1342, a corn oil-mono-di-triglyceride, a polyoxyethylated oleic glyceride, a poloxamer, or a combination thereof. In preferred embodiments, the emulsifier is polysorbate 80, sorbitan monooleate, or a combination thereof.

In other embodiments, the antiseptic is phenol, m-cresol, benzyl alcohol, 2-phenyloxyethanol, chlorobutanol, neomycin, benzethonium chloride, gluteraldehyde, beta-propiolactone, or a combination thereof.

In certain embodiments, the amino acid is alanine, aspartic acid, cysteine, isoleucine, glutamic acid, leucine, methionine, phenylalanine, pyrrolysine, serine, selenocysteine, threonine, tryptophan, tyrosine, valine, asparagine, L-arginine, histidine, glycine, glutamine, proline, or a combination thereof. In preferred embodiments, the amino acid is L-arginine, histidine, proline, or a combination thereof.

In some embodiments, the antioxidant is glutathione, ascorbic acid, cysteine, N-acetyl-L-tryptophanate, tocopherol, histidine, methionineor tocopherol, or a combination thereof.

In other embodiments, the protein is protamine, protamine sulfate, gelatin, or a combination thereof. In certain embodiments, the organic solvent is dimethyl sulfoxide, N-methyl-2-pyrrolidone, or a combination thereof. In still other embodiments, the preservative is methyl hydroxybenzoate, thimerosal, parabens, formaldehyde, castor oil, or a combination thereof. In certain other embodiments, the preservative is sodium nitrate, sulfur dioxide, potassium sorbate, sodium sorbate, sodium benzoate, benzoic acid, methyl hydroxybenzoate, thimerosal, parabens, formaldehyde, castor oil, or a combination thereof. The paraben can be a parahydroxybenzoate. In some embodiments, the bactericide is benzalkonium chloride (cationic surfactants), hypochlorites, peroxides, alcohols, phenolic compounds (e.g. carbolic acid), or a combination thereof.

In other embodiments, the fungicide is acibenzolar, 2-phenylphenol, anilazine, carvone, natamycin, potassium azide, or a combination thereof. In certain embodiments, the vitamin is thiamine, riboflavin, niacin, pantothenic acid, biotin, vitamin B6, vitamin B12, folate, niacin, ascorbic acid, calciferols, retinols, quinones, or a combination thereof.

A number of nutrient media, preferably serum free, alone or in combination, may be used in the present disclosure, including commercially available media or other media well known in the art. Examples of such media (all without serum or having had the serum removed) include ADC-1, LPM (Bovine Serum Albumin-free), F10 (HAM), F12 (HAM), DCCM1, DCCM2, RPMI 1640, BGJ Medium (Fitton-Jackson Modification), Basal Medium Eagle (BME—with the addition of Earle's salt base), Dulbecco's Modified Eagle Medium (DMEM-without serum), Glasgow Modification Eagle Medium (GMEM), Leibovitz L-15 Medium, McCoy's 5 A Medium, Medium M199 (M199E—with Earle's salt base), Medium M199 (M199H—with Hank's salt base), Minimum Essential Medium Eagle (MEM-E—with Earle's salt base), Minimum Essential Medium Eagle (MEM-H—with Hank's salt base) and Minimum Essential Medium Eagle (MEM-NAA—with non-essential amino acids), among numerous others. In addition, serum-containing nutrient media may also be used in compositions according to the present disclosure, but the use of serum-containing media is less preferred because of the possibility that the serum may be contaminated with microbial agents and because the patient may develop immunological reactions to certain antigenic components contained in the serum.

In some embodiments, the analgesic is paracetamol, histamine receptor antagonist (e.g., an H1 or an H2 blocker), NSAIDs, COX-2 inhibitors, Celecoxib, Rofecoxib, Valdecoxib, Parecoxib, Lumiracoxib, Etoricoxib, Firocoxib, acetaminophen, opiates, Dextropropoxyphene, Codeine, Tramadol, Anileridine, Pethidine, Hydrocodone, Morphine, Oxycodone, Methadone, Diacetylmorphine, Hydromorphone, Oxymorphone, Levorphanol, Buprenorphine, Fentanyl, Sufentanil, Etorphine, Carfentanil, dihydromorphine, dihydrocodeine, Thebaine, Papaverine, diproqualone, Flupirtine, Tricyclic antidepressants, Acetaminophen or lidocaine, or a combination thereof. In certain embodiments, the analgesic is acetaminophen or lidocaine.

In certain embodiments, the liquid further comprises at least one pharmaceutically acceptable additive, diluent, excipient, carrier, or a combination thereof. In certain other embodiments, the liquid further comprises a second agent. In other embodiments, the liquid further comprises a second diagnostic or therapeutic agent.

In some embodiments, the particles have less than 20% aggregation or less than 20% fragmentation of the therapeutic biologic, e.g., less than about 19, 18, 17, 16, 15, 14, 13, 12, 10, 9, 8, 7, 6, 5, 4, 3, 2, 1.9, 1.8, 1.7, 1.6, 1.5, 1.4, 1.3, 1.2, 1.1, 1, 0.9, 0.8, 0.7, 0.6, 0.5, 0.4, 0.3, 0.2, or 0.1%. In other embodiments, the particles have less than 10% aggregation or less than 10% fragmentation of the therapeutic biologic, e.g., less than about 9, 8, 7, 6, 5, 4, 3, 2, 1.9, 1.8, 1.7, 1.6, 1.5, 1.4, 1.3, 1.2, 1.1, 1, 0.9, 0.8, 0.7, 0.6, 0.5, 0.4, 0.3, 0.2, or 0.1%. In certain embodiments, the particles have about 3% to about 1% aggregation of the therapeutic biologic. In certain other embodiments, the particles have about 1% to about 0.5% aggregation of the therapeutic biologic. In preferred embodiments, the particles are substantially free from any aggregation of the therapeutic biologic. In still other embodiments, the particles have less than about 1% fragmentation of the therapeutic biologic. In certain preferred embodiments, the particles are substantially free from any fragmentation of the therapeutic biologic.

In certain embodiments, the methods described herein, may further include suspending the particles in a pharmaceutically acceptable medium, e.g., reconstitution of the dried particles. In some embodiments, the dissolution or reconstitution of the particles provides less than about 10% increase in aggregates of the diagnostic or therapeutic agent, e.g., a protein, (e.g., less than about 8%, less than about 5%, less than about 4%, less than about 3%, less than about 1%, less than about 0.5%, or less than about 0.1%) as compared to the therapeutic or diagnostic agent in the first liquid prior to processing. Exemplary methods of measuring aggregates include size exclusion high-performance liquid chromatography (SEC-HPLC), where the aggregate population is quantified by dividing the area under the peak corresponding to the aggregate population by the cumulative area contained beneath all peaks in the sample spectrum. Changes in aggregate percentage between two samples, e.g., Sample A and Sample B, are computed as the numerical difference in the respective aggregate percentages, i.e., by subtracting the aggregate percentage of Sample B from the aggregate percentage of Sample A, or vice versa. In certain other embodiments, the dissolution or reconstitution of the particles provides less than about 10% increase in fragments of the diagnostic or therapeutic agent, e.g., a protein, (e.g., less than about 8%, less than about 5%, less than about 4%, less than about 3%, less than about 1%, less than about 0.5%, or less than about 0.1%) as compared to the therapeutic or diagnostic agent in the first liquid prior to processing. Exemplary methods of measuring fragments include size exclusion high-performance liquid chromatography (SEC-HPLC), where the fragment population is quantified by dividing the area under the peak corresponding to the fragment population by the cumulative area contained beneath all peaks in the sample spectrum. Changes in fragment percentage between two samples, e.g., Sample A and Sample B, are computed as the numerical difference in the respective fragment percentages, i.e., by subtracting the fragment percentage of Sample B from the fragment percentage of Sample A, or vice versa.

In other embodiments, the process of particle formation provides less than a 50% change in charge variants in the population of a diagnostic or therapeutic agent, e.g., an antibody or an antibody fragment, (e.g., less than 40, 30, 20, 10, 8, 5, 4, 3, or 1%) as compared to the therapeutic or diagnostic agent prior to particle formation. In certain embodiments, the particles have less than about 50% change in charge variants of the therapeutic biologic, e.g., less than about 45, 40, 35, 30, 25, 20, 15, 10, 9, 8, 7, 6, 5, 4, 3, 2, 1, 0.5, 0.1%, compared to the starting biologic prior to particle formation. In preferred embodiments, the particles are substantially free from any change in charge variants of the therapeutic biologic compared to the starting biologic prior to particle formation.

In some embodiments, the residual moisture or solvent content of the dry component is less than about 7% by weight, e.g., less than about 6, 5, 4, 3, 2, 1.9, 1.8, 1.7, 1.6, 1.5, 1.4, 1.3, 1.2, 1.1, 1, 0.9, 0.8, 0.7, 0.6, 0.5, 0.4, 0.3, 0.2, or 0.1% by weight. In other embodiments, the particles have less than about 7% residual moisture by weight. In still other embodiments, the particles have less than about 5% residual moisture by weight. In certain embodiments, the particles have less than about 3% residual moisture by weight. In preferred embodiments, the particles have than about 1% residual moisture by weight.

In other embodiments, the particles have about 1% to about 7% residual moisture by weight. In still other embodiments, the particles have about 1% to about 5% residual moisture by weight. In certain embodiments, the particles have about 1% to about 3% residual moisture by weight. In preferred embodiments, the particles are substantially free from any residual moisture by weight.

In some embodiments, the particles have greater than about 60% therapeutic biologic by weight, e.g., greater than about 65, 70, 75, 80, 85, 86, 87, 88, 89, 90, 91, 92, 93, 94, 95, 96, 97, 98, 99, 99.1, 99.2, 99.3, 99.4, 99.5, 99.6, 99.7, 99.8, 99.9% therapeutic biologic by weight. In other embodiments, the particles have greater than about 90% therapeutic biologic by weight. In certain embodiments, the particles have greater than about 95% therapeutic biologic by weight. In still other embodiments, the particles have greater than about 98% therapeutic biologic by weight. In preferred embodiments, the particles have greater than about 98% therapeutic biologic by weight. In certain preferred embodiments, the particles have greater than about 99% therapeutic biologic by weight.

The concentration of the therapeutic biologic in the composition is typically of about 20 mg/mL to about 650 mg/mL, e.g., about 20, 30, 50, 75, 100, 125, 150, 175, 200, 225, 250, 275, 300, 325, 350, 375, 400, 425, 450, 475, 500, 525, 550, 575, 600, 625 mg/mL to about 650 mg/mL. The therapeutic biologic in the composition may have about 0.5 to about 1.0 activity per unit, about 0.75 to about 1.0 activity per unit, or about 0.9 to about 1.0 activity per unit. Activity is measured relative to the same therapeutic biologic prior to particle formation. In preferred embodiments, the therapeutic biologic has an activity per unit of about 0.5 to about 1.0.

In some embodiments, the compositions described herein, use a concentration of the therapeutic biologic in the composition of about 20 mg/mL to about 650 mg/mL, e.g., about 20, 30, 50, 75, 100, 125, 150, 175, 200, 225, 250, 275, 300, 325, 350, 375, 400, 425, 450, 475, 500, 525, 550, 575, 600, 625 mg/mL to about 650 mg/mL; about 20 mg/mL to about 625 mg/mL, e.g., about 20, 30, 50, 75, 100, 125, 150, 175, 200, 225, 250, 275, 300, 325, 350, 375, 400, 425, 450, 475, 500, 525, 550, 575, 600 mg/mL to about 625 mg/mL; about 20 mg/mL to about 600 mg/mL, e.g., about 20, 30, 50, 75, 100, 125, 150, 175, 200, 225, 250, 275, 300, 325, 350, 375, 400, 425, 450, 475, 500, 525, 550, 575 mg/mL to about 600 mg/mL; about 20 mg/mL to about 575 mg/mL, e.g., about 20, 30, 50, 75, 100, 125, 150, 175, 200, 225, 250, 275, 300, 325, 350, 375, 400, 425, 450, 475, 500, 525, 550 mg/mL to about 575 mg/mL; about 20 mg/mL to about 550 mg/mL, e.g., about 20, 30, 50, 75, 100, 125, 150, 175, 200, 225, 250, 275, 300, 325, 350, 375, 400, 425, 450, 475, 500, 525 mg/mL to about 550 mg/mL; about 20 mg/mL to about 525 mg/mL, e.g., about 20, 30, 50, 75, 100, 125, 150, 175, 200, 225, 250, 275, 300, 325, 350, 375, 400, 425, 450, 475, 500 mg/mL to about 525 mg/mL; about 20 mg/mL to about 500 mg/mL, e.g., about 20, 30, 50, 75, 100, 125, 150, 175, 200, 225, 250, 275, 300, 325, 350, 375, 400, 425, 450, 475 mg/mL to about 500 mg/mL; about 20 mg/mL to about 475 mg/mL, e.g., about 20, 30, 50, 75, 100, 125, 150, 175, 200, 225, 250, 275, 300, 325, 350, 375, 400, 425, 450 mg/mL to about 475 mg/mL; about 20 mg/mL to about 450 mg/mL, e.g., about 20, 30, 50, 75, 100, 125, 150, 175, 200, 225, 250, 275, 300, 325, 350, 375, 400, 425 mg/mL to about 450 mg/mL; about 20 mg/mL to about 425 mg/mL, e.g., about 20, 30, 50, 75, 100, 125, 150, 175, 200, 225, 250, 275, 300, 325, 350, 375, 400 mg/mL to about 425 mg/mL; about 20 mg/mL to about 400 mg/mL, e.g., about 20, 30, 50, 75, 100, 125, 150, 175, 200, 225, 250, 275, 300, 325, 350, 375 mg/mL to about 400 mg/mL; about 20 mg/mL to about 375 mg/mL, e.g., about 20, 30, 50, 75, 100, 125, 150, 175, 200, 225, 250, 275, 300, 325, 350 mg/mL to about 375 mg/mL; about 20 mg/mL to about 350 mg/mL, e.g., about 20, 30, 50, 75, 100, 125, 150, 175, 200, 225, 250, 275, 300, 325 mg/mL to about 350 mg/mL; about 20 mg/mL to about 325 mg/mL, e.g., about 20, 30, 50, 75, 100, 125, 150, 175, 200, 225, 250, 275, 300 mg/mL to about 325 mg/mL; or about 20 mg/mL to about 300 mg/mL, e.g., about 20, 30, 50, 75, 100, 125, 150, 175, 200, 225, 250, 275 mg/mL to about 300 mg/mL. In other embodiments, the concentration of the therapeutic biologic in the composition is about 30 mg/mL to about 500 mg/mL. In certain embodiments, the concentration of the therapeutic biologic in the composition is about 100 mg/mL to about 500 mg/mL. In still other embodiments, the concentration of the therapeutic biologic in the composition is about 200 mg/mL to about 400 mg/mL. In preferred embodiments, the concentration of the therapeutic biologic in the composition is about 300 mg/mL to about 400 mg/mL. In certain preferred embodiments, the concentration of the therapeutic biologic in the composition is about 350 mg/mL to about 400 mg/mL.

In other embodiments, the composition has a viscosity of less than about 200 mPa·s, less than about 150 mPa·s, less than about 125 mPa·s, less than about 100 mPa·s, less than about 75 mPa·s, less than about 75 mPa·s, less than about 70 mPa·s, less than about 65 mPa·s, less than about 60 mPa·s, less than about 55 mPa·s, less than about 50 mPa·s, less than about 45 mPa·s, less than about 40 mPa·s, less than about 35 mPa·s, less than about 30 mPa·s, less than about 25 mPa·s, less than about 20 mPa·s, less than about 19 mPa·s, less than about 18 mPa·s, less than about 17 mPa·s, less than about 16 mPa·s, less than about 15 mPa·s, less than about 14 mPa·s, less than about 13 mPa·s, less than about 12 mPa·s, less than about 11 mPa·s, less than about 10 mPa·s, less than about 9.5 mPa·s, less than about 9 mPa·s, less than about 8.5 mPa·s, less than about 8 mPa·s, less than about 7.5 mPa·s, less than about 7 mPa·s, less than about 6.5 mPa·s, less than about 6 mPa·s, less than about 5.5 mPa·s, less than about 5 mPa·s, less than about 4.5 mPa·s, less than about 4 mPa·s, less than about 3.5 mPa·s, less than about 3 mPa·s, less than about 2.5 mPa·s, less than about 2 mPa·s, less than about 1.5 mPa·s, less than about 1 mPa·s, less than about 0.5 mPa·s, less than about 0.1 mPa·s, less than about 0.05 mPa·s, or less than about 0.01 mPa·s (one millipascal-second). In other embodiments, the composition has a viscosity of about 0.01 mPa·s to about 10,000 mPa·s, e.g., from about 0.01 mPa·s to about 1,000 mPa·s, from about 0.01 mPa·s to about 100 mPa·s, from about 0.01 mPa·s to about 50 mPa·s, from about 0.01 mPa·s to about 25 mPa·s, from about 0.01 mPa·s to about 10 mPa·s, from about 0.01 mPa·s to about 5 mPa·s, or from about 0.01 mPa·s to about 1 mPa·s. In certain embodiments, the viscosity of the composition can range from about 0.27 mPa·s to about 200 mPa·s, e.g., about 0.27 mPa·s to about 50 mPa·s, about 1 mPa·s to about 30 mPa·s, or about 20 mPa·s to about 50 mPa·s. In still other embodiments, the viscosity of the composition ranges from about 0.27 mPa·s to about 200 mPa·s, e.g., about 0.27 mPa·s to about 100 mPa·s, about 0.27 mPa·s to about 50 mPa·s, about 0.27 mPa·s to about 30 mPa·s, about 1 mPa·s to about 20 mPa·s, or about 1 mPa·s to about 15 mPa·s. The term "viscosity" is used to describe the property of a fluid acting to resist shearing flow. For the purposes of the present disclosure, viscosity can be determined using a rheometer, e.g., AR-G2 Rheometer (TA Instruments, USA), fitted with a cone and plate (2°/40 mm) at 25° C. at a specified shear rate. In certain embodiments, the viscosity is measured at a shear rate in the Newtonian regime. The term "Newtonian regime" means a range of shear rates which are linearly proportional or nearly linearly proportional to the local strain rate at every point. In some embodiments, the viscosity is measured at a shear rate of about 100 s$^{-1}$ or greater, e.g., at about 1000 s$^{-1}$ or greater than about 1000 s$^{-1}$. The composition may include from about 5 to about 90% particles by volume, e.g., e.g., about 20 to about 90%, about 40 to about 80%, about 50 to about 60%, or about 70 to about 90%. The composition may have a concentration of the therapeutic biologic from about 0.0001 to about 1000 mg/mL, e.g., from about 100 to about 900, about 150 to about 800, or about 200 to about 700 mg/mL. Methods of controlling viscosity include temperature regulation and viscosity modifying additives. Mixtures of liquids may also be used to control viscosity. The units "mPa·s" and "cP" are used herein, interchangeably in the broadest sense.

In some embodiments, the composition has a viscosity of less than about 50 mPa·s. In other embodiments, the composition has a viscosity of less than about 30 mPa·s. In still other embodiments, the composition has a viscosity of less than about 20 mPa·s. In certain other embodiments, the composition has a viscosity of less than about 10 mPa·s. In certain embodiments, the composition has a viscosity of less than about 5 mPa·s. In preferred embodiments, the composition has a viscosity of less than about 3 mPa·s. In certain preferred embodiments, the composition has a viscosity of less than about 2.5 mPa·s.

In other embodiments of the composition described herein, the plurality of particles has a polydispersity index from about 0.002 to about 1.000, e.g., from about 0.003, 0.004, 0.005, 0.006, 0.007, 0.008, 0.009, 0.010, 0.020, 0.030, 0.040, 0.050, 0.060, 0.070, 0.080, 0.090, 0.100, 0.200, 0.300, 0.400, 0.500, 0.600, 0.700, 0.800, 0.900 to about 1.000. In certain embodiments, the plurality of particles has a polydispersity index from about 0.002 to about 0.900.

In certain embodiments of the disclosure described herein, high concentrations of the therapeutic biologic in the particles and high concentrations of particles in the liquid are possible. In some embodiments, the latter may be achieved by mixing particles of various sizes.

In preferred embodiments according to the disclosure as described herein, the composition comprising a plurality of particles has improved stability of the therapeutic biologic compared to an aqueous composition comprising the therapeutic biologic in monomeric form.

In other embodiments, the particles of the disclosure can be suspended in an aqueous liquid carrier, non-aqueous liquid carrier, e.g., an organic liquid, an ionic liquid carrier, a gel carrier, or a combination thereof to form a suspension composition. The medium for suspension may further include, e.g., a carbohydrate, a pH adjusting agent, a salt, a chelator, a mineral, a polymer, a surfactant, an amino acid, an oligopeptide, a biologic excipient, a chemical excipient, an antiseptic, an antioxidant, a paraben, a bactericide, a fungicide, a vitamin, a preservative, an analgesic, and/or nutrient media. In some embodiments, each of the other components can be, independently, at about 0.0001 to about 99% (w/v) of the medium, e.g., at about 0.0001 to about 90% (w/v), at about 0.0001 to about 50% (w/v), at about 0.0001 to about 10% (w/v), at about 0.0001 to about 1% (w/v), or at about 0.0001 to about 0.1% (w/v). In certain embodiments, the disclosure provides a plurality of particles described herein, suspended in a liquid. The liquid may be an organic solvent, ionic liquid, an aqueous liquid, or a combination thereof. The liquid may further include a second diagnostic or therapeutic agent.

In some embodiments, insoluble particulate matter with characteristic sizes greater than or equal to about 100 μm that persist upon dissolution in an aqueous liquid are referred to as Visible Particles (VP). In preferred embodiments of the disclosure described herein, the composition is substantially free of Visible Particles (VP). In certain preferred embodiments, the aqueous liquid is water, aqueous buffer or a physiologically relevant aqueous liquid. In other embodiments, insoluble particulate matter which is visible to the naked eye under prescribed lighting conditions persist upon reconstitution of the particles of the disclosure into a liquid pharmaceutical composition. Insoluble particulates of this type, are sometimes referred to as Visible Particles (VPs), and are typically greater than about 100 μm in size. VPs are present in quantities from about 0 to about 1 per about 1 mL, e.g., from about 0 to about 0.01 per about 1 mL, from about 0 to about 0.001 per about 1 mL, or about 0 to about 0.0001 per about 1 mL. Exemplary methods of measuring VPs include analysis of the therapeutic or diagnostic agent by visual inspection against and black and white background for 5 seconds under illumination between about 2000 and about 3750 lux in accordance with USP<790> after reconstitution and dilution of the therapeutic or diagnostic agent to a standard concentration, e.g., about 100 mg/mL or about 1 mg/mL. In some embodiments, fewer than 65 samples in 10,000 (0.65%) are rejected on the basis of USP<790>. Alternate inspection strategies are light-obscuration, automated optical imaging systems, or X-ray imaging in accordance with USP <1790>.

In other embodiments, insoluble particulate matter with characteristic sizes from about 1 μm to about 100 μm that persist upon dissolution in an aqueous liquid are referred to as Subvisible Particles (SvPs). SvPs are present in quantities from about 0 to 100,000,000 per about 1 mL, e.g., from about 0 to about 10,000,000 per about 1 mL, from about 0 to about 1,000,000 per about 1 mL, from about 0 to about 500,000 per about 1 mL, from about 0 to about 100,000 per about 1 mL, from about 0 to about 50,000 per about 1 mL, from about 0 to about 10,000 per about 1 mL, from about 0 to about 6,000 per about 1 mL, from about 0 to about 1,000 per about 1 mL, from about 0 to about 600 per about 1 mL, from about 0 to about 250 per about 1 mL, from about 0 to about 100 per about 1 mL, from about 0 to about 60 per about 1 mL, or from about 0 to about 10 per about 1 mL. In other embodiments, the count of particles with characteristic size greater than or equal to 10 μm is from about 0 to about 6,000 per about 1 mL, e.g., from about 0 to about 1,000 per about 1 mL, from about 0 to about 100 per about 1 mL, from about 0 to about 10 per about 1 mL, from about 0 to about 5 per about 1 mL, from about 0 to about 3 per about 1 mL, or from about 0 to about 1 per about 1 mL. In certain embodiments, the count of particles with characteristic size greater than or equal to 25 μm is from about 0 to about 600 per about 1 mL, e.g., from about 0 to about 100 per about 1 mL, from about 0 to about 10 per about 1 mL, from about 0 to about 3 per about 1 mL, from about 0 to about 1 per about 1 mL, from about 0 to about 0.5 per about 1 mL, or from about 0 to about 0.1 per about 1 mL. Exemplary methods of measuring SvPs include analysis of the therapeutic biologic with a Coulter Counter, HIAC Royco, or micro-flow imaging system after reconstitution and dilution of the therapeutic biologic to a standard concentration, e.g., about 100 mg/mL or about 1 mg/mL. In still other embodiments, the composition has a concentration of insoluble subvisible particles of about 0 per about 1 mL to about 100,000,000 per about 1 mL of greater than about 10 m particles upon dissolution in an aqueous liquid. In certain embodiments, the composition has a concentration of insoluble subvisible particles of about 0 per about 1 mL to about 6000 per about 1 mL of greater than about 10 μm particles upon dissolution in an aqueous liquid. In preferred embodiments, the composition has a concentration of insoluble subvisible particles of about 0 per about 1 mL to about 600 per about 1 mL of greater than about 25 μm particles upon dissolution in an aqueous liquid. In certain preferred embodiments, the composition is substantially free of insoluble subvisible particles upon dissolution in an aqueous liquid. In preferred embodiments, the aqueous liquid is water, aqueous buffer or a physiologically relevant aqueous liquid.

In some embodiments, insoluble particulate matter with characteristic sizes from about 100 nm to about 1 μm that persist upon dissolution in an aqueous liquid are referred to as submicron particles (SMP) and sometimes known as nanoparticles. Quantitatively, SMPs are present in quantities from about 0 to $5\times10^{12}$ per about 1 mL, e.g., from about 0 to about $0.5\times10^{12}$ per about 1 mL, from about 0 to about $50\times10^{9}$ per about 1 mL, from about 0 to about $10\times10^{9}$ per about 1 mL, from about 0 to about $5\times10^{9}$ per about 1 mL, from about 0 to about $0.5\times10^{9}$ per about 1 mL, from about 0 to about $50\times10^{6}$ per about 1 mL, from about 0 to about $1\times10^{6}$ per about 1 mL, from about 0 to about 500,000 per about 1 mL, from about 0 to about 200,000 per about 1 mL, from about 0 to about 100,000 per about 1 mL, from about 0 to about 10,000 per about 1 mL, from about 0 to about 5000 per about 1 mL, or from about 0 to about 1000 per about 1 mL. Exemplary methods of measuring SMPs quantitatively include analysis of the therapeutic biologic with a NanoSight, micro-flow imaging system, asymmetric field flow fractionation coupled to a multi-angle laser light scattering (AF4 MALS), or Dynamic Light Scattering (DLS) after reconstitution and dilution of the therapeutic biologic to a standard concentration, e.g., about 100 mg/mL, about 1 mg/mL, or about 1 µg/mL. Qualitatively, SMPs are within a range comparable to the starting monomeric therapeutic biologic solution. In preferred embodiments, the composition is substantially free of submicron particles (SMP) upon dissolution in an aqueous liquid. In certain preferred embodiments, the aqueous liquid is water, aqueous buffer or a physiologically relevant aqueous liquid. Qualitatively, as described herein, SMPs are within a range comparable to the feed solution.

In certain embodiments, the suspension includes insoluble particulate matter smaller than or equal to 1 m. The suspension can have a concentration of insoluble particles with a characteristic size greater than or equal to about 100 nm is about 1 to $5\times10^{12}$ per about 1 mL in suspension, or have a concentration of insoluble particles with a characteristic size less than or equal to about 1 µm is about 1 to $5\times10^{12}$ per about 1 mL in suspension. In still other embodiments, the suspension of particles may include insoluble particulate matter larger than or equal to about 1 µm in size. In certain other embodiments, the number of insoluble particles is from about 0 to about 100,000,000 per about 1 mL, e.g., less than about 10,000,000, 1,000,000, 100,000, 10,000, 1000, 100, 10, or about 1 per about 1 mL. For example, the number of insoluble particles greater than about 10 µm is from about 0 to about 6,000 per about 1 mL, e.g., less than about 5,000, about 4,000, about 3,000, about 2,000, about 1,000, about 500, about 100, about 10, or about 1 per about 1 mL, and/or the number of insoluble particles greater than about m is from about 0 to about 600 per about 1 mL, e.g., less than about 500, about 400, about 300, about 200, about 100, about 50, about 10, or about 1 about 1 per about 1 mL.

In some embodiments, the disclosure provides a composition, e.g., a suspension or dried form, containing a plurality of particles that include an agent, e.g., a therapeutic or diagnostic agent. The composition preferably has a concentration of insoluble particles, e.g., SvPs, of between about 0 and about 100,000,000 per about 1 mL in suspension or upon reconstitution. In other embodiments, the concentration of insoluble particles is between about 0 and about 1,000,000 per about 1 mL in suspension or upon reconstitution. In still other embodiments, the concentration of insoluble particles is between about 0 and about 10,000 per about 1 mL in suspension or upon reconstitution. In certain other embodiments, the concentration of insoluble particles with a characteristic size greater than or equal to about 10 am is between about 0 to about 6,000 per about 1 mL in suspension or upon reconstitution. In certain embodiments, the concentration of insoluble particles with a characteristic size greater than or equal to about 25 am is between about 0 to about 600 per about 1 mL in suspension or upon reconstitution.

In other embodiments, after dissolution or reconstitution of the particles following storage, SvPs are present in quantities from about 0 to about 100,000,000 per about 1 mL, e.g., from about 0 to about 10,000,000 per about 1 mL, from about 0 to about 1,000,000 per about 1 mL, from about 0 to about 500,000 per about 1 mL, from about 0 to about 100,000 per about 1 mL, from about 0 to about 50,000 per about 1 mL, from about 0 to about 10,000 per about 1 mL, from about 0 to about 6,000 per about 1 mL, from about 0 to about 1,000 per about 1 mL, from about 0 to about 600 per about 1 mL, from about 0 to about 250 per about 1 mL, from about 0 to about 100 per about 1 mL, from about 0 to about 60 per about 1 mL, or from about 0 to about 10 per about 1 mL. In some embodiments, the count of particles with characteristic size greater than or equal to about 10 µm is from about 0 to about 6,000 per about 1 mL, e.g., from about 0 to about 1,000 per about 1 mL, from about 0 to about 100 per about 1 mL, from about 0 to about 10 per about 1 mL, from about 0 to about 5 per about 1 mL, from about 0 to about 3 per about 1 mL, or from about 0 to about 1 per about 1 mL. In certain embodiments, the count of particles with characteristic size greater than or equal to about 25 µm is from about 0 to about 600 per about 1 mL, e.g., from about 0 to about 100 per about 1 mL, from about 0 to about 10 per about 1 mL, from about 0 to about 3 per about 1 mL, from about 0 to about 1 per about 1 mL, from about 0 to about 0.5 per about 1 mL, or from about 0 to about 0.1 per about 1 mL. In still other embodiments, after dissolution or reconstitution of the particles following storage, the therapeutic or diagnostic agent retains from about 0.5 to about 1.0 activity, e.g., from about 0.75 to about 1.0 activity, from about 0.9 to about 1.0 activity, from about 0.95 to about 1.0 activity, from about 0.99 to about 1.0 activity, or from about 0.999 to about 1.0 activity. In certain other embodiments, dissolution or reconstitution of the particles following storage provides less than about a 10% increase in aggregates of the agent, e.g., a protein, (e.g., less than about 8%, less than about 5%, less than about 4%, less than about 3%, less than about 1%, less than about 0.5%, or less than about 0.1%) as compared to the agent in the first liquid prior to processing. In certain embodiments, the dissolution or reconstitution of the particles after storage provides less than about a 10% increase in fragments of the agent, e.g., a protein, (e.g., less than about 8%, less than about 5%, less than about 4%, less than about 3%, less than about 1%, less than about 0.5%, or less than about 0.1%) as compared to the therapeutic or diagnostic agent in the first liquid prior to processing. In some embodiments, the dissolution or reconstitution of the particles following storage provides less than about a 50% change in charge variants in the population of the agent, e.g., an antibody or an antibody fragment, (e.g., less than about 40, 30, 20, 10, 8, 5, 4, 3, or about 1%) as compared to the therapeutic or diagnostic agent prior to particle formation.

In still other embodiments, after dissolution or reconstitution of the particles following storage, SvPs are present in quantities from about 0 to about 100,000,000 per about 1 mL, e.g., from about 0 to about 10,000,000 per about 1 mL, from about 0 to about 1,000,000 per about 1 mL, from about 0 to about 500,000 per about 1 mL, from about 0 to about 100,000 per about 1 mL, from about 0 to about 50,000 per about 1 mL, from about 0 to about 10,000 per about 1 mL, from about 0 to about 6,000 per about 1 mL, from about 0 to about 1,000 per about 1 mL, from about 0 to about 600 per about 1 mL, from about 0 to about 250 per about 1 mL, from about 0 to about 100 per about 1 mL, from about 0 to about 60 per about 1 mL, or from about 0 to about 10 per about 1 mL. In certain embodiments, the count of particles with characteristic size greater than or equal to about 10 μm is from about 0 to about 6,000 per about 1 mL, e.g., from about 0 to about 1,000 per about 1 mL, from about 0 to about 100 per about 1 mL, from about 0 to about 10 per about 1 mL, from about 0 to about 5 per 1 mL, from about 0 to about 3 per about 1 mL, or from about 0 to about 1 per about 1 mL. In certain other embodiments, the count of particles with characteristic size greater than or equal to about 25 m is from about 0 to about 600 per about 1 mL, e.g., from about 0 to about 100 per about 1 mL, from about 0 to about 10 per about 1 mL, from about 0 to about 3 per about 1 mL, from about 0 to about 1 per about 1 mL, from about 0 to about 0.5 per about 1 mL, or from about 0 to about 0.1 per about 1 mL. In some embodiments, dissolution or reconstitution of the particles following storage provides less than about a 10% increase in aggregates of the diagnostic or therapeutic agent, e.g., a protein, (e.g., less than about 8%, less than about 5%, less than about 4%, less than about 3%, less than about 1%, less than about 0.5%, or less than about 0.1%) as compared to the therapeutic or diagnostic agent in the first liquid prior to processing. In other embodiments, the dissolution or reconstitution of the particles after storage provides less than about a 10% increase in fragments of the diagnostic or therapeutic agent, e.g., a protein, (e.g., less than about 8%, less than about 5%, less than about 4%, less than about 3%, less than about 1%, less than about 0.5%, or less than about 0.1%) as compared to the therapeutic or diagnostic agent in the first liquid prior to processing. In certain other embodiments, the dissolution or reconstitution of the particles following storage provides less than about 50% change in charge variants in the population of a diagnostic or therapeutic agent, e.g., an antibody or an antibody fragment, (e.g., less than about 40, about 30, about 20, about 10, about 8, about 5, about 4, about 3, or about 1%) as compared to the therapeutic or diagnostic agent prior to particle formation.

In certain embodiments, the particles of the disclosure can be suspended in an aqueous liquid, an organic liquid, an ionic liquid, a gel, or a combination thereof to form a suspension formulation. The medium for suspension may further include, e.g., a carbohydrate, a pH adjusting agent, a salt, a chelator, a mineral, a polymer, a surfactant, an amino acid, an oligopeptide, a biologic excipient, a chemical excipient, an antiseptic, an antioxidant, a paraben, a bactericide, a fungicide, a vitamin, a preservative, an analgesic, and/or nutrient media. In some embodiments, each of the other components is, independently, at about 0.0001 to about 99% (w/v) of the medium, e.g., at about 0.0001 to about 90% (w/v), at about 0.0001 to about 50% (w/v), at about 0.0001 to about 10% (w/v), at about 0.0001 to about 1% (w/v), or at about 0.0001 to about 0.1% (w/v).

For aqueous suspension formulations, high concentration trehalose solutions can stabilize the particles in suspension and prevent premature dissolution. The sugar acts as a steric stabilizer if adsorbed onto the particle surface but if non-absorbing can also act as a "crowder" molecule. A crowder molecule may function by enhancing depletion repulsions. This stabilizing effect has also been described for other crowding agents in water such as (i) polymers, e.g., PEG 200, PEG 300, PEG 3350, PEG 8000, PEG 10000, PEG 20000, polyoxamers, polyvinylpyrrolidone, polyacrylic acids, poly(vinyl) polymers, polyesters, polyaldehydes, tert-polymers, polyamino acids, and hydroxyethylstarch, etc. (note that these may be used alone or in combination); (ii)

organic molecules, e.g., N-methyl-2-pyrrolidone (Miller et al. J. Pharm. Sci., 2012, 101, 3763-3778), and (iii) sugars and sugar alcohols such as sorbitol, sucrose, and mannitol, among others. Other "crowding agents" include salts such as ammonium sulfate which can compete for water of hydration, and water soluble organic liquids such as N-methyl pyrrolidone (NMP) which can lower the solvent dielectric constant and produce excluded volume effects. In preferred embodiments, the crowding agent is PEG 3350, Dextran 40k, or Dextran 6k.

In some embodiments, the surfactant in the suspension liquid (either aqueous and non-aqueous) acts as a charge stabilizer. The surfactant adsorbs onto the surface of the particles to control electrostatic interactions between them. The repulsive electrostatic force generated upon the addition of surfactant to the suspension is sufficient in some embodiments to prevent significant aggregation of the particles. The surfactant can also prevent attachment to the container. In other embodiments, a polymer can be added to the suspension liquid, to act as a steric stabilizer.

In certain embodiments, the therapeutic or diagnostic agent has about 0.5 to about 1.0 activity per unit, e.g., about 0.75 to about 1.0 activity per unit, or about 0.9 to about 1.0 activity per unit (e.g., about 0.99 activity per unit).

In certain preferred embodiments, the present disclosure as described herein, concerns a highly concentrated composition comprising a plurality of particles comprising at least one therapeutic biologic suspended in a low viscosity pharmaceutically acceptable liquid carrier, wherein the composition upon dissolution in water, buffers or other physiologically relevant aqueous liquids, e.g., biological fluids in the patients' body, have a substantially similar turbidity compared to a similar aqueous composition comprising monomeric therapeutic biologics. The term "turbidity" means the cloudiness or haziness of a fluid caused by individual particles that remain insoluble after dissolution at the desired concentration in water, buffer or other physiologically relevant aqueous liquids, e.g., biological fluids in the patients' body. As used herein, "physiologically relevant" conditions as may be encountered inside a mammal or human, can apply. The skilled person will be able to determine the set of conditions most appropriate for testing in accordance with the ultimate application of the compositions described herein. In some embodiments, the composition upon dissolution in an aqueous liquid has a substantially similar turbidity compared to an aqueous composition comprising monomeric therapeutic biologics. In preferred embodiments, the composition upon dissolution in an aqueous liquid is substantially free of turbidity. In certain preferred embodiments, the aqueous liquid is water, aqueous buffer or a physiologically relevant aqueous liquid.

In some embodiments, the particles of the disclosure can be reconstituted into a liquid pharmaceutical composition to assess the turbidity or turbidance (USP <855>). Turbidity may be measured in units of FTU (Formazin Turbidity Units). This is achieved by comparing the turbidity of a sample with that of a formazine suspension. Turbidity may also be measured as Nephelometric Turbidity Units (NTU) where 1NTU=1FTU. In other embodiments, when 10 mg of particles are dissolved in 1 mL of liquid, turbidity can be between about 0 to about 4000 FTU, about 0 to about 1000 FTU, about 0 to about 500 FTU, about 0 to about 50 FTU, about 0 to about 20 FTU, about 0 to about 10 FTU, about 0 to about 5 FTU, about 0 to about 1 FTU, about 0 to about 0.1 FTU, or about 0 to about 0.01 FTU. In certain embodiments, the composition has a turbidity of between about 0 to about 4000 Formazin Turbidity Units (FTU). In certain other embodiments, the composition upon dissolution in an aqueous liquid has a substantially similar turbidity compared to an aqueous composition comprising the therapeutic biologic in monomeric form. In preferred embodiments, the composition upon dissolution in an aqueous liquid is substantially free of turbidity. In certain preferred embodiments, the aqueous liquid is water, aqueous buffer or a physiologically relevant aqueous liquid.

In other embodiments, the disclosure concerns highly concentrated compositions of low turbidity comprising a carbohydrate, a pH adjusting agent, a salt, a surfactant, a protein stabilizer, an emulsifier, an amino acid, and a plurality of particles comprising a therapeutic biologic, in a non-aqueous liquid carrier. In preferred embodiments, the disclosure concerns highly concentrated compositions of low turbidity comprising trehalose, arginine hydrochloride, sodium succinate, succinic acid, citric acid, sodium citrate, histidine, histidine hydrochloride, sodium chloride, hydroxypropyl beta-cyclodextrin, polysorbate, polysorbate 80 or sorbitan monooleate, and a plurality of particles comprising an antibody, in ethyl oleate. In certain preferred embodiments, the composition upon dissolution in water, aqueous buffer or any physiologically relevant aqueous liquid is substantially free of turbidity.

The composition comprising a plurality of particles comprising at least one therapeutic biologic described herein, can be prepared in a number of ways, as well as any methods of forming the particles disclosed in, for example, PCT/US2017/063150, PCT/US2018/043774, PCT/US2019/033875, and U.S. 62/799,696, each of which is hereby incorporated by reference in its entirety.

Methods of the Disclosure

The methods described herein, are generally provided for forming particles, the method comprising: a) providing droplets comprising a first liquid and an agent; b) contacting the droplets with a second liquid; c) allowing the droplets to dry; and d) removing the first and second liquids, thereby forming particles comprising an agent, wherein the particles comprise less than about 25% internal void spaces and the circularity of the particles is from about 0.10 to about 1.00 after removing the first and second liquids. As disclosed herein, the agent may be a therapeutic or diagnostic agent. In certain embodiments, the therapeutic agent has an activity per unit of about 0.5 to about 1.0. In certain preferred embodiments, the therapeutic agent is a therapeutic biologic. In preferred embodiments, the therapeutic biologic has an activity per unit of about 0.5 to about 1.0. In other embodiments, the first liquid contains an agent to produce particles for non-therapeutic or non-diagnostic use.

In some embodiments, the particles have less than about 25% internal void spaces after removing the first and second liquids, e.g., less than about 24, 20, 15, 10, 9, 8, 7, 6, 5, 4, 3, 2, 1, 0.5, or 0.1% internal void spaces after removing the first and second liquids. In certain embodiments, the particles may include less than 10% internal void spaces after removing the first and second liquids, less than 5% internal void spaces after removing the first and second liquids, less than 1% internal void spaces after removing the first and second liquids, less than 0.1% internal void spaces after removing the first and second liquids, or less than 0.01% internal void spaces after removing the first and second liquids. In preferred embodiments, the particles are substantially free from any internal void spaces after removing the first and second liquids.

In other embodiments, the circularity of the particles is at least about 10% after removing the first and second liquids, e.g., at least about 20, 30, 40, 50, 55, 60, 65, 70, 75, 80, 85, 90, 91, 92, 93, 94, 95, 96, 97, 98, 99, or about 100% after removing the first and second liquids. In some embodiments, the circularity of the particle is at least about 88% after removing the first and second liquids. In certain embodiments, the circularity of the particles is at least about 90% after removing the first and second liquids. In still other embodiments, the circularity of the particles is at least about 93% after removing the first and second liquids. In preferred embodiments, the circularity of the particles is at least about 97% after removing the first and second liquids.

In some embodiments, the circularity of the particles is from about 0.10 to about 1.00 after removing the first and second liquids, e.g., from about 0.20, 0.30, 0.40, 0.50. 0.60, 0.70, 0.75, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, or 0.99 to about 1.00 after removing the first and second liquids. In certain embodiments, the circularity of the particles is from about 0.88 to about 1.00 after removing the first and second liquids. In still other embodiments, the circularity of the particles is from about 0.90 to about 1.00 after removing the first and second liquids. In certain other embodiments, the circularity of the particles is from about 0.93 to about 1.00 after removing the first and second liquids. In preferred embodiments, the circularity of the particles is from about 0.97 to about 1.00 after removing the first and second liquids.

In other embodiments, the sphericity of the particles is at least about 50% after removing the first and second liquids, e.g., at least about 55, 60, 65, 70, 75, 80, 85, 90, 91, 92, 93, 94, 95, 96, 97, 98, 99, or about 100% after removing the first and second liquids. In some embodiments, the sphericity of the particles is from about 0.10 to about 1.00 after removing the first and second liquids, e.g., from about 0.20, 0.30, 0.40, 0.50. 0.60, 0.70, 0.75, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, or 0.99 to about 1.00 after removing the first and second liquids. In preferred embodiments, the sphericity of the particles is about 1.00 after removing the first and second liquids.

In certain embodiments, the sphericity of the particles may range from about 0.10 to about 1.00 after removing the first and second liquids, e.g., at least about 0.20, about 0.40, about 0.60, or about 0.80 to about 1.00 after removing the first and second liquids.

In preferred embodiments, the particles have a substantially smooth surface after removing the first and second liquids.

In some embodiments, the particles have a diameter between about 0.1 to about 1000 μm after removing the first and second liquids, e.g., about 0.1 to about 900, 800, 700, 600, 500, 400, 300, 200, 100, 90, 80, 70, 60, 50, 45, 40, 35, 30, 25, 20, 19, 18, 17, 16, 15, 14, 13, 12, 11, 10, 9, 8, 7, 6, 5, 4, 3, 2, 1, 0.9, 0.8, 0.7, 0.6, 0.5, 0.4, 0.3, or about 0.2 μm after removing the first and second liquids. In certain embodiments, the particles have a diameter between about 1 to about 100 μm after removing the first and second liquids, e.g., about 2, 3, 4, 5, 6, 7, 8, 9, 10, 11, 12, 13, 14, 15, 16, 17, 18, 19, 20, 25, 30, 35, 40, 45, or 50 to about 100 μm after removing the first and second liquids. In still other embodiments, the particles have a diameter between about 4 to about 100 μm after removing the first and second liquids. In certain other embodiments, the particles have a diameter between about 10 to about 100 μm after removing the first and second liquids. In preferred embodiments, the particles have a diameter between about 20 to about 50 μm after removing the first and second liquids. In certain preferred embodiments, the particles are intentionally controlled in its diameter. In some embodiments, the particles have diameters from about 0.1 to about 1000 μm after removing the first and second liquids, e.g., about 1 to about 400 μm, about 1 to about 200 μm, about 1 to about 100 μm, about 1 to about 50 μm, about 1 to about 25 μm, about 1 to about 10 μm, about 10 to about 100 μm, about 50 to about 100 μm, about 50 to about 75 μm, or about 75 to about 100 μm after removing the first and second liquids. In other embodiments, the particles have diameters from about 1 to about 100 μm after removing the first and second liquids, e.g., from about 4 to about 100 μm, from about 10 to about 100 μm, or from about 20 to about 50 μm after removing the first and second liquids.

In other embodiments, the particles have a surfactant content of less than about 10% by mass after removing the first and second liquids, e.g., less than about 9, 8, 7, 6, 5, 4, 3, 2, 1, 0.9, 0.8, 0.7, 0.6, 0.5, 0.4, 0.3, 0.2, 0.1, 0.09, 0.08, 0.07, 0.06, 0.05, 0.04, 0.03, 0.02, 0.01, 0.009, 0.008, 0.007, 0.006, 0.005, 0.004, 0.003, 0.002, 0.001% by mass after removing the first and second liquids. In some embodiments, the particles have a surfactant content of less than about 5% by mass after removing the first and second liquids. In certain embodiments, the particles have a surfactant content of less than about 3% by mass after removing the first and second liquids. In still other embodiments, the particles have a surfactant content of less than about 0.1% by mass after removing the first and second liquids. In certain other embodiments, the particles have a surfactant content of less than about 0.01% by mass after removing the first and second liquids. In some embodiments, the particles have a surfactant content of less than about 0.001% by mass after removing the first and second liquids. In preferred embodiments, the particles have a surfactant content of less than about 1% by mass after removing the first and second liquids. In certain preferred embodiments, the particles are substantially free from any surfactant content after removing the first and second liquids.

In some embodiments, the surfactant content of the particles is from 0 to 10 wt % after removing the first and second liquids, e.g., from 0 to 5 wt %, from 0 to 3 wt %, from 0 to 2 wt %, from 0 to 1 wt %, from 0 to 0.5 wt %, from 0 to 0.2 wt %, from 0 to 0.1 wt %, from 0 to 0.01 wt %, or from 0 to 0.001 wt % after removing the first and second liquids.

In other embodiments, the particles exhibit a skeletal density from about 1.00 to about 6.00 g/cm³ after removing the first and second liquids, e.g., from about 1.00 to about 5.00 g/cm³, from about 1.00 to about 3.00 g/cm³, from about 1.00 to about 2.00 g/cm³, from about 1.00 to about 1.50 g/cm³, from about 1.30 to about 1.50 g/cm³, from about 1.32 to about 1.50 g/cm³, or from about 1.10 to about 1.40 g/cm³ after removing the first and second liquids. In some embodiments, the particles exhibit a skeletal density from about 0.10 to about 5.00 g/cm³ after removing the first and second liquids, e.g., from about 0.10 to about 2.50 g/cm³, from about 0.10 to about 1.40 g/cm³, from about 0.50 to about 1.40 g/cm³, or from about 1.00 to about 1.40 g/cm³ after removing the first and second liquids. In certain embodiments, the particles have a skeletal density of about 0.09 to about 1.60 g/cm³ after removing the first and second liquids. In still other embodiments, the particles have a skeletal density of about 1.30 to about 1.58 g/cm³ after removing the first and second liquids. In preferred embodiments, the particles have a skeletal density of about 1.32 to about 1.50 g/cm³ after removing the first and second liquids.

In certain embodiments, the particles have a skeletal density of about 1000 mg/mL to about 1500 mg/mL after removing the first and second liquids, e.g., about 1050 mg/mL to about 1500 mg/mL, about 1100 mg/mL to about 1500 mg/mL, about 1150 mg/mL to about 1500 mg/mL, about 1200 mg/mL to about 1500 mg/mL, about 1250 mg/mL to about 1500 mg/mL, about 1300 mg/mL to about 1500 mg/mL, about 1310 mg/mL to about 1500 mg/mL, about 1320 mg/mL to about 1500 mg/mL, about 1330 mg/mL to about 1500 mg/mL, about 1340 mg/mL to about 1500 mg/mL, about 1350 mg/mL to about 1500 mg/mL, about 1360 mg/mL to about 1500 mg/mL, about 1370 mg/mL to about 1500 mg/mL, about 1380 mg/mL to about 1500 mg/mL, about 1390 mg/mL to about 1500 mg/mL, about 1400 mg/mL to about 1500 mg/mL, about 1410 mg/mL to about 1500 mg/mL, about 1420 mg/mL to about 1500 mg/mL, about 1430 mg/mL to about 1500 mg/mL, about 1440 mg/mL to about 1500 mg/mL, about 1450 mg/mL to about 1500 mg/mL, about 1460 mg/mL to about 1500 mg/mL, about 1470 mg/mL to about 1500 mg/mL, about 1480 mg/mL to about 1500 mg/mL, or about 1490 mg/mL to about 1500 mg/mL after removing the first and second liquids.

In some embodiments, the particles can be characterized by a glass transition temperature of about 0° C. to 250° C. after removing the first and second liquids, e.g., of about 34° C. to 200° C., of about 50° C. to 200° C., of about 60° C. to 200° C., of about 40 to about 160° C., of about 50 to about 110° C., of about 60 to about 100° C., or of about 75 to about 80° C. after removing the first and second liquids. In other embodiments, the particles have a glass transition temperature of about 40 to about 160° C. after removing the first and second liquids. In still other embodiments, the particles have a glass transition temperature of about 50 to about 110° C. after removing the first and second liquids. In certain embodiments, the particles have a glass transition temperature of about 60 to about 100° C. after removing the first and second liquids. In preferred embodiments, the particles have a glass transition temperature of about 75 to about 80° C. after removing the first and second liquids. In still other embodiments, the particles are heated to about ±30° C., e.g., to about ±20, ±10, 5, ±1° C., of the glass transition temperature of the particles during drying.

In certain embodiments, the particles have a glass transition temperature that is higher than about 160° C. after removing the first and second liquids. In certain other embodiments, the particles have a glass transition temperature that is higher than about 90° C. after removing the first and second liquids. In certain preferred embodiments, the particles have a glass transition temperature that is higher than about 50° C. after removing the first and second liquids.

In other embodiments, the particles further comprise a carbohydrate, a pH adjusting agent, a salt, a chelator, a mineral, a polymer, a surfactant, a protein stabilizer, an emulsifier, an antiseptic, an amino acid, an antioxidant, a protein, an organic solvent, a paraben, a bactericide, a fungicide, a vitamin, a preservative, a nutrient media, an oligopeptide, a biologic excipient, a chemical excipient, or a combination thereof. In certain embodiments, the particle further comprises a carbohydrate, a pH adjusting agent, a salt, a surfactant, a protein stabilizer, an emulsifier, an amino acid, or a combination thereof.

In some embodiments, the particles have less than 20% aggregation or less than 20% fragmentation of the therapeutic biologic after removing the first and second liquids, e.g., less than about 19, 18, 17, 16, 15, 14, 13, 12, 10, 9, 8, 7, 6, 5, 4, 3, 2, 1.9, 1.8, 1.7, 1.6, 1.5, 1.4, 1.3, 1.2, 1.1, 1, 0.9, 0.8, 0.7, 0.6, 0.5, 0.4, 0.3, 0.2, or 0.1% after removing the first and second liquids. In other embodiments, the particles have less than 10% aggregation or less than 10% fragmentation of the therapeutic biologic after removing the first and second liquids, e.g., less than about 9, 8, 7, 6, 5, 4, 3, 2, 1.9, 1.8, 1.7, 1.6, 1.5, 1.4, 1.3, 1.2, 1.1, 1, 0.9, 0.8, 0.7, 0.6, 0.5, 0.4, 0.3, 0.2, or 0.1% after removing the first and second liquids. In certain embodiments, the particles have about 3% to about 1% aggregation of the therapeutic biologic after removing the first and second liquids. In certain other embodiments, the particles have about 1% to about 0.5% aggregation of the therapeutic biologic after removing the first and second liquids. In preferred embodiments, the particles are substantially free from any aggregation of the therapeutic biologic after removing the first and second liquids. In still other embodiments, the particles have less than about 1% fragmentation of the therapeutic biologic after removing the first and second liquids. In certain preferred embodiments, the particles are substantially free from any fragmentation of the therapeutic biologic after removing the first and second liquids.

In other embodiments, the process of particle formation provides less than a 50% change in charge variants in the population of a diagnostic or therapeutic agent after removing the first and second liquids, e.g., an antibody or an antibody fragment after removing the first and second liquids, (e.g., less than 40, 30, 20, 10, 8, 5, 4, 3, or 1% after removing the first and second liquids) as compared to the therapeutic or diagnostic agent prior to particle formation. In certain embodiments, the particles have less than about 50% change in charge variants of the therapeutic biologic after removing the first and second liquids, e.g., less than about 45, 40, 35, 30, 25, 20, 15, 10, 9, 8, 7, 6, 5, 4, 3, 2, 1, 0.5, 0.1% after removing the first and second liquids, compared to the starting biologic prior to particle formation. In preferred embodiments, the particles are substantially free from any change in charge variants of the therapeutic biologic after removing the first and second liquids compared to the starting biologic prior to particle formation.

In some embodiments, the particles have less than about 3% of residual first and second liquids by mass remaining after removing the first and second liquids, e.g., less than about 2, 1.9, 1.8, 1.7, 1.6, 1.5, 1.4, 1.3, 1.2, 1.1, 1, 0.9, 0.8, 0.7, 0.6, 0.5, 0.4, 0.3, 0.2, 0.1, 0.09, 0.08, 0.07, 0.06, 0.05, 0.04, 0.03, 0.02, 0.01, 0.009, 0.008, 0.007, 0.006, 0.005, 0.004, 0.003, 0.002, or 0.001% by mass remaining after removing the first and second liquids. In other embodiments, the particles have less than about 3% residual moisture by mass remaining after removing the first and second liquids. In still other embodiments, the particles have less than about 2% residual moisture by mass remaining after removing the first and second liquids. In certain other embodiments, the particles have less than about 1% residual moisture by mass remaining after removing the first and second liquids. In certain other embodiments, the particles have less than about 0.1% of residual first and second liquids by mass remaining after removing the first and second liquids. In some preferred embodiments, the particles have less than about 0.01% of residual first and second liquids by mass remaining after removing the first and second liquids. In certain preferred embodiments, the particles have less than about 0.001% of residual first and second liquids by mass remaining after removing the first and second liquids. In preferred embodiments, the particles are substantially free from any residual first and second liquids by mass after removing the first and second liquids.

In other embodiments, the particles have greater than about 60% therapeutic biologic by weight after removing the first and second liquids, e.g., greater than about 65, 70, 75, 80, 85, 86, 87, 88, 89, 90, 91, 92, 93, 94, 95, 96, 97, 98, 99, 99.1, 99.2, 99.3, 99.4, 99.5, 99.6, 99.7, 99.8, 99.9% therapeutic biologic by weight after removing the first and second liquids. In some embodiments, the particles have greater than about 90% therapeutic biologic by weight after removing the first and second liquids. In certain embodiments, the particles have greater than about 95% therapeutic biologic by weight after removing the first and second liquids. In still other embodiments, the particles have greater than about 98% therapeutic biologic by weight after removing the first and second liquids. In preferred embodiments, the particles have greater than about 98% therapeutic biologic by weight after removing the first and second liquids. In certain preferred embodiments, the particles have greater than about 99% therapeutic biologic by weight after removing the first and second liquids.

As described herein, the particles may include both a core and a shell. In some embodiments, the particles do not include a shell. In some embodiments, the core is a gel core or dry solid-state core when no shell is present but may exist in the liquid state when the particles include a gel shell or dry solid-state shell. In other embodiments, the morphology of the particles is approximately spherical, mushroom-like, or raisin-like, among potentially other morphologies, depending on the conditions of particle formation. In certain embodiments the particle surfaces may have wrinkles or crenellations. When particles with core-shell architectures are employed, the individual layers may include the same or different agents, e.g., therapeutic or diagnostic agents, or no agents at all. Furthermore, layers with the same agents, e.g., therapeutic or diagnostic agents, may or may not include the agents in the same concentration.

In some embodiments, residual quantities of the first liquid in the particles after desiccation are from about 0 to about 0% by weight, e.g., from about 0 to about 5% by weight, from about 0 to about 3% by weight, from about 0 to about 1% by weight, from about 0.01 to about 5% by weight, from about 0.01 to about 3% by weight, or from about 0.01 to about 1% by weight. Exemplary methods of measuring residual solvent content include Karl Fischer titration, headspace gas chromatography mass spectrometry, and various weight-loss methods. In other embodiments, residual quantities of the second liquid in the particles after desiccation are from about 0 to about 10% by weight, e.g., from about 0 to about 5% by weight, from about 0 to about 3% by weight, from about 0 to about 1% by weight, about 0.01 to about 5% by weight, from about 0.01 to about 3% by weight, or from about 0.01 to about 1% by weight. Exemplary methods of measuring residual solvent content include Karl Fischer titration, headspace gas chromatography mass spectrometry, and various weight-loss methods. In certain embodiments, residual quantities of one or more shell liquids in the particles after desiccation are from about 0 to about 10% by weight, e.g., from about 0 to about 5% by weight, from about 0 to about 3% by weight, or from about 0 to about 1% by weight. Exemplary methods of measuring residual solvent content include Karl Fischer titration, headspace gas chromatography mass spectrometry, and various weight-loss methods.

In other embodiments, the particles have a residual net electrical charge of either polarity, i.e., net positive or net negative charge. In terms of magnitude, the particles may have from about 0 to about 10 billion charges, e.g., from about 0 to about 100 million charges, from about 0 to about 1 million charges, from about 0 to about 0.01 million charges, or from about 0 to about 100 charges. The magnitude of a charge is defined as the magnitude of charge carried by an electron, i.e., the elementary charge, $1.6 \times 10^{-19}$ Coulombs. Exemplary methods of measuring particle charge include those involving the analysis of particle motion in response to an externally applied electric field, e.g., electrical mobility. In some embodiments, the measuring can be done while particles are suspended in an insulating liquid such as an oil. In certain embodiments, the therapeutic or diagnostic agents have a zeta potential from about −90 to about 90 mV; e.g., from about −60 to about 60 mV, from about −40 to about 40 mV, from about −20 to about 20 mV, or from about −5 to about '5 mV. Exemplary methods of measuring zeta potential include reconstituting the therapeutic or diagnostic agents by dissolving the particles in water and analyzing the solution by electrophoretic light scattering, similarly to a dynamic light scattering (DLS) measurement which is performed in the presence of a positive or negative electric field.

In certain embodiments, the primary component of the particles, e.g., an agent, is characterized during the particle formation process by a Peclet from about 0 to about 10, e.g., from about 0 to about 9, from about 0 to about 8, from about 0 to about 7, from about 0 to about 6, from about 0 to about 5, from about 0 to about 4, from about 0 to about 3, from about 0 to about 2, from about 0 to about 1, from about 0 to about 0.5, from about 0 to about 0.25, or from about 0 to about 0.1. In certain other embodiments, the primary component of the particles, e.g., an agent, can be characterized during the particle formation process by an average diffusivity of the agent, from about 0 to about 10,000 $\mu m^2/s$, e.g., from about 0 to about 1,000 $\mu m^2/s$, from about 0 to about 100 $\mu m^2/s$, from about 0 to about 50 $\mu m^2/s$, from about 0 to about 25 $\mu m^2/s$, from about 0 to about 10 $\mu m^2/s$, from about 0 to about 5 $\mu m^2/s$, from about 0 to about 2.5 $\mu m^2/s$, or from about 0 to about 1 $\mu m^2/s$.

In some embodiments, the particles can be flowable. The Hausner ratio may be from about 1.0 to greater than about 3.0, e.g., from about 1.0 to about 3.0, from about 1.0 to about 2.0, from about 1.0 to about 1.70 (e.g., very poor), from about 1.0 to about 1.59, from about 1.0 to about 1.35, from about 1.0 to about 1.25, or from about 1.0 to about 1.11 (e.g., excellent). Exemplary methods of measuring the flowability of a powder include the tapped density method (Carr R. L. Chem. Eng., 1965; 72:163-168). Bulk density may first be obtained by adding a known mass of powder to a graduated cylinder. The density can be calculated as mass/volume. The same sample may then be mechanically tapped until further volume change is not observed. The tapped density can then be calculated as mass divided by the final volume of the powder. A comparison of tapped and bulk density may be used to index the ability of the powder to flow. In other embodiments, the Hausner ratio (unsettled apparent volume or bulk volume, $V_0$, divided by the final tapped volume, $V_f$) is a measure of the product's ability to settle and permits an assessment of the relative importance of interparticulate interactions. These interactions are less significant in free flowing powders. The bulk and tapped densities for such free flowing powders are close in value, such that the Hausner ratio is close to about 1.0.

In other embodiments, the particles have one or more of the following characteristics: a size from about 1 to about 50 μm; a solid core; a gel or solid shell; a density from about 1 to about 1.5 $g/cm^3$; a residual solvent content from about 0 to about 5 wt %; a porosity from about 0 to about 10%; a net electrical charge of either polarity, i.e., positive or negative charge, from about 0 to about 1 million charges; therapeutic or diagnostic components with a zeta potential from about −60 to about 60 mV; SvPs from about 0 to about 1,000,000 per mL upon reconstitution; a therapeutic or diagnostic agent loading from about 50 to about 100 wt % in which the activity of the therapeutic or diagnostic agents is from about 0.9 to about 1.0 upon reconstitution; a surfactant loading from about 0 to about 3 wt %; a primary component, e.g., the agent, for which the Peclet number was about 1 or less during the particle formation process; a primary component, e.g., an agent, for which the diffusivity was about 500 $\mu m^2/s$ or less during the particle formation process; less than about 10% aggregates upon reconstitution; less than about 10% fragments upon reconstitution; and/or a Hausner ratio between about 1.0 and about 1.35, or between about 1.0 and about 1.11.

The term "core-shell morphology" refers to a morphology having multiple layers that comprise different components and/or concentrations of components. A "dry" particle component, i.e., a dry core or a dry shell, including the agent or agents, has undergone a desiccation step or series of desiccation steps, such that its moisture or solvent content is substantially reduced in relation to that before any desiccation. As described herein, the particles may have a core-shell morphology, where the shell may include multiple layers. In certain embodiments, the core is solid, gel, or liquid. In some embodiments, the shell is a gel, in particular a hydrogel, ionogel, or organogel. In other embodiments, the shell is crystalline or semi-crystalline. In preferred embodiments, the particles have a morphology comprising a core and a shell.

In some embodiments, the particles have a morphology comprising a core and a shell, where the shell may include multiple layers. In certain embodiments, the core is solid, gel, or liquid. In some embodiments, the shell is a gel, in particular a hydrogel, ionogel, or organogel. Exemplary hydrogels, ionogels and organogels include collagen hydrogels, chitosan hydrogels, methylcellulose hydrogels, dextran hydrogels, alginate hydrogels, agarose hydrogels, poly(m-ethyl methacrylate) hydrogels, poly(amido amine) hydrogels, poly(ethyleneimine) hydrogels, polyethylene oxide hydrogels, gelatin hydrogels, hyaluronic acid hydrogels, 4-tert-butyl-1-aryl cyclohexanol organogels, L-lysine derivative organogels, poly(ethylene glycol) organogels, polycarbonate organogels, polyester organogels, polyalkene organogels, oxalyl amide derivative organogels, or a combinations thereof.

Particle Core: The core of each particle typically includes one or more therapeutic or diagnostic agents. The core is a solid-state dry core or gel when no shell is present but may exist in the liquid state when the particle includes a gel shell or solid-state dry shell. When a shell is present, the shell may include the therapeutic or diagnostic agent, while the core may not.

Particle Shell: Generally, any excipient is suitable as a shell material. Exemplary excipients include, but are not limited to, sugars, salts, and amino acids. Therapeutic agents, diagnostic agents, and biocompatible polymers may also be used to form the shell. This includes small molecule drugs. Non-limiting examples of hydrophilic biocompatible polymers include poly(vinyl alcohol), poly(acrylic acid), poly(acrylamide), poly(ethylene oxide), or co-polymers or a combination of any two or more of them. Hydrophilic polymers may be modified to adjust their characteristics. The shell component may alternatively or additionally include one or more biocompatible hydrophobic polymers. Hydrophobic polymers may be modified to adjust their characteristics. Non-limiting examples of hydrophobic polymers include polycaprolactam, poly(lactic acid), poly(glycolic acid), polycaprolactone, PLGA or co-polymers, or a combination of any two or more of them. In some embodiments, a PLGA (50:50) polymer is used as a shell to encapsulate a therapeutic, e.g., an antibody or an antibody fragment, in an amount just below its solubility limit. The polymer also may be prepared as a function of PLGA at various lactic acid-glycolic acid ratios, as well as be co-polymer with other polymers, e.g., chitosan, cellulose, etc.

In some embodiments, the thickness of the particle shell may range from about 0 to about 90% of the diameter of the particle. The shell does not have to be uniform of fully formed for encapsulation. In other embodiments, the interface between the shell and the core is partially blended, such that a clear line of demarcation does not exist. One or more therapeutic or diagnostic agents, as described herein, can be included in the particle shell. In still other embodiments, the therapeutic or diagnostic agents can be the same or different as those in the core. In certain other embodiments, the concentration of the therapeutic or diagnostic agent in the shell may be in the range about 0.0001 to about 2000 mg/mL (or crystalline density of the therapeutic or diagnostic agent, if higher).

Core-Shell Ratio: For those embodiments in which the particle includes a shell, a core-shell volume ratio between about 1:99 vol % and about 99:1% are expected to be most useful, e.g., about 10:90 vol % or about 90:10 vol % or about 95:5 vol %. Complete coverage is not always required for sufficient encapsulation. In certain embodiments, e.g., for highly concentrated cores, thick shells can be beneficial. In some embodiments, the core-shell ratio may be useful in the modulation of the release kinetics of the therapeutic or diagnostic agent or agents. In other embodiments, it may be advantageous to have a polydisperse system, e.g., for lowering the viscosity of a pharmaceutical suspension formulation comprising the particles. In this instance a variety of core-shell ratios may be of interest.

Droplets

Droplets as described herein, can be formed through any of several techniques that are known in the art. These include rotary atomization, pneumatic atomization, ultrasonic atomization, sonic atomization, vibrating mesh nebulization, jet atomization, microfluidic droplet generation, flow focusing, membrane emulsification, electrospray, or homogenization. The term "droplet" or "droplets" or "drops" refer to a material that has a liquid outer surface. In certain embodiments, the droplets of step a) are formed by electrospray, an ultrasonic atomizer, or a microfluidic device. In preferred embodiments, the droplets of step a) are formed in a microfluidic device. In certain preferred embodiments, the droplets formed in the microfluidic device are regularly spaced in the microfluidic device.

The term "feed solution" refers to a preparation of the therapeutic or diagnostic agents in the first liquid, either as a solution, a slurry, or some other liquid form. In some embodiments, the preparation contains excipients. In other embodiments, the preparation further contains a buffer.

In some embodiments, the first liquid is aqueous, an organic solvent, an ionic liquid, a hydrogel, an ionogel, or a combination thereof. In other embodiments, the first liquid is aqueous. In certain embodiments, the first liquid is water, 0.9% saline, lactated Ringer's solution, buffers, dextrose 5%, or a combination thereof. In certain other embodiments, the buffer is acetate buffer, histidine buffer, succinate buffer, HEPES buffer, tris buffer, carbonate buffer, citrate buffer, phosphate buffer, phosphate-buffered saline, glycine buffer, barbital buffer, cacodylate buffer, ammonium formate buffer, urea solution, or a combination thereof. In preferred embodiments, the first liquid is water.

In other embodiments, the organic liquid is acetone, acetonitrile, acyclic alkanes (e.g., hexanes, heptane, pentane), amyl acetate, butanol, butyl acetate, chlorobenzene, chloroform, cumene, cyclohexane, 1,2-dichloroethene, dichloromethane, diethyl ether, dimethoxyethane, dimethylacetamide, dimethylformamide, dimethyl sulfoxide, 1,4-dioxane, ethanol, 2-ethoxyethanol, ethyl acetate, ethyl nitrate, ethyleneglycol, hydrazine, isopropanol, methanol, methyl acetate, 2-methyl-1-butanol, 2-methyl-1-propanol, methylbutyl ketone, methylcyclohexane, methylethyl ketone, methylpyrrolidone, methyl tert-butyl ether, nitromethane, propanol, propyl acetate, sulfolane, propyleneglycol, tetrahydrofuran, tetralin, toluene, 1,1,2-tricholoroethane, triethylamine, xylene, benzyl benzoate, ethyl lactate, dimethyl isosorbide, dimethyl sulfoxide, glycofurol, diglyme, methyl tert-butyl ether, polyethylene glycol, 2-pyrrolidone, tetrahydrofurfuryl alcohol, trigylcerides, octyl acetate, ethanol, butanol, octanol, decanol, diglyme, tocopherol, octa-fluoropropane, (perfluorohexyl)octane, n-acetyltryptophan, trigylcerides, triglycerides of the fractionated plant fatty acids C8 and C10, propylene glycol diesters of saturated plant fatty acids C8 and C10, ethyl laurate, methyl caprylate, methyl caprate, methyl myristate, methyl oleate, methyl linoleate, dimethyl adipate, dibutyl suberate, diethyl sebacate, ethyl macadamiate, trimethylolpropane triisosterate, isopropyl laurate, isopropyl myristate, diethyl succinate, polysorbate esters, ethanol amine, propanoic acid, triacetin, citral, anisole, anethol, benzaldehyde, linalool, caprolactone, phenol, thioglycerol, dimethylacetamide, ethyl formate, ethyl hexyl acetate, eugenol, clove bud oil, diethyl glycol monoether, dimethyl isosorbide, isopropyl acetate, methyl isobutyl ketone, methyl tert-butyl ether, N-methyl pyrrolidone, perfluorodecalin, 2-pyrrolidone, ethyl oleate, ethyl caprate, dibutyl adipate, hexanoic acid, octanoic acid, diethyl glycol monoether, gamma-butyrolactone, polyoxyl 40 hydrogenated castor oil, polyoxyl 35 castor oil, propylene carbonate, octanol, hexanol, sorbitan monooleate, n-acetyltryptophan, solketal, an alkyl acetate, an aryl acetate, an aryl alkyl acetate, tolyl acetate, benzyl acetate, polysorbate 80, phenethyl acetate, phenyl acetate, glycerol, or a combination thereof. In other embodiments, the first liquid is an oil. In certain embodiments, the oil is coconut oil, cottonseed oil, fish oil, grape seed oil, hazelnut oil, hydrogenated vegetable oils, lime oil, olive oil, palm seed oil, peanut oil, peppermint oil, safflower oil, sesame oil, soybean oil, sunflower oil, walnut oil, silicon oil, mineral oil, or a combination thereof. In still other embodiments, the first liquid is an ionic liquid. In certain other embodiments, the ionic liquid contains (i) cations such as pyridinium, pyridazinium, pyrimidinium, pyrazinium, imidazolium, pyrazolium, thiazolium, oxazolium, triazolium, ammonium, sulfonium; and (ii) anions such as halides, sulfates, sulfonates, carbonates, phosphates, bicarbonates, nitrates, acetates, $PF_6—$, $BF_4—$, triflate, nonaflate, bis(triflyl)amide, trifluoroacetate, heptafluorobutanoate, haloaluminate, or a combination thereof.

In certain embodiments, the first liquid is a hydrogel, an ionogel, or a combination thereof. Exemplary hydrogels are prepared from polymers such as collagen, chitosan, methylcellulose, dextran, alginate, agarose, poly(methyl methacrylate), poly(amido amine), poly(ethyleneimine), polyethylene oxide, gelatin, hyaluronic acid, or a combination thereof, and may contain water, aqueous solutions, and other polar solvents. Exemplary organogels are prepared form organogelators such as 4-tert-butyl-1-aryl cyclohexanols, L-lysine derivatives, poly(ethylene glycol), polycarbonate, polyesters, polyalkenes, oxalyl amide derivatives containing alkyl ester groups, or low molecular weight compounds such as fatty acids and n-alkanes, and contain a non-polar solvent phase. Ionogels are analogous to organogels with the exception that the solvent phase is an ionic liquid.

In some embodiments, the concentration of the therapeutic agent in the first liquid as described herein, is about 10 mg/mL to about 650 mg/mL, e.g., about 20, 30, 50, 75, 100, 125, 150, 175, 200, 225, 250, 275, 300, 325, 350, 375, 400, 425, 450, 475, 500, 525, 550, 575, 600, 625 mg/mL to about 650 mg/mL; about 20 mg/mL to about 625 mg/mL, e.g., about 20, 30, 50, 75, 100, 125, 150, 175, 200, 225, 250, 275, 300, 325, 350, 375, 400, 425, 450, 475, 500, 525, 550, 575, 600 mg/mL to about 625 mg/mL; about 20 mg/mL to about 600 mg/mL, e.g., about 20, 30, 50, 75, 100, 125, 150, 175, 200, 225, 250, 275, 300, 325, 350, 375, 400, 425, 450, 475, 500, 525, 550, 575 mg/mL to about 600 mg/mL; about 20 mg/mL to about 575 mg/mL, e.g., about 20, 30, 50, 75, 100, 125, 150, 175, 200, 225, 250, 275, 300, 325, 350, 375, 400, 425, 450, 475, 500, 525, 550 mg/mL to about 575 mg/mL; about 20 mg/mL to about 550 mg/mL, e.g., about 20, 30, 50, 75, 100, 125, 150, 175, 200, 225, 250, 275, 300, 325, 350, 375, 400, 425, 450, 475, 500, 525 mg/mL to about 550 mg/mL; about 20 mg/mL to about 525 mg/mL, e.g., about 20, 30, 50, 75, 100, 125, 150, 175, 200, 225, 250, 275, 300, 325, 350, 375, 400, 425, 450, 475, 500 mg/mL to about 525 mg/mL; about 20 mg/mL to about 500 mg/mL, e.g., about 20, 30, 50, 75, 100, 125, 150, 175, 200, 225, 250, 275, 300, 325, 350, 375, 400, 425, 450, 475 mg/mL to about 500 mg/mL; about 20 mg/mL to about 475 mg/mL, e.g., about 20, 30, 50, 75, 100, 125, 150, 175, 200, 225, 250, 275, 300, 325, 350, 375, 400, 425, 450 mg/mL to about 475 mg/mL; about 20 mg/mL to about 450 mg/mL, e.g., about 20, 30, 50, 75, 100, 125, 150, 175, 200, 225, 250, 275, 300, 325, 350, 375, 400, 425 mg/mL to about 450 mg/mL; about 20 mg/mL to about 425 mg/mL, e.g., about 20, 30, 50, 75, 100, 125, 150, 175, 200, 225, 250, 275, 300, 325, 350, 375, 400 mg/mL to about 425 mg/mL; about 20 mg/mL to about 400 mg/mL, e.g., about 20, 30, 50, 75, 100, 125, 150, 175, 200, 225, 250, 275, 300, 325, 350, 375 mg/mL to about 400 mg/mL; about 20 mg/mL to about 375 mg/mL, e.g., about 20, 30, 50, 75, 100, 125, 150, 175, 200, 225, 250, 275, 300, 325, 350 mg/mL to about 375 mg/mL; about 20 mg/mL to about 350 mg/mL, e.g., about 20, 30, 50, 75, 100, 125, 150, 175, 200, 225, 250, 275, 300, 325 mg/mL to about 350 mg/mL; about 20 mg/mL to about 325 mg/mL, e.g., about 20, 30, 50, 75, 100, 125, 150, 175, 200, 225, 250, 275, 300 mg/mL to about 325 mg/mL; or about 20 mg/mL to about 300 mg/mL, e.g., about 20, 30, 50, 75, 100, 125, 150, 175, 200, 225, 250, 275 mg/mL to about 300 mg/mL. In other embodiments, the concentration of the therapeutic agent in the first liquid is about 10 mg/mL to about 500 mg/mL. In certain embodiments, the concentration of the therapeutic agent in the first liquid is about 10 mg/mL to about 100 mg/mL. In preferred embodiments, the concentration of the therapeutic agent in the first liquid is about 20 mg/mL to about 100 mg/mL. In other embodiments of the disclosure, the concentration of the therapeutic or diagnostic agent in the first liquid is from about 0.0001 to about 1000 mg/mL, e.g., about 100 to about 800, about 200 to about 700, about 200 to about 600, or about 300 to about 700 mg/mL. In still other embodiments, the particles have a mass loading of the therapeutic or diagnostic agent from about 1% to about 100%.

In other embodiments, the first liquid has a viscosity of less than about 200 mPa·s, less than about 150 mPa·s, less than about 125 mPa·s, less than about 100 mPa·s, less than about 75 mPa·s, less than about 75 mPa·s, less than about 70 mPa·s, less than about 65 mPa·s, less than about 60 mPa·s, less than about 55 mPa·s, less than about 50 mPa·s, less than about 45 mPa·s, less than about 40 mPa·s, less than about 35 mPa·s, less than about 30 mPa·s, less than about 25 mPa·s, less than about 20 mPa·s, less than about 19 mPa·s, less than about 18 mPa·s, less than about 17 mPa·s, less than about 16 mPa·s, less than about 15 mPa·s, less than about 14 mPa·s, less than about 13 mPa·s, less than about 12 mPa·s, less than about 11 mPa·s, less than about 10 mPa·s, less than about 9.5 mPa·s, less than about 9 mPa·s, less than about 8.5 mPa·s, less than about 8 mPa·s, less than about 7.5 mPa·s, less than about 7 mPa·s, less than about 6.5 mPa·s, less than about 6 mPa·s, less than about 5.5 mPa·s, less than about 5 mPa·s, less than about 4.5 mPa·s, less than about 4 mPa·s, less than about 3.5 mPa·s, less than about 3 mPa·s, less than about 2.5 mPa·s, less than about 2 mPa·s, less than about 1.5 mPa·s, less than about 1 mPa·s, less than about 0.5 mPa·s, less than about 0.1 mPa·s, less than about 0.05 mPa·s, or less than about 0.01 mPa·s (one millipascal-second). In other embodiments, the first liquid has a viscosity of about 0.01 mPa·s to about 10,000 mPa·s, e.g., from about 0.01 mPa·s to about 1,000 mPa·s, from about 0.01 mPa·s to about 100 mPa·s, from about 0.01 mPa·s to about 50 mPa·s, from about 0.01 mPa·s to about 25 mPa·s, from about 0.01 mPa·s to about 10 mPa·s, from about 0.01 mPa·s to about 5 mPa·s, or from about 0.01 mPa·s to about 1 mPa·s. In certain embodiments, the first liquid has a viscosity that can range from about 0.27 mPa·s to about 200 mPa·s, e.g., about 0.27 mPa·s to about 50 mPa·s, about 1 mPa·s to about 30 mPa·s, or about 20 mPa·s to about 50 mPa·s. In still other embodiments, the first liquid has a viscosity that ranges from about 0.27 mPa·s to about 200 mPa·s, e.g., about 0.27 mPa·s to about 100 mPa·s, about 0.27 mPa·s to about 50 mPa·s, about 0.27 mPa·s to about 30 mPa·s, about 1 mPa·s to about 20 mPa·s, or about 1 mPa·s to about 15 mPa·s. Methods of controlling viscosity include temperature regulation and viscosity modifying additives. Mixtures of liquids may also be used to control viscosity.

In some embodiments, the first liquid has a viscosity from about 0.01 to about 10,000 mPa·s. In other embodiments, the first liquid has a viscosity of less than about 100 mPa·s. In still other embodiments, the first liquid has a viscosity of less than about 10 mPa·s. In certain other embodiments, the first liquid has a viscosity of less than about 3 mPa·s. In certain embodiments, the first liquid has a viscosity of less than about 0.9 mPa·s. In preferred embodiments, the first liquid has a viscosity of less than about 0.5 mPa·s.

In certain embodiments, the first liquid further comprises a surfactant.

In some embodiments, the surfactant is polysorbate, magnesium stearate, sodium dodecyl sulfate, TRITON™ N-101, glycerin, polyoxyethylated castor oil, docusate, sodium stearate, decyl glucoside, nonoxynol-9, cetyltrimethylammonium bromide, sodium bis(2-ethylhexyl) sulfosuccinate, lecithin, sorbitan ester, or a combination thereof. In certain embodiments, the surfactant is polysorbate, docusate or lecithin. In preferred embodiments, the surfactant is polysorbate 20, polysorbate 60, or polysorbate 80. In certain preferred embodiments, the surfactant is polysorbate 20 or polysorbate 80. In certain other embodiments, the fatty acid ester of sorbitol is a sorbitan ester, e.g., span 20, span 40, span 60, or span 80.

In other embodiments, the second liquid is aqueous, an organic solvent, an ionic liquid, a hydrogel, ionogel, protein stabilizer, or a combination thereof. In some embodiments, the second liquid is aqueous. In preferred embodiments, the second liquid is an organic solvent.

In some embodiments, the organic solvent is benzyl alcohol, benzyl benzoate, castor oil, coconut oil, corn oil, cottonseed oil, fish oil, grape seed oil, hazelnut oil, hydrogenated palm seed oil, olive oil, peanut oil, peppermint oil, safflower oil, sesame oil, soybean oil, sunflower oil, vegetable oil, walnut oil, polyethylene glycol, glycofurol, acetone, diglyme, dimethylacetamide, dimethyl isosorbide, dimethyl sulfoxide, ethanol, ethyl acetate, butyl acetate, ethyl ether, ethyl lactate, isopropyl acetate, methyl acetate, methyl isobutyl ketone, methyl tert-butyl ether, N-methyl pyrrolidone, perfluorodecalin, 2-pyrrolidone, trigylcerides, tetrahydrofurfuryl alcohol, triglycerides of the fractionated plant fatty acids C8 and C10 (e.g., MIGLYOL® 810 and MIGLOYL® 812N), propylene glycol diesters of saturated plant fatty acids C8 and C10 (e.g., MIGLYOL® 840), ethyl oleate, ethyl caprate, dibutyl adipate, fatty acid esters, hexanoic acid, octanoic acid, triacetin, diethyl glycol monoether, gamma-butyrolactone, eugenol, clove bud oil, citral, limonene, or a combination thereof. In certain embodiments, the organic solvent is ethyl acetate or butyl acetate.

In still other embodiments, the organic solvent is acetone, acetonitrile, acyclic alkanes (e.g., hexanes, heptane, pentane), amyl acetate, butanol, butyl acetate, chlorobenzene, chloroform, cumene, cyclohexane, 1,2-dichloroethene, dichloromethane, diethyl ether, dimethoxyethane, dimethylacetamide, dimethylformamide, dimethyl sulfoxide, 1,4-dioxane, ethanol, 2-ethoxyethanol, ethyl acetate, ethyl nitrate, ethyleneglycol, hydrazine, isopropanol, methanol, methyl acetate, 2-methyl-1-butanol, 2-methyl-1-propanol, methylbutyl ketone, methylcyclohexane, methylethyl ketone, methylpyrrolidone, methyl tert-butyl ether, nitromethane, propanol, propyl acetate, sulfolane, propyleneglycol, tetrahydrofuran, tetralin, toluene, 1,1,2-trichloroethane, triethylamine, xylene, benzyl benzoate, ethyl lactate, dimethyl isosorbide, dimethyl sulfoxide, glycofurol, diglyme, methyl tert-butyl ether, polyethylene glycol, 2-pyrrolidone, tetrahydrofurfuryl alcohol, trigylcerides, octyl acetate, ethanol, butanol, octanol, decanol, diglyme, tocopherol, octa-fluoropropane, (perfluorohexyl)octane, n-acetyltryptophan, trigylcerides, triglycerides of the fractionated plant fatty acids C8 and C10, propylene glycol diesters of saturated plant fatty acids C8 and C10, ethyl laurate, methyl caprylate, methyl caprate, methyl myristate, methyl oleate, methyl linoleate, dimethyl adipate, dibutyl suberate, diethyl sebacate, ethyl macadamiate, trimethylolpropane triisosterate, isopropyl laurate, isopropyl myristate, diethyl succinate, polysorbate esters, ethanol amine, propanoic acid, triacetin, citral, anisole, anethol, benzaldehyde, linalool, caprolactone, phenol, thioglycerol, dimethylacetamide, ethyl formate, ethyl hexyl acetate, eugenol, clove bud oil, diethyl glycol monoether, dimethyl isosorbide, isopropyl acetate, methyl isobutyl ketone, methyl tert-butyl ether, N-methyl pyrrolidone, perfluorodecalin, 2-pyrrolidone, ethyl oleate, ethyl caprate, dibutyl adipate, hexanoic acid, octanoic acid, diethyl glycol monoether, gamma-butyrolactone, polyoxyl 40 hydrogenated castor oil, polyoxyl 35 castor oil, propylene carbonate, octanol, hexanol, sorbitan monooleate, n-acetyltryptophan, solketal, an alkyl acetate, an aryl acetate, an aryl alkyl acetate, tolyl acetate, benzyl acetate, polysorbate 80, phenethyl acetate, phenyl acetate, glycerol, or a combination thereof.

In certain embodiments, the organic solvent is acetonitrile, chlorobenzene, chloroform, cyclohexane, cumene, 1,2-dichloroethene, dichloromethane, 1,2-dimethoxyethane, N,N-dimethylacetamide, N,N-dimethylformamide, 1,4-dioxane, 2-ethoxyethanol, ethyleneglycol, formamide, hexane, methanol, 2-methoxyethanol, methylbutyl ketone, methylcyclohexane, methylisobutylketone, N-methylpyrrolidone, nitromethane, pyridine, sulfolane, tetrahydrofuran, tetralin, toluene, 1,1,2-trichloroethene, xylene, acetic acid, acetone, anisole, 1-butanol, 2-butanol, butylacetate, tert-butylmethyl ether, dimethyl sulfoxide, ethanol, ethylacetate, ethyl ether, ethyl formate, formic acid, heptane, isobutylacetate, isopropylacetate, methylacetate, 3-methyl-1-butanol, methylethyl ketone, 2-methyl-1-propanol, pentane, 1-pentanol, 1-propanol, 2-propanol, propylacetate, triethylamine, 1,1-diethoxypropane, 1,1-dimethoxymethane, 2,2-dimethoxypropane, isooctane, isopropyl ether, methylisopropyl ketone, methyltetrahydrofuran, petroleum ether, trichloroacetic acid, trifluoroacetic acid, decanol, 2-ethylhexylacetate, amylacetate, or a combination thereof.

In some embodiments, the second liquid is an ionic liquid. In certain embodiments, the second liquid is a protein stabilizer.

In other embodiments, the second liquid has a viscosity of less than about 200 mPa·s, less than about 150 mPa·s, less than about 125 mPa·s, less than about 100 mPa·s, less than about 75 mPa·s, less than about 75 mPa·s, less than about 70 mPa·s, less than about 65 mPa·s, less than about 60 mPa·s, less than about 55 mPa·s, less than about 50 mPa·s, less than about 45 mPa·s, less than about 40 mPa·s, less than about 35 mPa·s, less than about 30 mPa·s, less than about 25 mPa·s, less than about 20 mPa·s, less than about 19 mPa·s, less than about 18 mPa·s, less than about 17 mPa·s, less than about 16 mPa·s, less than about 15 mPa·s, less than about 14 mPa·s, less than about 13 mPa·s, less than about 12 mPa·s, less than about 11 mPa·s, less than about 10 mPa·s, less than about 9.5 mPa·s, less than about 9 mPa·s, less than about 8.5 mPa·s, less than about 8 mPa·s, less than about 7.5 mPa·s, less than about 7 mPa·s, less than about 6.5 mPa·s, less than about 6 mPa·s, less than about 5.5 mPa·s, less than about 5 mPa·s, less than about 4.5 mPa·s, less than about 4 mPa·s, less than about 3.5 mPa·s, less than about 3 mPa·s, less than about 2.5 mPa·s, less than about 2 mPa·s, less than about 1.5 mPa·s, less than about 1 mPa·s, less than about 0.5 mPa·s, less than about 0.1 mPa·s, less than about 0.05 mPa·s, or less than about 0.01 mPa·s (one millipascal-second). In other embodiments, the second liquid has a viscosity of about 0.01 mPa·s to about 10,000 mPa·s, e.g., from about 0.01 mPa·s to about 1,000 mPa·s, from about 0.01 mPa·s to about 100 mPa·s, from about 0.01 mPa·s to about 50 mPa·s, from about 0.01 mPa·s to about 25 mPa·s, from about 0.01 mPa·s to about 10 mPa·s, from about 0.01 mPa·s to about 5 mPa·s, or from about 0.01 mPa·s to about 1 mPa·s. In certain embodiments, the second liquid has a viscosity that can range from about 0.27 mPa·s to about 200 mPa·s, e.g., about 0.27 mPa·s to about 50 mPa·s, about 1 mPa·s to about 30 mPa·s, or about 20 mPa·s to about 50 mPa·s. In still other embodiments, the second liquid has a viscosity that ranges from about 0.27 mPa·s to about 200 mPa·s, e.g., about 0.27 mPa·s to about 100 mPa·s, about 0.27 mPa·s to about 50 mPa·s, about 0.27 mPa·s to about 30 mPa·s, about 1 mPa·s to about 20 mPa·s, or about 1 mPa·s to about 15 mPa·s. Methods of controlling viscosity include temperature regulation and viscosity modifying additives. Mixtures of liquids may also be used to control viscosity.

In certain embodiments, the second liquid further comprises a surfactant. In still other embodiments, the surfactant is polysorbate, magnesium stearate, sodium dodecyl sulfate, TRITON™ N-101, glycerin, polyoxyethylated castor oil, docusate, sodium stearate, decyl glucoside, nonoxynol-9, cetyltrimethylammonium bromide, sodium bis(2-ethyl-hexyl) sulfosuccinate, lecithin, sorbitan ester, or a combination thereof.

In some embodiments, the second liquid has a viscosity from about 0.01 to about 10,000 mPa·s. In other embodiments, the second liquid has a viscosity of less than about 10 mPa·s. In still other embodiments, the second liquid has a viscosity of less than about 5 mPa·s. In certain other embodiments, the second liquid has a viscosity of less than about 2 mPa·s. In certain embodiments, the second liquid has a viscosity of less than about 0.70 mPa·s. In preferred embodiments, the second liquid has a viscosity of less than about 0.40 mPa·s.

The droplets as described herein, may include a first liquid and one or more agents, e.g., a therapeutic and/or diagnostic agent. In certain embodiments, the therapeutic agent is a therapeutic biologic. In still other embodiments, the therapeutic biologic has an activity per unit of about 0.5 to about 1.0. In certain other embodiments, the concentration of the agent, e.g., a therapeutic or diagnostic agent, in the first liquid can be in the range of about 0.0001 to about 1000 mg/mL, e.g., about 100 to about 900 mg/mL, about 200 to about 800 mg/mL, about 200 to about 700 mg/mL, about 200 to about 600 mg/mL, or about 300 to about 500 mg/mL.

In some embodiments, the first liquid is aqueous or an organic solvent, and the second liquid is an oil, aqueous, or an ionic liquid. In other embodiments, the first liquid and/or the second liquid has a viscosity from about 0.01 mPa·s to about 10,000 mPa·s. In certain embodiments, the second liquid is a mixture of two or more liquids of different polarities, where the mixture includes liquids that have differing solubility with the first liquid. In still other embodiments, the first liquid or second liquid further includes a carbohydrate, a pH adjusting agent, a salt, a chelator, a mineral, a polymer, a surfactant, a protein stabilizer, an emulsifier, an antiseptic, an amino acid, an antioxidant, a protein, an organic solvent, a paraben, a bactericide, a fungicide, a vitamin, a preservative, a nutrient media, or a combination thereof. The term "polarity" or "polarities" refer to the overall solvation capability (solvation power) of the solvent, which in turn depends on the action of all possible, nonspecific and specific, intermolecular interactions between solute ions or molecules and solvent molecules, excluding, however, those interactions leading to definite chemical alterations of the ions of molecules of the solute (Chem. Rev., 1994, 94, 2319-2358). A prediction of solvent polarity may be made from their dielectric constant. Solvents with high dielectric constants are considered more polar and those with low dielectric constants are considered less polar or nonpolar (<~15).

In other embodiments, each of the other components is, independently, about 0.0001 to about 99% (w/v) of the first liquid, e.g., about 0.0001 to about 90% (w/v), about 0.0001 to about 50% (w/v), about 0.0001 to about 10% (w/v), about 0.0001 to about 1% (w/v), or about 0.0001 to about 0.1% (w/v). In certain embodiments, the amount of additional compound, i.e., excipient, present in the first liquid, second, liquid, or medium, is as shown Table 2.

TABLE 2

| Excipient | Range 1 | Range 2 | Range 3 | Range 4 |
|---|---|---|---|---|
| Carbohydrate | 10-30% | 3-50% | 1-80% | 0.3-99% |
| pH adjusting agent | 0.5-5% | 0.2-40% | 0.05-70% | 0.01-99% |

TABLE 2-continued

| Excipient | Range 1 | Range 2 | Range 3 | Range 4 |
|---|---|---|---|---|
| Salt | 10-50% | 3-70% | 1-85% | 0.3-99% |
| Chelator | 0.01-1% | 0.003-40% | 0.001-80% | 0.0003-99% |
| Mineral | 10-50% | 3-70% | 1-80% | 0.3-99% |
| Polymer | 10-60% | 3-75% | 1-85% | 0.3-99% |
| Surfactant | .01-1% | 0.003-40% | 0.001-80% | 0.0003-99% |
| Amino acids | 10-25% | 3-50% | 1-85% | 0.3-99% |
| Oligopeptide | 10-25% | 3-50% | 1-85% | 0.3-99% |
| Biologic | 10-70% | 3-70% | 1-85% | 0.3-99% |
| Chemical | 10-50% | 3-70% | 1-85% | 0.3-99% |
| Antiseptic | .5-10% | 0.2-50% | 0.05-70% | 0.02-99% |
| Antioxidant | 0.01-1% | 0.003-40% | 0.001-80% | 0.0003-99% |
| Paraben | 0.01-5% | 0.005-10% | 0.001-50% | 0.001-99% |
| Bactericide | 0.01-5% | 0.005-10% | 0.001-50% | 0.001-99% |
| Fungicide | 0.01-5% | 0.005-10% | 0.001-50% | 0.001-99% |
| Vitamin | 1-50% | 1-70% | 0.1-85% | 0.01-99% |
| Preservative | 10-50% | 3-70% | 1-85% | 0.3-99% |
| Analgesic | 0.01-5% | 0.005-10% | 0.001-50% | 0.001-99% |
| Nutrient media | 10-50% | 3-70% | 1-85% | 0.3-99% |
| Organic liquid | 0.001-2% | 0.0003-1% | 0.0001-10% | 0.00003-99% |

In some embodiments, the cohesive forces (e.g., interfacial tension) on the droplet surface in the second liquid pulls the droplets into a spherical shape which is maintained during the course of drying. In other embodiments, the sphericity of the particles ranges from about 0.1 to about 1, e.g., at least about 0.2, about 0.4, about 0.6, or about 0.8. In certain embodiments, the process can result in uniform particles with high sphericity (about >0.9) and roundness or circularity. Methods of measuring particle sphericity include image analysis of scanning electron micrographs of the particles in which the average roundness is calculated on the basis of the cross-sectional shapes of the particles projected onto the plane of the image. Such roundness or circularity factors can be extended to identify the corresponding sphericity.

In other embodiments, the droplet has a core-shell morphology in the which the first liquid (the droplet "core") is surrounded by one or more concentric layers of additional liquid (the droplet "shell(s)"), each of which may or may not be defined by a unique set of components and/or a unique concentration of components. Each shell liquid can be an aqueous liquid, an organic liquid, an oil, an ionic liquid, or a combination thereof and include one or more agents, e.g., therapeutic or diagnostic agents. The concentration of the agent, e.g., a therapeutic or diagnostic agent, in a shell liquid can be in the range of about 0.0001 to about 1000 mg/mL, e.g., about 100 to about 900 mg/mL, about 200 to about 800 mg/mL, about 200 to about 700 mg/mL, about 200 to about 600 mg/mL, or about 300 to about 500 mg/mL. The shell liquid can further include, e.g., a carbohydrate, a pH adjusting agent, a salt, a chelator, a mineral, a polymer, a surfactant, an amino acid, an oligopeptide, a biologic excipient, a chemical excipient, an antiseptic, an antioxidant, a paraben, a bactericide, a fungicide, a vitamin, a preservative, an analgesic, and/or nutrient media.

In some embodiments, a surfactant in the first liquid and/or the shell liquid(s) prevents coalescence of the droplets. In other embodiments, an oligopeptide excipient, a protein excipient, and/or the agent(s) themselves, e.g., therapeutic or diagnostic agents, act as surfactants. In other embodiments, one or more of the shell layers is a hydrogel, ionogel, organogel, or some combination thereof.

In certain embodiments the, the droplets are electrically charged. As a fraction of the Rayleigh limit, the droplets may on average be charged from about 0 to about 1, e.g., from about 0.1 to about 1.0, from about 0.2 to about 1.0, from about 0.3 to about 1.0, from about 0.4 to about 1.0, or from about 0.5 to about 1.0. In some embodiments, charging assists in the mitigation of droplet coalescence and/or in the control of various particle properties of interest. These include but are not limited to the morphology, the surface chemistry, and the crystallinity of select components. The term "Rayleigh limit" refers to the specific charge, e.g., in units of Coulombs per kilogram, corresponding to the point at which Coulombic repulsion overcomes the binding forces of surface tension in a drop, leading to Coulomb fission or shedding of charge from the drop through some other mechanism.

In some embodiments, the droplets of step a) is formed in a microfluidic device, e.g., where the droplets that are formed are regularly spaced. The droplets may be flowed through the device for a time sufficient for the particle to form.

In other embodiments, the second liquid has a density between that of the droplets and the particles. The droplets float on the second liquid, but the particles formed do not float on the second liquid. The first liquid evaporates to dry the droplets. In certain embodiments, the second liquid has a density greater than that of the droplets. The droplets and particles formed float on the second liquid. The first liquid evaporates to dry the droplets. In still other embodiments, the second liquid has a density lower than that of the droplets, and the droplets do not float on the second liquid. The first liquid disperses into the second liquid to dry the droplets.

Formation of Particles

The particles as described herein, can be formed by placing droplets that include a first liquid in contact with a second liquid that facilitates removal of the first liquid. In some embodiments, the droplets are formed in a separate medium and placed into contact with the second liquid thereafter, e.g., by dripping or spraying them into or onto the second liquid. In other embodiments, the droplets are formed within the second liquid, such that they are immediately in contact. Particle formation begins to take place when at least a subset of the components of the droplets begin to undergo precipitation or phase separation as the first liquid is removed. In preferred embodiments, the droplets are dried after contacting the droplets with a second liquid.

In some embodiments, particles are formed after the first liquid disperses throughout the second liquid, e.g., through a diffusion process. In other embodiments the second liquid may have varying degrees of miscibility with the first liquid and represent a weakly or negligibly solubilizing medium in relation to the components of the particles or a subset of the components of the particles, e.g., the therapeutic or diagnostic agents. The agents, e.g., therapeutic or diagnostic agents, are typically less soluble in the second liquid relative to the first liquid in the timeframe of or under the conditions of production, e.g., at least about 5, 10, 100, or about 1000 times less soluble. In still other embodiments, the second liquid is an aqueous liquid, an organic liquid, an oil, an ionic liquid, or a combination thereof. The second liquid can further include a carbohydrate, a pH adjusting agent, a salt, a chelator, a mineral, a polymer, a surfactant, an amino acid, an oligopeptide, a biologic excipient, a chemical excipient, an antiseptic, an antioxidant, a paraben, a bactericide, a fungicide, a vitamin, a preservative, an analgesic, a nutrient media, or a combination thereof. Exemplary aqueous liquids may contain stabilizers, e.g., crowding agents. These solutions, in certain embodiments, include excipients such as a salt (e.g., sodium chloride), sugars and sugar alcohols (e.g., sorbitol, dextran 40, dextran 6000, or trehalose), polymers (e.g., PEG 3350, PEG 300, PEG 8000, PEG 20k, Ficoll 400, Ficoll 70, or polyvinylpyrrolidone, e.g., Povidone), a protein (e.g., human serum albumin or bovine serum albumin), or a combination thereof. In still other embodiments, where the first and second liquids are aqueous, particles are obtained via osmotic drying of the droplets. The second liquid that is used to dry the particles, in certain embodiments, include a high concentration of a solute, e.g., at least about 0.03 osmol, at least about 0.2 osmol, at least about 1.0 osmol, or at least about 1.2 osmol.

In other embodiments, the surfactant in the second liquid helps to prevent coalescence of the droplets. In certain embodiments, an oligopeptide excipient, a protein excipient, the agent(s) themselves, e.g., therapeutic or diagnostic agents, or a combination thereof, act as surfactants.

The particle formation process can be appreciated by considering the dispersal of the first liquid in the second liquid, as described by the diffusion equation $\partial c_1(x, t)/\partial t = D_{12}\nabla^2 c_1(x, t)$, where $c_1(x, t)$ is the concentration of the first liquid at a location x and time t, and $D_{12}$ is the diffusivity of the first liquid in the second liquid. For spherically-symmetric dispersal (gradients along the spherical radius r only) the differential relationship becomes $$\frac{1}{D_{12}}\frac{\partial c_1}{\partial t} = \frac{\partial^2 c_1}{\partial r^2} + \frac{2}{r}\frac{\partial c_1}{\partial r} \qquad \text{Eq. 3}$$

subject to the boundary conditions $c_1(r_i, t) = c_{1,s}$ and $c_1(r \to \infty, t) = c_{1,0}$. The initial concentration $c_{1,s}$ of the first liquid at the edge of the drop, $r = r_i$, is the solubility limit of the first liquid in the second liquid while the concentration far from the drop is some initial saturation level $c_{1,0}$. The initial condition is $c_1(r, 0) = c_{1,0}$. After nondimensionalizing the equation using $\hat{r} = (r - r_i)/r_i$, $\hat{c}_1 = (c_1 - c_{1,0})/(c_{1,s} - c_{1,0})$, and $Fo = tD_{12}/r_i^2$, the change of variables $\hat{u} = (\hat{r} + 1)\hat{c}_1$ can be used to map the problem to Cartesian space, where Fo is the Fourier number. As used herein, the Fourier number (Fo) or Fourier modulus, is termed as a dimensionless number that is used for the characterization of heat conduction. This gives $\partial \hat{u}/\partial Fo = \partial^2 \hat{u}/\partial \hat{r}^2$, subject to $\hat{u}(0, Fo) = 1$ and $\hat{u}(\hat{r}, 0) = 0$, which is in the form of a well-known semi-infinite problem from heat and mass transfer that is readily solved in closed-form using Laplace transform methods. These methods yield the solution $$\hat{c}_1(\hat{r}, Fo) = \frac{1}{\hat{r} + 1}\left[1 - \text{erf}\left(\frac{\hat{r}}{2\sqrt{Fo}}\right)\right] \qquad \text{Eq. 4}$$

which describes the concentration of the first liquid in the second liquid at all locations outside of the drop at all times Fo. It follows that the dimensionless flux of the first liquid into the second liquid at the surface of the drop is $\hat{j} = -\partial \hat{c}_1/\partial \hat{r} = 1 + 1/\sqrt{\pi Fo}$. The time required for dispersal of the entirety of the first liquid comprising a given drop is, to a first approximation, $Fo^* = \rho_1/3c_{1,s}(1 - c_{1,0}/c_{1,s})$, where $\rho_1$ is the density of the first liquid. In some embodiments, the ratio $\rho_1/c_{1,s}$ is much greater than unity and so the characteristic dispersal time $Fo^*$ is large. The flux of the first liquid from the surface of the drop is therefore seen to approach a steady-state as the particle is formed. Under these conditions, the surface flux can be related to the time rate of change of droplet mass to describe the temporal evolution of the drop size, and therefore the timescale for particle formation, in the following way. The mass of a drop $m = 4\pi r_i^3 \rho_l/3$ is dispersed in the second liquid at a rate $dm/dt = 4\pi r_i^2 j$. Since $d(4\pi r_i^3 \rho_l/3)/dt = 4\pi r_i^2 \rho_l(dr_i/dt)$, the drop radius evolves at the related rate $dr_i/dt=-j/\rho$. After rescaling the problem with $\tilde{r}(Fo)=r_i(Fo)/r_i(0)=r_i/r_{i,0}$ and $Fo=tD_{12}/r_{i,0}^2$, substituting for the flux j gives $$\frac{d\tilde{r}}{dFo} = \frac{-1}{3Fo^*}\left[\frac{1}{\tilde{r}} + \frac{1}{\sqrt{\pi Fo}}\right] \qquad \text{Eq. 5}$$

The analytical solution $$\tilde{r}^2 = 1 - \frac{2}{3}\frac{Fo}{Fo^*} \qquad \text{Eq. 6}$$

is valid for long Fourier times $Fo^* \geq 0.2$ (F. Incropera, et al., Fundamentals of Heat and Mass Transfer, $6^{th}$ Ed., 2007). The approximate timescale for particle formation is therefore $Fo=1.5\ Fo^*$. The actual time will vary as a function of concentration of the solutes in the drop and their densities. For example, the ratio of the volume of the formed particle to volume of the initial drop is $V_p/V_D$ $(r_p/r_D)^3$. The particle volume can be written $m_p/\rho_p$, i.e., the particle mass divided by the particle density, and so this relationship implies $r_p/r_D=(c_{sol}/\rho_p)^{1/3}$ where $c_{sol}$ is the concentration of solutes (dissolved solids) in the drop. A drop with $c_{sol}/\rho_p=\frac{1}{8}$ will therefore produce a particle for which $r_p/r_D \approx \frac{1}{2}$. From Eq. 6, $Fo \approx (9/8)\ Fo^*$ in this instance. The actual drying or desiccation time may similarly vary on account of changes that take place in the drop as concentration of the solutes, precipitation of solutes, and/or phase separation begin to take place. Depending on the chosen process conditions, drying of the particles may occur over a period of nanoseconds to days. In certain embodiments where the first liquid is aqueous and where the second liquid is an organic solvent, drying times vary, e.g., between about 1 $\rho$s and about 1000 s depending on the solvent chemistry.

In other embodiments, the distribution of solutes within the drop during the particle formation process is relevant. In spherically-symmetric space, this distribution is described by (R. Vehring, J. Aerosol Sci., 2007, 38, 728-746)

$$\frac{\partial c_n}{\partial t} = \frac{D_n}{r_i^2}\left(\frac{\partial^2 c_n}{\partial R^2} + \frac{2}{R}\frac{\partial c_n}{\partial R}\right) + \frac{R}{r_i}\frac{\partial c_n}{\partial R}\frac{\partial r_i}{\partial t} \qquad \text{Eq. 7}$$

where $c_n$ is the concentration of the $n^{th}$ solute in the drop, $D_n$ is its characteristic diffusivity in the drop, e.g., the diffusivity may vary as a function of time (concentration) as the particle forms, and $R=r/r_{i,0}$ is the dimensionless radial coordinate. An analytical solution to Eq. 7 exists when $r_i(dr_i/dt)$ is constant. This implies $r_i^2=f(t)$. From Eq. 6, this is true in certain embodiments so long as the characteristic Fourier number $Fo^*$ is sufficiently long. Imposing this condition gives $$\frac{c_n}{\bar{c}_n} = \frac{\exp(Pe_n R^2/2)}{3\int_0^1 R^2 \exp(Pe_n R^2/2)dR} \qquad \text{Eq. 8}$$

where $\bar{c}_n$ is the mean concentration of the solute averaged over the volume of the drop at a given time. $Pe_n$ is the Peclet number of the $n^{th}$ solute, i.e., the ratio of the transport rate of the first liquid away from the drop to the solute transport rate within the drop. It is sometimes defined as $Pe_n=-r_i/D_n$ $(dr_i/dt)$. In view of Eq. 6, the Peclet number may take the form $$Pe_n = \frac{1}{3Fo^*}\frac{D_{12}}{D_n} \qquad \text{Eq. 9}$$

In some embodiments, Eq. 8 provides a useful estimation of the radial distribution of the components of the drop and the particle during the particle formation process. The surface concentration (R=1) of the solutes in particular is of interest, in some cases, since it may govern important aspects of the particle formation process. It typically is computed through a numerical integration of the denominator in Eq. 8. For reasonably low Peclet numbers (Pe<20), however, it can be approximated to an accuracy of $\pm 1\%$ by $$E_n = \left.\frac{c_n}{\bar{c}_n}\right|_{R=1} \approx 1 + \frac{Pe_n}{5} + \frac{Pe_n^2}{100} - \frac{Pe_n^3}{4000} \qquad \text{Eq. 10}$$

where $E_n$ is a surface enrichment factor.

In other embodiments, the second liquid disperses throughout the drop on the timescale of and under the conditions of particle formation. Similar to Eq. 3, the process can be described by $$\frac{1}{D_{21}}\frac{\partial c_2}{\partial t} = \frac{\partial^2 c_2}{\partial r^2} + \frac{2}{r}\frac{\partial c_2}{\partial r} \qquad \text{Eq. 11}$$

subject to the boundary conditions $\partial c_2/\partial r(0, t)=0$ and $c_2(r_i, t)=c_{2,s}$ on $r \in (0, r_i)$. Here $c_2(r, t)$ is the concentration of the second liquid inside the drop (radius $r_i$) at times t and $D_{21}$ is its diffusivity in the first liquid. The initial condition $c_2(r, 0)=c_{2,0}$ describes the initial concentration of the second liquid within the drop. After nondimensionalizing the equation using $\hat{r}=r/r_i$, $\hat{c}_2=(c_2-c_{2,s})(c_{2,0}-c_{2,s})$, and $Fo=tD_{21}/r_i^2$, the change of variables $\hat{u}=\hat{r}\hat{c}$ can be used to map the problem to Cartesian space as previously described herein. This gives $\partial\hat{u}/\partial t=\partial^2\hat{u}/\partial\hat{r}^2$ subject to $\hat{u}(0, Fo)=0$, $\hat{u}(1, Fo)=0$, and $\hat{u}(\hat{r}, 0)=\hat{r}$. Searching for a product solution of the form $\hat{u}=X(\hat{r})Y$ (Fo) yields, after separation of variables $$\bar{c}_2(\hat{r}, Fo) = 1 + 2\left(1 - \frac{c_{2,0}}{c_{2,s}}\right)\sum_{m=1}^{\infty}\frac{\cos m\pi}{m\pi}\frac{\sin m\pi\hat{r}}{\hat{r}}\exp(-m^2\pi^2 Fo) \qquad \text{Eq. 12}$$

where $\bar{c}_2=c_2/c_{2,s}$ is a rescaled form of the concentration. It can be shown from Eq. 12 that the timescale for saturation of the second liquid in the drop is $Fo_2^*=t_2^*D_{21}/r_i^2 \sim \frac{1}{3}$. The ratio of $t_2^*$ to the characteristic particle formation time $t_p^*$ is, therefore $$\frac{t_2^*}{t_p^*} = \frac{D_{12}}{D_{21}}\frac{c_{1,2}}{\rho_1}\left(1 - \frac{c_{1,0}}{c_{1,2}}\right) \qquad \text{Eq. 13}$$

where the particle formation time follows from $Fo^*=t_p^*D_{12}/r_i^2=\rho_1/3c_{1,s}(1-c_{1,0}/c_{1,s})$. In certain embodiments, $t_2^*/t_p^*$ is small, meaning that the drop saturates or nearly saturates with the second liquid on the timescale of and under the conditions of particle formation as described herein. In other embodiments, $t_2^*/t_p^*$ is large, meaning that the drop does not saturate or approach saturation with the second liquid on the timescale of and under the conditions of the disclosed particle formation.

In some embodiments, the second liquid has a Fourier number (Fo) of less than about 1.500 allowing the droplets to dry in about 60 seconds. In other embodiments, the second liquid has a Fourier number (Fo) of less than about 1.000 allowing the droplets to dry in about 60 seconds. In still other embodiments, the second liquid has a Fourier number (Fo) of less than about 0.500 allowing the droplets to dry in about 60 seconds. In certain other embodiments, the second liquid has a Fourier number (Fo) of less than about 0.208 allowing the droplets to dry in about 5 seconds. The skilled person, once apprised of the range to be set for the Fourier number, will be able, without undue burden, to adjust the process parameters accordingly.

In other embodiments as described herein, step b) further includes decreasing the temperature of the second liquid to about ±30° C. of the freezing point of the first liquid. In some embodiments, the boiling point of the second liquid at atmospheric pressure is from about 0° C. to about 200° C. In certain embodiments, step b) further comprises decreasing the temperature of the second liquid to a temperature within about 30° C. of the freezing point of the first liquid. In certain other embodiments, the boiling point of the second liquid at atmospheric pressure is from about 0 to about 200° C. In still other embodiments, the second liquid is a mixture of two or more liquids of different polarities. In certain preferred embodiments, the mixture comprises liquids having differing solubility Ratio of Second Liquid to First Liquid: The ratio of the second liquid to the first liquid during the particle formation process may be engineered to control embodiments of the particle formation process described herein. For complete or nearly complete dispersal of the first liquid, the ratio of second liquid to first liquid $V=V_2/V_1$ is chosen as $$V_0 = \frac{\rho_1}{c_{1,s} - c_{1,0}}.$$

Ratios either higher or lower than $V_0$ result in either faster or slower desiccation, respectively. In the former case, the second liquid has sufficient capacity to accept all of the first liquid and Eqs. 5-7 become increasingly exact as $V/V_0$ becomes large. In the latter case, the second liquid has insufficient capacity for the first liquid, such that primary desiccation results in partial but not complete drying of the drops. Subsequent washing and/or secondary desiccation steps can be useful in this case for reducing the quantity of the first liquid in the drops and for completing the particle formation process. In some embodiments, the liquid ratio ranges from about 0 to about 1000 times $V_0$, e.g., from about 0 to about 100 times $V_0$, from about 0 to about 10 times $V_0$, from about 0 to about 5 times $V_0$, from about 0 to about 2.5 times $V_0$, from about 0 to about 1 times $V_0$, from about 0 to about 0.5 times $V_0$, from about 0 to about 0.25 times $V_0$, or from about 0 to about 0.1 times $V_0$.

The term "primary desiccation" refers to a step by which a droplet comprising a first liquid is placed in contact with a second liquid and dried or desiccated by the second liquid, e.g., through dispersal of the first liquid in the second liquid, and/or through evaporation.

The term "secondary desiccation" refers to a post-processing step, e.g., after removal of the first and second liquids by which the residual moisture and/or solvent content of the particles is modified. Exemplary methods of secondary desiccation include vacuum drying, with or without the application of heat, lyophilization, fluidized bed drying, tray drying, belt drying, or slurry spray drying. Secondary desiccation may also be used to remove any washing liquids that are used to separate the particles from the second liquid. In preferred embodiments, the first and second liquids are removed through centrifugation, sieving, filtration, magnetic collection, solvent exchange, or decanting.

In certain embodiments, the methods as described herein, include removing the particles from the second liquid through centrifugation, sieving, filtration, magnetic collection, solvent exchange, inertial separation, hydrocyclone separation, or decanting.

In other embodiments, the methods as described herein, further comprises washing the particles after step d) with a washing fluid, e.g., an organic liquid, a supercritical fluid, a cryogenic liquid, or a combination thereof. In certain embodiments, the washing fluid is an organic liquid, a supercritical fluid, a cryogenic liquid, or a combination thereof.

The drying of the particles, e.g., removal of the first and second liquids to produce dry particles, can be performed through methods as described herein. These include, but are not limited to, warm gas evaporation, freeze drying, critical point drying, emulsion solvent evaporation, emulsion solvent diffusion, or a combination thereof. In certain embodiments, the particles are further dried by lyophilization or vacuum desiccation. In certain other embodiments, residual quantities of the first and second liquids in the particles after drying are from about 0 to about 10% by weight, e.g., from about 0 to about 5% by weight, or from about 0 to about 3% by weight, or preferably from about 0 to about 1% by weight. In still other embodiments, the particles have less than 10% by weight of the first liquid or the second liquid remaining after drying.

In certain other embodiments, the methods further include washing the particles with a third liquid. In preferred embodiments, the third liquid is an organic solvent. The third liquid may also be removed through evaporation, vacuum desiccation or lyophilization, e.g., vacuum drying, with or without the application of heat, lyophilization, fluidized bed drying, tray drying, belt drying, or slurry spray drying. In preferred embodiments, the particles are further dried by lyophilization or vacuum desiccation.

In some embodiments, warm gas evaporation is used to further dry the particles. In other embodiments, the particles are further dried by contacting the particles with a stream of gas. In certain embodiments, the gas has a temperature from about −80 to about 200° C. In certain other embodiments, the gas has a temperature from about 10 to about 40° C. In still other embodiments, the gas has a relative humidity from about 0 to about 100%.

In certain embodiments, the particles may or may not include residual first and/or second liquid as described herein.

Electrical Charging and Other Forms of Control: As described herein, the particles may be formed in the presence of an electric field. The particles produced in the presence of the electric field may have an average diameter less than or equal to the diameter of particles produced in the absence of an electric field. In certain embodiments, the particles include a net charge that substantially minimizes particle coalescence.

Droplets of the disclosure can be formed in an electrical field and in some instances, carry an electrical charge. In certain embodiments, the medium in which the droplets are formed, e.g., the second liquid, is typically a dielectric medium. In some embodiments, the electric field and/or electric charge on the drop is such that free charges and/or polar molecules move to the surface of the droplet of the first liquid on account of Coulombic effects. The former phenomenon, the localization of free charges at the interface between the first liquid and the dielectric medium in which the droplets are formed, produces a layer of surface charge. In other embodiments, such effects are leveraged to influence the structure and/or surface properties of the droplet and/or particle. This includes instances in which the surface charge is used to achieve spherical particle morphologies under conditions in which they would not otherwise be readily accessible, i.e., high Peclet numbers. In still other embodiments, coordination of the first liquid, which may be polar near the surface of the droplet, facilitates faster removal of the first liquid by the second liquid. It may also mitigate surface-related degradation events among the agents, e.g., the therapeutic or diagnostic agents, and relative to what is typical in the absence of an electric field, decreases the residual quantity of first liquid in the particle after drying.

In some embodiments, the electric field and/or electric charge is such that free charges and/or polar molecules move to the surface of the droplet of the first liquid based on Coulombic effects, and one or several components of the droplets crystallize, e.g., therapeutic agents, diagnostic agents, or any of the various excipients that the droplet may comprise. Crystal nucleation of the agent or other droplet component may be controlled to obtain a desired polymorph (A. Ziabicki, L. Jarecki, Macromolecular Symposia, 1996, 104, 65-87). In other embodiments, crystallization proceeds along a preferential direction, e.g., along an electric field line.

Core-shell particles may also be produced from droplets including a first liquid alone, i.e., in the absence of any shell liquids, through the agency of a net charge or an electric field. In some embodiments, this is achieved by leveraging the proclivity of certain polar molecules and free charges to arrange themselves at the surface of the droplet when it carries net electrical charge and/or when an external electric field is applied. In other embodiments, this produces a localization of the therapeutic or diagnostic agents, either towards the core of the droplet or its surface, which can be preserved during desiccation. In certain embodiments, this involves a deterministic stratification of various agents (e.g., therapeutic agents, diagnostic agents, excipients) throughout the thickness of the particle. In still other embodiments, non-therapeutic components, e.g., a salt (e.g., sodium chloride) or a sugar (e.g., sucrose), are driven to the surface, preferentially with the electric field, to form a thin shell around the particle, crystalline or otherwise. This shell may have protective effects or provide a measure of control over the pharmacokinetics. In certain other embodiments, portions of the droplet components are localized at the particle surface without necessarily forming a uniform or continuous shell.

In other embodiments, the particles are formed in the presence of an electric field. In some embodiments, the particles formed in the presence of the electric field have an average diameter less than or equal to the diameter of particles produced in the absence of an electric field. In certain embodiments, the particles comprise a net charge.

Coalescence: Controlling the degree of coalescence during the particle formation process can be important for achieving a desired particle size distribution. Control of coalescence can be achieved in several ways. These include the use of surfactants, droplet charging, controlled droplet propagation, mixing, or a combination thereof. In some embodiments, the latter methods are preferred because they help to mitigate the amount of surfactant required to stabilize the droplets on the timescale of and under the conditions of particle formation. Such mitigation can be advantageous since it limits the amount of surfactant which may reside in the particles, thereby enhancing the weight fraction of other components of the particles including the agent(s), e.g., therapeutic or diagnostic agent(s). In other embodiments, the weight fraction of a surfactant in the particles is from about 0 to about 50%, e.g., from about 0 to about 10%, from about 0 to about 5%, from about 0 to about 3%, from about 0 to about 1%, from about 0 to about 0.5%, from about 0 to about 0.01%, or from about 0 to about 0.001%. Exemplary methods of quantifying the degree of coalescence include measuring the volume-weighted mean particle size and comparing this to the volume-weighted mean size estimated on the basis of the initial drop size distribution, i.e., the drop size distribution before any coalescence occurs. The measured mean size is from about 1 to about 5 times the estimated mean size, e.g., from about 1 to about 3 times the estimated mean size, from about 1 to about 2 times the estimated mean size, from about 1 to about 1.5 times the estimated mean size, from about 1 to about 1.2 times the estimated mean size, or from about 1 to about 1.1 times the estimated mean size.

As described herein, the use of surfactants can be a method for stabilizing liquid-liquid systems. In some embodiments, the droplets are stabilized on the timescale of and under the conditions of particle formation by addition of an appropriate surfactant to the first and/or second liquid. In terms of the critical micelle concentration (CMC), the concentration of the surfactant is from about 0.01 to about 100 times the CMC, e.g., from about 0.1 to about 10 times the CMC, from about 1 to about 5 times the CMC, or about 1 to about 3 times the CMC. In other embodiments, the concentration of the surfactant is from about 0.0001 to about 100 mg/mL, e.g., from about 0.001 to about 10 mg/mL, from about 0.01 to about 10 mg/mL, or from about 0.01 to about 1 mg/mL. As used herein, the term "critical micelle concentration", or "CMC", refers to the concentration of surfactants in a liquid above which micelles form and above which all additional surfactants added to the system go to micelles.

In some embodiments, charge on the droplets mitigates coalescence. In other embodiments, the effect is leveraged as an alternative to surfactants that may be added to the first liquid and/or the second liquid. In certain embodiments, this effect complements the use of surfactants in the first liquid and/or second liquid in a way that reduces the concentration required for the desired stabilization. In terms of the critical micelle concentration (CMC), the concentration of the surfactant is from about 0 to about 10 times the CMC, e.g., from about 0 to about 3 times the CMC, from about 0 to about 1 times the CMC, from about 0 to about 0.5 times the CMC, from about 0 to about 0.1 times the CMC, from about 0 to about 0.01 times the CMC, or about 0 to about 0.001 times the CMC. In certain other embodiments, the concentration of the surfactant is from about 0 to about 10 mg/mL, e.g., from about 0 to about 1 mg/mL, from about 0 to about 0.1 mg/mL, from about 0 to about 0.01 mg/mL, or from about 0 to about 0.001 mg/mL.

In certain embodiments, droplets are formed in a device, e.g., a microfluidic device, having at least one channel, where the properties of an individual channel are engineered to control the residence time of the droplets in the channel. In some embodiments, the drops flow in a train and experience limited drop-drop interactions in the channel. The residence time can be designed such that coalescence is mitigated regardless of the surfactant content of either the first liquid or the second liquid once drops and/or particles are collected from the channel or the drop train is otherwise disrupted in a way that enhances drop-drop interactions. In other embodiments, the residence time is on the order of or long with respect to the characteristic particle formation time from Eq. 6, e.g., from about 0.5 Fo* to about 150 Fo*, from about 0.5 Fo* to about 15 Fo*, from about 0.5 Fo* to about 7.5 Fo*, from about 0.5 Fo* to about 4.5 Fo*, from about 0.5 Fo* to about 3.0 Fo*, or from about 0.5 Fo* to about 1.5 Fo*. In certain other embodiments, the particles are substantially formed during residence in the individual channel. In still other embodiments, the residence time is less than the characteristic particle formation time from Eq. 6 but still sufficient for the formation of a proto-particle, e.g., from about 0.0001 Fo* to about 0.5 Fo*, from about 0.001 Fo* to about 0.5 Fo*, from about 0.01 Fo* to about 0.5 Fo*, from about 0.05 Fo* to about 0.5 Fo*, or from about 0.1 Fo* to about 0.5 Fo*. The proto-particle has surface properties, e.g., a thin layer of an enriched solute, that discourage coalescence in spite of potential drop-drop interactions that may occur during the particle formation process.

In some embodiments, a solute m with a Peclet number $Pe_m$ is used to engineer the required residence time for proto-particle formation. The solute is loaded in the drop at an initial concentration $c_{m,0}$ and will effectively prevent coalescence when it reaches a critical surface enrichment cm*. From Eq. 8, $c_m^*/\bar{c}_m = f(Pe_m)$ at R=1. The average concentration in the drop $\bar{c}_m$ can be computed as $\bar{c}_m = c_{m,0}(V_0/V) = c_{m,0}/\bar{r}^3$. From Eq. 6, this implies that the critical surface enrichment will be reached around about a time of approximately $$Fo = \frac{3}{2}Fo^*\left[1 - \left(\frac{c_{m,0}}{c_m} * f(Pe_m)\right)^{2/3}\right] \qquad \text{Eq. 14}$$

In other embodiments, coalescence is controlled even when the drop production frequency associated with the channel is very high. The drop production frequency associated with the channel can be from about 1 Hz to about 10 MHz, e.g., from about 10 Hz to about 10 MHz, from about 100 Hz to about 10 MHz, from about 1 kHz to about 10 MHz, or from about 10 kHz to about 10 MHz. In certain embodiments, an appropriate surfactant is added to the first liquid and/or the second liquid to further assist in the control of coalescence. In terms of the critical micelle concentration (CMC), the concentration of the surfactant is from about 0 to about 10 times the CMC, e.g., from about 0 to about 3 times the CMC, from about 0 to about 1 times the CMC, from about 0 to about 0.5 times the CMC, from about 0 to about 0.1 times the CMC, from about 0 to about 0.01 times the CMC, or about 0 to about 0.001 times the CMC. In certain other embodiments, the concentration of the surfactant is from about 0 to about 10 mg/mL, e.g., from about 0 to about 1 mg/mL, from about 0 to about 0.1 mg/mL, from about 0 to about 0.01 mg/mL, or from about 0 to about 0.001 mg/mL. The use of stirring or a motion of the second liquid, e.g., such as in continuous stirred tank reactor or a linear flow channel, may also be useful during drying to mitigate coalescence. In preferred embodiments, the net charge substantially minimizes particle coalescence.

Sterility: Sterility is a critical facet of pharmaceutical compositions because it affects the safety with which the composition may be administered. For example, many particle formulations, particularly microparticle formulations, achieving sterility can be a challenge since common sterilization techniques, e.g., sterile filtration, are not compatible. Sterile filtration steps typically involve a membrane through which only those components of the filtered liquid which are, for example, 200 nm in size or smaller may pass. Particle formulations with solids greater than 200 nm in size are therefore filtered rather than sterilized. In some embodiments, formulations of the disclosure are subjected to an alternative process of terminal sterilization prior to use or administration. The effectiveness of these sterilization protocols and of the process in reducing bioburden may be assessed following regulatory guidelines, e.g., those listed in USP Chapter <71>, Ph. Eur. Chapter, Sterility: 2.6.1, 21 CFR 610.12, ICH Q4B ANNEX 8(R1), ICH Q5A, etc. Exemplary methods of demonstrating compliance include incubating about 1 mL of the drug product per container in an appropriate growth media (Soybean-Casein Digest Medium, Tryptic Soy Broth, Fluid Thioglycollate Medium) for a period of about 14 days to ensure no microbial growth in about 1 in about 1000 million units of the drug product, or about 1 in about 1 million units of the drug product. As disclosed herein, a "sterile" formulation is aseptic or free from living microorganisms and their spores.

In some embodiments, the terminal sterilization step involves gamma irradiation. In other embodiments, the sterilization step required to inactivate at least about 2-4 $\log_{10}$ of viral microbial contaminants is about 10 kGy, about 20 kGy, about 40 kGy, about 60 kGy, or about 100 kGy. In certain embodiments, the particles comprise an antioxidant or a scavenger to mitigate the harmful effects of any degradation products which are generated as a result of the sterilization step.

In other embodiments, the terminal sterilization step involves a transient thermal treatment. In some embodiments, the formulation is exposed to temperatures from about 60 to about 200° C., e.g., from about 60 to about 180° C., from about 60 to about 160° C., from about 60 to about 140° C., from about 60 to about 130° C., from about 60 to about 120° C., or from about 60 to about 110° C. In certain embodiments, the exposure occurs over a period from about 1 to about 144 hours, e.g., from about 1 to about 120 hours, from about 1 to about 100 hours, from about 1 to about 90 hours, from about 1 to about 72 hours, from about 1 to about 48 hours, from about 1 to about 36 hours, or from about 1 to about 24 hours. For example, dry heat sterilization can be performed at a temperature of about 80° C. for about 72 hours, about 160° C. for about two hours, or about 170° C. for about one hour. In certain other embodiments, pasteurization is performed at about 60° C. for about 10 hours.

In some embodiments, the sterilization is ensured by using beta radiation, X-ray sterilization, steam sterilization, solvent-detergent inactivation steps, supercritical $CO_2$ mediated sterilization, low pH holds, ultraviolet C exposure, or ethylene oxide mediated sterilization of the formulation. In other embodiments, the terminal sterilization step is performed at low temperatures from about −100 to about 60° C. In certain embodiments, the supercritical $CO_2$ further includes additives (e.g., hydrogen peroxide, water, acetic anhydride, etc.) intended to effectively inactivate microorganisms, including bacterial spores.

In other embodiments, the second liquid is chosen such that its presence in the drop during particle formation helps to facilitate process sterility. In some embodiments, the second liquid is an antimicrobial or contains such a compound which is contained within the particle. This compound may persist inside the particles even after a secondary drying step. Organic liquids that can be used as a second liquid with antimicrobial activity may include, but are not limited to acetates (e.g., ethyl acetate) and alcohols (e.g., ethanol, phenol), or the like. The second liquid may also contain antimicrobial excipients, e.g., phenolic substances, benzalkonium chloride, linalool, coumarin, peroxides, active chlorine, alkalis, or a combination thereof.

In some embodiments, the use of nano-filtration membranes for the inlet process streams, e.g., for use on the first liquid and/or the second liquid prior to particle formation, contributes to a reduction of the bio-burden on the process. In other embodiments, combinations of the preceding sterility measures are employed to reach appropriate bio-burden levels.

As described herein, the particles may be sterilized after formation, e.g., by irradiation, pasteurization, freezing, or irradiation by gamma radiation. In certain embodiments, the methods as described herein, further comprises sterilization of the particles after the first and second liquids are removed. In certain preferred embodiments, the sterilization occurs by irradiation, pasteurization, or freezing. In preferred embodiments, the irradiation is by gamma radiation.

Control of Particle Properties

Properties of the particles can be controlled by modulating the drying rate of the droplets, the Peclet numbers of the components of the droplets, the concentrations of the components of the droplets, the particle formation dynamics following solute precipitation or phase separation within the droplet, the electric charge on the droplets, and/or the properties of the electric field in which the droplets may be disposed. In certain embodiments, the modulation influences the size, morphology, density, porosity, composition, surface energy properties of the particles, and help to establish the distribution of components within the particles and to regulate important physicochemical properties which may be difficult to address when drying without the second liquid, e.g., in air, as with conventional spray drying. These properties include the dissolution rates of the particles and their flow properties (R. Vehring, Pharmaceutical Res., 2008, 25, 999-1022).

The methods described herein, are generally provided for controlling the morphology of particles, the method comprising: a) providing droplets comprising a first liquid and an agent; b) contacting the droplets with a second liquid under a specified Peclet number; c) allowing the droplets to dry; and d) removing the first and second liquids, wherein the specified Peclet number controls the morphology of the particles.

In one aspect, the disclosure provides a method of controlling the morphology of particles, the method comprising: a) providing droplets comprising a first liquid and an agent; b) contacting the droplets with a second liquid comprising a plasticizer having a specified Peclet number; c) allowing the droplets to dry; and d) removing the first and second liquids, wherein the plasticizer controls the morphology of the particles.

In another aspect, the disclosure provides a method of controlling the morphology of particles, the method comprising: a) providing droplets comprising a first liquid and an agent; b) contacting the droplets with a second liquid; c) allowing the droplets to dry; and d) removing the first and second liquids, wherein the Peclet number of the second liquid controls the morphology of the particles.

As disclosed herein, the agent may be a therapeutic or diagnostic agent. In certain embodiments, the therapeutic agent has an activity per unit of about 0.5 to about 1.0. In certain preferred embodiments, the therapeutic agent is a therapeutic biologic. In preferred embodiments, the therapeutic biologic has an activity per unit of about 0.5 to about 1.0.

In other embodiments, the first or second liquid further comprises a plasticizer that controls the morphology of the particles. Exemplary plasticizers include sucrose, xylitol, sorbitol, fructose, triglyceride, pectin, glycerol, triethylcitrate, ethyl acetate, citric acid, oleic acid, hydroxypropyl cellulose, methyl pyrrolidone polyethylene glycol, polypropylene glycol, polysorbate 80, diethyl phthalate and other phthalate derivatives, castor oil, triacetin, water, chlorpheniramine, 1-butyl-3-methyl imidazolium dioctyl sulfosuccinate, hexyl acetate, water, 2-ethylhexyl acetate, triethyl citrate, dibutyl sebacate, benzyl alcohol, benzyl benzoate, dimethylacetamide, various aqueous liquids, organic liquids, oils, ionic liquids, polysaccharides, sugars, diols, polyols, fatty acids, fatty acid esters, esters, surfactants, or a combination thereof. In certain embodiments, the plasticizer is sucrose, xylitol, sorbitol, fructose, triglyceride, pectin, glycerol, triethylcitrate, ethyl acetate, citric acid, oleic acid, hydroxypropyl cellulose, methyl pyrrolidone polyethylene glycol, polypropylene glycol, polysorbate 20, polysorbate 60, polysorbate 80, fatty acid ester of sorbitol, diethyl phthalate and other phthalate derivatives, castor oil, triacetin, water, chlorpheniramine, 1-butyl-3-methyl imidazolium dioctyl sulfosuccinate, hexyl acetate, 2-ethylhexyl acetate, triethyl citrate, dibutyl sebacate, benzyl alcohol, benzyl benzoate, dimethylacetamide, or a combination thereof. In preferred embodiments, the plasticizer is polysorbate 20, polysorbate 60, or polysorbate 80. In certain preferred embodiments, the plasticizer is polysorbate 20 or polysorbate 80. In certain other embodiments, the fatty acid ester of sorbitol is a sorbitan ester, e.g., span 20, span 40, span 60, or span 80.

In some embodiments, the particles may include less than 10% internal void spaces after removing the first and second liquids, less than 5% internal void spaces after removing the first and second liquids, less than 1% internal void spaces after removing the first and second liquids, less than 0.1% internal void spaces after removing the first and second liquids, or less than 0.01% internal void spaces after removing the first and second liquids. In preferred embodiments, the particles are substantially free from any internal void spaces after removing the first and second liquids.

In other embodiments, the circularity of the particles is from about 0.88 to about 1.00 after removing the first and second liquids. In still other embodiments, the circularity of the particles is from about 0.90 to about 1.00 after removing the first and second liquids. In certain other embodiments, the circularity of the particles is from about 0.93 to about 1.00 after removing the first and second liquids. In preferred embodiments, the circularity of the particles is from about 0.97 to about 1.00 after removing the first and second liquids.

In some embodiments, the sphericity of the particles may range from about 0.10 to about 1.00 after removing the first and second liquids, e.g., at least about 0.20, about 0.40, about 0.60, or about 0.80 to about 1.00 after removing the first and second liquids.

In preferred embodiments, the particles have a substantially smooth surface after removing the first and second liquids.

In some embodiments, the particles have diameters from about 1 to about 100 μm after removing the first and second liquids, e.g., from about 4 to about 100 μm, from about 10 to about 100 μm, or from about 20 to about 50 μm after removing the first and second liquids.

In other embodiments, the particles have a surfactant content of less than about 5% by mass after removing the first and second liquids. In certain embodiments, the particles have a surfactant content of less than about 3% by mass after removing the first and second liquids. In still other embodiments, the particles have a surfactant content of less than about 0.1% by mass after removing the first and second liquids. In certain other embodiments, the particles have a surfactant content of less than about 0.01% by mass after removing the first and second liquids. In some embodiments, the particles have a surfactant content of less than about 0.001% by mass after removing the first and second liquids. In preferred embodiments, the particles have a surfactant content of less than about 1% by mass after removing the first and second liquids.

In some embodiments, the particles exhibit a skeletal density from about 1.00 to about 6.00 g/cm³ after removing the first and second liquids, e.g., from about 1.00 to about 5.00 g/cm³, from about 1.00 to about 3.00 g/cm³, from about 1.00 to about 2.00 g/cm³, from about 1.00 to about 1.50 g/cm³, from about 1.30 to about 1.50 g/cm³, from about 1.32 to about 1.50 g/cm³, or from about 1.10 to about 1.40 g/cm³ after removing the first and second liquids. In other embodiments, the particles exhibit a skeletal density from about 0.10 to about 5.00 g/cm³ after removing the first and second liquids, e.g., from about 0.10 to about 2.50 g/cm³, from about 0.10 to about 1.40 g/cm³, from about 0.50 to about 1.40 g/cm³, or from about 1.00 to about 1.40 g/cm³ after removing the first and second liquids. In certain embodiments, the particles have a skeletal density of about 0.09 to about 1.60 g/cm³ after removing the first and second liquids. In still other embodiments, the particles have a skeletal density of about 1.30 to about 1.58 g/cm³ after removing the first and second liquids. In preferred embodiments, the particles have a skeletal density of about 1.32 to about 1.50 g/cm³ after removing the first and second liquids.

In other embodiments, the particles have a skeletal density of about 1000 mg/mL to about 1500 mg/mL after removing the first and second liquids, e.g., about 1050 mg/mL to about 1500 mg/mL, about 1100 mg/mL to about 1500 mg/mL, about 1150 mg/mL to about 1500 mg/mL, about 1200 mg/mL to about 1500 mg/mL, about 1250 mg/mL to about 1500 mg/mL, about 1300 mg/mL to about 1500 mg/mL, about 1310 mg/mL to about 1500 mg/mL, about 1320 mg/mL to about 1500 mg/mL, about 1330 mg/mL to about 1500 mg/mL, about 1340 mg/mL to about 1500 mg/mL, about 1350 mg/mL to about 1500 mg/mL, about 1360 mg/mL to about 1500 mg/mL, about 1370 mg/mL to about 1500 mg/mL, about 1380 mg/mL to about 1500 mg/mL, about 1390 mg/mL to about 1500 mg/mL, about 1400 mg/mL to about 1500 mg/mL, about 1410 mg/mL to about 1500 mg/mL, about 1420 mg/mL to about 1500 mg/mL, about 1430 mg/mL to about 1500 mg/mL, about 1440 mg/mL to about 1500 mg/mL, about 1450 mg/mL to about 1500 mg/mL, about 1460 mg/mL to about 1500 mg/mL, about 1470 mg/mL to about 1500 mg/mL, about 1480 mg/mL to about 1500 mg/mL, or about 1490 mg/mL to about 1500 mg/mL after removing the first and second liquids.

In some embodiments, the particles can be characterized by a glass transition temperature of about 0° C. to about 250° C. after removing the first and second liquids, e.g., of about 34° C. to about 200° C., of about 50° C. to about 200° C., of about 60° C. to about 200° C., of about 40 to about 160° C., of about 50 to about 110° C., of about 60 to about 100° C., or of about 75 to about 80° C. after removing the first and second liquids.

In other embodiments, the particles further comprise a carbohydrate, a pH adjusting agent, a salt, a chelator, a mineral, a polymer, a surfactant, a protein stabilizer, an emulsifier, an antiseptic, an amino acid, an antioxidant, a protein, an organic solvent, a paraben, a bactericide, a fungicide, a vitamin, a preservative, a nutrient media, an oligopeptide, a biologic excipient, a chemical excipient, or a combination thereof. In certain embodiments, the particle further comprises a carbohydrate, a pH adjusting agent, a salt, a surfactant, a protein stabilizer, an emulsifier, an amino acid, or a combination thereof.

In some embodiments, the particles have less than 20% aggregation or less than 20% fragmentation of the therapeutic biologic after removing the first and second liquids, e.g., less than about 19, 18, 17, 16, 15, 14, 13, 12, 10, 9, 8, 7, 6, 5, 4, 3, 2, 1.9, 1.8, 1.7, 1.6, 1.5, 1.4, 1.3, 1.2, 1.1, 1, 0.9, 0.8, 0.7, 0.6, 0.5, 0.4, 0.3, 0.2, or 0.1% after removing the first and second liquids. In other embodiments, the particles have less than 10% aggregation or less than 10% fragmentation of the therapeutic biologic after removing the first and second liquids, e.g., less than about 9, 8, 7, 6, 5, 4, 3, 2, 1.9, 1.8, 1.7, 1.6, 1.5, 1.4, 1.3, 1.2, 1.1, 1, 0.9, 0.8, 0.7, 0.6, 0.5, 0.4, 0.3, 0.2, or 0.1% after removing the first and second liquids. In certain embodiments, the particles have about 3% to about 1% aggregation of the therapeutic biologic after removing the first and second liquids. In certain other embodiments, the particles have about 1% to about 0.5% aggregation of the therapeutic biologic after removing the first and second liquids. In preferred embodiments, the particles are substantially free from any aggregation of the therapeutic biologic after removing the first and second liquids. In still other embodiments, the particles have less than about 1% fragmentation of the therapeutic biologic after removing the first and second liquids. In certain preferred embodiments, the particles are substantially free from any fragmentation of the therapeutic biologic after removing the first and second liquids.

In other embodiments, the particles have less than about 50% change in charge variants of the therapeutic biologic after removing the first and second liquids, e.g., less than about 45, 40, 35, 30, 25, 20, 15, 10, 9, 8, 7, 6, 5, 4, 3, 2, 1, 0.5, 0.1% after removing the first and second liquids, compared to the starting biologic prior to particle formation. In preferred embodiments, the particles are substantially free from any change in charge variants of the therapeutic biologic after removing the first and second liquids compared to the starting biologic prior to particle formation.

In some embodiments, the particles have less than about 3% residual moisture by mass remaining after removing the first and second liquids. In other embodiments, the particles have less than about 2% residual moisture by mass remaining after removing the first and second liquids. In certain other embodiments, the particles have less than about 1% residual moisture by mass remaining after removing the first and second liquids. In still other embodiments, the particles have less than about 0.1% of residual first and second liquids by mass remaining after removing the first and second liquids. In some preferred embodiments, the particles have less than about 0.01% of residual first and second liquids by mass remaining after removing the first and second liquids. In certain preferred embodiments, the particles have less than about 0.001% of residual first and second liquids by mass remaining after removing the first and second liquids. In preferred embodiments, the particles are substantially free from any residual first and second liquids by mass after removing the first and second liquids.

In other embodiments, the particles have greater than about 90% therapeutic biologic by weight after removing the first and second liquids. In certain embodiments, the particles have greater than about 95% therapeutic biologic by weight after removing the first and second liquids. In still other embodiments, the particles have greater than about 98% therapeutic biologic by weight after removing the first and second liquids. In preferred embodiments, the particles have greater than about 98% therapeutic biologic by weight after removing the first and second liquids. In certain preferred embodiments, the particles have greater than about 99% therapeutic biologic by weight after removing the first and second liquids.

In some embodiments, the first liquid is aqueous, an organic solvent, an ionic liquid, a hydrogel, an ionogel, or a combination thereof. In other embodiments, the first liquid is aqueous. In certain embodiments, the first liquid is water, 0.9% saline, lactated Ringer's solution, buffers, dextrose 5%, or a combination thereof. In certain other embodiments, the buffer is acetate buffer, histidine buffer, succinate buffer, HEPES buffer, tris buffer, carbonate buffer, citrate buffer, phosphate buffer, phosphate-buffered saline, glycine buffer, barbital buffer, cacodylate buffer, ammonium formate buffer, urea solution, or a combination thereof. In preferred embodiments, the first liquid is water.

In other embodiments, the concentration of the therapeutic agent in the first liquid is about 10 mg/mL to about 500 mg/mL. In certain embodiments, the concentration of the therapeutic agent in the first liquid is about 10 mg/mL to about 100 mg/mL. In preferred embodiments, the concentration of the therapeutic agent in the first liquid is about 20 mg/mL to about 100 mg/mL.

In some embodiments, the first liquid has a viscosity of less than about 200 mPa·s, less than about 150 mPa·s, less than about 125 mPa·s, less than about 100 mPa·s, less than about 75 mPa·s, less than about 75 mPa·s, less than about 70 mPa·s, less than about 65 mPa·s, less than about 60 mPa·s, less than about 55 mPa·s, less than about 50 mPa·s, less than about 45 mPa·s, less than about 40 mPa·s, less than about 35 mPa·s, less than about 30 mPa·s, less than about 25 mPa·s, less than about 20 mPa·s, less than about 19 mPa·s, less than about 18 mPa·s, less than about 17 mPa·s, less than about 16 mPa·s, less than about 15 mPa·s, less than about 14 mPa·s, less than about 13 mPa·s, less than about 12 mPa·s, less than about 11 mPa·s, less than about 10 mPa·s, less than about 9.5 mPa·s, less than about 9 mPa·s, less than about 8.5 mPa·s, less than about 8 mPa·s, less than about 7.5 mPa·s, less than about 7 mPa·s, less than about 6.5 mPa·s, less than about 6 mPa·s, less than about 5.5 mPa·s, less than about 5 mPa·s, less than about 4.5 mPa·s, less than about 4 mPa·s, less than about 3.5 mPa·s, less than about 3 mPa·s, less than about 2.5 mPa·s, less than about 2 mPa·s, less than about 1.5 mPa·s, less than about 1 mPa·s, less than about 0.5 mPa·s, less than about 0.1 mPa·s, less than about 0.05 mPa·s, or less than about 0.01 mPa·s (one millipascal-second).

In other embodiments, the first liquid further comprises a surfactant. In certain embodiments, the surfactant is polysorbate, docusate or lecithin. In preferred embodiments, the surfactant is polysorbate 20, polysorbate 60, or polysorbate 80. In certain preferred embodiments, the surfactant is polysorbate 20 or polysorbate 80. In certain other embodiments, the fatty acid ester of sorbitol is a sorbitan ester, e.g., span 20, span 40, span 60, or span 80.

In some embodiments, the second liquid is aqueous, an organic solvent, an ionic liquid, a hydrogel, ionogel, protein stabilizer, or a combination thereof. In other embodiments, the second liquid is aqueous. In preferred embodiments, the second liquid is an organic solvent.

In other embodiments, the organic solvent is benzyl alcohol, benzyl benzoate, castor oil, coconut oil, corn oil, cottonseed oil, fish oil, grape seed oil, hazelnut oil, hydrogenated palm seed oil, olive oil, peanut oil, peppermint oil, safflower oil, sesame oil, soybean oil, sunflower oil, vegetable oil, walnut oil, polyethylene glycol, glycofurol, acetone, diglyme, dimethylacetamide, dimethyl isosorbide, dimethyl sulfoxide, ethanol, ethyl acetate, butyl acetate, ethyl ether, ethyl lactate, isopropyl acetate, methyl acetate, methyl isobutyl ketone, methyl tert-butyl ether, N-methyl pyrrolidone, perfluorodecalin, 2-pyrrolidone, trigylcerides, tetrahydrofurfuryl alcohol, triglycerides of the fractionated plant fatty acids C8 and C10 (e.g., MIGLYOL® 810 and MIGLOYL® 812N), propylene glycol diesters of saturated plant fatty acids C8 and C10 (e.g., MIGLYOL® 840), ethyl oleate, ethyl caprate, dibutyl adipate, fatty acid esters, hexanoic acid, octanoic acid, triacetin, diethyl glycol monoether, gamma-butyrolactone, eugenol, clove bud oil, citral, limonene, or a combination thereof. In certain embodiments, the organic solvent is ethyl acetate or butyl acetate.

In certain embodiments, the organic solvent is acetonitrile, chlorobenzene, chloroform, cyclohexane, cumene, 1,2-dichloroethene, dichloromethane, 1,2-dimethoxyethane, N,N-dimethylacetamide, N,N-dimethylformamide, 1,4-dioxane, 2-ethoxyethanol, ethyleneglycol, formamide, hexane, methanol, 2-methoxyethanol, methylbutyl ketone, methylcyclohexane, methylisobutylketone, N-methylpyrrolidone, nitromethane, pyridine, sulfolane, tetrahydrofuran, tetralin, toluene, 1,1,2-trichloroethene, xylene, acetic acid, acetone, anisole, 1-butanol, 2-butanol, butylacetate, tert-butylmethyl ether, dimethyl sulfoxide, ethanol, ethylacetate, ethyl ether, ethyl formate, formic acid, heptane, isobutylacetate, isopropylacetate, methylacetate, 3-methyl-1-butanol, methylethyl ketone, 2-methyl-1-propanol, pentane, 1-pentanol, 1-propanol, 2-propanol, propylacetate, triethylamine, 1,1-diethoxypropane, 1,1-dimethoxymethane, 2,2-dimethoxypropane, isooctane, isopropyl ether, methylisopropyl ketone, methyltetrahydrofuran, petroleum ether, trichloroacetic acid, trifluoroacetic acid, decanol, 2-ethylhexylacetate, amylacetate, or a combination thereof.

In some embodiments, the second liquid is an ionic liquid. In certain embodiments, the second liquid is a protein stabilizer.

In other embodiments, the second liquid has a viscosity of less than about 200 mPa·s, less than about 150 mPa·s, less than about 125 mPa·s, less than about 100 mPa·s, less than about 75 mPa·s, less than about 75 mPa·s, less than about 70 mPa·s, less than about 65 mPa·s, less than about 60 mPa·s, less than about 55 mPa·s, less than about 50 mPa·s, less than about 45 mPa·s, less than about 40 mPa·s, less than about 35 mPa·s, less than about 30 mPa·s, less than about 25 mPa·s, less than about 20 mPa·s, less than about 19 mPa·s, less than about 18 mPa·s, less than about 17 mPa·s, less than about 16 mPa·s, less than about 15 mPa·s, less than about 14 mPa·s, less than about 13 mPa·s, less than about 12 mPa·s, less than about 11 mPa·s, less than about 10 mPa·s, less than about 9.5 mPa·s, less than about 9 mPa·s, less than about 8.5 mPa·s, less than about 8 mPa·s, less than about 7.5 mPa·s, less than about 7 mPa·s, less than about 6.5 mPa·s, less than about 6 mPa·s, less than about 5.5 mPa·s, less than about 5 mPa·s, less than about 4.5 mPa·s, less than about 4 mPa·s, less than about 3.5 mPa·s, less than about 3 mPa·s, less than about 2.5 mPa·s, less than about 2 mPa·s, less than about 1.5 mPa·s, less than about 1 mPa·s, less than about 0.5 mPa·s, less than about 0.1 mPa·s, less than about 0.05 mPa·s, or less than about 0.01 mPa·s (one millipascal-second).

Morphology: The morphology of the particle can be an important consideration for certain applications in particle formation, e.g., concentrated pharmaceutical suspension formulations, as described herein. In order to minimize the apparent viscosity of the suspension at a given particle concentration, it is advantageous to minimize the degree to which the particles comprise internal void spaces or exhibit irregular shapes. Consider the Krieger-Dougherty equation (Y Papir and I. Krieger, J. Colloid Interface Sci., vol. 34, no. 1, 1970), which discloses the relative viscosity of the suspension $\eta = (1 - \phi/\phi_m)^{-B\phi_m}$. Here, 11 is the ratio of the apparent viscosity of the suspension to the viscosity of the of suspension medium in the absence of particles. $\phi$ is the effective volume fraction of solids, $\phi_m$ is the maximum packing fraction of solids, i.e., the maximum value that $\phi$ can take as $\eta$ becomes unbounded, and B is a coefficient describing particle-particle interactions. The minimum value for B, the so-called Einstein value of 2.5, corresponds to non-interacting hard spheres. For particles with a porosity $\alpha$, the actual volume fraction of solids is related to the effective volume fraction $\phi$ through $\phi_{act} = (1 - \alpha)\phi$, indicating that any non-zero porosity tends to limit concentration at a given viscosity. Similarly, irregularly shaped particles, in certain embodiments, tend to reduce $\phi_m$ relative to its value for spherical particles and/or to increase the interaction coefficient B, both of which are typified by disadvantageous effects on the concentration versus the viscosity profile of the suspension. For other applications, e.g., inhalable pharmaceutical composition, a high porosity and/or low particle density are desirable for achieving certain aerodynamic properties that facilitate advantageous pharmacokinetics. Dispersibility of the powder in air can also be promoted through the use of particles with rough or faceted surface features (R. Vehring, J. Aerosol Sci., 2007, 38, 728-746). Control over various morphological properties, e.g., sphericity, surface features, porosity, etc., can be important for practical application of the particles as described herein.

In some embodiments, the Peclet number is regulated in the interest of controlling the particle morphology. The term "Peclet number" refers to the ratio of the rate of a solvent mass transport process outside of a droplet or particle to the rate of a solute mass transport process inside a droplet or particle. Exemplary Peclet numbers as described herein, during the drying period are about 1 or less, indicating a regime where transport of solutes within the drop is fast as compared to the radial velocity of the receding droplet surfaces. Such Peclet numbers tend to correlate with regular, spherical particle morphologies. For Peclet numbers of about 1 or greater, the droplet surface tends to move fast in relation to the solutes, thereby leading to an enriched layer of solute near the surface of the drop (Eq. 10). Situations of this type typically correlate with irregular particle morphologies, i.e., morphologies which are less smooth, less spherical, and/or more porous than those associated with lower Peclet numbers. Such morphologies may comprise raisin-like features (high roughness) and/or a central void space.

The Peclet number can be regulated in several different ways. From Eq. 9, various properties of the liquid-liquid system can be modulated. Such properties include at least the solubility of the first liquid in the second liquid $c_{1,s}$ as well as the initial saturation level of the second liquid $c_{1,0}$. Furthermore, the diffusivities $D_{12}$ and $D_n$ may be controlled. Parameters which influence these properties and which are amenable to external control include the temperature, viscosity, and/or polarity of the first liquid and/or the second liquid, as well as the surface tension at the interface between the first liquid and the second liquid.

In other embodiments, the Peclet number of step b) is less than about 500. In some embodiments, the Peclet number of step b) is less than about 10. In certain embodiments, the Peclet number of step b) is less than about 5. In still other embodiments, the Peclet number of step b) is less than about 3. In certain other embodiments, the Peclet number of step b) is less than about 2. In preferred embodiments, the Peclet number of step b) is less than about 1.

In some embodiments, the solubility $c_{1,s}$ of the first liquid in the second liquid can be controlled. In other embodiments, the solubility of the first liquid in the second liquid ranges from about 0 g/L to fully miscible, e.g., from about 0 to about 250 g/L, from about 0 to about 100 g/L, from about 0 to about 50 g/L, from about 0 to about 25 g/L, from about 0 to about 10 g/L, from about 0 to about 9 g/L, from about 0 to about 8 g/L, from about 0 to about 7 g/L, from about 0 to about 6 g/L, from about 0 to about 5 g/L, from about 0 to about 4 g/L, from about 0 to about 3 g/L, from about 0 to about 2 g/L, or from about 0 to about 1 g/L. Methods of controlling the solubility as described herein, can include temperature regulation. In certain embodiments, mixtures of liquids are used to control solubility. In still other embodiments, the first liquid is placed in contact with the second liquid, and the solubility is adjusted thereafter by modifying the composition of the second liquid, e.g., by adjusting the relative ratios of the components of the second liquid.

In other embodiments, the saturation level $c_{1,0}$ of the first liquid in the second liquid is controlled. The saturation level ranges from about 0 to about 100%, e.g., from about 0 to about 50%, from about 0 to about 10%, from about 0 to about 5%, or from about 0 to about 1%.

In some embodiments, the temperature of the first and/or second liquid can be controlled. The first liquid and the second liquid may be kept at the same temperature or at different temperatures. In other embodiments, the temperature of each liquid is, independently, from about −100 to about 300° C., e.g., from about −20 to about 180° C., from about 0 to about 100° C., from about 0 to about 50° C., from about 0 to about 40° C., from about 0 to about 30° C., from about 0 to about 20° C., from about 0 to about 10° C., or from about 0 to about 5° C. In preferred embodiments, the temperature of each liquid is from about 0 to about 20° C., from about 0 to about 10° C., or from about 0 to about 5° C.

In other embodiments, the viscosity of the first and/or second liquid is controlled. In some embodiments, the viscosity of the first liquid and/or the second liquid affects a coefficient of diffusion or dispersal of the first liquid in the second liquid, e.g., $D_{12}$, thereby regulating the drying rate and Peclet number. The viscosity of each liquid may be, independently, from about 0.01 mPa·s to about 10,000 mPa·s, e.g., from about 0.01 to about 1,000 mPa·s, from about 0.01 to about 100 mPa·s, from about 0.01 to about 50 mPa·s, from about 0.01 to about 25 mPa·s, from about 0.01 to about 10 mPa·s, from about 0.01 to about 5 mPa·s, or from about 0.01 to about 1 mPa·s. Methods of controlling viscosity may include temperature regulation and viscosity modifying additives, e.g., polymers. Mixtures of liquids may also be used to control viscosity.

In some embodiments, the solvent polarity of the first liquid and/or second liquid is controlled. In other embodiments, the first liquid has a dielectric constant from about 1 to about 200, e.g., from about 1 to about 180, from about 10 to about 140, from about 30 to about 120, from about 50 to about 100, or from about 70 to about 80. In still other embodiments, the second liquid has a dielectric constant from about 1 to about 200, e.g., from about 1 to about 10, from about 1 to about 80, from about 1 to about 50, from about 1 to about 40, from about 1 to about 30, from about 1 to about 20, from about 1 to about 10, from about 1 to about 7, from about 1 to about 5, or from about 1 to about 3. Mixtures of various liquids may be used to control polarity.

In other embodiments, the surface tension at the interface between the first liquid and the second liquid is controlled. In some embodiments, the surface tension is from about 0 to about 100 mN/m, e.g., from about 0 to about 70 mN/m, from about 0 to about 60 mN/m, from about 0 to about 50 mN/m, from about 0 to about 40 mN/m, from about 0 to about 30 mN/m, from about 0 to about 20 mN/m, from about 0 to about 10 mN/m, from about 0 to about 9 mN/m, from about 0 to about 8 mN/m, from about 0 to about 7 mN/m, from about 0 to about 6 mN/m, from about 0 to about 5 mN/m, from about 0 to about 4 mN/m, from about 0 to about 3 mN/m, from about 0 to about 2 mN/m, or from about 0 to about 1 mN/m.

In some embodiments, the second liquid is a mixture of two or more liquids. In other embodiments, the mixture is used to tune the viscosity and/or polarity of the second liquid. In certain embodiments, the mixture is used to tune the solubility of the first liquid in the second liquid. Since such properties can affect the rate and Peclet number associated with the drying process, they may be used to directly control various particle properties (e.g., size, morphology, density, etc.) through simple adjustment of the relative ratios of the liquids comprising the mixture. For example, a two-part mixture for which the first liquid is more soluble in one component (Component A) than the other (Component B). In certain other embodiments, increasing the relative quantify of Component B will yield particles which are smoother, more spherical, and/or less porous than what would otherwise be achievable using only Component A. In still other embodiments, for two-part mixtures, one liquid in the mixture has a concentration from about 0 to about 99.9999 vol %, e.g., from about 0 to about 99 vol %, from about 0 to about 95 vol %, from about 0 to about 90 vol %, from about 0 to about 75 vol %, from about 0 to about 50 vol %, from about 0 to about 25 vol %, from about 0 to about 10 vol %, from about 0 to about 5 vol %, from about 0 to about 1 vol %, or from about 0 to about 0.0001 vol %. Exemplary two-part mixtures include, but are not limited to benzyl benzoate/acetone (e.g., about 5-30% benzyl benzoate, such as about 5:95, about 10:90, about 15:85, about 20:80, about 25:75, or about 30:70), isopropyl alcohol/sesame oil (e.g., about 35-65% isopropyl alcohol, such as about 35:65, about 40:60, about 45:55, about 50:50, about 55:45, about 60:40, or about 65:35), hexanes/ethanol (e.g., about 10-35% hexanes, such as about 10:90, about 15:85, about 20:80, about 25:75, about 30:70, or about 35:65), toluene/acetonitrile (e.g., about 10-35% toluene, such as about 10:90, about 15:85, about 20:80, about 25:75, about 30:70, or about 35:65), cottonseed oil/butyl acetate (e.g., about 10-35% cottonseed oil, such as about 10:90, about 15:85, about 20:80, about 25:75, about 30:70, or about 35:65), toluene/ethyl acetate (e.g., about 10-35% toluene, such as about 10:90, about 15:85, about 20:80, about 25:75, about 30:70, or about 35:65), diethyl ether/isopropanol (e.g., about 5-30% diethyl ether, such as about 5:95, about 10:90, about 15:85, about 20:80, about 25:75, or about 30:70), tetrahydrofuran/pentane (e.g., about 35-65% THF, such as about 35:65, about 40:60, about 45:55, about 50:50, about 55:45, about 60:40, or about 65:35), safflower oil/methanol (e.g., about 25-55% safflower oil, such as about 25:75, about 30:70, about 35:65, about 40:60, about 45:55, about 50:50, or about 55:45), and lime oil/acetone (about 5-30% lime oil, such as about 5:95, about 10:90, about 15:85, about 20:80, about 25:75, or about 30:70). As described herein, choosing the appropriate liquid combinations and ratios, e.g., components of the second liquid, can control the particle drying speed and Peclet number.

The mixture comprising the second liquid may also include a surfactant. In some embodiments, the surfactant helps to establish an interface between the first and second liquids, and in other embodiments, to regulate the drying speed and Peclet number. In certain embodiments, the surfactant limits coalescence of the drops during the drying process and/or mitigate damage to the agents, e.g., therapeutic or diagnostic agents, at the interface between the first liquid and the second liquid. The concentration of the surfactant in the second liquid ranges from about 0 to about 100 vol %, e.g., from about 0 to about 50 vol %, from about 0 to about 25 vol %, from about 0 to about 10 vol %, from about 0 to about 5 vol %, from about 0 to about 1 vol %, from about 0 to about 0.1 vol %, from about 0 to about 0.01 vol %, from about 0 to about 0.001 vol %, or from about 0 to about 0.0001 vol %. Exemplary mixtures of second liquid and surfactant include, but are not limited to Polysorbate 80/ethyl acetate (e.g., about 0.5:95.5, such as about 0.1:99.9, about 1:99, about 2.5:97.5, about 5:95, about 10:90, about 20:80), Span 20/ethyl acetate (about 0.5:95.5, such as about 0.1:99.9, about 1:99, about 2.5:97.5, about 5:95, about 10:90, about 20:80), Polysorbate 20/ethyl acetate (e.g., about 0.5:95.5, such as about 0.1:99.9, about 1:99, about 2.5:97.5, about 5:95, about 10:90, about 20:80), Polysorbate 80/butyl acetate (e.g., about 0.5:95.5, such as about 0.1:99.9, about 1:99, about 2.5:97.5, about 5:95, about 10:90, about 20:80), Polysorbate 80/isopropanol (e.g., about 0.5:95.5, such as about 0.1:99.9, about 1:99, about 2.5:97.5, about 5:95, about 10:90, about 20:80), or Polysorbate 80/cottonseed oil/ethyl acetate (e.g., about 0.5:20:79.5, such as about 0.1:20:79.9, about 1:30:69, about 2.5:10:87.5, about 5:5:90, about 10:5:75, about 20:20:60).

Careful selection of the solute mixture or concentrations in the first liquid can also be useful for influencing the ultimate particle morphology. In other embodiments, a component of the drop is typified by a diffusivity D, (corresponding Peclet number $Pe_n$) and/or a solubility limit in the first liquid which causes it to the precipitate or phase separate at the surface of the drop, with respect to other components of the drop, during the particle formation process. This phenomenon can be leveraged to prematurely enrich the surface (Eq. 10) in the interest of creating a shell that buckles to form a faceted or "raisin-like" particle (high roughness). Such morphologies can be typical of high Peclet number particle formation processes and can help to facilitate enhanced particle dispersibility properties (R. Vehring, J. Aerosol Sci., 2007, 38, 728-746). In certain embodiments, enrichment of select components at the drop surface leads to a shell that does not subsequently buckle during the particle formation process (low roughness). In certain other embodiments, a spherical particle morphology (typical of low Peclet number processes) can be recovered in spite of the premature surface enrichment of the select component or components.

As disclosed herein, it may be further understood by considering that the evolution of the shell as the first liquid continues to diffuse out of the proto-particle depends largely on the mechanical properties of the shell and the interfacial forces acting upon it. In some embodiments, the shell is stiff and able to withstand deformation under the interfacial forces, such that a spherical particle morphology (typical of low Peclet number processes) are recovered despite the surface enrichment of the select component or components. In other embodiments, the shell deforms plastically under the interfacial forces, resulting in shell buckling and subsequent low density, substantially smooth surface particle morphologies. In certain other embodiments, the final particle morphology is modified not only by tuning the Peclet number, but also by manipulating the mechanical properties or interfacial forces. Mechanical properties of proto-particle shells can be altered by changing the solutes and their concentrations within the droplet, modifying the degree to which shells are plasticized by the first or the second liquid, inclusion of a plasticizer or antiplasticizer, or by manipulating the processing temperature during particle formation. Interfacial forces at the interface between the first liquid and the proto-particle shell, or the interface between the second liquid and the proto-particle shell, can be altered by changing the composition of the first liquid or the second liquid, inclusion of surfactants within the first liquid or the second liquid, or by manipulating the processing temperature during particle formation.

In some embodiments, effective plasticization requires the use of a plasticizer in the first liquid and/or the second liquid at a temperature at about or higher than the glass transition temperature of the plasticizer. Controlling the temperature of the plasticizer during the particle formation process can most readily be achieved by controlling the temperature of the first liquid and/or the second liquid. In other embodiments, effective plasticization is leveraged to achieve a smoother, more spherical, and/or less porous particle morphology in instances where a component of the first liquid, e.g., an agent, is typified by a Peclet number greater than 1, and where the absence of effective plasticization would otherwise lead to particle morphologies which are more characteristic of high Peclet number processes. In certain embodiments, particle morphologies which are characteristic of high Peclet number processes are observed in spite of the fact that a component of the first liquid, e.g., an agent, is typified by a Peclet number less than 1. In certain other embodiments, effective plasticization is utilized to recover a smoother, more spherical, and/or less porous particle morphology. As a result, plasticization can be a potentially viable mechanism for achieving smoother, more spherical, and/or less porous particles regardless of the Peclet numbers of the components.

In other embodiments, various aqueous liquids, organic liquids, oils, ionic liquids, polysaccharides, sugars, diols, polyols, fatty acids, fatty acid esters, esters, surfactants, or a combination thereof, are employed as effective plasticizers under appropriate processing conditions. Exemplary plasticizers include, but are not limited to sucrose, xylitol, sorbitol, fructose, triglyceride, pectin, glycerol, triethylcitrate, ethyl acetate, citric acid, oleic acid, hydroxypropyl cellulose, methyl pyrrolidone polyethylene glycol, polypropylene glycol, polysorbate 80, diethyl phthalate or other phthalate derivatives, castor oil, triacetin, water, chlorpheniramine, 1-butyl-3-methyl imidazolium dioctyl sulfosuccinate, hexyl acetate, water, 2-ethylhexyl acetate, triethyl citrate, dibutyl sebacate, benzyl alcohol, benzyl benzoate, dimethylacetamide, or a combination thereof.

Like plasticization, increasing the total solute load of the first liquid can be useful for achieving smoother, more spherical, and/or less porous particles in instances where the dynamics of particle formation are such that surface buckling may be likely to prevail at the nominal solute concentration. Similarly, decreasing the solute load of the first liquid can be leveraged to induce or encourage buckling when it might not otherwise prevail at the nominal solute load.

In some embodiments, the rate at which the second liquid is introduced to the drops of the first liquid is leveraged to control embodiments of the particle formation process. For example, a second liquid with a low characteristic drying time Fo* (and thus having a high corresponding Peclet number) can be placed in contact with the first liquid at a controlled rate to achieve a lower effective Peclet number. Such control can be useful in certain embodiments for achieving a desired morphology, e.g., a continuous spherical morphology, with second liquids which would not otherwise facilitate the requisite Peclet regime. In other embodiments, drops of the first liquid are formed in a medium which has a limited capacity for dispersal of the first liquid, i.e., V is less than $V_0$. A second liquid with a low characteristic Fo* can be gradually added thereafter until sufficient first liquid has been removed from the particles.

Purposeful integration of particle porosity can be advantageous for select applications. In some embodiments, the second liquid is dispersed at least partially in the first liquid before undergoing phase separation or emulsification on the timescale of and under the conditions of particle formation. In certain embodiments, the concentration of any components in the drop, including any dispersed second liquid, typically increases as the first liquid disperses throughout the second liquid. In certain other embodiments, phase separation or emulsification owes to the inability of the second liquid in the drop to diffuse away as the concentration approaches the saturation limit $c_{2,s}$. The extent to which phase separation or emulsification takes places can be a function of the choice of agent(s), e.g., therapeutic or diagnostic agents, and/or excipients. In still other embodiments, the phenomenon is related to the formation of a skin, i.e., an enriched surface layer (Eq. 10), comprising one or more components of the drop that traps or encapsulates at least a portion of the second liquid. Subsequent removal of the trapped second liquid can produce particles with internal void spaces and porosity.

For certain applications, e.g., concentrated pharmaceutical suspension, particle morphologies which exhibit a satisfactory smoothness, sphericity, and/or porosity may be achieved using one or more of the methodologies disclosed herein. This can be facilitated by ensuring that the main component or components of the first liquid, e.g., the agent(s), are typified by sufficiently low Peclet numbers. The Peclet numbers may be from about 0 to about 10, e.g., from about 0 to about 9, from about 0 to about 8, from about 0 to about 7, from about 0 to about 6, from about 0 to about 5, from about 0 to about 4, from about 0 to about 3, from about 0 to about 2, from about 0 to about 1, from about 0 to about 0.5, from about 0 to about 0.25, or from about 0 to about 0.1.

In certain embodiments, judicious control of the disclosed methods is useful for achieving low Peclet numbers even in instances where a component or components of the first liquid, e.g., the agent(s), are characterized by a low diffusivity. Since alternative approaches to desiccation, e.g., conventional spray drying, are restricted to regimes of high drying rate, corresponding Peclet numbers for low diffusivity components are often large, meaning that certain morphologies of interest may not be accessible. Therefore, the methods described herein, can afford unique Peclet control for select components, e.g., large biomolecules. Depending on the processing conditions, low Peclet numbers may be achieved when the diffusivity of the component is from about 0 to about 10,000 $\mu m^2/s$, e.g., from about 0 to about 1,000 $\mu m^2/s$, from about 0 to about 100 $\mu m^2/s$, from about 0 to about 50 $\mu m^2/s$, from about 0 to about 25 $\mu m^2/s$, from about 0 to about 10 $\mu m^2/s$, from about 0 to about 5 $\mu m^2/s$, from about 0 to about 2.5 $\mu m^2/s$, or from about 0 to about 1 $\mu m^2/s$.

Surface Properties: The surface characteristics of the particle can also be important for certain applications of the methods as described herein. For example, surface roughness and surface chemistry can be important for promoting dispersibility (R. Vehring, J. Aerosol Sci., 2007, 38, 728-746) and/or regulating the kinetics of dissolution. Surface energy can also be important for ensuring that the particles are wetted in a given medium, e.g., the continuous phase of a pharmaceutical suspension formulation, such that they disperse rather than exhibit a strong proclivity for flocculation (M. Bowen, et al., J. Pharm. Sci., vol. 101, no. 12, 2012).

In one aspect, the disclosure provides a method of controlling the surface properties of particles, the method comprising: a) providing droplets comprising a first liquid, a first component, and a second component, wherein the first component is present in an amount closer to its solubility limit than the second component, the first component has a higher Peclet number than the second component, or a combination thereof; b) contacting the droplets with a second liquid; c) allowing the droplets to dry; and d) removing the first and second liquids, thereby forming particles, wherein the first component is enriched at the surface of the particles relative to the second component.

In some embodiments, various parameters which are amenable to external control during the particle formation process are leveraged to influence the surface chemistry and/or surface energy of the particles. These include, but are not limited to the temperature, viscosity, surface tension, and/or polarity of the first and/or second liquid. In other embodiments, the second liquid is a mixture of two or more liquids of different polarities. In certain embodiments, the mixture comprises liquids having differing solubility.

In other embodiments, the droplet is surrounded by a halo of the first liquid as it disperses throughout the second liquid during particle formation. From Eq. 4, the distribution $\hat{c}_1$ of the first liquid in the second liquid approaches $(\hat{r}+1)^{-1}$ outside of the drop at long Fourier times Fo. In some embodiments, one or more of the components of the drop are soluble in the halo, e.g., therapeutic or diagnostic agents and/or excipients, under the conditions of particle formation. Unlike particle formation methodologies, such as spray drying (R. Vehring, J. Aerosol Sci., 2007, 38, 728-746), the methods described herein, facilitates coordination of select components outside of the interface between the drop and the second liquid during particle formation. In certain embodiments, this phenomenon is leveraged to decorate the surface of the particle with select components. In certain other embodiments, the surface decoration is used to functionalize the surface and/or modulate its energy, among other things.

Similar to the morphology methods as described herein, careful selection of the solute mixture and concentration can be useful for influencing the surface composition and energy. In some embodiments, a component of the drop is typified by a diffusivity $D_n$ (corresponding Peclet number $Pe_n$) and/or a solubility limit in the first liquid which causes it to the precipitate or phase separate at the surface of the drop, preferentially, with respect to other components of the drop, during the particle formation process. In other embodiments, this phenomenon is leveraged to decorate the surface of the particle with select components. In certain embodiments, the surface decoration is used to functionalize the surface and/or modulate its energy. In certain other embodiments, a core-shell structure is produced when a high Peclet number component forms a shell around an inner core of a component or components with lower Peclet numbers.

In some embodiments, core-shell droplets are utilized to produce particles comprising a core-shell structure that is intended to control the surface roughness, chemistry, and/or energy. The shell may also play an important role in pharmacokinetics. Droplets of the disclosure as described herein, may include one or more shell layers, each of which may or may not be typified by a unique solvent and have a unique composition of solutes, e.g., therapeutic agents, diagnostic agents, or excipients. When the droplets include one or more liquid (shell) layers, particle formation requires drying of at least the outermost layer of the droplet, but may also involve drying of one or more inner layers. In other embodiments, the outermost layer of the core-shell droplet is dried through methods of the disclosure to produce particles with a solid-shell and non-solid, i.e., liquid or gel-like, inner layers. In certain embodiments, all layers of the core-shell droplet are dried through methods of the disclosure to produce particles with solid layers.

In other embodiments, the particles have a morphology comprising a core and a shell. In other embodiments, the shell comprises one or more layers. In still other embodiments, the shell is a gel. In certain embodiments, the gel is a hydrogel, ionogel, or organogel. In certain other embodiments, the shell is crystalline or semi-crystalline. In certain preferred embodiments, the core is solid, gel, or liquid.

In some embodiments, crystalline or semi-crystalline shells are useful for some methods described herein, since the crystalline or semi-crystalline surface material is typified by a lower energy state than the corresponding amorphous matter. For example, crystalline surface matter can help to mitigate particle-particle interactions and enhance dispersibility. In other embodiments, the shell need not necessarily be continuous or fully encapsulating and may instead comprise discrete crystalline surface domains. In certain embodiments, the components or components of the drop which are controlled in such a way that they reside at the particle surface, are elected on the basis of their amenability to crystallization under the conditions of particle formation as described herein.

In other embodiments, the second liquid is a mixture of, e.g., two or more liquids of different polarities. In some embodiments, the solubility of the first liquid in one component of the mixture differs from the solubility of the first liquid in another component or components of the mixture. In still other embodiments, where the first liquid disperses into the second, the morphology of the particles produced can be controlled by adjusting the ratio of the liquids in the mixture. For example, a mixture including a higher vol % of the lower solubility can give rounder or circular particles. One liquid in the mixture can be from about 1 to about 99 vol %, e.g., about 1-10 vol %, about 5-25 vol %, about 10-30 vol %, about 15-50 vol %, about 20-60 vol %, about 30-75 vol %, about 40-80 vol %, about 50-99 vol %, or about 75-99 vol %, with the balance being the other liquid or liquids. Exemplary mixtures are benzyl benzoate/acetone (e.g., about 5-30% benzyl benzoate, such as about 5:95, about 10:90, about 15:85, about 20:80, about 25:75, or about 30:70), isopropyl alcohol/sesame oil (e.g., about 35-65% isopropyl alcohol, such as about 35:65, about 40:60, about 45:55, about 50:50, about 55:45, about 60:40, or about 65:35), hexanes/ethanol (e.g., about 10-35% hexanes, such as about 10:90, about 15:85, about 20:80, about 25:75, about 30:70, or about 35:65), toluene/acetonitrile (e.g., about 10-35% toluene, such as about 10:90, about 15:85, about 20:80, about 25:75, about 30:70, or about 35:65), cottonseed oil/butyl acetate (e.g., about 10-35% cottonseed oil, such as about 10:90, about 15:85, about 20:80, about 25:75, about 30:70, or about 35:65), toluene/ethyl acetate (e.g., about 10-35% toluene, such as about 10:90, about 15:85, about 20:80, about 25:75, about 30:70, or about 35:65), diethyl ether/isopropanol (e.g., about 5-30% diethyl ether, such as about 5:95, about 10:90, about 15:85, about 20:80, about 25:75, or about 30:70), tetrahydrofuran/pentane (e.g., about 35-65% THF, such as about 35:65, about 40:60, about 45:55, about 50:50, about 55:45, about 60:40, or about 65:35), safflower oil/methanol (e.g., about 25-55% safflower oil, such as about 25:75, about 30:70, about 35:65, about 40:60, about 45:55, about 50:50, or about 55:45), and lime oil/ acetone (about 5-30% lime oil, such as about 5:95, about 10:90, about 15:85, about 20:80, about 25:75, or about 30:70). In certain other embodiments, the first liquid or the second liquid has a viscosity from about 0.01 mPa·s to about 10,000 mPa·s, e.g., from about 0.01 to about 1,000 mPa·s, from about 0.01 to about 100 mPa·s, from about 0.01 to about 50 mPa·s, from about 0.01 to about 25 mPa·s, from about 0.01 to about 10 mPa·s, from about 0.01 to about 5 mPa·s, or from about 0.01 to about 1 mPa·s. In certain preferred embodiments, the first liquid or the second liquid further comprises a surfactant.

Composition and Degradation Products: In some embodiments, a component is added to the first liquid to limit the influx of the second liquid under the conditions of particle formation. Limiting the penetration of the second liquid can be useful, e.g., for minimizing the amount of residual second liquid in the particle after formation and/or mitigating the degree to which unwanted degradation products form as a result of interactions between components of the first liquid and the second liquid. In other embodiments, the component is added to mitigate the diffusivity of the second liquid in the drop $D_{21}$, enforcing a disparity in relation to $D_{12}$. In certain embodiments, the component is added to limit the solubility $c_{2,s}$. In still other embodiments, the component is added to achieve a combination of such effects.

In other embodiments, the second liquid is chosen such that its presence in the drop during particle formation helps to stabilize the agent(s), e.g., therapeutic or diagnostic agents. The therapeutic or diagnostic agent may undergo changes in molecular size through the irreversible association of two or more molecules. In some embodiments, the presence of second liquid in the drop during particle formation at various stages throughout the process decreases the tendency of the therapeutic or diagnostic agent to undergo this irreversible self-association by several potential mechanisms including, but not limited to, either an increase in the activation energy for the transition state of the rate limiting step of the irreversible self-association reaction, or a change the interfacial activity of the therapeutic or diagnostic agent at the air-liquid, liquid-solid, or liquid-liquid interface, etc.

For example, in a given solvent, it may be thermodynamically favorable to bury exposed hydrophobic or charged regions on the surface of the therapeutic or diagnostic agent, to prevent self-association. The changes in self-association tendency of the therapeutic or diagnostic agent due to the addition of the second liquid may be due to the direct interaction of the second liquid molecules with association prone regions of the therapeutic or diagnostic agent, resulting in reduced exposure of these association prone regions. In certain embodiments, the second liquid affects the interaction of first liquid with the therapeutic agent, and/or of the first liquid with itself, thereby affecting the tendency for self-association between the therapeutic or diagnostic molecules. The difference in interfacial adsorption affinity for the second liquid molecules as compared to the therapeutic or diagnostic agent may also affect the interface mediated formation of irreversible self-associated therapeutic or diagnostic agent through either competitive inhibition of interfacial adsorption of the therapeutic or diagnostic agent or limiting the reversible or irreversible self-association of therapeutic or diagnostic agent adsorbed at the interface. In certain other embodiments, the use of second liquid for the stabilization of therapeutic or diagnostic agent through the process followed by subsequent removal of the second liquid can reduce the excipient burden in the final powder or suspension formulation. A reduction in excipient burden would further increase the dosage of therapeutic or diagnostic agents while minimizing the delivery volume, shortening administration time, and/or reducing pain.

In some embodiments, the excipients in the droplets are soluble in the second liquid under the conditions of particle formation. In other embodiments, this leads to leaching of the excipients and changes to the relative ratios of components as particles are formed from the droplets, e.g., the droplets have a higher excipient to agent ratio than the particles on account of excipient loss (H. C Shum, Biomicrofluidics, 2012, 6 (1), 012808). To counteract this activity, excipients can be added to the second liquid at appropriate concentrations. This can help to prevent concentration gradients and/or other driving forces that may, in some embodiments, lead to leaching. In certain embodiments, the second liquid includes, e.g., a carbohydrate, a pH adjusting agent, a salt, a chelator, a mineral, a polymer, a surfactant, an amino acid, an oligopeptide, a biologic excipient, a chemical excipient, an antiseptic, an antioxidant, a paraben, a bactericide, a fungicide, a vitamin, a preservative, an analgesic, and/or nutrient media, or a combination thereof.

For select applications, e.g., concentrated pharmaceutical suspension formulations, leaching of excipients or other components of the drop can be advantageous. Select components may be useful for the particle formation process but less desirable from stability, particle composition, or various other standpoints. For example, an appreciable concentration of surfactant may be advantageous for mitigating coalescence during particle formation but disadvantageous in that it decreases the weight fraction of the agent(s), e.g., therapeutic or diagnostic agents, in the particle. Maximizing the weight fraction of the agent(s) can be desirable when forming concentrated pharmaceutical suspension formulations from the particles or applying them in various other ways. In some embodiments, a subset of the components of the drop, e.g., a surfactant, are at least slightly soluble in the second liquid. In other embodiments, the second liquid is leveraged to extract at least a portion of these components from the drops or particles.

The conditions of particle formation as described herein, including the total desiccation time for the droplet, can also be engineered to provide sufficient conditions for crystal formation among one or more of the components of the droplets. In some embodiments, the majority of the matter comprising the particles is in a crystalline state while in other embodiments, only a fraction of the matter crystallizes. In certain embodiments, the remaining matter is in a semi-crystalline or amorphous state. In certain other embodiments, all of the matter comprising the particles is semi-crystalline, amorphous, or some combination thereof. Coordinating the location of crystalline domains can be advantageous for certain methods as described herein. For example, crystalline domains at the surface of the particles may be useful for minimizing particle-particle interactions and enhancing dispersibility. In still other embodiments, the crystalline domains at the surface may be typified by lower energy states than corresponding amorphous matter. In certain preferred embodiments, the Peclet number of the material to be crystallized is controlled such that it preferentially resides at the particle surface.

Methods of Droplet and Particle Handling

Droplets of the disclosure can be placed in contact with a second liquid in one of several ways. In some embodiments, the droplets are formed within the second liquid, such that they are immediately in contact with one another. In other embodiments, the droplets are formed in a separate medium and placed into contact with the second liquid thereafter, e.g., by dripping or spraying them into or onto the second liquid. This medium can be, e.g., air, an inert gas, vacuum, or a third liquid in which the first liquid is at least partially immiscible under the conditions of particle formation. In certain embodiments, the second liquid is contained in a vessel where the droplets are collected. The term "vessel" refers to a container for a second liquid. Exemplary embodiments include an open bath, a closed bath, or a microfluidic junction, i.e., the tubing or channels within which and through which microfluidic droplet generation may proceed.

The droplets and particles described herein, can have different densities, e.g., the solid particles can have a higher density than the liquid droplets. The density of the droplets and the particles may be higher, lower, or substantially the same as the second liquid. In some embodiments, the second liquid is contained in a vessel and chosen such that its density is between that of the droplets and the solid particles. In certain embodiments, droplets are dispersed in a medium, e.g., air, inert gas, or vacuum, and collected with the second liquid. The droplets float on the interface between the second liquid and the medium in which they are dispersed, such that the formation of particles is at least partially assisted by evaporation of the first liquid into the medium. In still other embodiments the temperature, pressure, and vapor content (of the first liquid) and of the medium in which the droplets are dispersed can be regulated to control the evaporation characteristics. The temperature of the medium during evaporation is from about −100 to about 300° C., e.g., from about −100 to about 200° C., from about −100 to about 150° C., from about −100 to about 100° C., from about −75 to about 75° C., from about −40 to about 40° C., from about −30 to about 30° C., from about −20 to about 20° C., from about −10 to about 10° C., or from about −4 to about 4° C. The pressure of the medium during evaporation can be from about $10^{-6}$ atm to about 10 atm, e.g., from about $10^{-6}$ atm to about 1 atm, from about $10^{-5}$ atm to about 1 atm, from about $10^{-4}$ atm to about 1 atm, or from about $10^{-3}$ atm to about 1 atm. The vapor content (of the first liquid) and of the medium during evaporation, relative to the saturation point, can be from about 0 to about 100%, e.g., from about 0 to about 50%, from about 0 to about 25%, from about 0 to about 10%, from about 0 to about 5%, from about 0 to about 2%, from about 0 to about 1%, from about 0 to about 0.5%, from about 0 to about 0.1%, or from about 0 to about 0.01%. In certain other embodiments, the droplet density can increase during evaporation, leading to the particles that sink into the second liquid.

In some embodiments, the droplets of step a) are formed by electrospray, an ultrasonic atomizer, a microfluidic device. In other embodiments, the droplets of step a) are formed in a microfluidic device. In certain embodiments, the droplets formed in the microfluidic device are regularly spaced in the microfluidic device.

In certain embodiments, an electric field and/or magnetic field is used to guide or steer charged and/or magnetic droplets into and through a second liquid. Such techniques are particularly useful when spraying droplets into a medium, e.g., air, and collecting them in a vessel of the second liquid. In certain other embodiments, the electric and/or magnetic field is useful for overcoming buoyancy and/or surface tension effects. The forces associated with the electric and/or magnetic fields are such that the droplets can be driven into the second liquid in instances where the surface tension and/or density of the second liquid would otherwise make it difficult.

In some embodiments, the droplets are charged. In other embodiments, the charge on the droplets or particles is all or partially dissipated before, during, or after desiccation by means of, e.g., contacting the droplets or particles with an electrode. In certain embodiments, the charge on the droplets or particles is intentionally preserved, either completely or in part, by preventing direct contact between an electrode and the droplets or particles.

In other embodiments, the droplets are formed using a microfluidic device. In some embodiments, a microfluidic source produces droplets, wherein the first liquid is co-flowed with at least a partially immiscible liquid, i.e., a third liquid, to form droplets. The droplets can be collected in a vessel containing a second liquid, in which they dry to form particles. In certain embodiments, the first liquid and third liquid are different but miscible. In still other embodiments, the first liquid is co-flowed directly with the second liquid, such that an intermediate liquid is obviated. Droplets may be formed by methods, whereby flow in the microfluidic system remains Stokesian, typified by a low Reynolds number, or through inertial microfluidic technologies (J. Zhang et al. Lab Chip. 2016, 16, 10-34).

In some embodiments, a surfactant is added to the second liquid to decrease the surface tension. Such effects are useful for facilitating entry of the droplets into the second liquid when the droplets are first dispersed in a medium and then collected with a vessel of the second liquid.

In other embodiments, the droplets are dried after contacting the droplets with a second liquid. In some embodiments, the second liquid includes or be in contact with a drying substance, i.e., a desiccant, to absorb the first liquid or otherwise sequester it, e.g., by reaction. Such substances are useful for ensuring a uniform, steady-state degree of saturation of the first liquid in the second liquid during drying. Exemplary desiccants include, but are not limited to celite, molecular sieves, phosphorous pentoxide, magnesium sulfate, silica, calcium chloride, activated charcoal, or potassium carbonate.

In some embodiments, the second liquid has a Fourier number (Fo) of less than about 1.500 allowing the droplets to dry in about 60 seconds. In other embodiments, the second liquid has a Fourier number (Fo) of less than about 1.000 allowing the droplets to dry in about 60 seconds. In still other embodiments, the second liquid has a Fourier number (Fo) of less than about 0.500 allowing the droplets to dry in about 60 seconds. In certain other embodiments, the second liquid has a Fourier number (Fo) of less than about 0.208 allowing the droplets to dry in about 5 seconds.

In other embodiments as described herein, step b) further comprises decreasing the temperature of the second liquid to a temperature within about 30° C. of the freezing point of the first liquid. In certain other embodiments, the boiling point of the second liquid at atmospheric pressure is from about 0 to about 200° C. In still other embodiments, the second liquid is a mixture of two or more liquids of different polarities. In certain preferred embodiments, the mixture comprises liquids having differing solubility.

Post-Processing

In some embodiments, the particles or proto-particles are removed from the second liquid via centrifugation, sieving, filtration, magnetic collection, solvent exchange, inertial separation, hydrocyclone separation, or decanting. In other embodiments, the particles are removed from the second liquid through a solvent exchange washing procedure. After removal of most of the second liquid (e.g., after centrifugation and supernatant decanting), another liquid may be added which is volatile, miscible with the second liquid, and in which the particles are not soluble under the conditions of washing. In still other embodiments, the second liquid can be replaced with a volatile washing liquid that is easier to remove. Additional cycles of concentration, supernatant removal, and backfilling with the washing liquid may lead to substantial reduction of the content of the second liquid. The washing liquid may be subsequently evaporated, e.g., by application of heat and/or vacuum, or removed via lyophilization. In certain embodiments, the washing liquid is an organic liquid. In certain other embodiments, the washing liquid is a supercritical fluid, e.g., supercritical $CO_2$, a cryogenic fluid, e.g., liquid nitrogen, or a mixture of one of these liquids and an organic liquid. In some embodiments, the boiling point of the washing liquid at atmospheric pressure is from about −200 to about 200° C., e.g., from about −200 to about 100° C., from about −200 to about 75° C., or from about −200 to about 50° C. In certain preferred embodiments, the first and second liquids are removed through centrifugation, sieving, filtration, magnetic collection, solvent exchange, or decanting.

In other embodiments, a subset of the components of the drop, e.g., a surfactant, are at least slightly soluble in the washing liquid. In certain embodiments, the washing liquid is leveraged to extract at least a portion of these components from the drops or particles. Select components may be useful during the particle formation process but less desirable from stability, particle composition, or various other standpoints. For example, an appreciable concentration of surfactant may be advantageous for mitigating coalescence during particle formation but disadvantageous in that it decreases the weight fraction of the agent(s), e.g., therapeutic or diagnostic agents, in the particle. Maximizing the weight fraction of the agent(s) can be desirable when forming concentrated pharmaceutical suspension formulations from the particles or applying them in various other ways.

In some embodiments, the methods as described herein, further comprises washing the particles after step d) with a washing fluid, e.g., an organic liquid, a supercritical fluid, a cryogenic liquid, or a combination thereof. In certain embodiments, the washing fluid is an organic liquid, a supercritical fluid, a cryogenic liquid, or a combination thereof.

The particles can be subjected to one or more secondary desiccation steps after separation from the second liquid. Such steps can be utilized to remove washing liquid, and/or to modulate residual quantities of the first liquid in the particles. In some embodiments, residual quantities of the second liquid persist in the particles after primary desiccation. In other embodiments, secondary drying is useful for reducing quantities to a desired level. Exemplary methods of secondary desiccation include vacuum drying with or without application of heat, lyophilization, fluidized bed drying, slurry spray drying, tray drying, belt drying, or air drying on a filter membrane.

In some embodiments, secondary desiccation is achieved by flowing a drying gas over a bed of particles atop a filtration element. In certain embodiments, the drying gas is helium, air, nitrogen or argon. In preferred embodiments, the drying gas is helium or air. The temperature, pressure, flow rate, or vapor content of the drying gas may be controlled during the drying time to achieve a desired rate of desiccation, a desired temperature difference relative to the glass transition temperature, or a desired equilibrium content of the first liquid or the second liquid at the conclusion of the secondary desiccation step. In other embodiments, the time required to achieve a desired level of desiccation is lower than that which corresponds to alternative secondary desiccation techniques, e.g., lyophilization, spray drying, or fluidized bed drying. Similarly, the percentage of material recovery may be greater.

In other embodiments, the primary desiccation step, the washing step, and/or the secondary desiccation step are facilitated by modulating the temperature of particles relative to their glass transition temperature. Under certain conditions, quantities of the first liquid, the second liquid, the washing liquid, and/or various components of the drop or particle, e.g., a surfactant, become trapped in a "glassy" matrix during particle formation (Richardson, H. et al., The European Physical Journal E, 12, no. 1 (2003): 87-91). This can make extraction of various liquids or drop or particle components challenging. In some embodiments, removal of various trapped liquids or drop or particle components can be facilitated by bringing the temperature of the drop or particle in proximity to the glass transition temperature for a period of time. Proximity to the glass transition enhances mobility within the drop or particle and permits liberation of the trapped liquids or drop or particle components at a substantially enhanced rate relative to what is typically seen at temperatures well below that of the transition. With respect to the glass transition temperature, the temperature of the drop or particles during this step can be within about ±30° C., within about ±20° C., within about ±10° C., within about ±5° C., within about ±2° C., or within about ±1° C. The duration for which the sample must be held in this proximity can vary as a function of the mobility of the liquid or component to be extracted and the conditions of extraction, e.g., the temperature, flow rate, and humidity of the drying gas, but can be from about 0 to about 24 hours, from about 0 to about 12 hours, from about 0 to about 6 hours, from about 0 to about 3 hours, from about 0 to about 1 hour, from about 0 to about 0.5 hours, from about 0 to about 0.25 hours, or from about 0 to about 0.1 hours.

The volatility of the second liquid can contribute to the ease and expedience with which it may be removed from the particle after primary desiccation. In some embodiments, a second liquid with high volatility is chosen in the interest of minimizing the time and energy required for reaching a desired residual quantity of the second liquid during post-processing. In other embodiments, the boiling point of the second liquid at atmospheric pressure is from about 0 to about 100° C., e.g., from about 0 to about 80° C., or from about 0 to about 75° C. In certain embodiments, the conditions under which primary desiccation occurs are controlled such that the desiccation time and Peclet number provide for particle characteristics of interest, e.g., a desired morphology. Such conditions include at least the temperature of the second liquid and its initial saturation level with respect to the first liquid, $c_{1,0}$. For example, a volatile second liquid can be sufficiently cooled, e.g., to about the freezing point of the first liquid or slightly higher, to depress the saturation level $c_{1,s}$ and reach a Peclet number regime of around about 1 or lower. Particles of a regular spherical morphology can be produced, after which the second liquid is removed during post-processing with relative ease in comparison to alternative second liquids of a much higher boiling point.

In some embodiments, a shell is added to the particles after secondary desiccation through a spray dry process. The dry particles can be suspended in a medium within which a shell material is dissolved to form a process slurry. The process slurry is spray dried by atomizing the slurry and evaporating the medium with a drying gas. The dissolved shell material condenses on the surfaces of the particles as the medium is removed to form a shell layer. In other embodiments, the microstructure of the atomized slurry is controlled to achieve a desired particle size distribution of the final coated powder. In certain embodiments, the concentration of the shell solute and the dry particles are selected to achieve a desired average shell thickness and shell to core mass ratio.

In other embodiments, the particle shell (either native or added in a post-processing step) is tailored for a specific application or applications. For example, PLGA particles may be functionalized with poly(ethylene glycol) (PEG). This results in a particle surface that is almost invisible to mononuclear phagocyte system (Acta Biomater., 73, 2018, 38-51). In some embodiments, poly(lactic-co-glycolic acid) (PLGA) shells are functionalized with carboxyl groups, allowing for the covalent attachment of proteins, antibodies, peptides, and small molecules.

In some embodiments, the particles are further dried by lyophilization or vacuum desiccation.

In other embodiments, warm gas evaporation is used to further dry the particles. In still other embodiments, the particles are further dried by contacting the particles with a stream of gas. In certain embodiments, the gas has a temperature from about −80 to about 200° C. In certain other embodiments, the gas has a temperature from about 10 to about 40° C. In some other embodiments, the gas has a relative humidity from about 0 to about 100%.

In some embodiments, the particles are formed in the presence of an electric field. In other embodiments, the particles formed in the presence of the electric field have an average diameter less than or equal to the diameter of particles produced in the absence of an electric field. In certain embodiments, the particles comprise a net charge.

In other embodiments, the net charge substantially minimizes particle coalescence.

In some embodiments, the methods as described herein, further comprises sterilization of the particles after the first and second liquids are removed. In certain embodiments, the sterilization occurs by irradiation, pasteurization, or freezing. In certain preferred embodiments, the irradiation is by gamma radiation.

Methods of Use

The pharmaceutical compositions including suspensions or dry forms of the disclosure may be administered in a suitable dosage that may be adjusted as required, depending on the clinical response. Compositions may also be used cosmetically. The dosage of the pharmaceutical composition can vary depending on factors, such as the pharmacokinetics of the therapeutic or diagnostic agents; the mode of administration; the age, health, and weight of the recipient; the nature and extent of the symptoms; the frequency of the treatment, and the type of concurrent treatment, if any; and the clearance rate of the therapeutic or diagnostic agents in the animal to be treated. Administration may occur daily, weekly, every two weeks, every three weeks, monthly, or any other suitable interval. In general, satisfactory results may be obtained when the therapeutic or diagnostic agent is administered to a human at a dosage of, for example, between about 0.01 mg/kg and about 70 mg/kg (measured as the solid form). In some embodiments, the dosage may range from about 0.01 mg/kg to 1 about mg/kg. Dose ranges include, for example, between about 30 mg and about 5000 mg. In other embodiments, at least about 30, about 100, about 500, about 1000, about 2000, or about 5000 mg of the compound that is administered. Preferred dose ranges include, e.g., between about 1-30 mg/kg, or about 1-10 mg/kg.

The volume delivered will depend on the indication and the route of delivery. In some embodiments, a dose of more than about 0.5 mL, e.g., more than about 2 mL, of a pharmaceutical composition having a viscosity less than about 50 mPa·s, e.g., less than about 30 mPa·s, is administered, e.g., injected into skin of an animal. In other embodiments, a dose of more than about 1.5 mL, e.g., more than about 5 mL, of a pharmaceutical composition having a viscosity less than about 50 mPa·s, e.g., less than about 30 mPa·s, is administered, e.g., injected into skin of an animal.

The pharmaceutical composition may be administered by any suitable method, for example, by auricular, buccal, conjunctival, cutaneous, dental, electro-osmotical, endocervical, endosinusial, endotracheal, enteral, epidural, extraamniotical, extracorporeal, infiltration, interstitial, intra-abdominal, intra-amniotical, intra-arterial, intra-articular, intrabiliary, intrabronchial, intrabursal, intracameral, intracardial, intracartilaginous, intracaudal, intracavernous, intracavitary, intracerebral, intracisternal, intracorneal, intracoronal, intracoronary, intracorporus cavernosum, intradermal, intradiscal, intraductal, intraduodenal, intradural, intraepidermal, intraesophageal, intragastrical, intragingival, intrailleal, intralesional, intraluminal, intralymphatical, intramedullar, intrameningeal, intramuscular, intraocular, intraovarian, intrapericardial, intraperitoneal, intrapleural, intraprostatical, intrapulmonary, intrasinal, intraspinal, intrasynovial, intratendinous, intratesticular, intrathecal, intrathoracic, intratubular, intratumor, intratympanic, intrauterine, intravascular, intravenous, intravenous bolus, intravenous drip, intraventricular, intravesical, intravitreal, iontophoresis, irrigation, laryngeal, nasal, nasogastrical, occlusive dressing technique, ophthalmical, oral, oropharyngeal, parenteral, percutaneous, periarticular, peridural, perineural, periodontal, rectal, inhalation, retrobulbar, soft tissue, subarachnoidial, subconjunctival, subcutaneous, sublingual, submucosal, topical, transdermal, transmucosal, transplacental, transtracheal, transtympanic, ureteral, urethral, or vaginal administration.

In some embodiments, a pharmaceutical suspension formulation is formed to improve the injectability of certain therapeutic or diagnostic agents. Specifically, the suspension may exhibit lower viscosity than an aqueous solution of comparable therapeutic or diagnostic agent loading, thereby reducing the forces required to administer the suspension with a standard injector device, i.e., the breakaway and glide forces. In other embodiments, particles in suspension provide a means for replacing the intermolecular interactions that prevail in regular solution, e.g., aqueous solution, with less onerous effects, e.g., excluded volume effects. In certain other embodiments, this permits the performance of the suspension to approximately obey the Einstein Equation for the viscosity of solutions (E. W. J. Mardles, Nature, 1940, 145, 970):

$$\eta = \eta_0(1 + 2.5\phi) \qquad \text{Eq. 15}$$

where $\eta$ is the apparent viscosity of the suspension, $\eta_0$ is the viscosity of the suspension carrier medium, and $\phi$ is the volume fraction of the solutes or particles. In certain embodiments, particularly those involving high volume fraction, $\phi$, the performance of the suspensions approximately obeys other equations such as the Krieger-Dougherty equation or the Frankel-Acrivos equation (S. Mueller, E. W. Llewellin, H. M. Mader, Proc. Royal Soc. A, 2010, 466, 1201-1228), amongst others. In still other embodiments, the suspension formulation provides a means of enhancing the stability of certain therapeutic or diagnostic agents at a given concentration, e.g., as compared to an aqueous formulation, and improving the injectability concurrently. In certain preferred embodiments, in which the injectability is not necessarily improved, the suspension formulation enhances the stability properties of the therapeutic or diagnostic at a given concentration. In some embodiments, powder formulations enhance the stability of certain therapeutic or diagnostic agents, e.g., as compared to an aqueous formulation. The term "powder formulation" refers to a solid formulation including solid particles in the absence of a carrier liquid. In other embodiments, the powder formulation is suitable for powder injection, e.g., with a PORTAL PRIME™ device.

In certain embodiments, the particles can be suspended in a non-aqueous or aqueous liquid, thereby forming a non-aqueous or aqueous suspension. In certain other embodiments, the process of generating non-aqueous or aqueous suspensions with therapeutic or diagnostic agents does not significantly alter the structure or bioactivity of the agents. In addition, the present disclosure allows for the delivery of higher doses of therapeutic or diagnostic agents while minimizing the delivery volume, shortening administration time, and/or reducing pain.

The term "injectability" refers to the relative ease with which a liquid formulation can be administered to a subject through the use of an injection device. In some embodiments, the injectability is determined by measuring the viscosity of the formulation at various shear rates. In other embodiments, the injectability is determined by measuring the breakaway and/or glide forces required to actuate a standard injection device consisting of a syringe barrel, a plunger, and, optionally, a needle. In certain embodiments, the injectability of the suspension formulation is superior to that of an aqueous formulation with about the same concentration of therapeutic or diagnostic agents. The term "injection breakaway force" refers to the force required to overcome friction between the syringe barrel and plunger of a standard injection device before ejection of the contents of the syringe can take place at a steady rate. The force is applied at the outward-facing end of the syringe plunger shaft and directed along the axis of the syringe barrel. The contents of the syringe are optionally ejected through a syringe needle of prescribed gauge and length. In some embodiments, the injection breakaway force is measured through a load cell placed at the outward-facing end of the syringe plunger during actuation. The term "injection glide force" refers to the force required to maintain a steady ejection of the contents of a standard injection device. The force is applied at the outward-facing end of the syringe plunger shaft and directed along the axis of the syringe barrel. The contents of the syringe are optionally ejected through the tip of a syringe needle of prescribed gauge and length. In some embodiments, the injection glide force is measured through a load cell placed at the outward-facing end of the syringe plunger during actuation.

In some embodiments, the particles are manufactured and collected for use in a needle-free injector or in an inhalation or other nasal delivery system. In other embodiments, the particles are stored as a dry powder. In certain embodiments, the dry powder is reconstituted shortly before administration of a formulation in which the therapeutic or diagnostic agents are dissolved in an aqueous or non-aqueous solution. Such a paradigm is beneficial in some cases for circumventing the relative instability or degradation of certain therapeutic or diagnostic agents stored in an aqueous or non-aqueous solution form, rather than a dry powder form.

Needle-free injection systems may involve administration of liquids, suspensions, powders, or projectiles. Exemplary needle-free injection systems include those made by Portal Instruments and PharmaJet (Stratis), among others. Powders are suitable for long term storage and can be injected at home without reconstitution or extensive user preparation using such systems. Needle-free injection system incorporating powders often require an injection chamber filled with solid drug and a nozzle for firing the solid drug particles into the skin. In some embodiments, the particles exit the nozzle with a gas stream and impinge the skin surface. This leads to small perforations or holes in which the particles are deposited. They penetrate the stratum corneum before being distributed completely into the stratum corneum and viable epidermis. Particles for needle-free injection may have a density from about 0.1 to about 5 $g/cm^3$ (in the case of magnetic nanoparticle inclusion), e.g., from about 0.1 to about 2.5 $g/cm^3$, from about 0.1 to about 1.4 $g/cm^3$, from about 0.5 to about 1.4 $g/cm^3$, or from about 1.0 to about 1.4 $g/cm^3$. The mean diameter greater of the particles can be from about 1 to about 100 μm, e.g., from about 4 to about 100 μm, from about 10 to about 100 μm, or from about 20 to about 50 μm.

In some embodiments, the particles are administered via a dual-chamber syringe device such as LYOTWIST™. The particles exist as a dry powder in one chamber of the device while the second chamber is occupied by an aqueous or non-aqueous carrier liquid. The components of the two chambers are mixed briefly before administration.

In other embodiments, a chamber of a device containing powder, e.g., a dual-chamber device, is filled with a slurry comprising particles of the disclosure. The particles are suspended in a continuous phase which is compatible with lyophilization, such that it can be subsequently removed from the device through this means. This provides for a method of metering a desired amount of powder into each device which may in some embodiments be more facile than alternative powder filling approaches.

In some embodiments, surfaces of the administration device that come into contact with the pharmaceutical suspension formulation, e.g., the inner wall of a syringe chamber, exhibit surface energies that discourages adhesion by the particles. In other embodiments, the surfaces have an oil coating, e.g., a silicone oil coating, which helps to impart this effect. Mitigation of surface adhesion by the particles is useful for maximizing dose recovery upon administration, among other things.

In other embodiments, particles will settle or sediment out of the suspension medium over some period of time after transfer to a container closure system. Flocculation may also take place. Resuspension and/or reversal of flocculation may be required to facilitate proper use or administration of the formulation. In some embodiments, manual agitation of the container closure may be sufficient for this purpose. In certain embodiments, the container closure system may be agitated for use through external means, e.g., vortex or sonic agitation. In still other embodiments, the container closure system itself may incorporate a means for vortexing, soni- cating, or otherwise agitating the formulation in such a way that flocs are reduced and/or particles are sufficiently resus- pended for proper use.

In certain embodiments, the composition further com- prises at least one pharmaceutically acceptable additive, diluent, excipient, carrier, or a combination thereof. In certain embodiments, one or more therapeutic or diagnostic agents can be in the particles and/or outside of the particles, i.e., in the suspension medium. The therapeutic or diagnostic agent included in the suspension medium can be the same or different than that employed in the particle. The one or more therapeutic or diagnostic agent can reduce pain or inflam- mation during administration. The concentration of the therapeutic agent in the pharmaceutical composition outside of the particles can range, e.g., from about 0.0001 to about 1000 mg/mL.

The term "injectability" or "syringeability", refers to the relative ease with which a liquid composition or formulation can be administered to a subject through the use of an injection device. In some embodiments, the injectability is determined by measuring the viscosity of the composition or formulation at various shear rates. In other embodiments, the injectability is determined by measuring the breakaway and/or glide forces required to actuate a standard injection device consisting of a barrel, a plunger, and a needle. In preferred embodiments, the injectability of the composition comprising a plurality of particles comprising at least one therapeutic biologic as described herein, is superior to that of an aqueous composition or formulation with about the same concentration of aqueous monomeric therapeutic bio- logics.

The term "injection breakaway force" refers to the force required to overcome friction between the syringe barrel and plunger of a standard injection device before ejection of the contents of the syringe can take place at a steady rate. The force is applied at the outward-facing end of the syringe plunger shaft and directed along the axis of the syringe barrel. The contents of the syringe are ejected through a syringe needle of prescribed gauge and length. In certain embodiments, the injection breakaway force is measured through a load cell placed at the outward-facing end of the syringe plunger during actuation.

The term "injection glide force" or "syringe force" refers to the force required to maintain a steady ejection of the contents of a standard injection device. The force is applied at the outward-facing end of the syringe plunger shaft and directed along the axis of the syringe barrel. The contents of the syringe are ejected through a syringe needle of pre- scribed gauge and length. In certain embodiments, the injection breakaway force is measured through a load cell placed at the outward-facing end of the syringe plunger during actuation. The term "Newtonian regime" or "N"

means a range of shear rates which are linearly proportional or nearly linearly proportional to the local strain rate at every point.

In some embodiments, the composition is capable of being dispensed using a syringe force of about 2 N to about 80 N. In other embodiments, the composition is capable of being dispensed using a syringe force of about 2 N to about 40 N.

In other embodiments, the composition is capable of being dispensed using a syringe force of about 3 N to about 80 N. In other embodiments, the composition is capable of being dispensed using a syringe force of about 3 N to about 40 N.

The disclosure generically described, will be more readily understood by reference to the following examples, which are included merely for purposes of illustration of certain aspects and embodiments of the present disclosure, and are not intended to be limiting.

EXEMPLIFICATION

Abbreviations

Å angstrom
aa amino acids
BSA bovine serum albumin
° C. degrees Celsius
cm centimeter
d day
DCM dichloromethane
DIPEA diisopropylethylamine
DMA N,N-dimethylaniline
DMF dimethyl formamide
DMSO dimethyl sulfoxide
DTE dithioerythritol
DTT dithiothreitol
EDT 1,2-ethanedithiol
EDTA Ethylenediaminetetraacetic acid
Eq. equation
eq. equivalent
Et ethyl
g gram
h hour
HPLC high performance liquid chromatography
Hz hertz
IV intravenous
kJ kilojoules
LC-MS liquid chromatograph mass spectrometry
m meta
mAb monoclonal antibody
MALDI-MS matrix-assisted laser desorption ionization mass spectrometry
Me methyl
MHz megahertz
min minute
μg microgram
μL microliter
μm micrometer
μM micromolar
mg milligram
mL milliliter
mm millimeter
mM millimolar
mol mole
nm nanometer
NMP N-methylpyrrolidone
p para PBS phosphate-buffered saline
PEG polyethylene glycol
PEGA polyethylene glycol polyacrylamide
ppm parts per million
ps picosecond
RP-HPLC reversed phase-high performance liquid chro-
    matography
rpm revolutions per minute
s second
SC subcutaneous
sec second
SEM scanning electron microscopy
t tertiary
tert tertiary
UHMW ultrahigh molecular weight polyethylene
ug micrometer
UTW ultra thin wall
UV ultraviolet
V volts
vol % volume percent
wt % weight percent

Materials

A biosimilar of Roche's Rituximab was purchased from a vendor that provided the antibody in an aqueous composition consistent with the FDA-label defined as 10 mg/mL rituximab, 9 mg/mL sodium chloride, 7.35 mg/mL sodium citrate dihydrate, and 0.7 mg/mL polysorbate 80. Composition of custom "feed solutions" used for processing particles were produced through modifying the FDA-label formulation by desalting followed by concentrating and adding desired excipients. All excipients used in particle composition have been used in existing approved biologics injections.

Human IgG (IRHUGGF-LY, >97%) and bovine IgG (IRBVGGF) were obtained from Innovative Research as a lyophilized powder or as an aqueous solution. The antibody products (mAb1, mAb2, mAb3, mAb4) were obtained in aqueous solution. The latter three mAbs were used as received while mAb1 was reformulated based on conditions of interest. Concentration columns were procured from Millipore Sigma (AMICON®Amicon® Ultra 15 mL Filters for Protein Purification and Concentration with a 3 kDa cut off) and used where necessary to: (i) reach the desired protein concentration, and (ii) exchange buffer/excipients before particle formation. ZEBA™ desalting columns (THERMO FISHER SCIENTIFIC™, Cat. No.: 87773) were also used to remove salt from solutions in certain instances. Typically, the ratio of residual salt to agent in the desalted solutions (wt/wt) was <1%. All excipients were purchased from Sigma-Aldrich and used as received.

Desiccation liquids, i.e., second liquids, including benzyl benzoate, various alcohols, various acetates, oils, ionic liquids, surfactants, and aqueous media comprising different forms of polyethylene glycol (PEG) were used as appropriate. Benzyl benzoate is an organic liquid, largely immiscible with water, which exhibits a density (d=1.12 g/cm³) that typically brackets that of the liquid feed solution (d≈1 g/cm³ in the case of water) and the density of solid proteins, i.e., the density of the dry protein powder (d≈1.25-1.35 g/cm³). It therefore served as a medium upon which drops floated while undergoing primary desiccation via dispersal of the first liquid in the benzyl benzoate and evaporation of the first liquid in the surrounding medium, e.g., air (typically of order several seconds or less). The desiccated particles sunk thereafter, such that a spatial separation was generated between wet incoming drops and processed particles. Such separation helped to mitigate particle coalescence, among other phenomena. The remaining liquids typically exhibited a density less than or approximately that of the feed solution. Drops did not tend to float, and primary desiccation was therefore driven primarily by dispersal of the first liquid in the second liquid. All desiccation ("second") liquids, e.g., acetonitrile, chlorobenzene, chloroform, cyclohexane, cumene, 1,2-dichloroethene, dichloromethane, 1,2-dimethoxyethane, N,N-dimethylacetamide, N,N-dimethylformamide, 1,4-dioxane, 2-ethoxyethanol, ethyleneglycol, formamide, hexane, methanol, 2-methoxyethanol, methylbutyl ketone, methylcyclohexane, methylisobutylketone, N-methylpyrrolidone, nitromethane, pyridine, sulfolane, tetrahydrofuran, tetralin, toluene, 1,1,2-trichloroethene, xylene, acetic acid, acetone, anisole, 1-butanol, 2-butanol, butylacetate, tert-butylmethyl ether, dimethyl sulfoxide, ethanol, ethylacetate, ethyl ether, ethyl formate, formic acid, heptane, isobutylacetate, isopropylacetate, methylacetate, 3-methyl-1-butanol, methylethyl ketone, 2-methyl-1-propanol, pentane, 1-pentanol, 1-propanol, 2-propanol, propylacetate, triethylamine, 1,1-diethoxypropane, 1,1-dimethoxymethane, 2,2-dimethoxypropane, isooctane, isopropyl ether, methylisopropyl ketone, methyltetrahydrofuran, petroleum ether, trichloroacetic acid, trifluoroacetic acid, decanol, 2-ethylhexylacetate, amylacetate, except for the ionic liquids were purchased from Sigma Aldrich and used as received. The ionic liquids were purchased from TCI America and used as received.

Methods

Particle Formation: Unless otherwise noted, an electrospray apparatus was used to form drops for desiccation and particle formation. In most instances this apparatus comprised a Sono-Tek 120 kHz ultrasonic atomizer charged by a Matsusada EQ-30P1-LCt or EQ-30N1-LCt high voltage DC power supply, while in others it was replaced by a small blunt disposable syringe needle (VWR International). A Harvard Apparatus Model 33 dual-channel syringe pump was utilized for pumping the feed solution. The drops generated by the apparatus were collected for desiccation by a vessel containing the second liquid, typically under conditions of continuous stirring. Thermal management of the second liquid was utilized in the preparation of select samples. The distance between the surface of the second liquid in the vessel and the tip of the drop source was typically 10-20 cm.

Lyophilization: The particles for lyophilized samples, i.e., samples marked as having gone through a secondary desiccation step involving freeze drying, were loaded into either microcentrifuge or 15 mL conical tubes and subjected to snap freezing by immersion in liquid nitrogen for approximately 10 min. The samples were then loosely covered and transferred to either a Virtis Advantage or a Labconco FreeZone lyophilizer for approximately 24 hours at a pressure of approximately 10-50 mTorr.

Microscopy: Particle sizing was measured using FLOW-CAM™; a dynamic image analysis instrument. Samples were diluted to about 1 mg/mL in isopropanol and passed through a thin channel. Images of particles were recorded and analyzed according to size and shape.

ImageJ Measurements: Particles diameters were measured using ImageJ analysis on SEM images. The analysis was performed on the 600× images. The ImageJ Particle Analysis tool was run on the image, identifying objects with a circularity of >0.8 and size>0.5 um with each object outlines. These outlines were visually inspected for good fit. Any mis-identified particles were manually rejected and any missed particles were manually included and measured using the ImageJ diameter tool.

Accelerated Storage Protocol: All samples were transferred to WHEATON™ E-Z ex-traction round-bottom glass vials for aging (2 mL or 4 mL volume, depending on sample). The glass vials were sealed with parafilm, placed in an oven at 40° C., and visually inspected on a daily basis over the aging period to ensure integrity.

Viscosity Measurements: Apparent suspension viscosity was measured using an AR-G2 rheometer (TA Instruments) and a 25 mm plate at 25° C. Measurements were taken at 1000 s$^{-1}$ (experimental limit due to edge effects), which is below the shear rates experienced in 27-gauge needles, but in the Newtonian regime for the suspensions. Each measurement was repeated three times (about 60 s intervals between repeats) to assess short-term physical stability of the suspensions. Prior to each measurement calibration standards were recorded to validate instrument settings.

Syringeability Measurements: Syringe force was measured during 0.1 mL/s ejection of a 1 mL suspension (400 mg/mL particle) using a custom force sensor apparatus and a 1-mL NORM-JECT®model syringe with a 27-gauge ultra-thin-wall needle (TSK).

Karl Fischer: Testing for moisture content was undertaken using Karl Fischer analysis. Approximately 100 mg of particles was heated to 105° C. in an oven and released water was determined coulometrically.

Skeletal Density: Skeletal density was measured by gas pycnometry. The gas was nitrogen and the particle mass was 0.0413 g.

Particle Dissolution: Phosphate-buffered saline (PBS) was added to dry particle samples to produce a final concentration of 10 mg/mL (particle mass/mL of solution). Samples were placed on a VWR™ angular rocker with a speed setting of "35" and angle setting of "15". At 1, 10, 20, 30, 40, 50, 60, 90, and 120 minutes a 10 µL aliquot was removed from the sample vial and the absorbance at 280 nm was measured and recorded. The mAb concentration was plotted against time for all samples.

Salt Content: Salt content was recorded by measuring sodium content using Inductively Coupled Plasma Optical Emission Spectroscopy (ICP-OES). A calibration curve was prepared using a sodium standard (ICPTRACECERT®, 1000 mg/L). Quality control was completed using a diluted standard solution at 100 ppm sodium. A sample of particles (~15 mg) dissolved in 2 vol % nitric acid (10 mL) was then analyzed, resulting in an intensity lower than the instrument detection limit of ~0.5 ppm for sodium. This indicated a sodium content of less than 0.034 wt % and a total salt content (assuming sodium citrate and sodium chloride to have been removed equally) of less than 0.1 wt %.

Size Exclusion Chromatography (SEC) Measurements: The quantification of size variants in select samples was determined by size exclusion chromatography. The analysis utilized an ADVANCEBIO™ SEC-3 column, 7.8 mm ID×30 cm, 3 µm (AGILENT™) run on an HPLC system (1260 Infinity II, AGILENT™). The mobile phases were 25 mM potassium phosphate and 0.25 M potassium chloride at pH 6.8. The chromatography was run isocractically at a flow rate of 1.0 mL/min for 15 minutes. The column temperature was maintained at ambient 25° C. and the eluent absorbance was monitored at 280 nm. Each monoclonal antibody was diluted with its respective formulation buffer to 1 mg/mL. The injection volume was 10 µL. 20 µL Injections of samples (1 mg/mL) were run at a flow rate of 1 mL/min in SEC buffer (25 mM phosphate, 250 mM NaCl pH 6.8) for 15 minutes on an AGILENT ADVANCEBIO™ SEC (300 mm×2.7 um, 300 Å column). Peak analysis was performed by auto-integrating using the following parameters: slope sensitivity=0.5, peak width=0, height reject=0, area reject=0, shoulders off, area percent reject 0, standard tangent skim mode, advanced baseline correction, 0 for front peak skim height ratio, 0 for tail peak skim height ratio, 0 for peak to valley ratio, and 0 for skim valley ratio.

Differential Scanning Fluorimetry (DSF) Measurements: The melting temperature of the protein before and after formulation, as well as at various time points of 40° C. storage, were assessed using a QUANTSTUDIO™ 6 Flex instrument. Five microliters (5 µL) of samples (1 mg/mL), prepared after dialysis, were loaded onto a 96-well thermal cycler plate in quadruplicate. To each well, 12.5 µL of ultrapure deionized water and 2.5 µL of SYPRO® Orange dye (8×) were added. After a 5-minute incubation, samples were run from 25° C. to 99° C. at a ramp rate of 0.05° C./s. Melting temperature was calculated using the PROTEIN THERMAL SHIFT™ Software (THERMO FISHER™, version 1.3) using a Boltzmann fit.

Circular Dichroism (CD) Measurements: The degree of preservation of the secondary structure (alpha helices and beta sheets) of the protein before and after formulation, as well as at various time points of 40° C. storage, was assessed using a JASCO™ J-815 instrument. Four hundred microliters (400 µL) of sample (0.5 mg/mL), prepared after dialysis, was loaded into a quartz cuvette (1 mm path length). Samples were scanned over the 190-260 nm range. Diluent buffer was used as blank subtraction for each sample. The following instrument settings were used:

Photometric mode: CD, HT
Measure range: 260-190 nm
Data pitch: 0.5 nm
Sensitivity: Standard
D.I.T.: 4 sec
Bandwidth: 1.00 nm
Start mode: Immediately
Scanning speed: 100 nm/min
Shutter control: Auto
Baseline correction: None
CD detector: PMT
PMT voltage: Auto Cation Exchange Chromatography (CIEX) Measurements: Charge variant analysis was performed for each sample on days 0, 7 and 30 under accelerated storage conditions, using an AGILENT BIOMAB™ NP5, 4.6×250 mm, PEEK ion exchange column. Samples were prepared at 1 mg/mL concentration after overnight dialysis in water. Buffer A was prepared with: 30 mM phosphate, pH: 6.3, and NaCl: 0 mM. Buffer B was prepared with: Buffer A: 30 mM phosphate, pH 6.3 plus NaCl: 175 mM. The samples were run in a gradient starting with 100% Buffer A, ramping up to a 100% Buffer B over a course of 20 min, after which the gradient was set to return to 100% Buffer A and 0% Buffer B in the next 1 min. The system re-equilibrated in 100% Buffer A for 10 min before the injection of the next sample. Integration was performed as a manual skim peak mode according to the AGILENT™ data applications protocol.

Monoclonal Antibody Binding Assay (Flow Cytometry): Monoclonal antibodies from select samples were assessed for cellular binding ability utilizing cells that express the appropriate cell surface receptors. Cells were incubated for 30 minutes at 4° C. with monoclonal antibodies at respective concentrations and then spun down at 2000 rpm followed by washing with PBS three times. Cells were then incubated with secondary goat anti-human Fab antibody fluorescently labeled with PE for 30 minutes at 4° C. The cells were then spun down at 2000 rpm followed by washing with PBS, three times. The cells were then re-suspended and then analyzed on an ATTUNE™ Flow Cytometer (INVITRO-GEN™). 1 Million Raji cells (100 μL per well) were plated per well in a 96 well 'V-bottom' plate and 10 μL of mAb Label, particle, or suspension at a starting concentration of 200 μL was added to the wells. The dilution factor for the mAb label, particle and suspension was 3×. The plate was incubated at 4° C. for 30 min. The plate was centrifuged at 2000 rpm for 5 min and was washed 3 times with PBS. 100 μL of PE-conjugated goat anti-human IgG was added as the secondary antibody at a 1:200 dilution. The plate was centrifuged at 2000 rpm for 5 min and was washed 3 times with PBS. The cells were then resuspended in 200 μL of cold PBS for analysis on a Life Technologies ATTUNE™ NXT flow cytometer.

Scanning Electron Microscopy: Electron micrographs were collected for select samples with either a HITACHI™ TM3030Plus or a TM1000 tabletop microscope. The samples were immobilized on conductive tape and examined in a low-vacuum anti-charging environment, obviating the need for sample preparation.

Image Analysis: Select microscopy images were chosen for further analysis on the basis of (i) minimal particle overlapping, (ii) good contrast between the particles and the background, and (iii) a resolution providing for particle occupancies of at least 10 pixels. This allowed for particles to be easily identified and reduced resolution-based error. A binary threshold was applied to separate the particles from background, and a watershed segmentation algorithm was applied to ensure that individual particles were measured separately. The ImageJ tool "Analyze Particles" was then applied on the binary picture with the following parameters: circularity between 0.5 and 1.0; size between 5 and infinity square microns; exclude on edges; fill holes. The outlines of the identified particles were overlaid onto the original image. Particles which were misidentified, such as clusters that were identified as a single particle or particles whose outlines do not match the particle, were then discarded. Missing particles were measured by manually tracing the particle's outline and using ImageJs Measure tool.

Density Analysis: The skeletal density of particles from select samples was determined by examining approximately 0.1 g of powder with an ACCUPYC™ 111340 gas displacement pycnometry system.

Water Content Analysis: The residual moisture in particles from select samples was determined by placing approximately 0.1 g of powder in a vacuum oven with a Karl Fischer titrator and heating the sample.

ELISA Assay: ELISA assay was used on select samples to detect human antibody in a denaturation sensitive manner. Human IgG was first plated in PBS for 1 hour, followed by washing with wash buffer (PBS+0.05% Tween20) three times for 4 minutes, followed by blocking with 2% BSA (Sigma) in wash buffer for 45 minutes, followed by incubation with dilute (20 μg/mL) protein A-HRP (ABCAM™) for 45 minutes, followed by wash buffer three times for 3 minutes, followed by incubation with TMB (ABCAM™) for 10 minutes, finally followed by quenching of the reaction with STOP solution (ABCAM™). The colorimetric readout was conducted on a THERMO MULTISKAN™ Spectrum.

Subvisible Particle (SvP) Analysis: Subvisible particles (SvPs) were analyzed with a Fluid Imaging Technologies FLOWCAM™ PV-100 system. Samples for analysis were reconstituted in sterile centrifuge tubes with filtered water (MILLI-Q™) to the concentration of interest. Three sets of samples were investigated thereafter. These included (i) a sample of the diluent used for reconstitution, (ii) an aliquot of the feed solution used for the particle formation process, i.e., a sample of the first liquid, and (iii) the reconstituted material.

Accelerated Storage: Storage was carried out under accelerated conditions for select samples by maintaining them at an elevated temperature (40° C.) for defined periods of time in an incubator or oven. Samples were kept in 2 mL or 4 mL WHEATON™ glass vials and sealed with paraffin film.

Helium Ion Microscopy (HIM): Ion micrographs were collected for select samples using an HIM instrument. The source energy, working distance, and aperture size were typically, 29 keV, 9 mm, and 10 microns, respectively. For select samples, a focused gallium ion beam was used to section particles for analysis of the internal structure. Tilted samples were ablated with a source current, dwell time, and cut spacing of 300 pA, 0.5-1 μs, and 2-5 nm, respectively.

X-Ray Photoelectron Spectroscopy (XPS): A small amount of powder was deposited onto hydrocarbon tape attached to a piece of silicon wafer and gently pressed to form a compact uniform bed. Excess loose powder was removed by lightly tapping the edge of the wafer piece. Specimens were prepared just before analysis. XPS measurements were performed with a KRATOS AXIS ULTRA™ spectrometer using monochromatic Al Kα X-rays (1486.6 eV). For each sample, a survey spectrum was acquired from an area of approximately 2 mm by 1 mm (pass energy=160 eV; 225 W power), from which the surface elemental composition was determined. Charge compensation was achieved using a beam of magnetically focused electrons as a flood current. The standard photoelectron take-off angle used for analysis is 90° giving a sampling depth in the range 5-8 nm. The surface elemental compositions were analyzed using a quantification model that assumes homogeneity of the probed sample volume.

Inverse Gas Chromatography (IGC): Powdered samples were analyzed using inverse gas chromatography. Cylindrical columns were packed with 200 to 300 mg of powdered samples to make up a stationary phase. Following an inert gas purge, a series of gas probes was injected on the column. Determination of the retention volume for each probe enabled evaluation of the dispersive and polar components of the surface energy for each sample.

X-Ray Diffraction (XRD): Samples were packed into 0.7 mm diameter glass capillaries. The powder patterns were measured on a PANALYTICAL EMPYREAN™ diffractometer equipped with an incident-beam focusing mirror and an X'CELERATOR™ detector. The patterns (1-50° 2θ, 0.0167113° steps, 4 sec/step, ¼° divergence slit, 0.02 radian Soller slits) were measured using Mo Ká radiation. If static electricity effects (for the case of evaluating a lyophilization control this occurred after grinding in a mortar and pestle) prevented packing the sample into a capillary, its powder pattern was measured from a flat plate specimen on a BRUKER™ D2 Phase diffractometer equipped with a LYNXEYE™ position-sensitive detector. The pattern was measured using Cu Kα radiation from 5-100° 2θ in 0.0202144° steps, counting for 1.0 sec/step. The standard instrument settings (30 kV, 10 mA, 0.6 mm divergence slit, 2.5° Soller slits, and 3 mm scatter screen height) were employed.

Microflow Particle Sizing (MPS): Flow imaging microscopy for particle size analysis was carried out using a FLOWCAM™ PV-100. To investigate size and dispersity of particles, 5 mg of powder were dispersed in 10 mL of dry isopropanol via sonication. The isopropanol continuous phase prevented the particles from dissolving, i.e., prevented reconstitution. 0.3 mL was injected into the cell and images of the particles were taken using a flow rate of 0.15 mL/minute. Particles with a circularity greater than 0.9 were reported in the analysis and any double images were removed from the analysis, to give a size distribution and dispersity of particles in the range from 1 to 100 μm.

Dynamic Vapor Sorption (DVS): Powders were analyzed using dynamic water vapor sorption. Approximately 50 mg of powdered sample was loaded into the pan of the instrument's microbalance. The sample was held isothermally at 22° and the sample mass was monitored throughout the measurement. Following a 0% RH purge to remove surface water, the relative humidity (RH) in the sample chamber was ramped at a constant rate of 4% RH per hour up to 90% RH. The sample was held at 90% RH for one hour, then the RH was reduced to 0% as a step change. The sample was held at 0% RH for one hour, after which the measurement was terminated.

Dynamic Scanning Calorimetry (DSC): Powdered samples were analyzed using dynamic scanning calorimetry. Masses of 5 to 10 mg of powdered samples were loaded into aluminum crucibles and sealed hermetically. Crucibles were loaded into the instrument, and the heat flow into the samples was monitored while the temperature was ramped from 30 to 250° C. at a constant rate of 5° C./minute.

Antibody-Dependent Cell-Mediated Cytotoxicity (ADCC): Using an ADCC luciferase-based kit (PRO-MEGA™-G7015), target cells were plated in a 96 well plate (25 μL per well; 12,500 cells per 25 μL). 25 μL of antibody solution (2 μg/mL starting concentration) was added to each well, after which a 3× serial dilution was carried out. Effector cells were added (25 μL per well; 75,000 cells per 25 μL) and the plate was incubated at 37° C. for 6 h in an incubator. The plate was then equilibrated at RT for 15 min before addition of 30 μL Luciferin reagent to each well. 12,500 Cells per well at a 25 μL volume of Raji cells were plated in 96 well plate, followed by addition of 25 μL of mAb with a starting concentration of 2 μg/mL was added and a 3× serial dilution was made thereon. 75,000 cells per well at a 25 μL volume per well of Effector cells were added and the plate was incubated at 37° C. for 6 h in an incubator. The plate was then equilibrated at RT for 15 min. 30 μL Luciferin reagent was added to each well. The luminescence was measured using a THERMO SCIENTIFIC VARIOS-KAN™ LUX luminometer.

USP <790>: According to the USP <790> standard, samples of dissolved particles were visually observed against a white and black background under lighting conditions greater than 2000 lux. Matte-finished high density polyethylene sheets were selected for the background to reduce glare. The illuminance at the viewing point was confirmed with a lux meter (Dr. Meter, LX1330B). The samples were swirled before being held up to the backgrounds and viewed for 5 sec.

EXAMPLES

The methods disclosed herein, have been utilized in separate instances to prepare particles including at least one of several agents, e.g., whole human IgG or bovine IgG, or one of several monoclonal antibodies. Various analytical techniques were applied to assess the physical characteristics of the particles themselves as well as the structural and functional properties of the processed agents. Scanning electron microscopy and associated image analysis were used to study the particle morphology and size distribution, respectively. Various morphologies and distributions of components were achieved by controlling the properties of the first liquid and/or the second liquid. In some instances, the processing conditions conferred smooth particles of high sphericity and/or facile control of the mean particle size over a broad range with low dispersity. In certain cases, the particle surfaces were also decorated with components, e.g., excipients, in a controlled fashion. Density and water content measurement demonstrated that the particles approached crystalline packing efficiencies and retained very low levels of residual moisture after post-processing. The functional properties of the agents were also preserved, as evidenced by ELISA and binding assays performed on reconstituted material. This was corroborated by size exclusion HPLC analysis indicating that the process had a minimal or even remedial effect on the degree of inter-protein association. Finally, investigation of the insoluble particle populations upon reconstitution revealed very few insoluble artifacts, particularly as compared to alternative particle formation procedures.

Example 1

A solution of sodium chloride (30 mg/mL) and a surfactant (0.1% w/w) was prepared and processed using a rotary membrane emulsification system. The system consisted of a porous glass membrane with a median pore size of 5 micrometers, a 10 mm outer diameter, a 9 mm inner diameter, and an overall length of 4 mm coupled to a liquid pump via a tubular shaft and a rotary union fitting. Rotational motion was imparted to the membrane using an overhead mixer. The membrane was immersed in 300 mL of a second liquid which was stirred using a magnetic stir bar within a glass vessel. The membrane was rotated at approximately 900 rpm while 3.0 mL of the feed solution was pumped through the membrane at 1.5 mL/min. Dehydrated particles were separated from the second liquid using a 0.5 micrometer membrane filter and vacuum dried to remove residual solvents. SEM images revealed identifiable particulate matter.

Example 2

Human IgG powder was reconstituted in deionized water to a protein concentration of approximately 60 mg/mL. The solution was desalted and quantities of an amino acid (12 mg/mL), a carbohydrate (3 mg/mL), a salt (2.1 mg/mL), and a surfactant (1.8 mg/mL) were added. A flow focusing apparatus was utilized to form drops of the solution in a flow of ethyl acetate. The flow focusing apparatus comprised a tube-in-tube assembly, i.e., a coaxial assembly, in which an inner tube was stationed along the axis of an outer tube. The inner tube had inner and outer diameters of approximately 100 microns and 360 microns, respectively. The outer tube had inner and outer diameters of approximately ⅓₂" and ⅟₁₆", respectively. The tube-in-tube assembly was connected to a focusing capillary in such a way that the outlet of the inner tube and the inlet of the focusing capillary were spaced by an axial distance of approximately 1 mm. The focusing tube had inner and outer diameters of approximately 100 microns and 360 microns, respectively, with a length of approximately 10 cm. Ethyl acetate was pumped through the outer tube at a rate of approximately 3 mL/min while the solution was pumped through the inner tube at a rate of approximately 0.03 mL/min. Flow from the outlet of the focusing tube was collected in a vessel containing approximately 200 mL of ethyl acetate held near room temperature under conditions of gentle stirring. After primary desiccation, particles were collected and vacuum dried to remove residual liquid. SEM images revealed identifiable particulate matter.

Example 3

Human IgG powder was reconstituted in deionized water to a protein concentration of approximately 50 mg/mL and desalted. A solution of ethyl acetate comprising an appropriate surfactant at an appropriate concentration for mitigating coalescence was prepared. A sample of the human IgG solution was atomized and collected with a stainless steel vessel containing a volume $5V_0$ of the ethyl acetate solution held near room temperature under conditions of gentle stirring. A second sample of the human IgG solution was atomized and collected with a stainless steel vessel containing a volume $V_0$ of the ethyl acetate solution held near room temperature under conditions of gentle stirring. A third sample of the human IgG solution was atomized and collected with a stainless steel vessel containing a volume $0.5V_0$ of the ethyl acetate solution held near room temperature under conditions of gentle stirring. A fourth sample of the human IgG solution was atomized and collected with a stainless steel vessel containing a volume $0.1V_0$ of the ethyl acetate solution held near room temperature under conditions of gentle stirring. After primary desiccation, all samples were collected and vacuum dried to remove residual liquid. SEM images reveal identifiable particulate matter for all samples.

Example 4

Figure 1B:
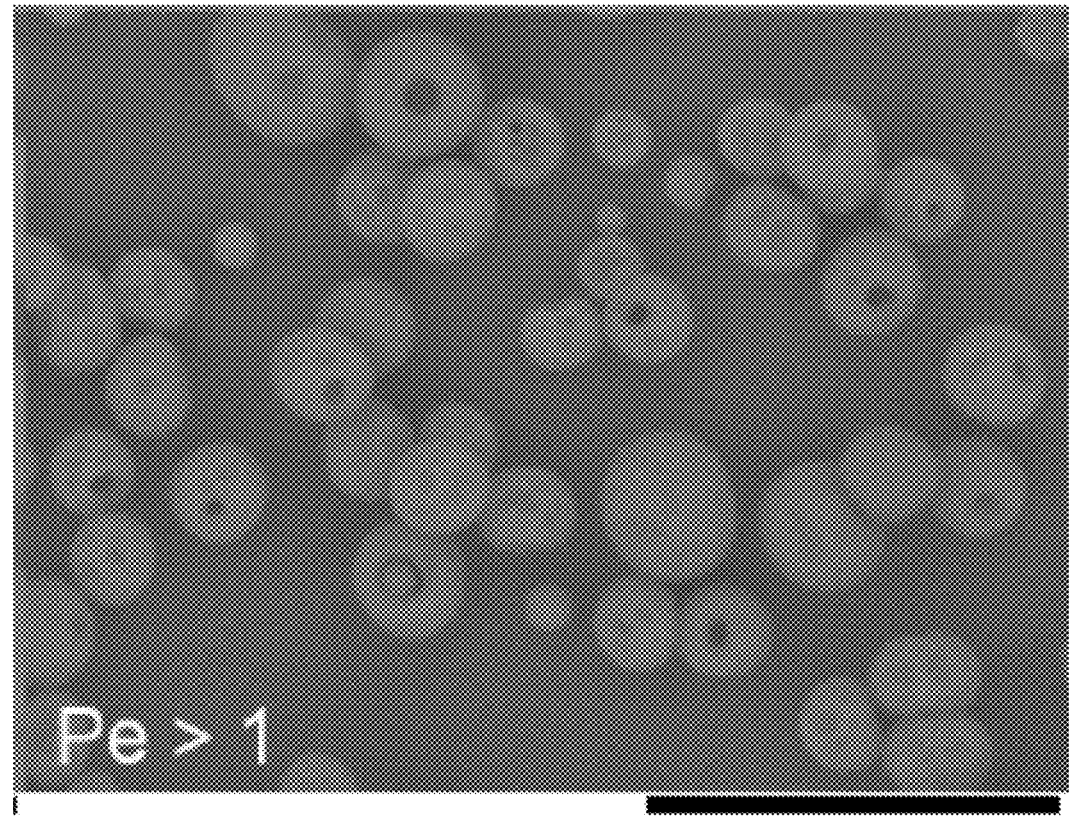
FIG. 1B shows an image of human IgG particles produced using a second liquid for which the Peclet number was substantially higher than 1.

Human IgG powder was reconstituted in deionized water to a protein concentration of approximately 60 mg/mL. The solution was desalted and quantities of an amino acid (4 mg/mL), a carbohydrate (1 mg/mL), a salt (0.7 mg/mL), and a surfactant (0.6 mg/mL) were added. A sample of the solution was atomized and collected with a stainless steel vessel containing a volume of a second liquid (second liquid A) greater than $V_0$. The Peclet number was less than 1. The circularity was calculated to be 0.896, the roughness was 4.637. A second sample of the solution was atomized and collected with a stainless steel vessel containing a volume of a second liquid (second liquid B) greater than $V_0$. The Peclet number was greater than 1. The circularity was calculated to be 0.925, the roughness was 6.991. After primary desiccation, particle from both samples were collected, washed, and vacuum dried to remove residual liquid. SEM images revealed identifiable particulate matter, and that the Peclet number afforded a degree of control over the particle morphology. The lower Peclet number was associated with smooth spheroidal particles (FIG. 1A) while the higher Peclet number was associated with particles comprising an internal void space and wrinkled surfaces (FIG. 1B).

Example 5

Human IgG powder is reconstituted in deionized water to a protein concentration of approximately 50 mg/mL. The solution is desalted. Two solutions of ethyl acetate are prepared, one neat (second liquid A) and another comprising a quantity of PLGA at a concentration of 50 mg/mL (second liquid B). The PLGA functions as a viscosity modifying additive. A sample of the human IgG solution is atomized and collected with a stainless steel vessel comprising a volume greater than $V_0$ of the second liquid A held at room temperature under conditions of gentle stirring. A second sample of the human IgG solution is atomized and collected with a stainless steel vessel comprising a volume greater than $V_0$ of second liquid B held near room temperature under conditions of gentle stirring. After primary desiccation, particles from both samples are collected, washed, and vacuum dried to remove residual liquid. SEM images reveal identifiable particulate matter, and that the viscosity-modifying additive affords a degree of control over the particle morphology. Second liquid A is associated with particles comprising an internal void space and wrinkled surfaces. Second liquid B is associated with particles comprising lesser degrees of internal void spaces and lesser degrees of surface wrinkles.

Example 6

Figure 2A:
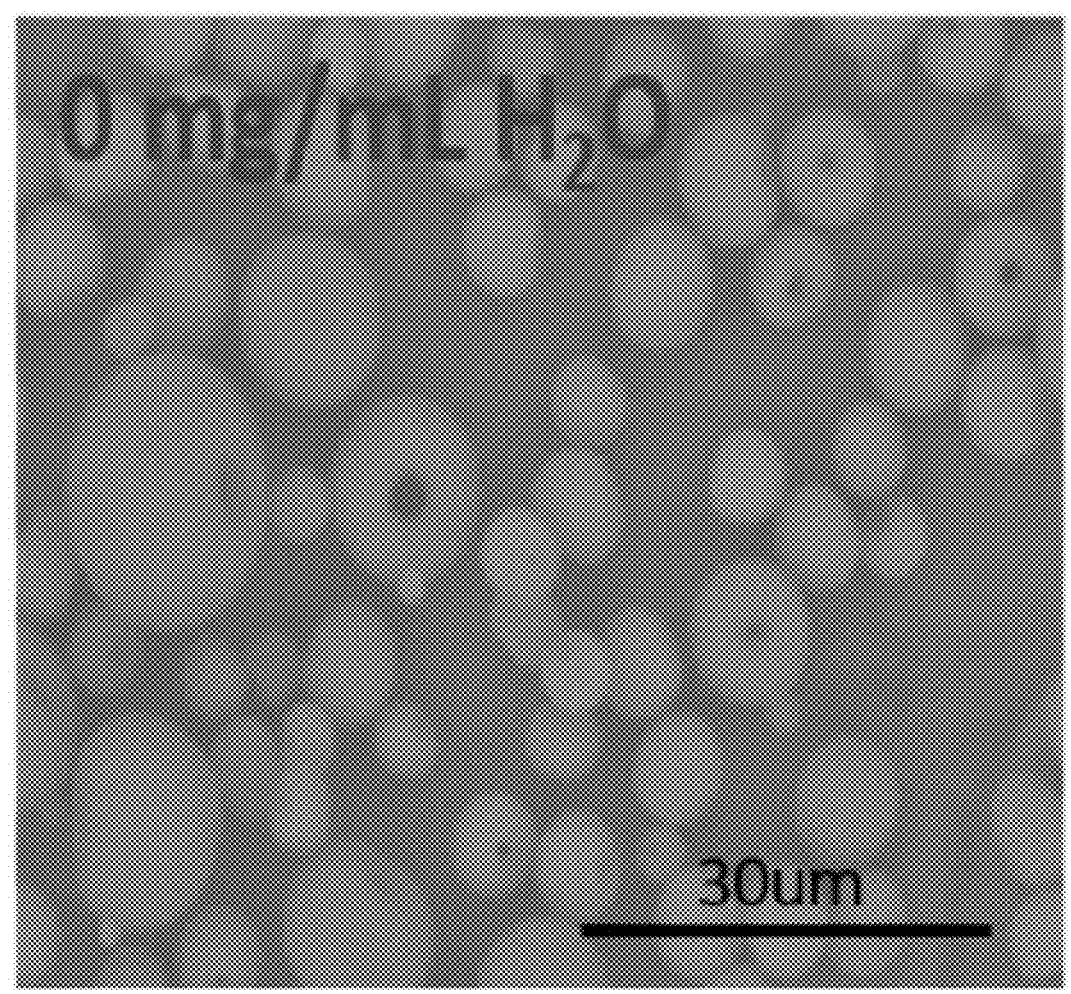
FIGS. 2A-2C show images of human IgG particles formed through methods of the disclosure using several second liquids having varying levels of presaturation with respect to the first liquid.
Figure 2B:
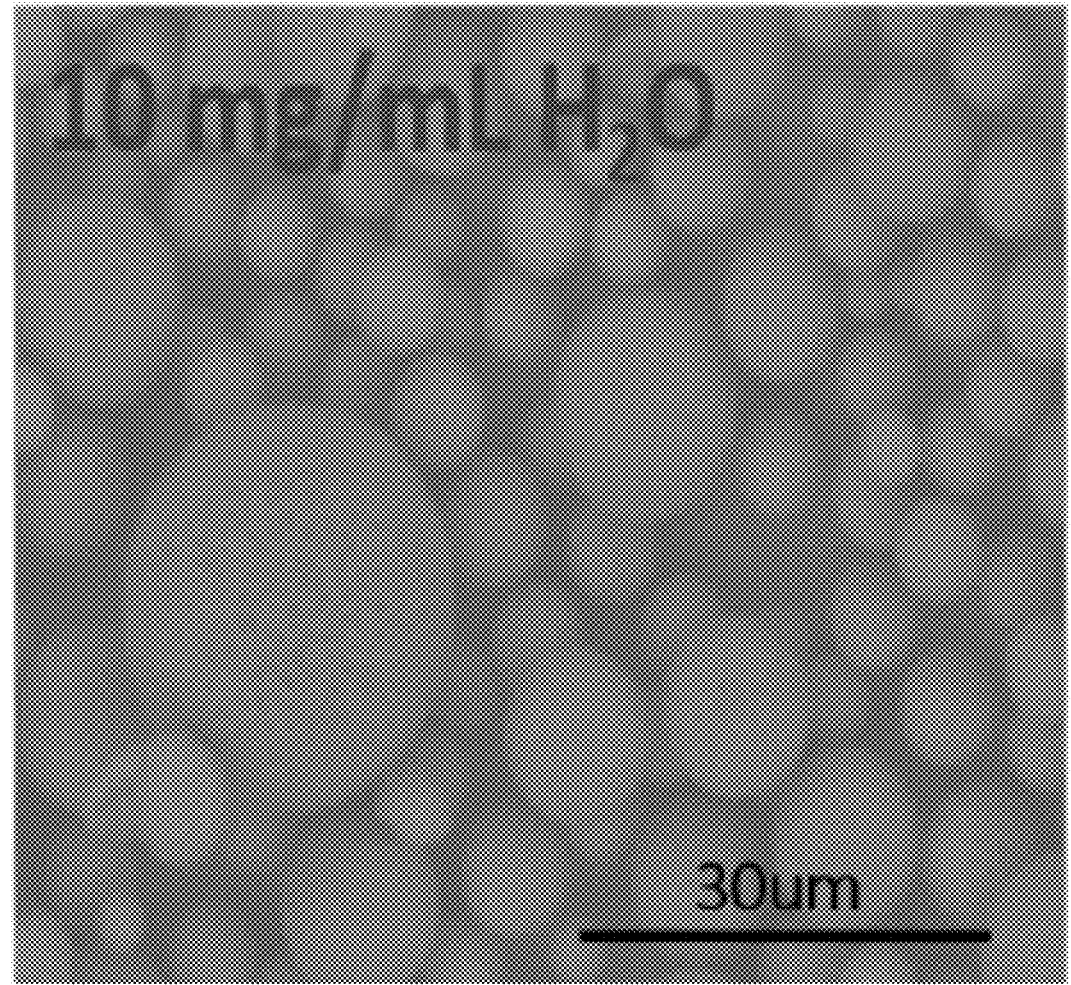
Figure 2C:
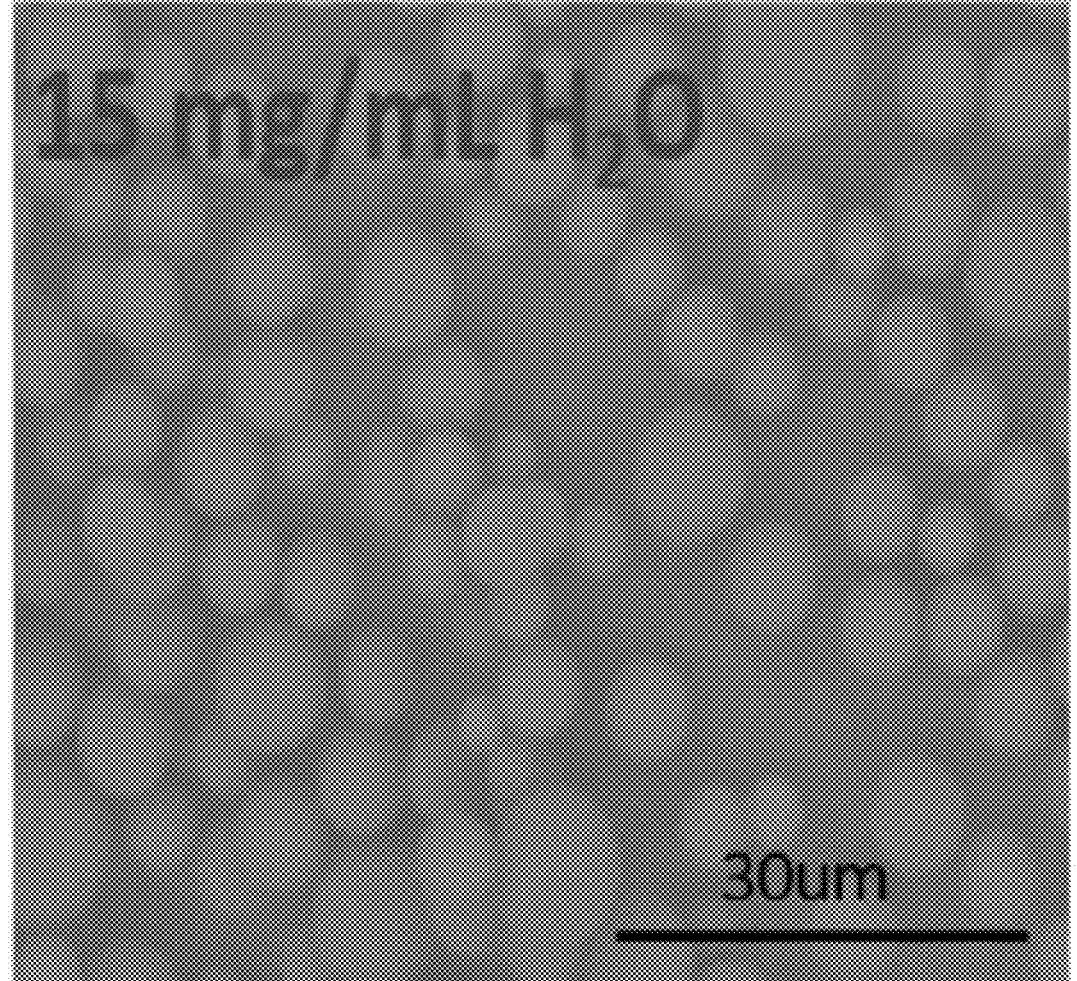

Human IgG powder was reconstituted in deionized water to a protein concentration of approximately 20 mg/mL. The solution was desalted and quantities of an amino acid (4 mg/mL), a carbohydrate (1 mg/mL), a salt (0.7 mg/mL), and a surfactant (0.6 mg/mL) were added. Three solutions of ethyl acetate were prepared, one neat (second liquid A), one comprising deionized water at a concentration of 10 mg/mL (second liquid B), and another comprising deionized water at a concentration of 15 mg/mL (second liquid C). A sample of the human IgG solution was atomized and collected with a stainless steel vessel containing a volume greater than $V_0$ of the second liquid A held at room temperature under conditions of gentle stirring. A second sample of the human IgG solution was atomized and collected with a stainless steel vessel containing a volume greater than $V_0$ of second liquid B held near room temperature under conditions of gentle stirring. A third sample of the human IgG solution was atomized and collected with a stainless steel vessel containing a volume greater than $V_0$ of second liquid C held near room temperature under conditions of gentle stirring. After primary desiccation, particles from all samples were collected, washed, and vacuum dried to remove residual liquid. SEM images revealed identifiable particulate matter, and that the pre-saturation of the second liquid afforded a degree of control over the particle morphology. Second liquid A was associated with particles comprising an internal void space (FIG. 2A) having a circularity of 0.900 and a roughness of 4.306. Second liquid B was associated with particles comprising lesser degrees of internal void spaces (FIG. 2B) having a circularity of 0.970 and a roughness of 2.510. Second liquid C was associated with particles comprising still lesser degrees of internal void spaces (FIG. 2C) having a circularity of 0.884 and a roughness of 2.186.

Example 7

A solution of human IgG was prepared by reconstituting human IgG powder in deionized water to a protein concentration of approximately 10 mg/mL (first liquid A). A second solution of human IgG was prepared by reconstituting human IgG powder in deionized water to a protein concentration of approximately 30 mg/mL (first liquid B). A third solution of human IgG was prepared by reconstituting human IgG powder in deionized water to a protein concentration of approximately 100 mg/mL (first liquid C). All three solutions were desalted. The solutions were atomized separately and collected with stainless steel vessels containing a volume of ethyl acetate greater than $V_0$ held near room temperature under conditions of gentle stirring. The Peclet number was around about 1 or higher. After primary desiccation, particles from all samples were collected, washed, and vacuum dried to remove residual liquid. SEM images reveal identifiable particulate matter and indicate that the solute concentration of the first liquid afforded a degree of control over the particle morphology. First liquid A was associated with highly wrinkled, raisin-like particles. First liquid B was associated with particles comprising an internal void space and surfaces which were wrinkled to a lesser degree. First liquid C, in comparison to first liquid B, was associated with particles comprising lesser degrees of internal void spaces and lesser degrees of surface wrinkles.

Example 8

Human IgG powder was reconstituted in deionized water to a protein concentration of approximately 50 mg/mL and desalted. A solution of ethyl acetate was prepared which comprises a quantity of surfactant that was sufficient for stabilizing droplets of the first liquid on the timescale of and under the conditions of particle formation. A sample of the first liquid (sample A) was atomized and collected in a stainless steel vessel containing a volume of the ethyl acetate solution greater than $V_0$ was held near room temperature under conditions of gentle stirring. The Peclet number was around about 1 or higher. A second sample of the first liquid (sample B) was atomized and collected in a stainless steel vessel containing a volume of ethyl acetate solution less than $V_0$ was held near room temperature under conditions of gentle stirring. An additional volume of ethyl acetate was added to the vessel at a controlled rate to achieve an effective Peclet number around about 1 or less. After primary desiccation, particles from both samples were collected, washed, and vacuum dried to remove residual liquid. SEM images revealed identifiable particulate matter and indicated that the rate of introduction of the ethyl acetate afforded a degree of control over the particle morphology. Sample A was associated with particles comprising an internal void space and wrinkled surfaces. Sample B was associated with particles comprising a smooth, spheroidal morphology with lesser degrees of internal void spaces and lesser degrees of surfaces wrinkles.

Example 9

Figure 3A:
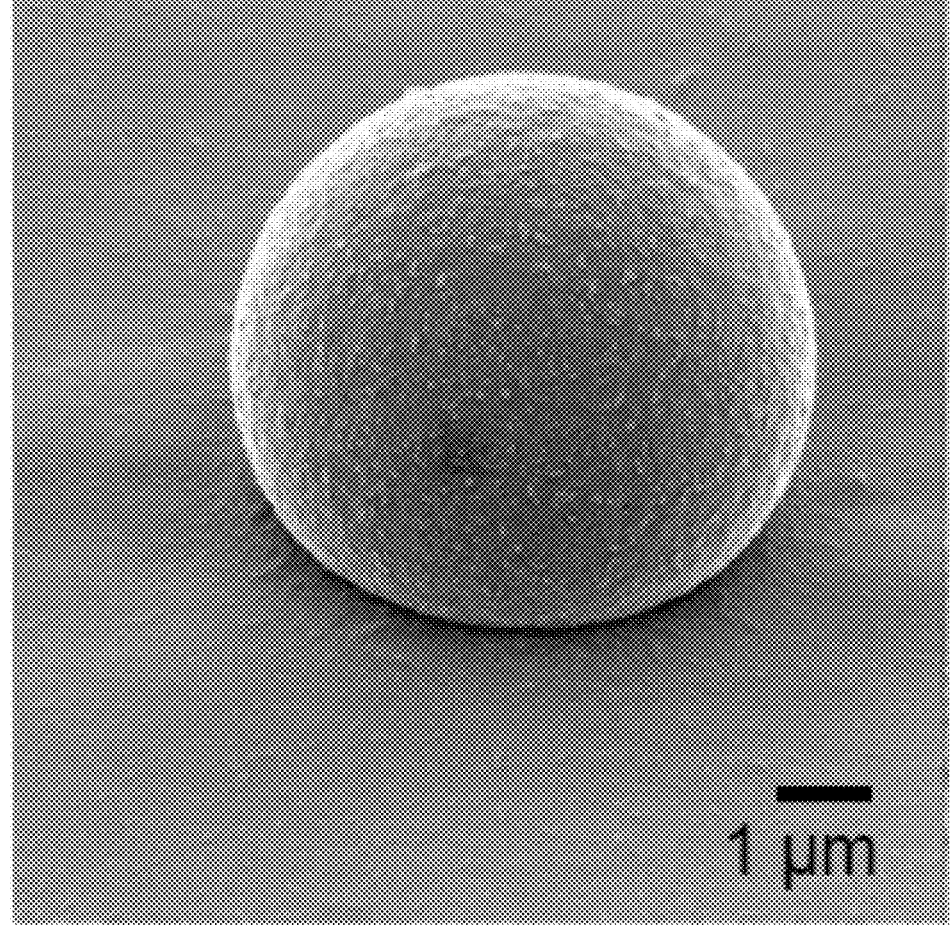
FIG. 3A shows an image of a human IgG particle surface formed through methods of the disclosure.
Figure 3B:
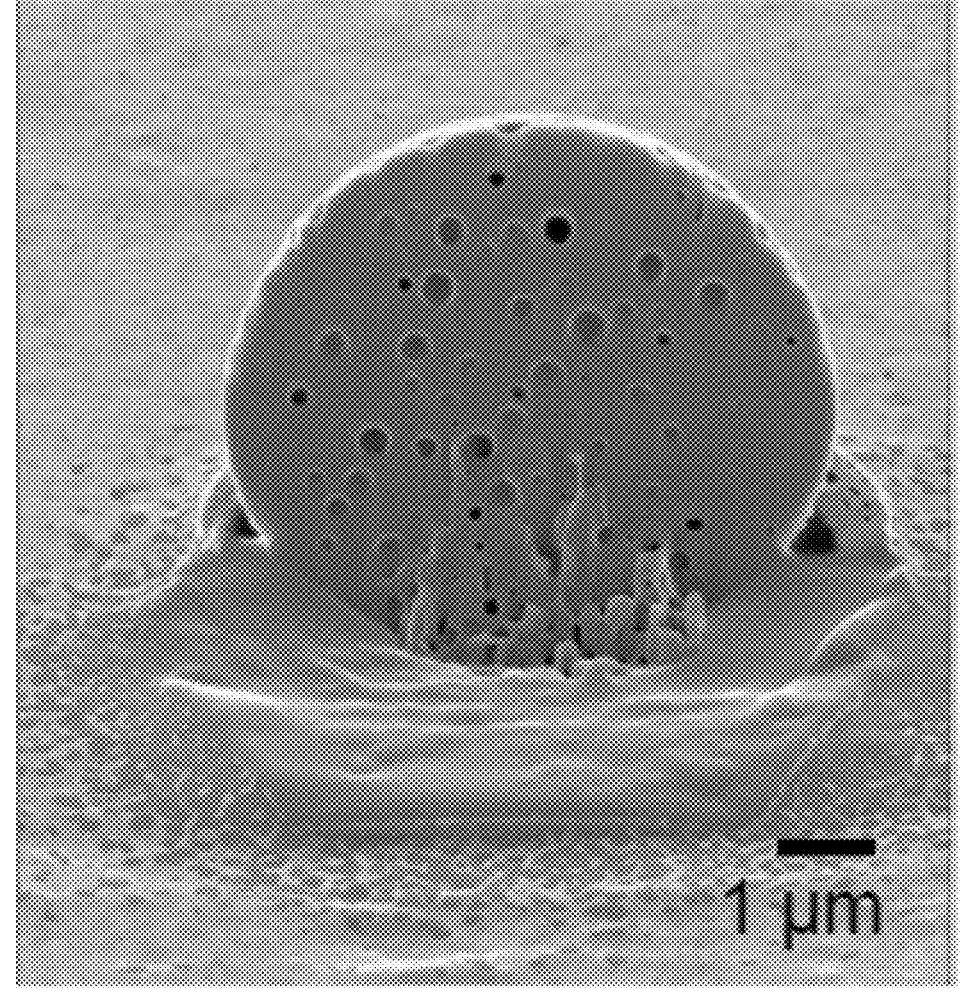
FIG. 3B shows an image of a human IgG particle sectioned to reveal the internal cross-section.

Human IgG powder was reconstituted in deionized water to a protein concentration of approximately 60 mg/mL. The solution was desalted and quantities of an amino acid (4 mg/mL), a carbohydrate (1 mg/mL), a salt (0.7 mg/mL), and a surfactant (0.6 mg/mL) were added. The solution was atomized and collected with a stainless steel vessel containing a volume of 2-ethylhexyl acetate greater than $V_0$ held near room temperature under conditions of gentle stirring. After primary desiccation, particles were collected, washed, and vacuum dried to remove residual liquid. HIM images revealed identifiable particulate matter. Cross-sections of the particles indicated the presence of numerous circular pores (void fraction of 10.8%) with diameters on the order of 100 nm (FIGS. 3A-3B) having a circularity of 0.872 and a roughness of 9.904. The pores have resulted from an intra-droplet emulsification event characterized by:
1. Diffusional ingress of the second liquid into the first liquid early in the droplet lifetime, with concentration approaching the saturation limit.
2. Supersaturation and nanodroplet nucleation of the second liquid within the droplet later in the droplet lifetime. The nanodroplets form templates for the pores.

3. Diffusional egress of the second liquid during washing, secondary dehydration, or sample preparation, resulting in porosity.

Example 10

A solution of human IgG was prepared by reconstituting human IgG powder in deionized water to a protein concentration of approximately 50 mg/mL (first liquid A). The solution was desalted. A second solution of human IgG was prepared by reconstituting human IgG powder in deionized water to a protein concentration of approximately 50 mg/mL. The solution was desalted and a quantity of an amino acid was added at a concentration that was at least 90% of the solubility limit, i.e., the amino acid was closer to its solubility limit than the human IgG was to its solubility limit (first liquid B). A third solution of human IgG was prepared by reconstituting human IgG powder in deionized water to a protein concentration of 50 mg/mL. The solution was desalted and a quantity of an amino acid characterized by a Peclet number greater than that of the human IgG is added (first liquid C). The solutions were atomized separately and collected with stainless steel vessels containing a volume of 2-ethylhexyl acetate greater than $V_0$ held near room temperature under conditions of gentle stirring. After primary desiccation, particles from all samples were collected, washed, and vacuumed dried to remove residual liquid. SEM images reveal identifiable particulate matter and indicate that the concentration, solubility, and Peclet numbers of the amino acids in the first liquids afforded a degree of control over the particle morphology. First liquid A was associated with smooth, spheroidal particles that were largely devoid of internal void spaces. First liquids B and C were associated with highly wrinkled, raisin-like particles. The shift in morphology may have to do with premature surface enrichment or precipitation and crystallization of the amino acid excipients.

Example 11

Human IgG powder was reconstituted in deionized water to a protein concentration of approximately 20 mg/mL and desalted. Quantities of an amino acid (4 mg/mL), a carbohydrate (1 mg/mL), a salt (0.7 mg/mL), and a surfactant (0.6 mg/mL) were added. A sample of the solution (sample A) was directly lyophilized. A second sample of the solution (sample B) was atomized and collected with a stainless steel vessel containing a volume of 2-ethylhexyl acetate greater than $V_0$ held near room temperature under conditions of gentle stirring. After primary desiccation, particles were collected, washed, and vacuum dried until the residual moisture content was similar to that of sample A. Both samples were analyzed by XPS. The results indicate a difference in surface elemental composition and thus the surface distribution of components relative to the average composition in the two samples.

| Element | Sample A Atomic % | Sample B Atomic % |
| --- | --- | --- |
| Carbon | 64.7 | 70.5 |
| Oxygen | 19.7 | 16.2 |
| Nitrogen | 15.1 | 12.8 |
| Sodium | 0.12 | 0.09 |
| Chlorine | 0.14 | 0.09 |
| Sulfur | 0.31 | 0.29 |

Example 12

Figure 4:
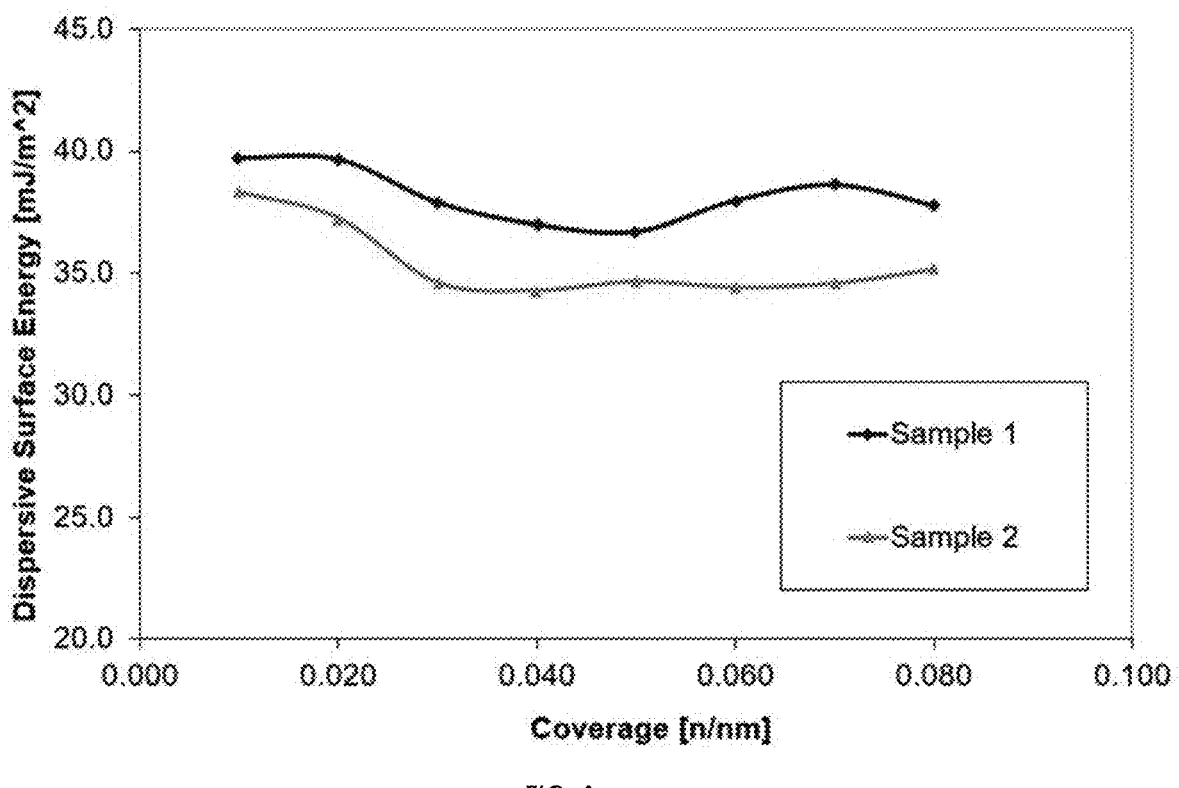
FIG. 4 shows a graph of the dispersive surface energy profiles for particles formed in second liquids of varying polarity.

Human IgG powder was reconstituted in deionized water to a protein concentration of approximately 20 mg/mL and desalted. Quantities of an amino acid (4 mg/mL), a carbohydrate (1 mg/mL), a salt (0.7 mg/mL), and a surfactant (0.6 mg/mL) were added. A sample of the solution (sample 1) was atomized and collected with a stainless steel vessel containing a volume of a second liquid (second liquid A) greater than $V_0$ held near room temperature under conditions of gentle stirring. A second sample of the solution (sample 2) was atomized and collected with a stainless steel vessel containing a volume of a second liquid (second liquid B) greater than $V_0$ held near room temperature under conditions of gentle stirring. After primary desiccation, particles were collected, washed, and vacuum dried. IGC analysis revealed that sample 1 had a substantially larger dispersive surface energy in comparison to sample 2 (FIG. 4). The result demonstrates that the surface energies of the particles can be modified by selection of the second liquid. This has implications for the behavior of the particles in a pharmaceutical suspension formulation since the surface energy will affect the colloidal stability, the relative viscosity, the redispersibility, and the adhesive interactions with container closure components.

Example 13

Figure 5:
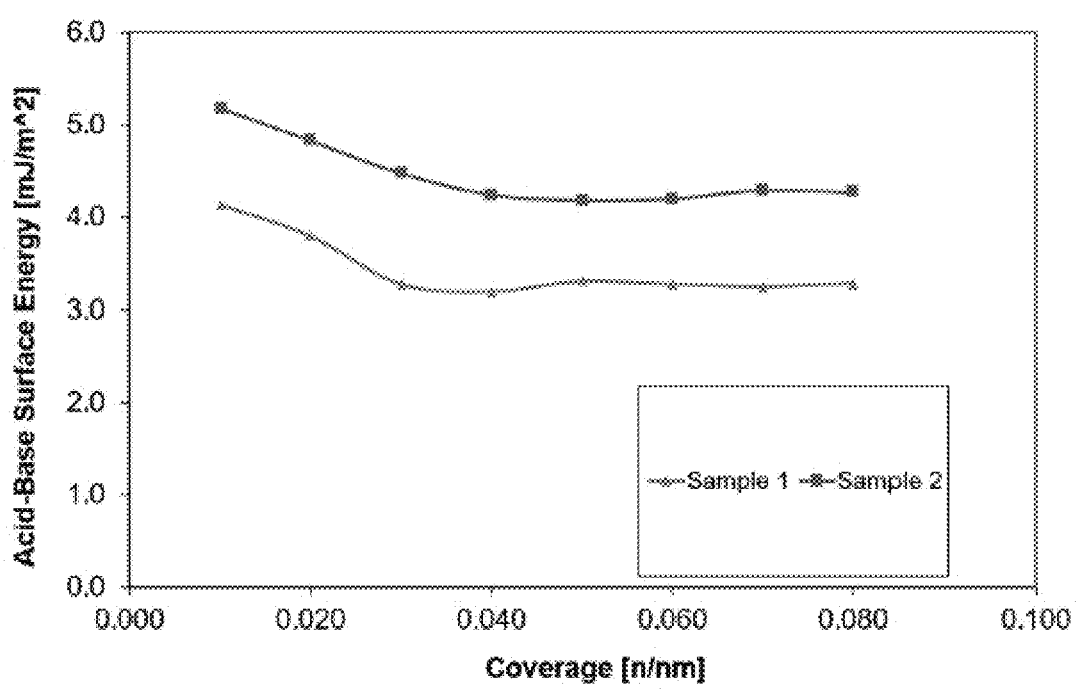
FIG. 5 shows a graph of the acid-base surface energy profiles for particles formed in second liquids of varying polarity and acid-base properties.

A solution of human IgG (sample 1) was prepared by reconstituting human IgG powder in deionized water to a protein concentration of approximately 20 mg/mL. The solution was desalted and quantities of an amino acid (4 mg/mL), a carbohydrate (1 mg/mL), a salt (0.7 mg/mL), and a surfactant (0.6 mg/mL) were added. A second solution of human IgG (sample 2) was prepared by reconstituting human IgG powder in deionized water to a concentration of approximately 20 mg/mL. The solution was desalted and a quantity of salt (6.3 mg/mL) was added. The solutions were atomized separately and collected with stainless steel vessels containing a volume of a second liquid greater than $V_0$ held near room temperature under conditions of gentle stirring. After primary desiccation, particles from all samples were collected, washed, and vacuum dried to remove residual liquid. IGC analysis revealed that sample 1 had a substantially lower polar surface energy in comparison to sample 2 (FIG. 5). This result demonstrates that the surface energies of particles can be altered by modifications to the type or quantity of the excipients which are utilized.

Example 14

Human IgG powder was reconstituted in deionized water to a protein concentration of approximately 50 mg/mL and desalted. A quantity of an excipient (10 mg/mL) was added to the solution, after which it was atomized and collected with a stainless steel vessel containing a volume of a second liquid greater than $V_0$ held near room temperature under conditions of gentle stirring. After primary desiccation, particles were collected, washed, and vacuum dried to remove residual liquid. The first liquid had a solubility limit in the second liquid of $c_{1,s}$. The excipient had a solubility limit in a saturated mixture of the first liquid in the second liquid, i.e., a solution in which the first liquid was at or near the limit of solubility, which was greater than that of the human IgG. This allowed it to solubilize in the saturated second liquid surrounding the droplet during particle formation, such that it preferentially resided at the surface. XPS analysis revealed a high quantity of the excipient on the surface relative to the quantify of the human IgG.

Example 15

A solution of human IgG was prepared by reconstituting human IgG powder in deionized water to a protein concentration of approximately 50 mg/mL (first liquid A). The solution was desalted and a quantity of an amino acid (4 mg/mL) was added at a concentration far from its solubility, i.e., farther from its solubility limit than the human IgG is to its solubility limit. The Peclet number of the amino acid was similar to that of the human IgG. A second solution of human IgG was prepared by reconstituting human IgG powder in deionized water to a protein concentration of approximately 50 mg/mL. The solution was desalted and a quantity of an amino acid was added at a concentration that was at least 90% of the solubility limit, i.e., closer to its solubility limit than the human IgG was to its solubility limit (first liquid B). A third solution of human IgG was prepared by reconstituting human IgG powder in deionized water to a protein concentration of 50 mg/mL. The solution was desalted and a quantity of an amino acid characterized by a Peclet number greater than that of the human IgG was added (first liquid C). The solutions were atomized separately and collected with stainless steel vessels containing a volume of 2-ethylhexyl acetate greater than $V_0$ held near room temperature under conditions of gentle stirring. After primary desiccation, particles from all samples were collected, washed, and vacuumed dried to remove residual liquid. XPS measurements revealed that the concentration, solubility, and Peclet numbers of the amino acids in the first liquids afforded a degree of control over the particle surface properties. In comparison to first liquid A, first liquids B and C were associated with much greater surface enrichment of their amino acids. The increased surface enrichment was a byproduct of proximity of the amino acid to its solubility limit in the first liquid (first liquid B) or a high Peclet number relative to other components in the first liquid (first liquid C).

Example 16

Human IgG powder was reconstituted in deionized water to a protein concentration of approximately 50 mg/mL and desalted. PLGA was dissolved in ethyl acetate at a concentration of approximately 50 mg/mL or another concentration below the limit of solubility. A coaxial atomizer was used to generate core-shell drops for which the core comprises the human IgG solution and the shell comprises the PLGA solution. The drops were collected with a stainless steel vessel comprising a volume of deionized water greater than $V_0$ (measured with respect to the shell liquid) held near room temperature under conditions of gentle stirring. The shell liquid dispersed in the deionized water to form particles comprising a PLGA shell. After primary desiccation, particles were collected, washed, and vacuum dried to remove residual liquid. SEM images revealed identifiable particulate matter.

Example 17

Figure 6:
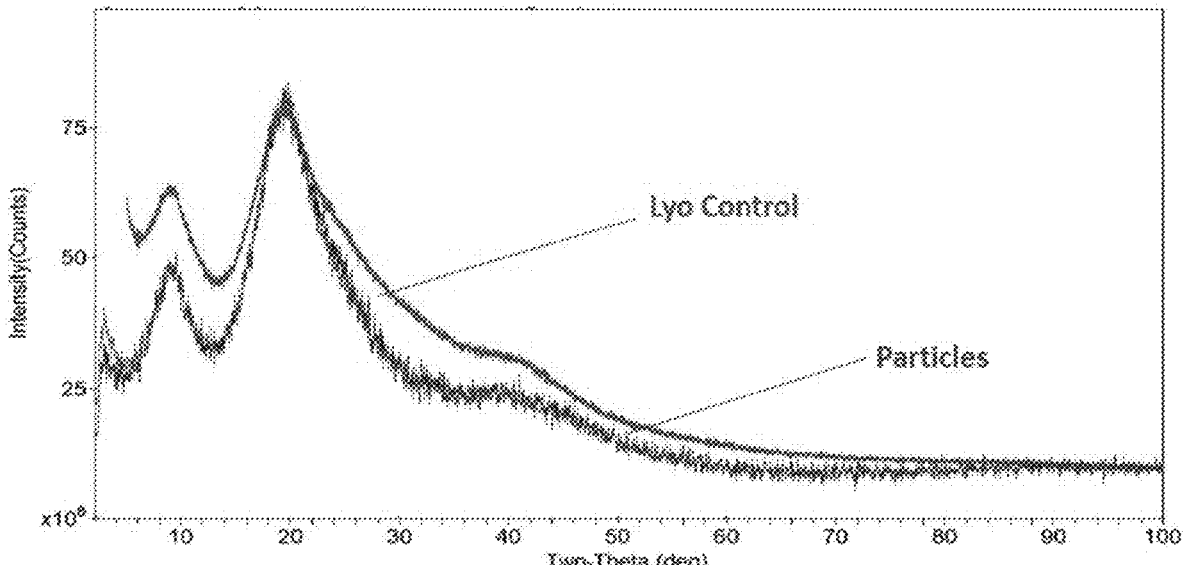
FIG. 6 shows a graph of the X-ray diffraction profiles for solid proteinaceous matter from a common first liquid compared to standard lyophilization matter.

Human IgG powder was reconstituted in deionized water to a protein concentration of approximately 60 mg/mL. The solution was desalted and quantities of an amino acid (12 mg/mL), a carbohydrate (3 mg/mL), a salt (2.1 mg/mL), and a surfactant (1.8 mg/mL) were added. A sample of the solution was atomized and collected with a stainless steel vessel containing a volume of 2-ethylhexyl acetate greater than $V_0$ held near room temperature under conditions of gentle stirring. After primary desiccation, particles were collected, washed, and vacuum dried to remove residual liquid. XRD analysis revealed no discernible Bragg peaks (FIG. 6), indicating an absence of crystalline material in spite of several excipients which are sometimes amenable to crystallization.

Example 18

Human IgG powder was reconstituted in deionized water to a protein concentration of approximately 60 mg/mL. The solution was desalted and quantities of an amino acid (12 mg/mL), a carbohydrate (3 mg/mL), a salt (2.1 mg/mL), and a surfactant (1.8 mg/mL) were added. A sample of the solution was atomized and collected with a stainless steel vessel containing a volume of a second liquid greater than $V_0$ held near room temperature under conditions of gentle stirring. The second liquid was chosen on the basis of a characteristic desiccation time that was long in relation to that of an alternative liquid such as 2-ethylhexyl acetate, e.g., Fo* was greater. After primary desiccation, particles were collected, washed, and vacuum dried to remove residual liquid. XRD analysis revealed Bragg peaks, indicating the presence of crystalline material. The crystalline material was potentially present on account of the protracted particle formation time relative to what alternative second liquids may afford, e.g., 2-ethylhexyl acetate.

Example 19

Human IgG powder was reconstituted in deionized water to a protein concentration of approximately 60 mg/mL. The solution was desalted and quantities of an amino acid (concentration equal to 95% of the solubility limit, about 12 mg/mL), a carbohydrate (3 mg/mL), a salt (2.1 mg/mL), and a surfactant (1.8 mg/mL) were added. The amino acid was selected on the basis of a propensity to crystallize and a relatively low solubility limit, the latter of which will cause it to precipitate early in the droplet desiccation process. A sample of the solution was atomized and collected with a stainless steel vessel containing a volume of a second liquid greater than $V_0$ held near room temperature under conditions of gentle stirring. After primary desiccation, particles were collected, washed, and vacuum dried to remove residual liquid. XRD analysis reveals Bragg peaks consistent with the amino acid, indicating the presence of crystalline amino acid. Further analysis revealed that the crystalline material was preferentially located near the surface of the particles, likely on account of the inability of the crystalline domains to efficiently diffuse during the particle formation process.

Example 20

Human IgG powder was reconstituted in deionized water to a protein concentration of approximately 50 mg/mL. The solution was desalted and quantities of two excipients are added at equal concentrations of 50 mg/mL (excipients A and B). The order of the Peclet numbers for the three components of the solution were such that human IgG<excipient A<excipient B, i.e., the human IgG had the lowest Peclet number and excipient B had the highest Peclet number. The solution was atomized and collected with a stainless steel vessel containing a volume of a second liquid greater than $V_0$ held near room temperature under conditions of gentle stirring. After primary desiccation, particles were collected, washed, and vacuum dried to remove residual liquid. A gallium focused ion beam (FIB) was used to cut one of the particles in half to reveal a cross-section of the particle interior. Auger electron spectroscopy (AES) was used to sample the composition of the cross-section along a line r extending between the center of the cross-section and an edge. XPS reveals that the human IgG had the highest local abundance at the center of the cross-section, that excipient A had the highest local abundance at the midway point of the line r, and that excipient B has the highest local abundance at the edge of the cross-section. The distribution of the abundances may be a reflection of the Peclet numbers of the solutes.

Example 21

Human IgG powder was reconstituted in deionized water to a protein concentration of approximately 50 mg/mL and desalted. A sample of the solution (sample A) was atomized and collected with a stainless steel vessel containing a volume of a second liquid (second liquid A) greater than $V_0$ held near room temperature under conditions of gentle stirring. Second liquid A had no known tendency to either stabilize or destabilize the human IgG. A second sample of the solution (sample B) was atomized and collected with a stainless steel vessel containing a volume of a second liquid (second liquid B) greater than $V_0$ held near room temperature under conditions of gentle stirring. Second liquid B was chosen on the basis of a known tendency to stabilize the human IgG. Such stabilization can be achieved by a reduction of the tendency of the therapeutic or diagnostic agent to deviate from its functional or native state; by a reduction of the tendency of the therapeutic or diagnostic agent to self-associate either reversibly or irreversibly; and/or by a reduction of the ability of the therapeutic or diagnostic agent to adsorb to various interfaces including air-liquid, liquid-solid, and liquid-liquid, etc. After primary desiccation, particles from both samples were collected, washed, and vacuum dried to remove residual liquid. Particles from both samples were then reconstituted in an appropriate medium for SEC and SvP analysis. SEC analysis revealed that sample B had fewer aggregates and/or fragments than sample A. SvP analysis revealed that sample B had fewer insoluble artifacts than sample A.

Example 22

Human IgG powder was reconstituted in deionized water to a protein concentration of approximately 50 mg/mL. The solution was desalted and a quantity of an excipient (1 mg/mL) was added. Several second liquids were prepared, each comprising ethyl acetate with quantities of the excipient dissolved at various concentrations between 0 mg/mL and the solubility limit. Samples of the human IgG solution were atomized and collected with stainless steel vessels, each containing a volume greater than $V_0$ of one of the several second liquids. The second liquids were held near room temperature under conditions of gentle stirring. After primary desiccation, particles from all samples were collected, washed, and vacuum dried. The samples were reconstituted to ascertain the ratio of human IgG to excipient in the particles by mass. The second liquid with 0 mg/mL excipient may correspond to particles with less excipient than expected while the second liquid with the excipient at the solubility limit may correspond to more excipient than anticipated. The results can be used to calibrate the concentration of the excipient in the second liquid to preserve the desired ratio of human IgG to excipient.

Example 23

Human IgG powder was reconstituted in deionized water to a protein concentration of approximately 25 mg/mL. The solution was desalted and quantities of a carbohydrate (6 mg/mL) and a surfactant (1 mg/mL) were added. The solution was atomized and collected with a stainless steel vessel containing a volume greater than $V_0$ of 2-ethylhexyl acetate, held near room temperature under conditions of gentle stirring. The resulting particles were washed using ethyl acetate, a wash liquid in which the surfactant was soluble. The amount of surfactant remaining in the particles was determined using an evaporative light scattering detector (ELSD). The weight fraction of surfactant in the particles was less than what would be anticipated on the basis of the composition of the first liquid.

Example 24

Human IgG powder was reconstituted in deionized water to a protein concentration of approximately 50 mg/mL and desalted. A sample of the solution (sample A) was atomized without an applied voltage and collected with a stainless steel vessel containing a volume greater than $V_0$ of a second liquid held near room temperature under conditions of gentle stirring. A second sample of the solution (sample B) was atomized with an applied voltage and collected with a stainless steel vessel containing a volume greater than $V_0$ of the same second liquid held near room temperature under conditions of gentle stirring. In both cases the Peclet number was about 1 or higher. Droplets of sample B, however, were charged to a high fraction of the Rayleigh limit. After primary desiccation, particles from the samples were collected, washed, and vacuum dried to remove residual liquid. SEM images revealed identifiable particulate matter and indicated that the droplet charge affords a degree of control over the particle morphology. Sample A was associated with particles comprising an internal void space and wrinkled surfaces. Sample B was associated with lesser degrees of internal void spaces and wrinkled surfaces.

Example 25

Human IgG powder was reconstituted in deionized water to a protein concentration of approximately 5 mg/mL and desalted. A sample of the solution (sample A) was atomized without an applied voltage and collected with a stainless steel vessel containing a volume greater than $V_0$ of a second liquid held near room temperature under conditions of gentle stirring. A second sample of the solution (sample B) was atomized with an applied voltage and collected with a stainless steel vessel containing a volume greater than $V_0$ of the same second liquid held near room temperature under conditions of gentle stirring. Droplets of sample B were charged to a high fraction of the Rayleigh limit. After primary desiccation, particles from the samples were collected, washed, and vacuum dried to remove residual liquid. SEM images reveal identifiable particulate matter and indicated that the droplet charge afforded a degree of control over the particle morphology. Sample A was associated with particles comprising wrinkled surfaces, likely on account of surface buckling during the particle formation process. Sample B was associated with lesser degrees of surface buckling, likely on account of Coulombic effects that act to preserve a more spherical morphology.

Example 26

A solution of human IgG (first liquid A) was prepared by reconstituting human IgG powder in deionized water to a protein concentration of approximately 50 mg/mL. The solution was desalted. A second solution of human IgG (first liquid B) was prepared by reconstituting human IgG powder in deionized water to a protein concentration of approximately 50 mg/mL. The solution was desalted and a quantity of an excipient (10 mg/mL) was added. A third solution of human IgG (first liquid C) was prepared by reconstituting human IgG powder in deionized water to a protein concentration of approximately 50 mg/mL. The solution was desalted and a quantity of the same excipient was added at a higher concentration (50 mg/mL). The excipient in first liquids B and C was chosen on account of the fact that it carried a net electrical charge in solution. The solutions were separately atomized with an applied voltage and collected with stainless steel vessels containing volumes greater than $V_0$ of a second liquid held near room temperature under conditions of gentle stirring. After primary desiccation, particles from the samples were collected, washed, and vacuum dried. XPS analysis revealed a high local abundance of the excipient on the surfaces of particles produced from first liquids B and C. The abundance was higher than what would be anticipated based on the ratio of human IgG to excipient in either solution. This suggests that the layer of surface charge on the drops was potentially comprised primarily of the excipient. SEM analysis further revealed that, for particle produced from first liquid C, the surface abundance of excipient was such that a continuous shell had been formed around the particle.

Example 27

Figure 7A:
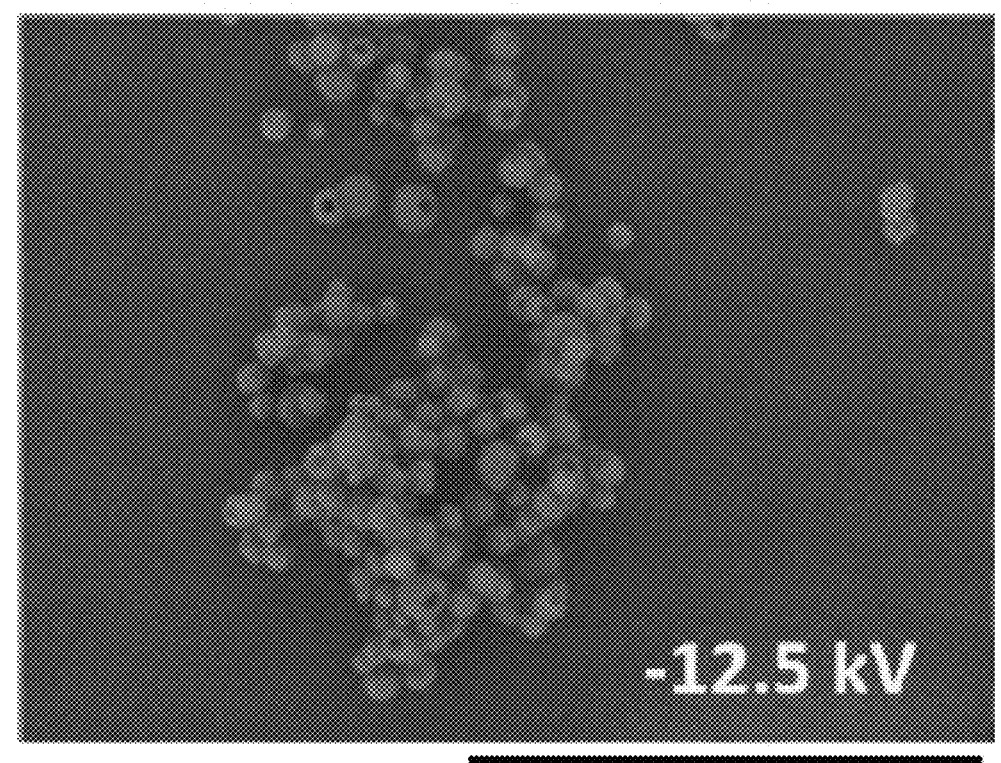
FIGS. 7A-7C show images of human IgG particles formed through methods of the disclosure at different voltages.
Figure 7B:
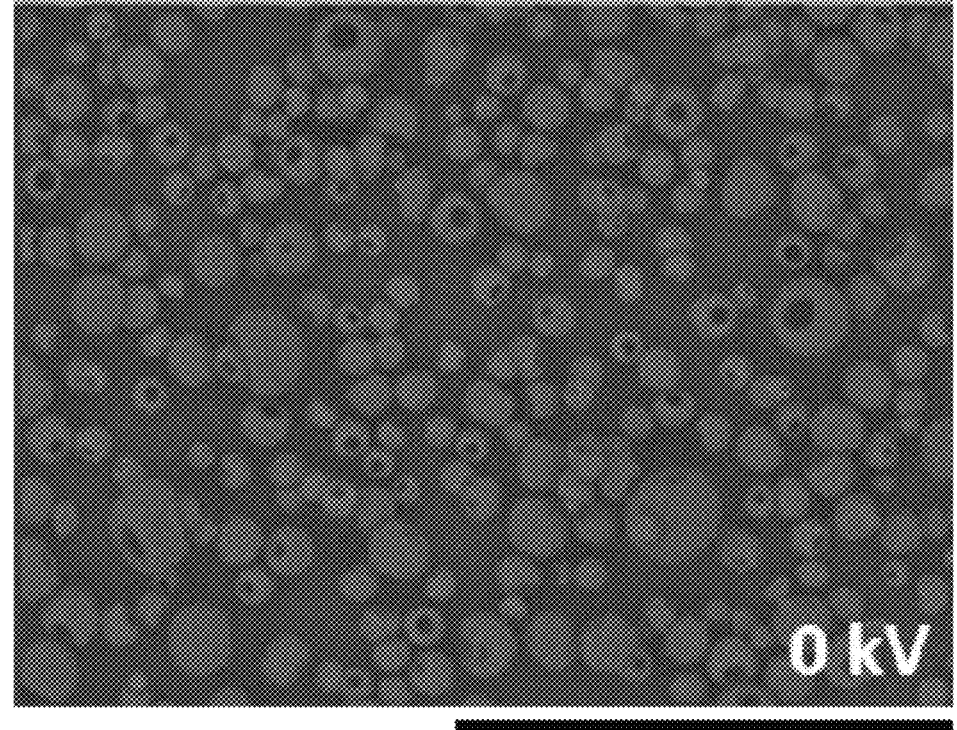
Figure 7C:
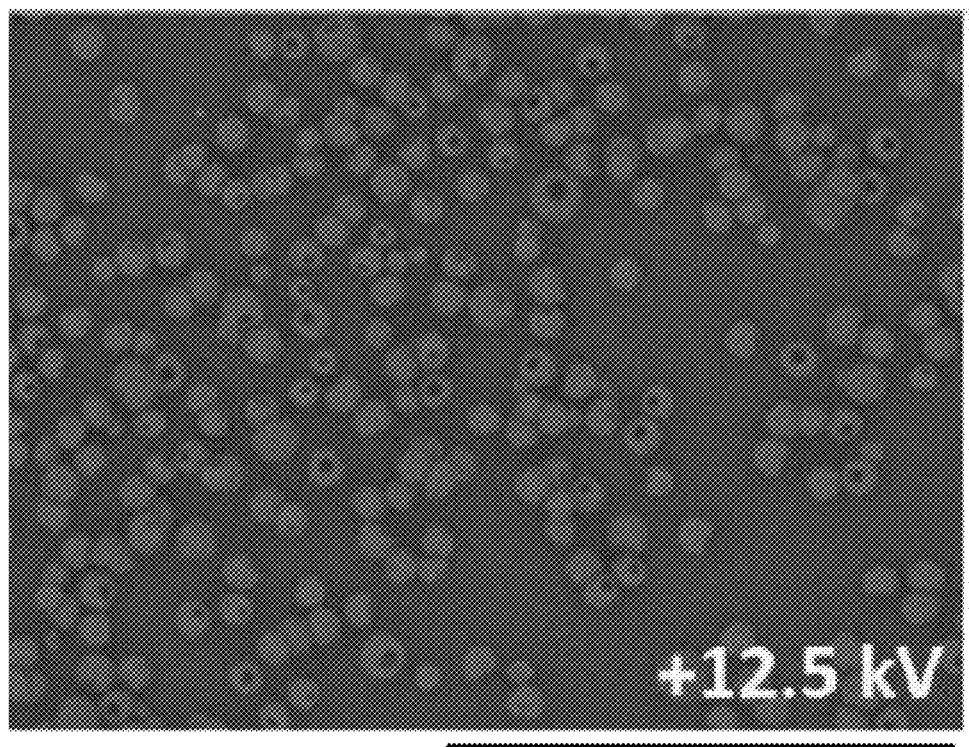
Figure 8:
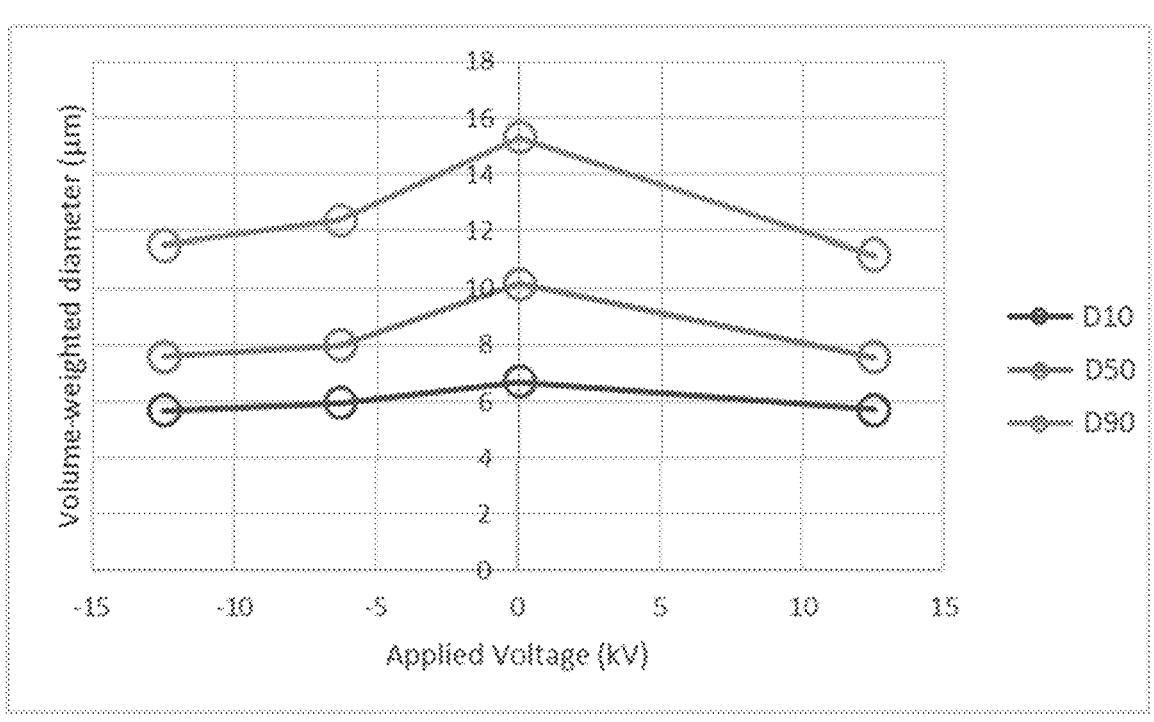
FIG. 8 shows a graph of volume-weighted size distributions for human IgG particles D10, D50, and D90, formed through methods of the disclosure at different voltages.

Human IgG powder was reconstituted in deionized water to a protein concentration of approximately 50 mg/mL and desalted. A sample of the solution (sample A) was ultrasonically atomized at a voltage of −12.5 kV and collected with a stainless steel vessel containing a volume greater than $V_0$ of 2-ethylhexyl acetate held near room temperature under conditions of gentle stirring. A second sample of the solution (sample B) was ultrasonically atomized at a voltage of −6.3 kV and collected with a stainless steel vessel containing a volume greater than $V_0$ of 2-ethylhexyl acetate held near room temperature under conditions of gentle stirring. A third sample of the solution (sample C) was ultrasonically atomized at a voltage of 0 kV and collected with a stainless steel vessel containing a volume greater than $V_0$ of 2-ethylhexyl acetate held near room temperature under conditions of gentle stirring. A fourth sample of the solution (sample D) was ultrasonically atomized at a voltage of +12.5 kV and collected with a stainless steel vessel containing a volume greater than $V_0$ of 2-ethylhexyl acetate held near room temperature under conditions of gentle stirring. After primary desiccation, particles from all samples were collected, washed, and vacuum dried to remove residual liquid. SEM images revealed identifiable particulate matter and suggested that the more highly charged samples were more monodisperse (FIGS. 7A-7C). The particles of FIG. 7A having a circularity of 0.921 and a roughness of 6.372. The particles of FIG. 7B having a circularity of 0.898 and a roughness of 5.587. The particles of FIG. 7C having a circularity of 0.921 and a roughness of 5.385. MPS analysis confirmed this result (FIG. 8), showing volume-weighted size distributions for human IgG particles formed through methods of the disclosure at different voltages. The D10, D50, and D90 values of the size distributions are shown. A smaller average particle size was found for the samples generated at higher voltage along with a narrower particle size distribution, as evidenced by the $10^{th}$, $50^{th}$, and $90^{th}$ percentile diameters of the cumulative volume distribution for each sample. The smaller average particle size may be attributable to the high electric field reducing the initial droplet size to a value below that which prevails for the ultrasonic atomizer alone. The narrower distribution may be attributable to the tendency of the charge on the drops to prevent coalescence.

Example 28

Human IgG powder was reconstituted in deionized water to a protein concentration of approximately 50 mg/mL and desalted. A sample of the solution (sample A) was processed using a microfluid junction that generates 10 micron drops at a frequency of greater than 10,000 Hz. The channel downstream of the junction ensured that droplets of the solution propagated in a train for a period of time which was approximately 10% of the characteristic desiccation time of the particles before exiting the system. A second sample of the solution (sample B) was processed using a second microfluid junction which generated 10 micron drops at a frequency greater than 10,000 Hz. The channel downstream of the junction ensured that droplets of the solution propagated in a train for a period of time which was approximately 100% of the characteristic desiccation time of the particles before exiting the system. A third sample of the solution (sample C) was processed using a third microfluid junction which produced 10 micron drops at a frequency greater than 10,000 Hz. The channel downstream of the junction ensured that droplets of the solution propagated in a train for a period of time which was approximately 500% of the characteristic desiccation time of the particles before exiting the system. For all samples, the drops or particles were collected in a small beaker (no stirring) as they exited the system and sufficient second liquid was provided to facilitate full desiccation, i.e., volumes greater than $V_0$ are provided. After primary desiccation, particles from all samples were collected, washed, and vacuum dried to remove residual liquid. SEM images revealed identifiable particulate matter. MPS analysis indicated that samples B and C were associated with lower average particle sizes. This is likely attributable to the extended residence time in the microfluidic channels. Once the drops or particles exited the channels, the drop or particle train was disrupted and drop-drop or particle-particle interactions can increase in frequency. This can lead to enhanced coalescence if the drops or particles were not sufficiently desiccated beforehand.

Example 29

Human IgG powder was reconstituted in deionized water to a protein concentration of approximately 50 mg/mL and desalted. A quantity of an excipient was added. The excipient was chosen on the basis of a high Peclet number which was greater than 1 and large in relation to that of the human IgG, such that it will enrich at the surface during particle formation. The excipient acted as an effective deterrent to coalescence when it reached a critical surface concentration. The timescale for reaching this critical concentration under the particle formation conditions of interest was approximately τ. A sample of the solution (sample A) was processed using a microfluid junction that generated 10 micron drops at a frequency of greater than 10,000 Hz. The channel downstream of the junction ensured that droplets of the solution propagated in a train for a period of time which was approximately 10% of r before exiting the system. A second sample of the solution (sample B) was processing using a second microfluid junction which generated 10 micron drops at a frequency greater than 10,000 Hz. The channel downstream of the junction ensured that droplets of the solution propagated in a train for a period of time which was approximately 100% of τ before exiting the system. A third sample of the solution (sample C) was processed using a third microfluid junction which produced 10 micron drops at a frequency greater than 10,000 Hz. The channel downstream of the junction ensured that droplets of the solution propagated in a train for a period of time which was approximately 500% of τ before exiting the system. For all samples, the drops or particles were collected in a small beaker (no stirring) as they exited the system and sufficient second liquid was provided to facilitate full desiccation, i.e., volumes greater than $V_0$ were provided. After primary desiccation, particles from all samples were collected, washed, and vacuum dried to remove residual liquid. SEM images revealed identifiable particulate matter. MPS analysis indicated that samples B and C were associated with lower average particle sizes. This was likely attributable to the extended residence time in the microfluidic channels. Once the drops or particles exited the channels, the drop or particle train was disrupted and drop-drop or particle-particle interactions can increase in frequency. This can lead to enhanced coalescence if the drops or particles do not exhibit sufficient surface enrichment of the coalescence-mitigating excipient at the time of interaction.

Example 30

Human IgG powder was reconstituted in deionized water to a protein concentration of approximately 50 mg/mL and desalted. Drops from the solution were formed using a membrane emulsification apparatus situated in a vessel containing a volume of second liquid which was initially saturated with water. The water saturation helped to prevent clogging of the membrane emulsification apparatus during drop formation. Once the drops have been formed, a volume of unsaturated second liquid greater than $V_0$ was added to the vessel to form particles. After primary desiccation, particles were collected, washed, and vacuum dried. SEM images revealed identifiable particulate matter.

Example 31

Figure 9:
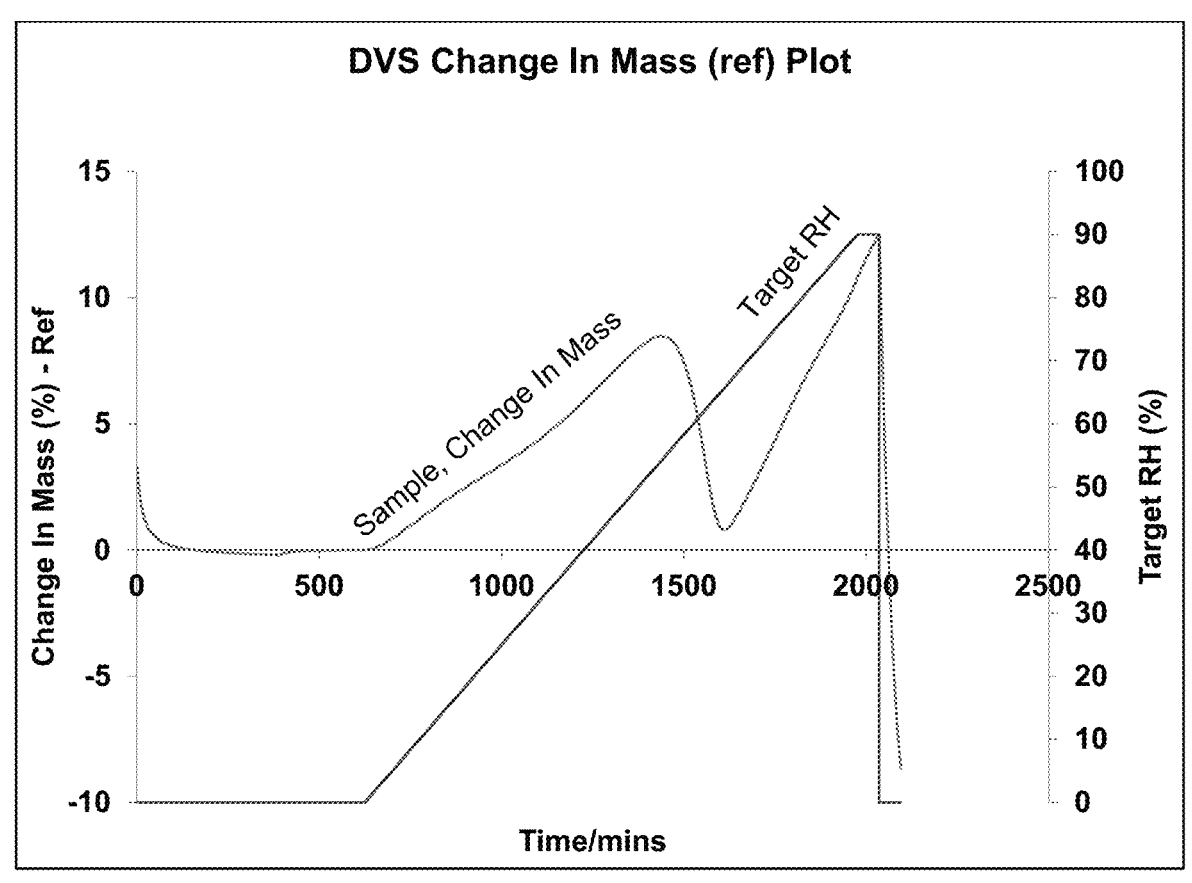
FIG. 9 shows a graph of a relationship between particle mass and environmental humidity for particles formed through methods of the disclosure at fixed temperature.

Human IgG powder was reconstituted in deionized water to a protein concentration of approximately 20 mg/mL. The solution was desalted and a salt (6 mg/mL) was added. The solution was atomized and collected with a stainless steel vessel containing a volume greater than $V_0$ of a second liquid held near room temperature under conditions of gentle stirring. After primary desiccation, particles were collected, washed, and vacuum dried to remove residual liquid. A DVS measurement was carried out on 50 mg of the particles while ramping the RH at a constant rate of 4% per hour. The measurement was conducted isothermally at about 22° C. At around a run time of 1450 minutes, when the RH was approximately 55%, a mass loss event consisting of an irreversible loss of approximately 10% of the total sample mass was observed (FIG. 9). Upon a step to 0% RH at the very end of the run, the sample mass was roughly 10% less than the initial sample mass conditioned in dry air. This indicated that the lost mass consisted of a non-aqueous volatile component, i.e., residual second liquid. The result demonstrates that liquid removal can be expedited in proximity to the glass transition temperature. The rationale is as follows.

1. Residual second liquid is trapped within the glassy amorphous phase as droplets solidify into particles. Though loss of volatile second liquid in dry gas is thermodynamically favored, this is retarded by the need of the glass to contract as solvent loss proceeds (Richardson, H. et al., The European Physical Journal E, 12, no. 1 (2003): 87-91). This imposes a compressive stress which the rigid glass withstands, and the rate of solvent loss is close to negligible even in dry air.

2. As the glass transition is approached, molecular mobility increases, the amorphous glass becomes rubbery, and the material is no longer able to support the compressive stress imposed by the loss of the second liquid. Loss of second liquid proceeds at a detectable rate.

In the context of the vapor sorption data presented in (FIG. 9), as water uptake proceeded during the RH ramping method. Thus the glass transition temperature was continually decreased as the RH increases. At roughly 55% RH, the sample was plasticized sufficiently such that the glass transition temperature was near the measurement temperature (22° C.), and the loss of second liquid proceeded rapidly.

Example 32

Human IgG powder was reconstituted in deionized water to a protein concentration of approximately 50 mg/mL and desalted. The solution was atomized and collected with a stainless steel vessel containing a volume greater than $V_0$ of a second liquid held near room temperature under conditions of gentle stirring. After primary desiccation, particles were collected and separated into two samples (samples A and B). Sample A was washed and vacuum dried for a period of 24 hours to remove residual liquid. Sample B was washed and then processed with a drying gas (helium, air, nitrogen or argon, preferably helium or air). The drying gas had a negligible RH and was operated at a temperature which was comparable to that of sample A during vacuum drying. The gas was set to flow over the particles of sample B for 3 hours at a rate of 50 standard liters per minute while they were immobilized on a filter. Karl Fischer analysis revealed that the residual quantity of the first liquid in sample B was less than the residual quantity of the first liquid in sample A in spite of the abbreviated processing time. The result indicated that air drying can be utilized to accelerate particle post-processing.

Example 33

Human IgG powder was reconstituted in deionized water to a protein concentration of approximately 50 mg/mL and desalted. A sample of the solution (sample A) was atomized and collected with a stainless steel vessel containing a volume greater than $V_0$ of a second liquid (second liquid #1) held near room temperature under conditions of gentle stirring. The Peclet number was around about 1 or lower and second liquid #1 had a boiling point greater than about 180° C. A second sample of the solution (sample B) was atomized and collected with a stainless steel vessel containing a volume greater than $V_0$ of a second liquid (second liquid #1)

held near 4° C. under conditions of gentle stirring. The Peclet number was lower than that which corresponds to sample A. A third sample of the solution (sample C) was atomized and collected with a stainless steel vessel containing a volume greater than $V_0$ of a second liquid (second liquid #2) held near room temperature under conditions of gentle stirring. The Peclet number was above 1 and second liquid #2 had a boiling point around about 80° C. A fourth sample of the solution (sample D) was atomized and collected with a stainless steel vessel containing a volume greater than $V_0$ of a second liquid (second liquid #2) held near 4° C. under conditions of gentle stirring. The Peclet number was around about 1 or lower. After primary desiccation, particles from all samples were collected, washed, and vacuum dried under comparable conditions to remove residual liquid. SEM images revealed identifiable particulate matter and indicated that samples with Peclet numbers around about 1 or lower (A, B, D) were associated with particles comprising a smooth, spherical morphology. Sample C, for which the Peclet number was around about 1 or higher, was associated with particles comprising internal void spaces and rougher surfaces. Gas chromatography with a flame ionization detector (GC-FID) analysis further revealed that samples C and D were associated with lower residual quantities of the second liquid, likely on account of the higher volatility of second liquid #2. The result indicated that Peclet number modulation of a more volatile second liquid can be useful for achieving a morphology of interest, e.g., a spherical morphology, while preserving ease of post-processing.

Example 34

Human IgG powder was reconstituted in deionized water to a protein concentration of approximately 50 mg/mL and desalted. The solution was atomized and collected with a stainless steel vessel containing a volume greater than $V_0$ of a second liquid held near room temperature under conditions of gentle stirring. After primary desiccation, particles were collected, washed, and vacuum dried to remove residual liquid. The resulting particles were re-suspended at a volume fraction of around about 0.02 in a solution of ethyl acetate containing 0.5 wt % poly(lactic-co-glycolic acid) (PLGA, 50:50, Mw=10,000) and 0.001 wt % oil red dye. The suspension was stirred for 1 hour to allow for binding of polymer to particle surface, after which the suspension was spray-dried with a conventional spray dry apparatus. The inlet temperature was around 130° C. The resulting spray-dried particles have a core-shell structure with a thin coating of PLGA, as determined by thermogravimetric analysis (for weight loss), and confocal microscopy. SEM images were collected.

Example 35

Figure 10:
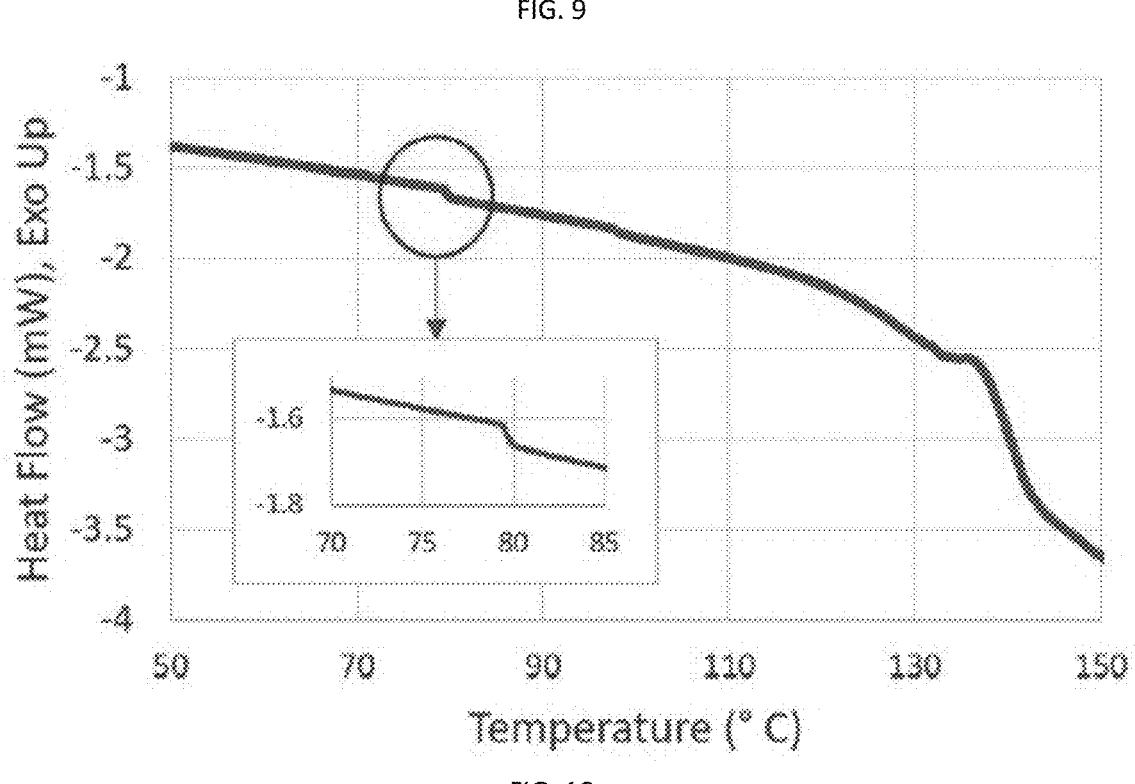
FIG. 10 shows a graph of a differential scanning calorimetry measurement used to measure the glass transition temperature for particles formed through methods of the disclosure.

Human IgG powder was reconstituted in deionized water to a protein concentration of approximately 25 mg/mL and desalted. The solution was atomized and collected with a stainless steel vessel containing a volume greater than $V_0$ of a second liquid held near room temperature under conditions of gentle stirring. After primary desiccation, particles were collected, washed, and vacuum dried to remove residual liquid. A sample of the dried powder was sealed hermetically in an aluminum crucible and analyzed using dynamic scanning calorimetry (5° C. ramp rate). A glass transition characterized by a shift in the specific heat capacity was observed (FIG. 10). The onset temperature of this transition was around about 79° C.

Example 36

Human IgG powder was reconstituted in deionized water to a protein concentration of approximately 25 mg/mL and desalted. The solution was atomized and collected with a stainless steel vessel containing a volume greater than $V_0$ of a second liquid held near room temperature under conditions of gentle stirring. After primary desiccation, particles were collected, washed, and vacuum dried to remove residual liquid. The samples were reconstituted in deionized water to a human IgG concentration of approximately 25 mg/mL. Visual inspection revealed no visible insoluble particulates (VPs) while analysis with a NanoSight revealed 100 submicron particles (SMPs) per mL. The turbidity of the solution was comparable to that of the first liquid prior to processing.

Example 37

Figure 11:
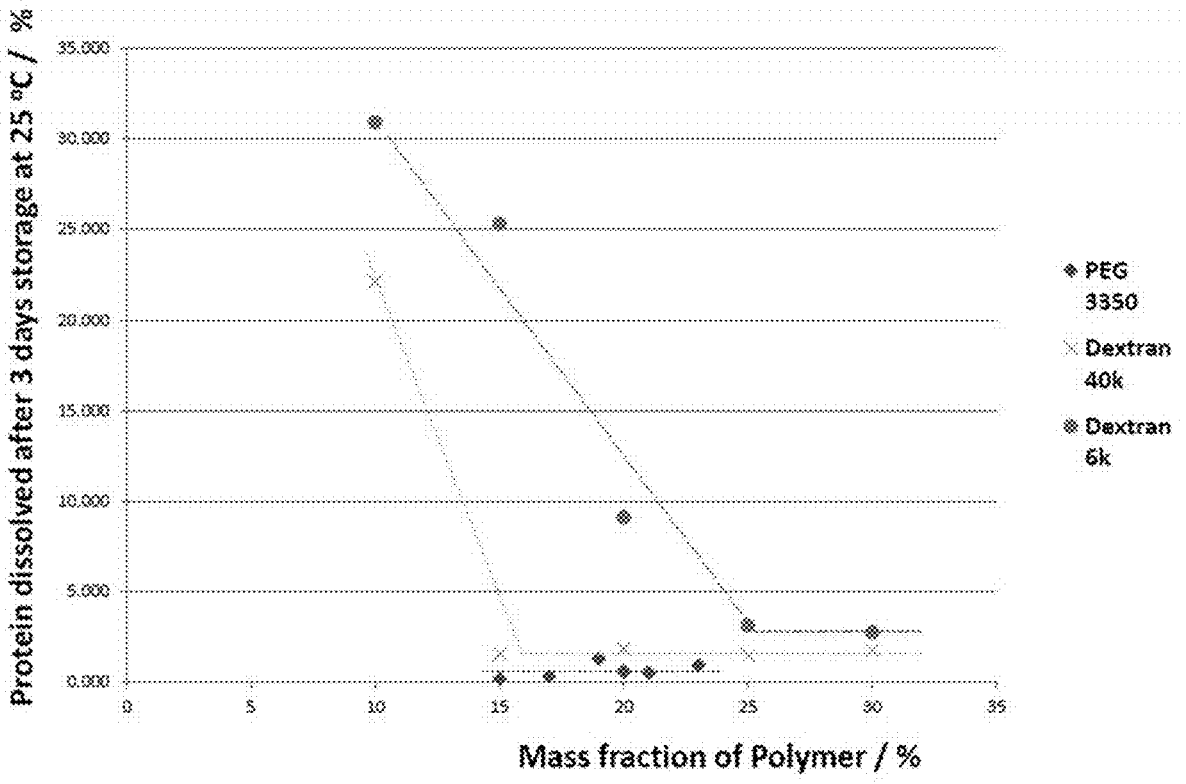
FIG. 11 shows a graph of the percentages of dissolved particles after storage for several suspensions of human IgG particles that were suspended in aqueous solutions comprising various crowding agents.

Human IgG particles were suspended in various aqueous solutions comprising the crowding agents PEG 3350, Dextran 40k, or Dextran 6k at various mass fractions. The suspensions were stored at room temperature for a period of three days before the fraction of dissolved particles was recorded. The measurement was facilitated by collecting, for each suspension, the concentration of human IgG in the aqueous continuous phase using a spectrophotometer. The results indicate that for each crowding agent there is a crowding agent mass fraction above which the dissolution of the particles can be substantially minimized during storage (FIG. 11).

Example 38

Figure 12:
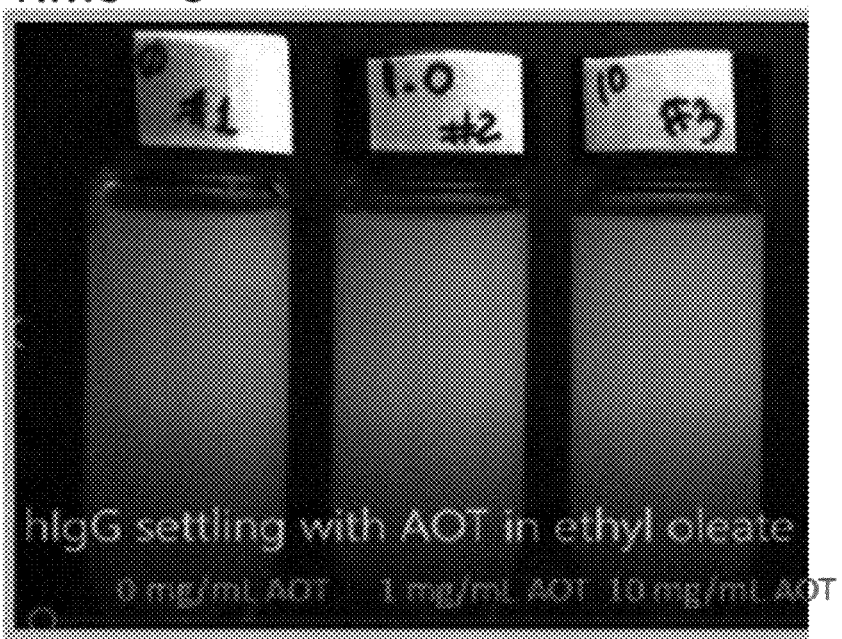
FIG. 12 shows pictures of the sedimentation and surface adhesion properties of human IgG particles that are suspended in a non-aqueous suspension medium.
Figure 12:
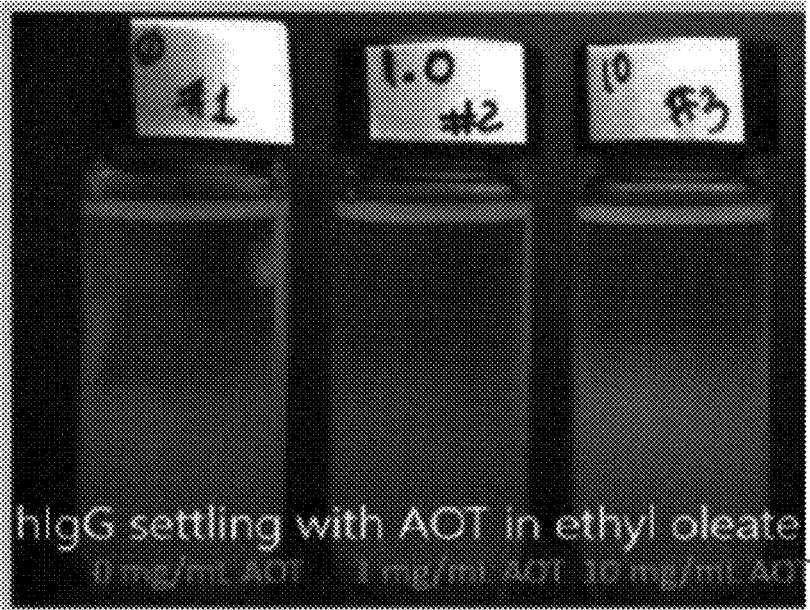

Human IgG powder was reconstituted in deionized water to a protein concentration of approximately 50 mg/mL. The solution was atomized and collected with a stainless steel vessel containing a volume greater than $V_0$ of a second liquid held near 40° C. under conditions of gentle stirring. After primary desiccation, particles were collected, washed, and vacuum dried to remove residual liquid. A first suspension (suspension A) was prepared thereafter in which the particles were loaded to a volume fraction of 0.2 in a vehicle. The vehicle comprised only ethyl oleate. A second suspension (suspension B) was prepared in which the particles were loaded to a volume fraction of 0.2 in a second vehicle. The second vehicle comprised dioctyl sulfosuccinate sodium salt (1 mg/mL) in ethyl oleate. A third suspension (suspension C) was prepared in which the particles were loaded to a volume fraction of 0.2 in a third vehicle. The third vehicle comprised dioctyl sulfosuccinate sodium salt (10 mg/mL) in ethyl oleate. The suspensions were placed in glass vials and observed for a period of time while sedimentation occurred (FIG. 12). The results indicated that the salt acted to mitigate particle adhesion to the vials walls and to protract the sedimentation time. The latter may owe to decreased flocculation facilitated by electrostatic particle interactions (repulsion).

Example 39

Human IgG particles comprising an amino acid (approximately 10 wt % of particle) and a surfactant (less than 1 wt % of particle) were suspended in ethyl acetate at a volume fraction of around 0.2. One mL of the suspension was used to fill a chamber of a syringe system before the ethyl acetate was removed through vacuum drying. The result was a powder-loaded chamber. The chamber can be back-filled with a pharmaceutically-acceptable suspension medium to produce a drug product.

Example 40

A suspension of human IgG particles was prepared in which the particles were loaded to a volume fraction of 0.2 in ethyl oleate. A sample of the suspension (sample A) was loaded into a glass vial that does not have a silicone oil coating. A sample of the suspension (sample B) was loaded into a glass vial that does have a silicone oil coating. The suspensions were observed for a period of time while sedimentation occurred. The results indicated that the silicone oil acts to mitigate particle adhesion to the vials walls.

Example 41

A suspension of human IgG particles was prepared in which the particles were loaded to a volume fraction of 0.2 in ethyl oleate. The suspension was loaded into a 1 mL glass syringe system and stored for a period of time that was long in relation to the characteristic sedimentation time of the particles. Prior to administration, the syringe system was agitated for 5 seconds in a sonic bath to resuspend the particles. Administration resulted in greater than 95% of the expected dose.

Example 42

Human IgG powder was reconstituted in deionized water to a protein concentration of approximately 25 mg/mL. The solution was desalted and spiked with 100 colony forming units of *Escherichia coli*, after which it was atomized and collected with a stainless steel vessel containing a volume greater than $V_0$ of a mixture of amyl acetate and phenol (10:1 ratio by volume) held near room temperature under conditions of gentle stirring. The phenol was chosen for its antimicrobial properties. After primary desiccation, particles were collected for sterility inspection. 10 mg of the desiccated particles were dissolved in 1 mL of sterile deionized water and incubated in Fluid Thioglycollate Medium for a period of 14 days to ensure no microbial growth.

Example 43

A solution of monoclonal antibody (60 mg/mL) and 30 mg/mL ascorbate in deionized water was spiked with 100 colony forming units of *Escherichia coli*. The solution was atomized and collected with a stainless steel vessel containing a volume greater than $V_0$ of a second liquid with no known sterilizing properties. After primary desiccation, particles were collected, washed, and vacuum dried before being placed in a suspension of benzyl benzoate at a protein loading of 300 mg/mL. The suspension was loaded into a 2.25 mL glass syringe. Gamma irradiation was then performed on the syringe using a MDS Nordian Gammacell 220 at a dose rate of 1.5 kGy/hr to a total of 14 kGy. After irradiation, particles were separated from the suspension continuous phase and dissolved in DI water. An ELISA assay established the preservation of antigen binding activity. After dissolution of the powder in 1 mL of deionized water, 1 mL of the dissolved powder was incubated in Fluid Thioglycollate Medium for a period of 14 days to ensure no microbial growth.

Example 44

Taq Polymerase (300 mg), sodium chloride (105 mg), and polyethylene glycol (PEG) 3350 (60 mg) were dissolved in DI water (5 mL). 100 colony forming units of *Escherichia coli* were spiked into this solution. The solution was atomized and collected with a stainless steel vessel containing a volume greater than $V_0$ of a second liquid with no known sterilizing properties. After primary desiccation, particles were collected, washed, and vacuum dried. The particles were then sterilized by using dry heat: 2 hr at 160° C. In other instances, the particles were stored at 80° C. for 72 hrs. Dissolution of 10 mg of powder was performed in 1 mL of deionized water. Preservation of protein function was confirmed by successfully performing polymerase chain reaction on DNA using the processed Taq polymerase. 1 mL of the dissolved powder was incubated in Fluid Thioglycollate Medium for a period of 14 days to ensure no microbial growth.

Example 45

Bovine Serum Albumin (0.1 g) was dissolved in DI water (4 mL) and 100 colony forming units of *Escherichia coli* were spiked into the solution. The solution was atomized and collected with a stainless steel vessel containing a volume greater than $V_0$ of a second liquid with no known sterilizing properties. After primary desiccation, particles were collected, washed, and vacuum dried. The particles were then placed in foil pouches and transferred to a 750 mL steel autoclave equipped with an inlet and outlet valve, pressure gauge, and safety valve. The autoclave was filled with $scCO_2$ (300 g liquid $CO_2$) and transferred to the supercritical (sc) state by heating the autoclave (38° C., 8.5 MPa). Particles were subjected to $scCO_2$ treatment for around 30 minutes before depressurization of the autoclave and collection of the sterile powder. After dissolution of 10 mg of powder in 1 mL of deionized water, 1 mL of the dissolved powder was incubated in Fluid Thioglycollate Medium for a period of 14 days to ensure no microbial growth.

Example 46

Figure 13:
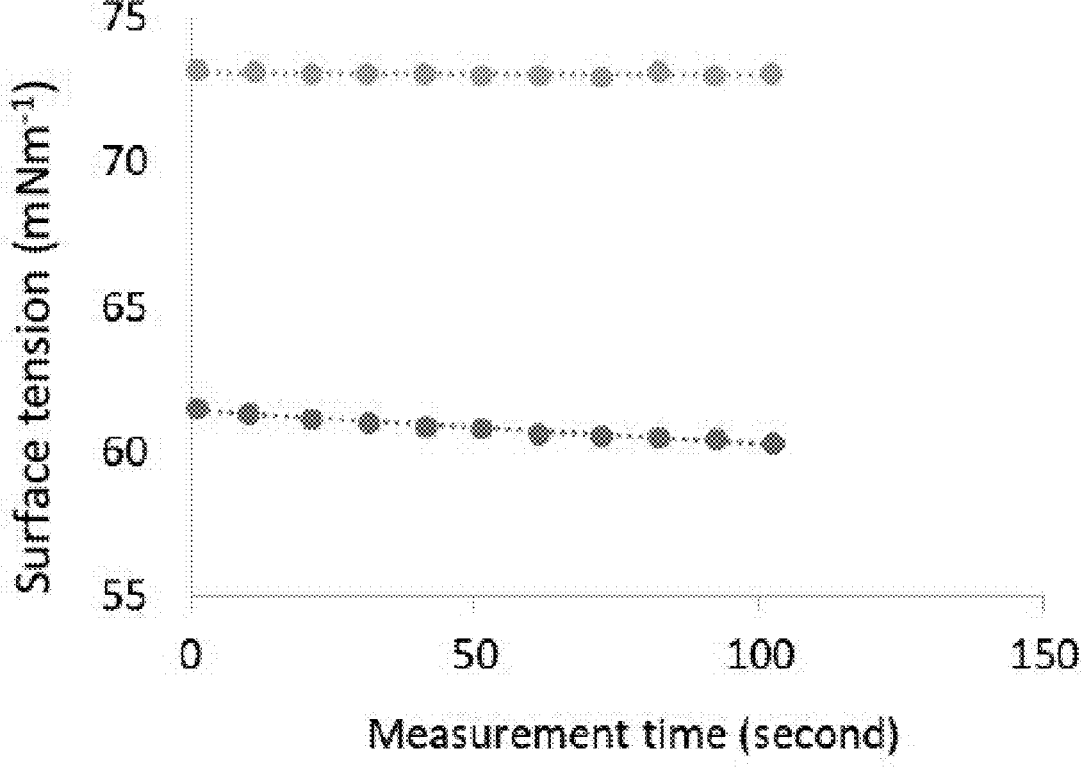
FIG. 13 shows a graph of the surface tension of the air-liquid interface for a neat deionized water solution and a solution of protein dissolved in deionized water at a concentration of 20 mg/mL.

A solution of protein (20 mg/mL) was prepared in deionized water. The surface tension (air-water) of this solution was measured using a KRÜSS™ K11 tensiometer fitted with a Wilhelmy plate. The surface tension was recorded until equilibrium was reached. The solution exhibited a decrease of approximately 10 mN/m as compared to neat deionized water. This demonstrated the ability of the surfactant to act as a surfactant (FIG. 13).

Example 47

A first solution of human IgG (first liquid A) was prepared by reconstituting human IgG powder in deionized water to a protein concentration of approximately 50 mg/mL. The solution was desalted. A second solution of human IgG (first liquid B) was prepared by reconstituting human IgG powder in deionized water to a protein concentration of approximately 50 mg/mL. The solution was desalted and a quantity of a plasticizer (5 mg/mL) was added. The solutions were separately atomized and collected with stainless steel vessels containing volumes greater than $V_0$ of a second liquid held under conditions of gentle stirring. In both cases, the temperature of the first liquid and the second liquid during the particle formation process was kept above the glass transition temperature of the plasticizer excipient in first liquid B. In both cases, these resulted in a Peclet number of greater than 1 for the human IgG in the first liquid. After primary desiccation, particles were collected, washed, and vacuum dried to remove residual liquid. SEM images revealed identifiable particulate matter and indicated that the plasticizer afforded control over the particle morphology. First liquid A was associated with particles comprising an internal void space and wrinkled surfaces. First liquid B was associated with particles comprising lesser degrees of internal void spaces and wrinkled surfaces.

Example 48

A first solution of human IgG (first liquid A) was prepared by reconstituting human IgG powder in deionized water to a protein concentration of approximately 50 mg/mL. The solution was desalted. A second solution of human IgG (first liquid B) was prepared by reconstituting human IgG powder in deionized water to a protein concentration of approximately 50 mg/mL. The solution was desalted and a quantity of a surfactant (2 mg/mL) was added. The solutions were separately atomized and collected with stainless steel vessels containing volumes greater than $V_0$ of a second liquid held under conditions of gentle stirring. In both cases, the temperature of the first liquid and the second liquid during the particle formation process was kept above the glass transition temperature of the surfactant excipient in first liquid B. In both cases, this resulted in a Peclet number of greater than 1 for the human IgG in the first liquid. After primary desiccation, particles were collected, washed, and vacuum dried to remove residual liquid. SEM images revealed identifiable particulate matter and indicated that the surfactant afforded control over the particle morphology. First liquid A was associated with particles comprising an internal void space and wrinkled surfaces. First liquid B was associated with particles comprising lesser degrees of internal void spaces and wrinkled surfaces. This may have to do with the surfactant effectively plasticizing the drop and the particle during the particle formation process, in addition to mitigating forces at the interface between the second liquid and the drop/particle. A sample of the particles produced from first liquid A were suspended in a non-aqueous medium in such a way that the average concentration of human IgG in the formulation was approximately 400 mg/mL (sample A). A sample of the particles produced from first liquid B were suspended in a separate volume of the same non-aqueous medium such that the average concentration of human IgG in the formulation was approximately 400 mg/mL (sample B). A sample for comparison was produced by reconstituting human IgG powder in deionized water to a protein concentration of approximately 400 mg/mL (sample C). The inherent viscosities of the non-aqueous medium and the deionized water (no protein load) were approximately 6 mPa·s and 1 mPa·s, respectively. The viscosities of all three samples were tested using a rheometer. In terms of increasing viscosity, the results indicated that sample B<sample A<sample C, i.e., that the particles from first liquid B provided the lowest formulation viscosity at the concentration of interest. This may be a byproduct of their smoother, more spherical morphology.

Example 49

Figure 14A:
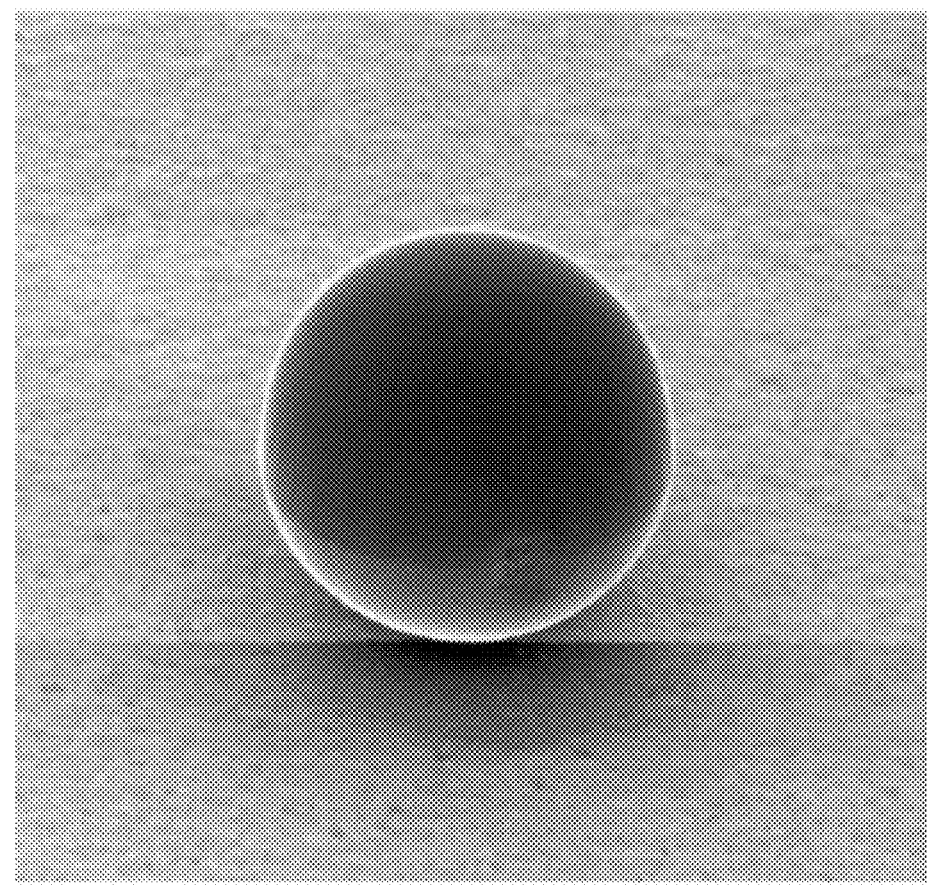
FIG. 14A shows an image of a human IgG particle surface formed through methods of the disclosure.
Figure 14B:
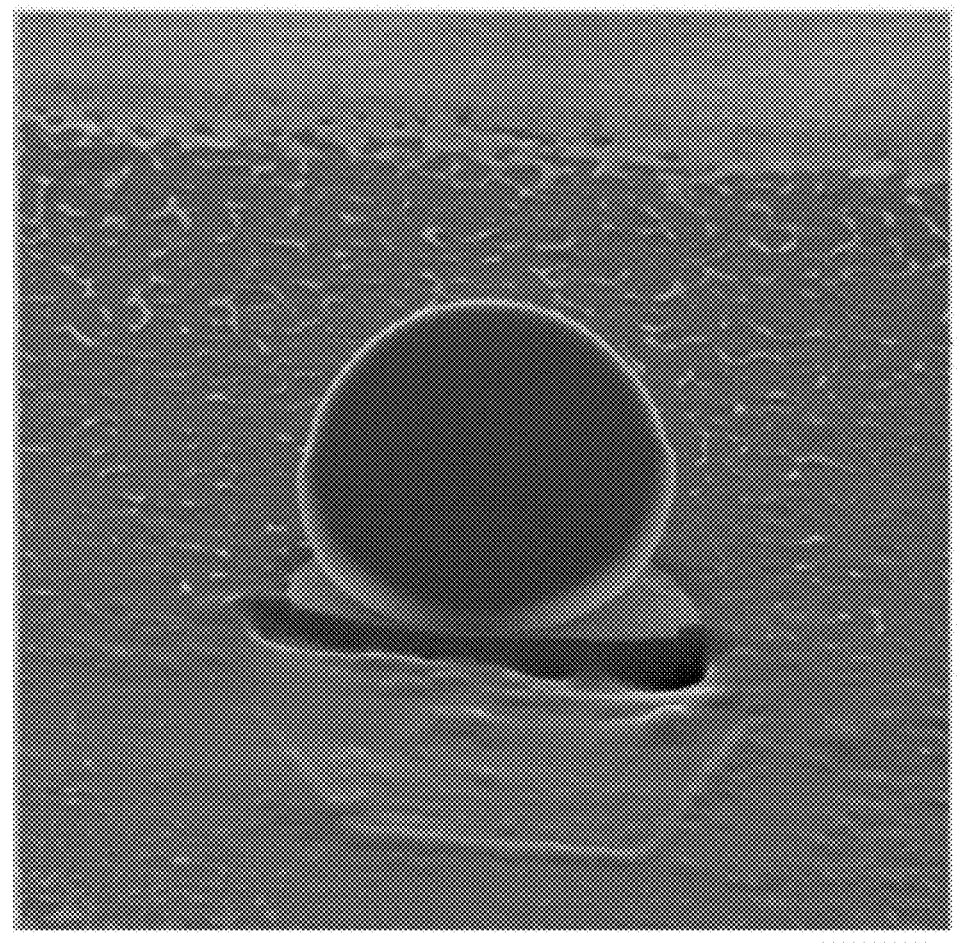
FIG. 14B shows an image of a human IgG particle sectioned to reveal the internal cross-section.

Human IgG powder was reconstituted in deionized water to a protein concentration of approximately 24 mg/mL. The solution was desalted, after which it was atomized and collected with a stainless steel vessel containing a volume greater than $V_0$ of butyl acetate held near room temperature under conditions of gentle stirring. After primary desiccation, particles were collected, washed, and vacuum dried to remove residual liquid. HIM images revealed identifiable particulate matter. Cross-sections of the particles indicated an absence of pores (substantially free from any internal void spaces) and a correspondingly low particle porosity (FIGS. 14A-14B) as compared to the particles of FIG. 3A. The particles were found to have a circularity of 0.900 and a roughness of 2.342 as compared to the particles of FIG. 3A.

DISCUSSION

As demonstrated in the exemplary material, particle morphology was manipulated variously and extensively by modifying the composition and properties of the first liquid and the second liquid during controlled particle formation. These parameters, in addition to judicious execution of the post-processing steps, were similarly employed to manipulate the particle composition, component distribution, and surface properties. In the case of particle formulations containing monoclonal antibodies, physiochemical analyses indicated agent activity was substantially preserved immediately following processing and on stability under thermal stress (7 days at 40° C.). Suspension formulations based on the particles exhibited low viscosity at high agent loading in addition to favorable dispersibility properties. The bioburden was low on account of sterility measures.

INCORPORATION BY REFERENCE

All publications and patents mentioned herein, are hereby incorporated by reference in their entirety as if each individual publication or patent was specifically and individually indicated to be incorporated by reference. In case of conflict, the present application, including any definitions herein, will control.

EQUIVALENTS

While specific aspects and embodiments of the subject disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations.

What is claimed is:

1. A composition comprising particles, wherein a plurality of the particles: comprise an antibody or fragment thereof and one or more excipients, wherein the one or more excipients comprises a surfactant; have less than about 7% residual moisture by weight; have a loading of the antibody or fragment thereof from about 75 wt % to about 100 wt %; and comprise less than about 0.1% internal void spaces, and wherein the composition comprises less than 5% aggregation of the antibody or fragment thereof.

2. The composition of claim 1, wherein the antibody or fragment thereof is an amorphous antibody or fragment thereof.

3. The composition of claim 1, wherein the composition comprises less than 3% aggregation of the antibody or fragment thereof.

4. The composition of claim 1, wherein the composition further comprises a sugar or an antioxidant.

5. The composition of claim 1, wherein the plurality of particles, upon contact with an aqueous solution, dissolve in the aqueous solution.

6. The composition of claim 1, wherein the plurality of particles are suspended in the composition.

7. The composition of claim 6, wherein the plurality of particles are suspended in an organic solvent comprising esters.

8. The composition of claim 6, wherein the plurality of particles are suspended in an organic solvent comprising a C1-C20 ester containing compound.

9. The composition of claim 1, wherein the plurality of particles have diameters from about 1 μm to about 25 μm.

10. The composition of claim 1, wherein the composition includes about 20 to about 90% particles by volume.

\* \* \* \* \*